US012692229B2

(12) United States Patent
Cutshall et al.

(10) Patent No.: US 12,692,229 B2
(45) Date of Patent: *Jul. 28, 2026

(54) MASP-2 INHIBITORS AND METHODS OF USE

(71) Applicant: Omeros Corporation, Seattle, WA (US)

(72) Inventors: Neil S. Cutshall, Snohomish, WA (US); Jennifer Lynn Gage, Kenmore, WA (US); Sara Rebecca Goldstein, Seattle, WA (US); Do Yeon Kwon, Seattle, WA (US); Thomas L. Little, Seattle, WA (US); Markus Metz, Bellevue, WA (US); Peter Kurt Nollert von Specht, Bainbridge Island, WA (US); Jennifer Tsoung, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 130 days.

This patent is subject to a terminal disclaimer.

(21) Appl. No.: 18/680,563

(22) Filed: May 31, 2024

(65) Prior Publication Data

US 2024/0317682 A1 Sep. 26, 2024

Related U.S. Application Data

(63) Continuation of application No. 17/112,873, filed on Dec. 4, 2020, now Pat. No. 12,030,853.

(60) Provisional application No. 62/943,629, filed on Dec. 4, 2019.

(51) Int. Cl.

| | |
|---|---|
| ***C07D 207/16*** | (2006.01) |
| ***A61K 31/40*** | (2006.01) |
| ***C07D 403/04*** | (2006.01) |
| ***C07D 413/04*** | (2006.01) |
| ***C07D 471/04*** | (2006.01) |

(52) U.S. Cl.

CPC ......... *C07D 207/16* (2013.01); *C07D 403/04* (2013.01); *C07D 413/04* (2013.01); *C07D 471/04* (2013.01)

(58) Field of Classification Search

CPC .. C07D 207/16; C07D 403/04; C07D 413/04; C07D 471/04; A61K 31/40

See application file for complete search history.

(56) References Cited

U.S. PATENT DOCUMENTS

| | | | |
|---|---|---|---|
| 4,331,647 | A | 5/1982 | Goldenberg |
| 4,816,567 | A | 3/1989 | Cabilly |
| 4,946,778 | A | 8/1990 | Ladner |
| 5,211,657 | A | 5/1993 | Yamada |
| 5,223,409 | A | 6/1993 | Ladner |
| 5,403,484 | A | 4/1995 | Ladner |
| 5,552,157 | A | 9/1996 | Yagi |
| 5,565,213 | A | 10/1996 | Nakamori |
| 5,567,434 | A | 10/1996 | Szoka, Jr. |
| 5,571,698 | A | 11/1996 | Ladner |
| 5,610,288 | A | 3/1997 | Rubenstein |
| 5,693,762 | A | 12/1997 | Queen |
| 5,718,709 | A | 2/1998 | Considine |
| 5,738,868 | A | 4/1998 | Shinkarenko |
| 5,739,119 | A | 4/1998 | Galli |
| 5,741,516 | A | 4/1998 | Webb |
| 5,759,829 | A | 6/1998 | Shewmaker |
| 5,789,573 | A | 8/1998 | Baker |
| 5,795,587 | A | 8/1998 | Gao |
| 5,801,154 | A | 9/1998 | Baracchini |
| 5,866,573 | A | 2/1999 | Sanderson |
| 6,515,011 | B2 | 2/2003 | Selnick |
| 6,649,592 | B1 | 11/2003 | Larson |
| 6,653,316 | B1 | 11/2003 | South |
| 7,015,230 | B1 | 3/2006 | South |
| 7,919,094 | B2 | 4/2011 | Schwaeble |
| 8,652,477 | B2 | 2/2014 | Schwaeble |
| 8,840,893 | B2 | 9/2014 | Schwaeble |
| 8,889,712 | B2 | 11/2014 | Borzilleri |
| 8,937,065 | B2 | 1/2015 | Becker et al. |
| 8,951,522 | B2 | 2/2015 | Demopulos |
| 9,011,860 | B2 | 4/2015 | Dudler |
| 9,469,608 | B2 | 10/2016 | Chobanian |
| 9,475,885 | B2 | 10/2016 | Dudler |
| 9,644,035 | B2 | 5/2017 | Demopulos |
| 11,299,479 | B1 | 4/2022 | Ashcraft |
| 11,584,714 | B2 | 2/2023 | Cutshall |
| 11,661,418 | B2 | 5/2023 | Cutshall |
| 11,807,641 | B2 | 11/2023 | Cicirelli |

(Continued)

FOREIGN PATENT DOCUMENTS

| | | | |
|---|---|---|---|
| AU | 2013201779 | A1 | 4/2013 |
| CA | 3147564 | A1 | 2/2021 |

(Continued)

OTHER PUBLICATIONS

Kenawy, H. I., et al., “Complement-Coagulation Cross-Talk: A Potential Mediator of the Physiological Activation of Complement by Low pH,” Front Immunol 6:215 (2015).

Kleywegt, G. J., et al., “Detection, delineation, measurement and display of cavities in macromolecular structures,” Acta Crystallogr D Biol Crystallogr 50(Pt 2):178-185 (1994).

Laskowski, R. A., et al., “LigPlot+: multiple ligand-protein interaction diagrams for drug discovery,” J Chem Inf Model 51(10):2778-2786 (2011).

(Continued)

*Primary Examiner* — Bruck Kifle

(74) *Attorney, Agent, or Firm* — CHRISTENSEN O’CONNOR JOHNSON KINDNESS PLLC

(57) ABSTRACT

The present disclosure provides, inter alia, compounds with MASP-2 inhibitory activity, compositions of such compounds, and methods of making and using such compounds.

18 Claims, No Drawings

Specification includes a Sequence Listing.

(56) References Cited

U.S. PATENT DOCUMENTS

| | | | | |
|---|---|---|---|---|
| 12,030,853 | B2 * | 7/2024 | Cutshall | C07D 207/16 |
| 12,195,427 | B2 | 1/2025 | Cutshall | |
| 2002/0019369 | A1 | 2/2002 | Li | |
| 2002/0119992 | A1 | 8/2002 | Selnick | |
| 2004/0072862 | A1 | 4/2004 | Bitler | |
| 2005/0004031 | A1 | 1/2005 | Subasinghe | |
| 2006/0002937 | A1 | 1/2006 | Schwaeble | |
| 2006/0128613 | A1 | 6/2006 | Ebetino et al. | |
| 2007/0172483 | A1 | 7/2007 | Schwaeble | |
| 2013/0266560 | A1 | 10/2013 | Demopulos | |
| 2013/0344073 | A1 | 12/2013 | Schwaeble | |
| 2015/0166675 | A1 | 6/2015 | Demopulos | |
| 2015/0315141 | A1 | 11/2015 | Chobanian | |
| 2017/0137537 | A1 | 5/2017 | Demopulos | |
| 2017/0166660 | A1 | 6/2017 | Schwaeble | |
| 2017/0189525 | A1 | 7/2017 | Brunskill | |
| 2017/0253667 | A1 | 9/2017 | Brunskill | |
| 2017/0267781 | A1 | 9/2017 | Demopulos | |
| 2017/0283508 | A1 | 10/2017 | Demopulos | |
| 2018/0105604 | A1 | 4/2018 | Brunskill | |
| 2019/0367452 | A1 | 12/2019 | Cutshall | |
| 2021/0171461 | A1 | 6/2021 | Cutshall | |
| 2021/0171512 | A1 | 6/2021 | Cutshall | |
| 2021/0171531 | A1 | 6/2021 | Cicirelli | |
| 2021/0179612 | A1 | 6/2021 | Cutshall | |
| 2023/0145071 | A1 | 5/2023 | Cutshall | |
| 2024/0092788 | A1 | 3/2024 | Cutshall | |
| 2024/0351980 | A1 | 10/2024 | Cutshall et al. | |
| 2024/0391917 | A1 | 11/2024 | Cutshall | |
| 2025/0011323 | A1 | 1/2025 | Cutshall | |
| 2025/0129020 | A1 | 4/2025 | Cutshall et al. | |
| 2025/0197349 | A1 | 6/2025 | Cutshall et al. | |
| 2025/0368604 | A1 | 12/2025 | Cutshall et al. | |
| 2025/0376443 | A1 | 12/2025 | Cutshall et al. | |

FOREIGN PATENT DOCUMENTS

| | | | |
|---|---|---|---|
| CL | 202003083 | | 5/2019 |
| CL | 202103105 | | 5/2019 |
| CL | 202000610 | | 4/2022 |
| CN | 1127509 | A | 7/1996 |
| CN | 104661676 | A | 5/2015 |
| CO | 5160330 | | 5/2002 |
| CO | 5170524 | A1 | 6/2002 |
| EP | 0321201 | | 6/1989 |
| EP | 0321201 | B1 | 12/1994 |
| JP | 20014515922 | A | 9/2001 |
| JP | 2004516286 | A | 6/2004 |
| JP | 2005514332 | | 5/2005 |
| JP | 2007535474 | A | 12/2007 |
| JP | 2010-515729 | A | 5/2010 |
| JP | 2014-506877 | A | 3/2014 |
| JP | 2014-520108 | A | 8/2014 |
| JP | 2017-508789 | A | 3/2017 |
| JP | 2022-552048 | A | 12/2022 |
| RU | 2014133019 | A | 2/2016 |
| WO | 1988004300 | A1 | 6/1988 |
| WO | 9111465 | | 8/1991 |
| WO | 199429336 | A1 | 12/1994 |
| WO | 1994029335 | | 12/1994 |
| WO | 1994029336 | | 12/1994 |
| WO | 1995023609 | A1 | 9/1995 |
| WO | 9961442 | | 12/1999 |
| WO | 0039124 | | 7/2000 |
| WO | 2000055188 | A1 | 9/2000 |
| WO | 0069834 | | 11/2000 |
| WO | 0179195 | | 10/2001 |
| WO | 01/87851 | | 11/2001 |
| WO | 01/89282 | A2 | 11/2001 |
| WO | 0187854 | | 11/2001 |
| WO | 0250056 | A1 | 6/2002 |
| WO | 2002050056 | A1 | 6/2002 |
| WO | 03028729 | | 4/2003 |
| WO | 03029224 | | 4/2003 |
| WO | 2004009664 | A2 | 1/2004 |
| WO | 2004032834 | A2 | 4/2004 |
| WO | 2005002627 | A2 | 1/2005 |
| WO | 2006101860 | | 9/2006 |
| WO | 2007135131 | | 11/2007 |
| WO | 2008/085608 | A1 | 7/2008 |
| WO | 2008085608 | | 7/2008 |
| WO | 2010141406 | A2 | 12/2010 |
| WO | 2012007777 | A1 | 1/2012 |
| WO | 2012/093101 | A1 | 7/2012 |
| WO | 2012139081 | A2 | 10/2012 |
| WO | 2012151481 | A1 | 11/2012 |
| WO | 2012172438 | | 12/2012 |
| WO | 2013106643 | A2 | 7/2013 |
| WO | 2014057068 | A1 | 4/2014 |
| WO | 2014/081618 | A1 | 5/2014 |
| WO | 2015103317 | A1 | 7/2015 |
| WO | 2015/130854 | A1 | 9/2015 |
| WO | 2017173290 | | 10/2017 |
| WO | 2018045054 | | 3/2018 |
| WO | 2019036460 | A1 | 2/2019 |
| WO | 2019055590 | A1 | 3/2019 |
| WO | 2021032933 | A1 | 8/2019 |
| WO | 2019186164 | | 10/2019 |
| WO | 2019211585 | A1 | 11/2019 |
| WO | 2019231933 | A2 | 12/2019 |
| WO | 2019231935 | A1 | 12/2019 |

OTHER PUBLICATIONS

Laskowski, R. A., "Surfnet: a program for visualizing molecular surfaces, cavities, and intermolecular interactions," JMol Graph 13(5):323-330, 307-328 (1995).
Laurie, A. T., et al., "Q-SiteFinder: an energy-based method for the prediction of protein-ligand binding sites," Bioinformatics 21(9):1908-1916 (2005).
Levitt, D. G., et al., "Pocket: a computer graphics method for identifying and displaying protein cavities and their surrounding amino acids," J Mol Graph 10(4):229-234 (1992).
Lin, C., et al., "Discovery and development of VX-950, a novel, covalent, and reversible inhibitor of hepatitis C virus NS3.4A serine protease," Infect Disord Drug Targets 6(1):3-16 (2006).
Moake, J. L., Merck Manual—Hematology and Oncology: Overview of Thrombotic Disorders [updated Oct. 17, 2019]. Available from: https://www.merckmanuals.com/professional/hematology-and-oncology/thrombotic-disorders/overview-of-thrombotic-disorders.
Nayal, M., et al., "On the nature of cavities on protein surfaces: application to the identification of drug-binding sites," Proteins 63(4):892-906 (2006).
Ni-NTA Superflow Cartridge Handbook: For manual or FPLC™ purification of His-tagged proteins: QIAGEN; 2007. 32 p.
Pedregosa, F., et al., "Scikit-learn: Machine Learning in Python," Journal of Machine Learning Research 12:2825-2830 (2011).
Peters, K. P., et al., "The automatic search for ligand binding sites in proteins of known three-dimensional structure using only geometric criteria," J Mol Biol 256(1):201-213 (1996).
Pettersen, E. F., et al., "UCSF Chimera—a visualization system for exploratory research and analysis," J Comput Chem 25(13):1605-1612 (2004).
Powers, J. C., et al., "Irreversible inhibitors of serine, cysteine, and threonine proteases," Chem Rev 102(12):4639-47S0 (2002).
Protein Data Bank [Internet], 3TVJ—Catalytic fragment of MASP-2 in complex with its specific inhibitor developed by directed evolution on SGCI scaffold. 2011 [cited Oct. 22, 2019], Available from: https://www.rcsb.org/structure/3tvj.
Ramot, Y., et al., "Drug-induced thrombosis-experimental, clinical, and mechanistic considerations," Toxicol Pathol 35(2):208-225 (2007).
Renne, T., et al., "In vivo roles of factor XII," Blood 120(22):4296-4303 (2012).
Schechter, I., et al., "On the size of the active site in proteases. I. Papain," Biochem Biophys Res Commun 27(2):157-162 (1967).
Smoum, R., et al., "Boron containing compounds as protease inhibitors," Chem Rev 112(7):4156-4220 (2012).

(56) References Cited

OTHER PUBLICATIONS

Uniprot.org [Internet], Identifier: 000187, Mannan-binding lectin serine protease 2. 2019 [cited Oct. 22, 2019], Available from: https://www.urjiprot.org/uniprot/O00187.

Venkatachalam, C. M., et al., "LigandFit: a novel method for the shape-directed rapid docking of ligands to protein active sites," J Mol Graph Model 21(4):289-307 (2003).

Verdonk, M. L., et al., "SuperStar: a knowledge-based approach for identifying interaction sites in proteins," JMol Biol 289(4):1093-1108 (1999).

Weisel, M., et al., "PocketPicker: analysis of ligand binding-sites with shape descriptors," Chem Cent J 1:7 (2007).

Weitz, J. I., et al., "Factors XI and XII as Targets for New Anticoagulants," Front Med (Lausanne) 4:19 (2017).

Young, W. B., et al., "Generation of potent coagulation protease inhibitors utilizing zinc-mediated chelation," Bioorg Med Chem Lett 16(3):710-713 (2006).

SciFinder; Chemical Abstracts Service: Columbus, OH; RN 1223890-82-1 [accessed Nov. 27, 2019]. Available from: https://scifinder.cas.org.

SciFinder; Chemical Abstracts Service: Columbus, OH; RN 1242003-50-4 [accessed Nov. 27, 2019]. Available from: https://scifinder.cas.org.

Zadlo-Dobrowolska et al., "Enzymatic Ugi Reaction with Amines and Cyclic Imines," Chem. Eur. J., 22:16684-16689 (2016).

Harmat et al., (2004), "The Structure of MBL-associated Serine Protease-2 Reveals that Identical Substrate Specificities of C1s and MASP-2 are Realized Through Different Sets of Enzyme-Substrate Interactions", JMB, 342(5) p. 1533-1546: XP004844933, https://www.dropbox.eom/s/6eto0ib57oqe8pq/D5.pdf?dl=0.

Szakacs et al., (Apr. 5, 2019), "Novel MASP-2 inhibitors developed via directed evolution of human TFPI1 are potent lectin pathway inhibitors", J. Biol. Chem., 294(20):8227-8237, XP055727499, DOI: http://dx.doi.org/10.1074/jbc.RA119.008315.

Hedstrom, L, "Serine protease mechanism and specificity," Chem Rev 102(12):4501-4524 (2002).

U.S. Appl. No. 62/688,611, filed Jun. 22, 2018, Demopulos et al.

Courtenay-Luck, N.S., "Genetic Manipulation of Monoclonal Antibodies," in Monoclonal Antibodies: Production, Engineering and Clinical Application, Ritter et al., (eds.) p. 166, Cambridge University Press, (1995).

Kelley, R.F., "Engineering Therapeutic Antibodies," in Protein Engineering. Principles and Practice, Cleland et al., (eds.) John Wiley & Sons, Inc., pp. 399-434, (1996).

Baines et al., "Purification of Immunoglobulin G, (IgG)," in Methods in Molecular Biology vol. 10: Immunochemical Protocols, Chapter 8, pp. 79-105, (1992).

Matsushita, M., et al., "The role of ficolins in innate immunity," Immunobiology, 205(4-5):490-497, (2002).

Tezel, G., et al., "Oxidative stress and the regulation of complement activation in human glaucoma" Invest Ophthalmol Vis Sci 51:5071-5082, (2010).

Harlow, E., et al., Antibodies: A Laboratory Manual, Cold Spring Harbor Laboratory, New York, (1988).

Heja, et al., "Monospecific Inhibitors Show That Both Mannan-binding Lectin-associated Serine Protease-1 (MASP-1) and -2 Are Essential for Lectin Pathway Activation and Reveal Structural Plasticity of MASP-2," The Journal of Biological Chemistry, 287(24):20290-20300 (2012).

Risitano, A.M., et al., "Complement fraction 3 binding on erythrocytes as additional mechanism of disease in paroxysmal nocturnal hemoglobinuria patients treated by eculizumab," Blood 113(17):4094-100, (2009).

Teh, C., et al., "M-ficolin is expressed on monocytes and is a lectin binding to N-acetyl-D-glucosamine and mediates monocyte adhesion and phagocytosis of *Escherichia coli*," Immunology 101:225-232, (2000).

Hansen, et al., "Collectin 11 (CL-11, CL-K1) is a MASP-I/3-associated plasma collectin with microbial-binding activity," J. Immunol 185(10):6096-6104, (2010).

Jack, D.L., et al., "Mannose-binding lectin enhances phagocytosis and killing of Neisseria meningitidis by human macrophages" J Leukoc Biol., 77(3):328-36, (2005).

Aoyagi et al., "Role of L-ficolin/mannose-binding lectin-associated serine protease complexes in the opsonophagocytosis of type III group B streptococci," J Immunol, 174(I):418-25, (2005).

Degn, S.E., et al., "MAp19, the alternative splice product of the MASP2 gene," J Immunol. Methods, 373(1-2):89-101, (2011).

Guessous, F., et al., "Shiga toxin 2 and lipopolysaccharide induce human microvascular endothelial cells to release chemokines and factors that stimulate platelet function," Infect. Immun, 73(12):8306-8316, (2005).

Kaufman, R.J., et al., "Improved vectors for stable expression of foreign genes in mammalian cells by use of the untranslated leader sequence from EMC virus," Nucleic Acids Research 19:4485-90, (1991).

Kaufman, R.J., "Selection and coamplification of heterologous genes in mammalian cells," Methods in Enzymology, 185:537-66, (1990).

Maniatis, A., et al., "Intermediate-dose melphalan for refractory myeloma," Blood 74(3):1177, (1989).

Shea, K. J., "Molecular Imprinting of Synthetic Network Polymers: The De Novo synthesis of Macromolecular Binding and Catalytic Sties," TRIP 2(5):166-173, (1994).

Registry(STN) [online], [Retrieved on Jul. 31, 2024]: CAS Registry No. 1348730-54-0, Entry Date Dec. 5, 2011, CAS Registry No. 1348728-96-0, Entry Date Dec. 5, 2011, CAS Registry No. 1348431-17-3, Entry Date Dec. 4, 2011, CAS Registry No. 1348395-03-8, Entry Date Dec. 4, 2011, CAS Registry No. 749177-11-5, Entry Date Sep. 21, 2004.

Lu, J., et al., "Collectins and ficolins: sugar pattern recognition molecules of the mammalian innate immune system," Biochim Biophys Acta 1572:387-400, (2002).

Jordan et al., "Inhibition of mannose-binding lectin reduces postischemic myocardial reperfusion injury," Circulation 104(12):1413-1418, (2001).

Maynard, Y., et al., "Characterization of a mannose and N-acetylglucosamine-specific lectin present in rat hepatocytes," J. Biol. Chem. 257:3788-3794, (1982).

Lee, R.T., et al., "Multivalent ligand binding by serum mannosebinding protein," Archiv. Biochem. Biophys. 299:129-136, (1992).

Collard et al., "Endothelial oxidative stress activates the lectin complement pathway: role of cytokeratin 1," Am. J. Pathol. 159(3):1045-1054, (2001).

Ji, Y.H., et al., "Activation of the C4 and C2 components of complement by a proteinase in serum bactericidal factor, Ra reactive factor," J. Immunol. 150:571-578, (1993).

Kilpatrick, D.C., et al., "Mannan-binding lectin: clinical significance and applications," Biochim Biophys Acta 1572:401-413, (2002).

Weis, W.I., et al., "Structure of a C-type mannose-binding protein complexed with an oligosaccharide," Nature 360:127-134, (1992).

Kalli, K.R., et al., "Therapeutic uses of recombinant complement protein inhibitors," Springer Semin. Immunopathol. 15:417-431, (1994).

Wallis, R., et al., "Localization of the serine protease-binding sites in the collagen-like domain of mannose-binding protein: indirect effects of naturally occurring mutations on protease binding and activation," J. Biol. Chem. 279:14065-73, (2004).

Wallis, R., et al., "Interaction of mannose-binding protein with associated serine proteases: effects of naturally occurring mutations," J. Biol. Chem. 275:30962-30969, (2000).

Sim, R.B., et al., "Innate Immunity," Biochem. Soc. Trans. 28:545-550, (2000).

Cech, T.R., et al., "Biological catalysis by RNA," Ann. Rev. Biochem. 55:599-629, (1986).

Clackson, T., et al., "Making antibody fragments using phage display libraries," Nature 352:624-628, (1991).

Chen, P.F., et al., "Development of the non-palindromic adaptor polymerase chain reaction (NPA-PCR) for the amplification of alpha- and beta-chain T-cell receptor cDNAs," Scand. J. Immunol. 35:539-549, (1992).

Bird, et al., "Single-chain antigen-binding proteins," Science 242(4877):423-426, (1988).

(56) References Cited

OTHER PUBLICATIONS

Climie, S., et al., "Chemical synthesis of the thymidylate synthase gene," Proc. Nat'l Acad. Sci. USA 87(2):633, (1990).
Carter, P., et al., "Humanization of an anti-pl85HER2 antibody for human cancer therapy," Proc. Nat'l. Acad. Sci. USA 89(10):4285-4289, (1992).
Altschul, S.F., et al., "Gapped BLAST and PSI-BLAST: a new generation of protein database search programs," Nucl. Acids Res. 25:3389-3402, (1997).
Makino, K., "A Microcapsule Self-Regulating Delivery System for Insulin," J. Controlled Release 12:235-239, (1990).
Lee, V.H.L., "Protease Inhibitors and Penetration Enhancers as Approaches to Modify Peptide Absorption," J. Controlled Release 13:213, (1990).
Jolliffe, L.K., et al., "Humanized antibodies: enhancing therapeutic utility through antibody engineering," Int'l Rev. Immunol. 10:241-250, (1993).
Jackson, D.Y., et al., "Potent alpha 4 beta 1 peptide antagonists as potential anti-inflammatory agents," J. Med. Chem 40:3359-68, (1997).
Hori, R., et al., "Enhanced bioavailability of subcutaneously injected insulin coadministered with collagen in rats and humans," Pharm. Res. 6:813, (1989).
Daha, M.R., et al., "C3 nephritic factor (C3NeF): stabilization of fluid phase and cell-bound alternative pathway convertase," J. Immunol. 116(1):1-7, (1976).
Greenspan, N.S., et al., "Idiotypes: structure and immunogenicity," FASEBJ. 7(5):437-444, (1993).
Deboer, A.G., et al., "Rectal Absorption Enhancement of Peptide Drugs," J. Controlled Release 13:241, (1990).
Fuertges, F., et al., "The Clinical Efficacy of Poly(Ethylene Glycol)-Modified Proteins," J. Controlled Release 11:139, (1990).
Singer, I.I., et al., "Optimal humanization of 1B4, an anti-CD18 murine monoclonal antibody, is achieved by correct choice of human V-region framework sequences," J. Immun. 150:2844, (1993).
Siegert, C.E., et al., "The relationship between serum titers of autoantibodies to Clq and age in the general population and in patients with systemic lupus erythematosus," Clin. Immunol. Immunopathol. 67:204-9, (1993).
Schwaeble, W., et al., "The mannan-binding lectin-associated serine proteases (MASPs) and MApl9: four components of the lectin pathway activation complex encoded by two genes," Immunobiology 205:455-466, (2002).
Ronn R et al, (2006), "Exploration of acyl sulfonamides as carboxylic acid replacements in protease inhibitors of the hepatitis C virus full-length NS3", Bioorganic, Elsevier, Amsterdam, NL, 14(2):544-559 , XP027992303, https://www.dropbox.com/s/qzqalozouacfevl/D11 pdf?dl=0.
Ambrus et al., "Natural substrates and inhibitors of mannan-binding lectin-associated serine protease-1 and -2: a study on recombinant catalytic fragments," J. Immunol. 170:1374-1382, (2003).
Berge et al., "Pharmaceutical salts," J. Pharm. Sei. 66( 1):1-19, Jan. 1977.
Berthoux et al., "Predicting the Risk for Dialysis or Death in IgA Nephropathy," J. Am. Soc. Nephrol. 22:752-761, 2011.
Goto et al., "A scoring system to predict renal outcome in IgA nephropathy: a nationwide 10-year prospective cohort study," Nephrol. Dial. Transplant. 24:3068-3074, Jun. 10, 2009.
Ho et al., "Blood and Marrow Transplant Clinical Trials Network Toxicity Committee Consensus Summary: Thrombotic Microangiopathy after Hematopoietic Stem Cell Transplantation," Biology of Blood and Marrow Transplantation 11:571-575, 2005.
Kozarcanin, H., et al., "The lectin complement pathway serine proteases (MASPs) represent a possible crossroad between the coagulation and complement systems in thromboinflammation," J Thromb Haemost 14(3):531-545 (2016).
Lange et al., "Orally active thrombin inhibitors. Part 2: Optimization of the P2-moiety," Biorganic & Medicinal Chemistry Letters 76:2648-2653, Feb. 3, 2006.
Noris M et al. "Genetic Atypical Hemolytic-Uremic Syndrome," Nov. 16, 2007 [Updated, Mar. 10, 2011]. In: Pagon RA, Bird TD, Dolan CR, et al., editors. GeneReviews™, Seattle, (WA): University of Washington, Seattle.
Parlow et al., "Design, Parallel Synthesis, ancl Crystal Structures of Pyrazinone Antithrombotics as Selective Inhibitors of the Tissue Factor Vila Complex," Journal of Medicinal Chemistry, 46(19):4050-4062 (2003).
Peterlin-Masic et al., "Metabolism-Directed Optimisation of Antithrombotics: The Prodrug Principle," Curr. Pharm. Des. 12(1):73-91, 2006.
Pétursson, "Protecting Groups in Carbohydrate Chemistry," Journal of Chemical Education 74(11):1297, Nov. 1997.
Rambaldi et al., "Endothelial injury and thrombotic microangiopathy in COVID-19: Treatment with the lectin-pathway inhibitor narsoplimab," Immunobiology 225(152001):1-10, 2020.
Reich et al., "Remission of Proteinuria Improves Prognosis in IgA Nephropathy," J. Am. Soc. Nephrol. 18:3177-3183,2007.
Ricklin et al., "Complement—a key system for immune surveillance and homeostasis," Nat. Immunol. 11(9):785-797, Sep. 2010.
Sanderson, et al., "Azaindoles: Moderately Basic P1 Groups for Enhancing the Selectivity of Thrombin Inhibitors," Biorganic & Medicinal Chemistry Letters, 13:795-798 (2003).
Schwaeble et al., "Targeting of mannan-binding lectin-associated serine protease-2 confers protection from myocardial and gastrointestinal ischemia/reperfusion injury," PNAS 108( 18):7523-7528, May 3, 2011.
Staas D D et al, "Discovery of potent, selective 4-fluoroproline-based thrombin inhibitors with improved metabolic stability", Bioorganic & Medicinal Chemistry,, vol. 14, No. 20, ISSN 0968-0896, (Oct. 15, 2006), pp. 6900-6916, (Oct. 15, 2006), XP027992972.
Trost et al., eds., "Comprehensive Organic Synthesis: Selectivity, Strategy & Efficiency in Moden Organic Chemistry" vol. 1, Pergamon Press, Oxford, United Kingdom, 1991.
Registry(STN) [online], [search date Aug. 15, 2024]: CAS Registry No. 1325176-10-0, Entry Date Aug. 29, 2011, CAS Registry No. 1321541-78-9, Entry Date Aug. 22, 2011, CAS Registry No. 1300407-49-1, Entry Date May 25, 2011, CAS Registry No. 1277113-31-1, Entry Date Apr. 8, 2011, CAS Registry No. 1277016-41-7, Entry Date Apr. 8, 2011, CAS Registry No. 1240647-23-7, Entry Date Sep. 13, 2010, CAS Registry No. 1009452-72-5, Entry Date Mar. 21, 2008.
Colligan, "Production of Monoclonal Antibodies," Current Protocols in Immunology, vol. 1., John Wiley & Sons, pp. 2.5.1-2.6.7, (1991).
Gal et al., "A true autoactivating enzyme. Structural insight into mannose-binding lectin-associated serine protease-2 activations," J. Biol. Chem. 280(39):33435-44, (2005).
Riechmann, L., et al., "Reshaping human antibodies for therapy," Nature 332:323-329, (1988).
Lee, W. A., "Permeation enhancers for the nasal delivery of protein and peptide therapeutics," Biopharm. 3:22-25, (1990).
Yoshihiro, I., et al., "An Insulin-Releasing System that is Responsive to Glucose," J. Controlled Release 10:195-203, (1989).
Green, J.A., et al., "Production of polyclonal antisera," In: Immunochemical protocols. Methods in molecular biology, vol. 10. Humana Press, Totowa, N.J., p. 1, (1992).
King, L.A., et al., "Propagation, titration and purification of AcMNPV in cell culture," The Baculovirus Expression System. A Laboratory Guide, Chapman and Hall Ltd., London, pp. 106-126, (1992).
Gastoldi, S., et al., "C5a/C5aR interaction mediates complement activation and thrombosis on endothelial cells in atypical hemolytic uremic syndrome (aHUS)," Immunobiology 217(11):1145-1146, (2012).
Abagyan, R., et al., "Biased probability Monte Carlo conformational searches and electrostatic calculations for peptides and proteins," JMol Biol 235(3):983-1002 (1994).
Abagyan, R., et al., "ICM—A new method for protein modeling and design: Applications to docking and structure prediction from the distorted native conformation," Journal of Computational Chemistry 15(5):488-506 (1994).

(56) References Cited

OTHER PUBLICATIONS

An, J., et al., "Pocketome via comprehensive identification and classification of ligand binding envelopes," Mol Cell Proteomics 4(6):752-761 (2005).
Biela, A., et al., "Ligand binding stepwise disrupts water network in thrombin: enthalpic and entropie changes reveal classical hydrophobic effect," J Med Chem 55(13):6094-6110 (2012).
Brady, G. P., Jr., et al., "Fast prediction and visualization of protein binding pockets with Pass," J Comput Aided Mol Des 14(4):383-401 (2000).
Brylinski, M., et al., "Prediction of functional sites based on the fuzzy oil drop model," PLoS Comput Biol 3(5):e94 [2007).
Brylinski, M., et al., "A threading-based method (FINDSITE) for ligand-binding site prediction and functional annotation," Proc Natl AcadSci USA 105(1):129-134 (2008).
Chang, D. T., et al., "MEDock: a web server for efficient prediction of ligand binding sites based on a novel optimization algorithm," Nucleic Acids Res 33(Web Server issue):W233-238 (2005).
Del Carpio, C. A., et al., "A new approach to the automatic identification of candidates for ligand receptor sites in proteins: (I). Search for pocket regions," J Mol Graph11(1):23-29, 42 (1993).
Delaney, J. S., "Finding and filling protein cavities using cellular logic operations," J Mol Graph 10(3):174-177,163 (1992).
Dundas, J., et al., "CASTp: computed atlas of surface topography of proteins with structural and topographical mapping of functionally annotated residues," Nucleic Acids Res 34(Web Server issue):W116-118 (2006).
Emsley, P., et al., "Features and development of Coot," Acta Crystallogr D Biol Crystallogr 66(Pt 4):486-501 (2010).
Fernández-Recio, J., "Prediction of protein binding sites and hot spots," Wiley Interdiscip Rev ComputMol Sci I (5):680-698 (2011).
Fukunishi, Y., et al., "Prediction of ligand-binding sites of proteins by molecular docking calculation for a random ligand library," Protein Sci 20(1):95-106 (2011).
Gelb, M. H., et al., "Substituted isatoic anhydrides: selective inactivators of trypsin-like serine proteases," J Med Chem 29(4):585-589 (1986).
Glaser, F., et al., "ConSurf: identification of functional regions in proteins by surface-mapping of phylogenetic information," Bioinformatics 19(1):163-164 (2003).
Goodford, P. J., "A computational procedure for determining energetically favorable binding sites on biologically important macromolecules," JMed Chem 28(7):849-857 (1985).
Greene, J., et al., "Chemical Function Queries for 3D Database Search," J Chem Inf Comput Sci 34(6):1297-1308 (1994).
Grutter, M. G., et al., "Crystal structure of the thrombin-hirudin complex: a novel mode of serine protease inhibition," EMBO J 9(8):2361-2365 (1990).
Halgren, T., "New method for fast and accurate binding-site identification and analysis," Chem Biol Drug Des 69(2):146-148 (2007).
Hendlich, M., et al., "LIGSITE: automatic and efficient detection of potential small molecule-binding sites in proteins," JMol Graph Model 15(6):359-363, 389 (1997).
Huang, B., et al., "LIGSITEcsc: predicting ligand binding sites using the Connolly surface and degree of conservation," BMC Struct Biol 6:19 (2006).
Katz, B. A., et al., "Design of potent selective zinc-mediated serine protease inhibitors," Nature 391(6667):608-612 (1998).
Sandhu U.S., "Protein engineering of antibodies," Crit. Rev. Biotech. 12:437-462, (1992).
Ravetch J.V., et al., "Fc receptors," Annu. Rev. Immunol. 9:457-492, (1991).
Rosenblatt, J., et al., "The Effect of Collagen Fiber Size Distribution on the Release Rate of Proteins from Collagen Matrices by Diffusion," J. Controlled Release 9:195, (1989).
Porter, R.R., "The hydrolysis of rabbit y-globulin and antibodies with crystalline papain," Biochem. J. 73:119, (1959).
Merrifield, R.B., "Solid Phase Peptide Synthesis. I. The Synthesis of a Tetrapeptide," in J. Amer. Chem. Soc. 85:2149-2154, (1963).
Presta, L.G., "Antibody engineering," Curr. Op. Struct. Biol. 2:593-596, (1992).
Lee, V.H.L., "Enzymatic Barriers to Peptide and Protein Absorption," Crit. Rev. Ther. Drug Carrier Sys. 5(2):69-97, (1988).
Yamakawa, I., et al., "Sustained release of insulin by double-layered implant using poly(D,L-lactic acid)," J. Pharm. Sci. 79:505, (1990).
Ohman, E.M., et al., "Early clinical experience with integrelin, an inhibitor of the platelet glycoprotein IIb/IIIa integrin receptor," European Heart J. 16:50-55, (1995).
Pack, P., et al., "Improved bivalent miniantibodies, with identical avidity as whole antibodies, produced by high cell density fermentation of *Escherichia coli*," Bio/Technology 11:1271, (1993).
Zhang, L., et al., "A discrete site modulates activation of I domains. Application to integrin alphaMbeta2," J. Biol. Chem. 271(47):29953-57, (1996).
Taylor, L.D., et al., "Human immunoglobulin transgenes undergo rearrangement, somatic mutation and class switching in mice that lack endogenous IgM," Int. Immun. 6:579, (1994).
Takakura, Y., et al., "Control of pharmaceutical properties of soybean trypsin inhibitor by conjugation with dextran. I: Synthesis and characterization," J. Pharm. Sci. 78:117, (1989).
Van de Winkel, J.G., et al., "Human IgG Fc receptor heterogeneity: molecular aspects and clinical implications," Immunol. Today 14:215-221, (1993).
Vaughan, T.J., et al., "Human antibodies by design," Nature Biotechnical 16:535-539, (1998).
Scatchard, G., "The Attraction of Proteins for Small Molecules and Ions," NY Acad. Sci. 51:660-672, (1949).
Green, L.L., et al., "Antigen-specific human monoclonal antibodies from mice engineered with human Ig heavy and light chain YACs," Nature Genet. 7:13-21, (1994).
Glover, G.I., et al., "Synthetic peptide inhibitors of complement serine proteases—I. Identification of functionally equivalent protease inhibitor sequences in serpins and inhibition of C1s and D," Mol. Immunol. 25:1261, (1988).
Fedor, M.J., et al., "Substrate sequence effects on "hammerhead" RNA catalytic efficiency," Proc. Natl. Acad. Sci. USA 87:1668-1672, (1990).
CAS RN: 2180351-81-7; Date entered STN Feb. 27, 2018; 5-Cyclopropyl-N-[2-[(2 furanylmethyl)amino]-2-oxoethyl]-1H-pyrazole-3-carboxamide.
Chobanian, H. R. et al., 'Improved Stability of Proline-Derived Direct Thrombin Inhibitors through Hydroxyl to Heterocycle Replacement', ACS Medicinal Chemistry Letters (2015), 6(5), 553-557.
Maiwald, A., et al., 'Changing the selectivity profile—from substrate analog inhibitors of thrombin and factor Xa to potent matriptase inhibitors', Journal of Enzyme Inhibition and Medicinal Chemistry (2016), 31(sup1), 89-97.
Li, H. et al., 'Identification of Potent and Selective Non-covalent Inhibitors of the Plasmodium falciparum Proteasome', Journal of the American Chemical Society (2014), 136(39), 13562-13565.
Meyer, D., et al., 'Identification of the first synthetic inhibitors of the type II transmembrane serine protease TMPRSS2 suitable for inhibition of influenza virus activation', Biochemical Journal (2013), 452(2), 331-343.
Isaacs, R.C.A., et al., 'P3 optimization of functional potency, in vivo efficacy and oral bioavailability in 3-aminopyrazinone thrombin inhibitors bearing non-charged groups at the P1 position', Bioorganic & Medicinal Chemistry Letters (2011), 21(5), 1532-1535.
Young, M.B., et al., 'Discovery and Evaluation of Potent P1 Aryl Heterocycle-Based Thrombin Inhibitors', Journal of Medicinal Chemistry (2004), 47(12), 2995-3008.
Endo, Y., "Collaboration of the lectin complement pathway with the blood coagulation system," Japanese Journal of Thrombosis and Hemostasis 22(4):164-170, 2011.
Ohkuma, K., et al., "Crosstalk between the two systems, blood coagulation and complement," Japanese Journal of Thrombosis and Hemostasis 22(4):171-185, 2011.
Belikov, V.G., "Pharmaceutical Chemistry", textbook, 2007, Moscow, "MEDpress-Inform", pp. 27-29.
Dyson G. and P. Mei, "Chemistry of synthetic drugs", translation from English, M: "Mir", 1964, pp. 12-19).

(56) References Cited

OTHER PUBLICATIONS

Kümmererer, K. Pharmaceuticals in the environment, Annual Review of Environment and Resources, 2010, V.35, p. 57-75, doi: 10.1146/annurev-environ-052809-16122.
Alexeev, V.V., Optical isomerism and pharmacologic activity of drugs. Soros Educational Journal, 1998, pp. 49-55.
Vorup-Jensen, T., et al., "Distinct pathways of mannan-binding lectin (MBL)- and Cl-complex autoactivation revealed by reconstitution of MBL with recombinant MBL-associated serine protease-2," J. Immunol. 165:2093-2100, (2000).
Wyatt et al., "IgA Nephropathy," N. Engl. J. Med. 368(25):2402-2414, Jun. 20, 2013.
Zipfel et al., "Deletion of Complement Factor H-Related Genes CFHR1 and CFHR3 Is Associated with Atypical Hemolytic Uremic Syndrome," PLoS Genet. 3(3):0387-0392, e41, Mar. 2007.
Nurbo et al., Bioorganic & Medicinal Chemistry (2008), 16(10), 5590-5605 and Supplementary Material on pp. S1-S8. (Year: 2008).
E-EROS Encyclopedia of Reagents for Organic Synthesis; "N-hydroxyacetamide—preparations, properties and applications"; Published Apr. 15, 2001; pp. 1-4, Conference 2008.
Shirk et al.; "Inhibitors of Factor VIIa/Tissue Factor"; Arteriosclerosis, Thrombosis, and Vascular Biology; Sep. 1, 2007; pp. 1895-1900; vol. 27, Issue 9.
Trujillo et al.; "Design, synthesis, and biological evaluation of pyrazinones containing novel P1 needles as inhibitors of TFA/IIa"; Bioorganic & Med Chem Letters; Aug. 15, 2007; pp. 4568-4574; vol. 17, Issue 16.
Clark J, E, Dudler T, Marber M,S, et al. Cardioprotection by an anti-MASP-2 antibody in a murine model of myocardial infarction. Open Heart 2018;5:e000652. doi:10.1136/ openhrt-2017-000652.
Orsini, F. et al., "Mannan binding lectin-associated serine protease-2 (MASP-2) critically contributes to post-ischemis brain injury independent of MASP-1," Journal of Neuroinflammation (2016)13:213; DOI 10.1186s/12974-016-0684-6.
Asgari, E. et al., "Mannan-binding lectin-associated serine protease 2 is critical for the development of renal ischemia reperfusion injury and mediates tissue injury in the absence of complement C4," The FASEB Journal Research Communication; May 19, 2014; pp. 3996-4003.
Alghadban, S. et al., "Absence of the Lectin Activation Pathway of the Complement Ameliorates Proteinuria-Induced Renal Injury," Front. Immunol. 10:2238; doi: 10.3389/fimmu.2019.02238.
Banda, N. K. et al., "Deconstructing the Lectin Pathway in the Pathogenesis of Experimental Inflammatory Arthritis: Essential Role of the Lectin Ficolin B and Mannose-Binding Protein-Associated Serine Protease 2," J Immunol (2017) 199 (5): 1835-1845; https://doi.org/10.4049/jimmunol.1700119.
Elhadad, S. et al. "MASP2 levels are elevated in thrombotic microangiopathies: association with microvascular endothelial cell injury and suppression by anti-MASP2 antibody narsoplimab," Clinical and Experimental Immunology, 203: 96-104.
Belcher, J. D. et al., "MASP-2 and MASP-3 inhibitors block complement activation, inflammation, and microvascular stasis in a murine model of vaso-occlusion in sickle cell disease," Translational Research, Nov. 2022; pp. 1-12.
Khaled, MD, S. K. et al., "Narsoplimab, a Mannan-Binding Lectin-Associated Serine Protease-2 Inhibitor, for the Treatment of Adult Hematopoietic Stem-Cell Transplantation-Associated Thrombotic Microangiopathy," Journal of Clinical Oncology; vol. 40, Issue 22; pp. 2247-2459.
Lafayette, R. A. et al., "Safety, Tolerability and Efficacy of Narsoplimab, a Novel MASP-2 Inhibitor for the Treatment of IgA Nephropathy," Kidney International Reports (2020) 5, 2032-2041.
Lafayette MD, R. A. et al. "Long-Term Phase 2 Efficacy of the MASP-2 Inhibitor Narsoplimab for Treatment of Severe IgA Nephropathy," ASN (2021).
Duncan, A.R., et al., "The binding site for Clq on IgG," Nature 332:738-740, (1988).
Dodds, A.W., "Small-scale preparation of complement components C3 and C4," Methods Enzymol. 223:46, (1993).
Haseloff, J., et al., "Simple RNA enzymes with new and highly specific endoribonuclease activities," Nature 334:585-591, (1988).
Matsushita, M., et al., "Activation of the classical complement pathway by mannose-binding protein in association with a novel C1s-like serine protease," J. Exp. Med. 176(6):1497-1502, (1992).
Morgan, B.P., "Clinical complementology: recent progress and future trends," Eur. J. Clinical Investig. 24(4):219-228, (1994).
Itakura, K., et al., "Synthesis and use of synthetic oligonucleotides," Annu. Rev. Biochem. 53:323, (1984).
Kuntz, I.D., et al., "Structure-based strategies for drug design and discovery," Science 257:1078, (1992).
Holmskov, U., et al., "Collections and ficolins: humoral lectins of the innate immune defense," Annu. Rev. Immunol. 21:547-578, (2003).
Ikeda, K., et al., "Serum lectin with known structure activates complement through the classical pathway," J. Biol. Chem. 262:7451-7454, (1987).
Jensen, J., et al., "Taming of transposable elements by homology-dependent gene silencing," Nat. Genet. 21(2):209-12, (1999).
Lloyd, B.H., et al., "Determination of optimal sites of antisense oligonucleotide cleavage within TNFalpha mRNA," Nucleic Acids Res. 29:3665-3673, (2001).
Desjarlais, R.L., et al., "Structure-based design of nonpeptide inhibitors specific for the human immunodeficiency virus 1 protease," PNAS 87:6644-6648, (1990).
Bae, Y.H., et al., "Insulin Permeation Through Thermo-Sensitive Hydrogels," J. Controlled Release 9:271, (1989).
Asano, M., et al., "In Vivo Characteristics of Low Molecular Weight Copoly(L-Lactice Acid/Glycolic Acid) Formulations with Controlled Release of Luteinizing Hormone-Releasing Hormone Agonist," J. Controlled Release 9:111-112, (1989).
Kohler, G., et al., "Continuous cultures of fused cells secreting antibody of predefined specificity," Nature 256:495, (1975).
Kuntz, I.D., et al., "A geometric approach to macromolecule-ligand interactions," J. Mol. Biol. 161:269-288, (1982).
Kuhlman, et al., "The human mannose-binding protein functions as an opsonin," J. Exp. Med. 169:1733, (1989).
Losman, M.J., et al., "Baboon anti-idiotype antibodies mimic a carcinoembryonic antigen epitope," Int. J. Cancer 46:310, (1990).
Lonberg, N., et al., "Antigen-specific human antibodies from mice comprising four distinct genetic modifications," Nature 368:856, (1994).
Marks, J.D., et al., "By-passing immunization. Human antibodies from V-gene libraries displayed on phage," J. Mol. Biol. 222:581-597, (1991).
Matsushita et al., "A novel human serum lectin with collagen- and fibrinogen-like domains that functions as an opsonin," J. Biol. Chem. 271 (5):2448-54, (1996).
Mariani, M., et al., "A new enzymatic method to obtain high-yield F(ab)2 suitable for clinical use from mouse IgGl," Mol. Immunol. 28:69-71, (1991).
Morrison, S.L., et al., "Chimeric human antibody molecules: mouse antigen-binding domains with human constant region domains," Proc. Nat'lAcad. Sci. USA 81:6851-6855, (1984).
Murayama, O., et al., "Novel peptide ligands for integrin alpha 6 beta 1 selected from a phage display library," J. Biochem. 120:445-51, (1996).
Nisonoff, A., et al., "Separation of univalent fragments from the bivalent rabbit antibody molecule by reduction of disulfide bonds," Arch. Biochem. Biophys. 89:230-244, (1960).
Scherr, M., et al., "Rapid determination and quantitation of the accessibility to native RNAs by antisense oligodeoxynucleotides in murine cell extracts," Nucleic Acids Res. 26:5079-5085, (1998).
Isaacs, J.D., et al., "Therapy with monoclonal antibodies. An in vivo model for the assessment of therapeutic potential," J. Immunol. 148(10):3062-3071, (1992).
Whitlow, M., et al., "Single-chain Fv Proteins and Their Fusion Proteins," Methods: A Companion to Methods in Enzymology 2:97-105, (1991).
Larrick, J.W., et al., "PCR Amplification of Antibody Genes," Methods: A Companion to Methods in Enzymology 2:106-110, (1991).

(56) References Cited

OTHER PUBLICATIONS

Jones, P.T., et al., "Replacing the complementarity-determining regions in a human antibody with those from a mouse," Nature 321:522-525, (1986).

Ward et al., "Genetic Manipulation and Expression of Antibodies," in Monoclonal Antibodies: Principles and Applications, Birch et al., (eds.) p. 137, Wiley-Liss, Inc., (1995).

Chen, C.B., et al., "Stoichiometry of complexes between mannose-binding protein and its associated serine proteases. Defining functional units for complement activation," J. Biol. Chem., 276(28):25894-25902, (2001).

Feinberg, H., et al., "Crystal structure of the CUB1-EGF-CUB2 region of mannose-binding protein associated serine protease-2," EMBO J. 22:2348-2359, (2003).

Lynch, N.J., et al., "L-ficolin specifically binds to lipoteichoic acid, a cell wall constituent of Gram-positive bacteria, and activates the lectin pathway of complement," J. Immunol. 172:1198-1202, (2004).

Stover, C.M., et al., "Two constituents of the initiation complex of the mannan-binding lectin activation pathway of complement are encoded by a single structural gene," J. Immunol. 162:3481-3490, (1999).

Stover, C.M., et al., "The rat and mouse homologues of MASP-2 and MApl9, components of the lectin activation pathway of complement," J. Immunol. 163:6848-6859, (1999).

Thiel, S., et al., "A second serine protease associated with mannan-binding lectin that activates complement," Nature 386:506-510, (1997).

Thiel, S., et al., "Interaction of Clq and mannan-binding lectin (MBL) with Clr, Cls, MBL-associated serine proteases 1 and 2, and the MBL-associated protein MApl9," J. Immunol. 165:878-887, (2000).

Thielens, N.M., et al., "Interaction properties of human mannan-binding lectin (MBL)-associated serine proteases-1 and -2, MBL-associated protein 19, and MBL," J. Immunol. 166:5068-5077, (2001).

Matsushita, M., et al., "Cutting edge: complement-activating complex of ficolin and mannose-binding lectin-associated serine protease," J. Immunol. 164:2281-2284, (2000).

Rodrigues, M.L., et al., "Engineering Fab' fragments for efficient F(ab)2 formation in *Escherichia coli* and for improved in vivo stability," J. Immunol. 151(12):6954-6961, (1993).

Riedermann, N.C., et al., "Complement in ischemia reperfusion injury," Am. J. Pathol. 162:363-367, (2003).

Matsushita, M., et al., "Activation of the lectin complement pathway by H-ficolin (Hakata antigen)," J. Immunol. 168 (7):3502-3506, (2002).

Stengaard-Pedersen, K., et al., "Inherited deficiency of mannan-binding lectin-associated serine protease 2," New England J. Med. 349:554-560, (2003).

Takahashi, M., et al., "A truncated form of mannose-binding lectin-associated serine protease (MASP)-2 expressed by alternative polyadenylation is a component of the lectin complement pathway," Int. Immunol. 11:859-863, (1999).

Moller-Kristensen, M., et al., "Levels of mannan-binding lectin-associated serine protease-2 in healthy individuals," J. Immunol Methods 282:159-167, (2003).

Dahl, M.R., et al., "MASP-3 and its association with distinct complexes of the mannan-binding lectin complement activation pathway," Immunity 15:127-35, (2001).

Petersen, S. V., et al., "An assay for the mannan-binding lectin pathway of complement activation," J. Immunol. Methods 257:107-116, (2001).

Liszewski, M.K., et al., "The Complement System," in Fundamental Immunology, Third Edition, Raven Press, Ltd., New York, (1993).

Collard, C.D., et al., "Complement activation after oxidative stress: role of the lectin complement pathway," Am J. Pathol 156(6):1549-56, (2000).

Daniel Ricklin et al: "Complement: key system for immune surveillance and homeostasis", Nature Immulogy, vol. 11, No. 9, Aug. 19, 2010 (Aug. 19, 2010), pp. 785-797, XP055306904, New York ISSN: 1529-2908, DOI: 10.1038/ni.1923.

CAS Reg No. 1316130-90-1; Date Entered STN: Aug. 11, 2011; 1H-Pyrazole-3-carboxamide, 5-(4-methoxyphenyl)-N-[2-[[(4-methoxyphenyl)methyl]amino]-2-oxoethyl]-1-phenyl-.

CAS Reg No. 789480-07-5; Date Entered STN: Nov. 28, 2004; Glycinamide, N-[[4-(aminoiminomethyl)phenyl]methyl]-2-(2-pyridinyl)glycyl-N-(3-pyridinylmethyl)-(9Cl).

CAS Reg No. 786631-78-5; Date Entered STN: Nov. 23, 2004; Glycinamide, N-[[4-(aminoiminomethyl)phenyl]methyl]-2-(1,3-benzodioxol-5-yl)glycyl-N-[(3,4-dimethoxyphenyl)methyl]-(9Cl).

CAS Reg No. 785766-56-5 ; Date Entered STN: Nov. 22, 2004; Alaninamide, N-[[4-(aminoiminomethyl)phenyl]methyl]-2-[4-(methoxycarbonyl)phenyl]glycyl-N-[(3,4-dimethoxyphenyl)methyl]-(9Cl).

Kiossowski, S., et al., 'Model Studies on the First Enzyme-Catalyzed Ugi Reaction', Org. Lett., vol. 15, No. 3, 2013.

CAS registry No. 1349763-94-5; date entered STN: Dec. 6, 2011; 1(2H)-Pyrazineacetamide, N-[[4-(aminoiminomethyl)phenyl]methyl]-6-(4-methylphenyl)-2-oxo-3-[(2-phenylethyl)amino]-.

CAS registry No. 1027369-96-5; date entered STN: Jun. 11, 2008; 1(2H)-Pyrazineacetamide, N-[[4-(aminoiminomethyl)phenyl]methyl]-6-[3-amino-5-[[(1-methylethyl)amino]carbonyl]phenyl]-3-(cyclopropylamino)-2-oxo-.

* cited by examiner

SEQUENCE LISTING

```
Sequence total quantity: 1
SEQ ID NO: 1            moltype = AA  length = 686
FEATURE                 Location/Qualifiers
source                  1..686
                        mol_type = protein
                        organism = Homo sapiens
SEQUENCE: 1
MRLLTLLGLL CGSVATPLGP KWPEPVFGRL ASPGFPGEYA NDQERRWTLT APPGYRLRLY  60
FTHFDLELSH LCEYDFVKLS SGAKVLATLC GQESTDTERA PGKDTFYSLG SSLDITFRSD  120
YSNEKPFTGF EAFYAAEDID ECQVAPGEAP TCDHHCHNHL GGFYCSCRAG YVLHRNKRTC  180
SALCSGQVFT QRSGELSSPE YPRPYPKLSS CTYSISLEEG FSVILDFVES FDVETHPETL  240
CPYDFLKIQT DREEHGPFCG KTLPHRIETK SNTVTITFVT DESGDHTGWK IHYTSTAQPC  300
PYPMAPPNGH VSPVQAKYIL KDSFSIFCET GYELLQGHLP LKSFTAVCQK DGSWDRPMPA  360
CSIVDCGPPD DLPSGRVEYI TGPGVTTYKA VIQYSCEETF YTMKVNDGKY VCEADGFWTS  420
SKGEKSLPVC EPVCGLSART TGGRIYGGQK AKPGDFPWQV LILGGTTAAG ALLYDNWVLT  480
AAHAVYEQKH DASALDIRMG TLKRLSPHYT QAWSEAVFIH EGYTHDAGFD NDIALIKLNN  540
KVVINSNITP ICLPRKEAES FMRTDDIGTA SGWGLTQRGF LARNLMYVDI PIVDHQKCTA  600
AYEKPPYPRG SVTANMLCAG LESGGKDSCR GDSGGALVFL DSETERWFVG GIVSWGSMNC  660
GEAGQYGVYT KVINYIPWIE NIISDF                                     686
```

MASP-2 INHIBITORS AND METHODS OF USE

CROSS-REFERENCE TO RELATED APPLICATIONS

This application is a continuation of U.S. application Ser. No. 17/112,873, filed Dec. 4, 2020, which claims the benefit of U.S. Provisional Patent Application No. 62/943,629, filed Dec. 4, 2019, the entire disclosures of which are hereby incorporated by reference in their entirety.

SEQUENCE LISTING

The sequence listing XML associated with this application is provided in XML format and is hereby incorporated by reference into the specification. The name of the XML file containing the sequence listing is 4278-P2US.CON2_Seq_List.xml. The XML file is 2415 bytes; was created on May 17, 2023; and is being submitted electronically via Patent Center with the filing of the specification.

BACKGROUND

The present disclosure is directed generally to compositions and methods that are useful in the field of medicine. More specifically, the disclosure provides synthetic inhibitors of mannan-binding lectin-associated serine protease-2 (MASP-2), including inhibitors that selectively inhibit MASP-2 over thrombin, compositions thereof, and methods for the manufacture and use thereof.

The complement system plays a role in the inflammatory response and becomes activated because of tissue damage or microbial infection. Complement activation must be tightly regulated to ensure selective targeting of invading microorganisms and avoid self-inflicted damage (Ricklin et al., Nat. Immunol. 11:785-797, 2010). Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and generally requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

Mannan-binding lectin-associated serine protease-2 (MASP-2) has been shown to be required for the function of the lectin pathway, one of the principal complement activation pathways (Vorup-Jensen et al., J. Immunol 165:2093-2100, 2000; Ambrus et al., J Immunol. 170: 1374-1382, 2003; Schwaeble et al., PNAS 108:7523-7528, 2011). Importantly, inhibition of MASP-2 does not appear to interfere with the antibody-dependent classical complement activation pathway, which is a critical component of the acquired immune response to infection. As described in U.S. Pat. No. 9,011,860 (assigned to Omeros Corporation), which is hereby incorporated by reference, discloses a fully human monoclonal antibody targeting human MASP-2 has been generated which binds to human MASP-2 with high affinity and blocks the lectin pathway complement activity and is therefore useful to treat various lectin complement pathway-associated diseases and disorders.

MASP-2-dependent complement activation has been implicated as contributing to the pathogenesis of numerous acute and chronic disease states. Therefore, a need exists for compounds that are suitable for administration/treatment of subject suffering from MASP-2 complement pathway-associated diseases and disorders, including diseases that are not suitably or efficiently treated with large molecule biologic inhibitors.

SUMMARY

One embodiment provides a compound having the following Structure (I):

(I)

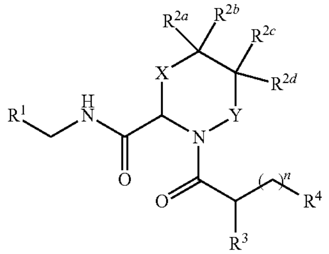

or a stereoisomer, tautomer, or pharmaceutically acceptable salt thereof, wherein $R^1$, $R^{2a}$, $R^{2b}$, $R^{2c}$, $R^{2d}$, $R^3$, $R^4$, and n are as defined herein.

Another embodiment provides a compound having the following Structure (II):

(II)

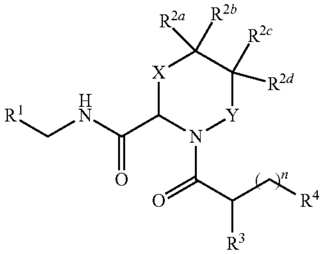

or a stereoisomer, tautomer, or pharmaceutically acceptable salt thereof, wherein $R^1$, $R^{2a}$, $R^{2b}$, $R^{2c}$, $R^{2d}$, $R^3$, $R^4$, and n are as defined herein.

Another embodiment provides a compound having the following Structure (III):

(III)

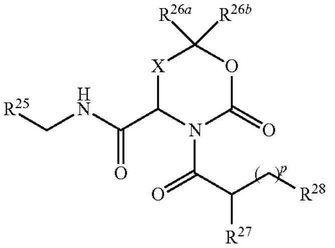

or a stereoisomer, tautomer, or pharmaceutically acceptable salt thereof, wherein $R^{25}$, $R^{26a}$, $R^{26b}$, $R^{27}$, $R^{28}$, and p are as defined herein.

Additional embodiments of the present disclosure provide a pharmaceutical composition comprising a compound of Structure (I), (II) or (III), or a stereoisomer, tautomer, or pharmaceutically acceptable salt thereof, and at least one pharmaceutically acceptable carrier or excipient.

The compounds of Structures (I), (II) and (III) are useful in the treatment of MASP-2-associated diseases and disorders, and in the manufacture of medicaments for treating MASP-2-associated diseases and disorders. Accordingly, other embodiments of the disclosure provide methods of treating a MASP-2-associated disease and disorder comprising administering to a patient a therapeutically effective amount of a compound of Structure (I), (II) or (III), or a stereoisomer, tautomer, or pharmaceutically acceptable salt thereof.

These and other aspects, objects and embodiments will become more apparent when read with the detailed description and figures which follow.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DETAILED DESCRIPTION

I. Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter of the present disclosure, suitable methods and materials are described below. In addition, the materials, methods, and examples are illustrative only and not intended to be limiting.

In certain embodiments herein, reference is made to features and aspects of the disclosure, including method steps. All possible combinations of such features and aspects within the embodiments of the disclosure are included, at least to the extent that such combinations are non-contradictory. For example, if an embodiment presents aspects A, B, and C, it is understood that this also discloses embodiments including both aspects A and B, both aspects B and C, and both aspects A and C, as well as an embodiment with aspects A, B, and C.

The terms "a," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art.

The terms "about" and "approximately" refer to an acceptable degree of error for the quantity measured given the nature or precision of the measurements. Typical, exemplary degrees of error are within ±20 percent (%); preferably, within ±10%; and more preferably, within ±c5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written support for a claim limitation of, e.g., "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11 mg/kg" is equivalent to "about 7, about 9, or about 11 mg/kg."

The term "MASP-2" refers to mannan-binding lectin-associated serine protease-2. Human MASP-2 protein with UniProt accession code 000187 (SEQ ID NO:1). The Serine Protease Domain ('B-chain'=Mannan-binding lectin serine protease 2 B chain, based on UniProtKB-O00187 (MASP-2_HUMAN)) includes residues 445 to 686 (or consists of residues 445 to 686).

The term "MASP-2-dependent complement activation" refers to MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

The term "MASP-2-dependent complement-associated disease or disorder" refers to a disease or disorder that is associated with MASP-2-dependent complement activation.

The term "MASP-2-associated disease or disorder" refers to a disease or disorder that is associated with activation or activity of MASP-2, including MASP-2-dependent complement-associated disease or disorders, and wherein inhibition of MASP-2 is or is expected to be therapeutically beneficial.

The term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

The term "classical pathway" refers to complement activation that is triggered by an antibody bound to a foreign particle and requires binding of the recognition molecule Clq.

Amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile), leucine (Leu), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either His, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further sub-classed as follows: by "uncharged hydrophilic" amino acid is meant either Ser, Thr, Asn or Gln. By "acidic" amino acid is meant either Glu or Asp. By "basic" amino acid is meant either Lys, Arg or His.

The term "conservative amino acid substitution" is illustrated by a substitution among amino acids within each of the following groups:

(1) glycine, alanine, valine, leucine, and isoleucine;

(2) phenylalanine, tyrosine, and tryptophan;

(3) serine and threonine;
(4) aspartate and glutamate;
(5) glutamine and asparagine; and
(6) lysine, arginine and histidine.

The term "a subject" includes all mammals, including without limitation, humans, non-human primates, dogs, cats, horses, sheep, goats, cows, rabbits, pigs, and rodents.

"Mammal" includes humans and both domestic animals such as laboratory animals and household pets, (e.g., cats, dogs, swine, cattle, sheep, goats, horses, rabbits), and non-domestic animals such as wildlife and the like.

The terms "small molecule" and "small organic molecule" refers to a small carbon-containing molecule that has a molecular weight of about 2500 daltons or lower. In some embodiments, a small molecule has a molecular weight of about 2000 daltons or lower. In some embodiments, a small molecule has a molecular weight of about 1500 daltons or lower. In some embodiments, a small molecule has a molecular weight of about 1000 daltons or lower. In some embodiments, a small molecule has a molecular weight of about 750 daltons or lower. In some embodiments, a small molecule has a molecular weight of about 500 daltons or lower. In some embodiments, a small molecule has a molecular weight of about 50 daltons or greater. In some embodiments, a small molecule has a molecular weight of about 75 daltons or greater. In some embodiments, a small molecule has a molecular weight of about 100 daltons or greater. In some embodiments, a small molecule has a molecular weight of about 150 daltons or greater. In some embodiments, a small molecule has a molecular weight of about 250 daltons or greater. In some embodiments, small molecules may have a molecular weight in the range from about 50 daltons to about 500 daltons, from about 50 daltons to about 750 daltons, from about 50 daltons to about 1000 daltons, from about 50 daltons to about 1500 daltons, from about 50 daltons to about 2000 daltons, or from about 50 daltons to about 2500 daltons. When the term "compound" is used herein, the term is explicitly intended to include small molecule compounds as defined herein (including any of the embodiments thereof).

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In some embodiments, a disease is a pathological condition of an organ, a body part, or a system resulting from various causes, such as infection, genetic defect, or environmental stress that is characterized by an identifiable group of symptoms.

"Therapeutically effective amount," "effective amount," or "effective dose" refers to that amount of a compound of the disclosure that, when administered to a mammal (e.g., a human), is sufficient to effect treatment, as defined below, of a disease or condition in the mammal, preferably a human. The amount of a compound of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

The term "subcutaneous administration" refers to administration of a formulation under all layers of the skin of a subject.

The term "histidine" specifically includes L-histidine unless otherwise specified.

The term "isotonic" refers to a formulation that has essentially the same osmotic pressure as human blood. Isotonic formulations will generally have an osmotic pressure from about 250 to about 350 mOsmol/L. Isotonicity can be measured using a vapor pressure or freezing point depression osmometer, for example.

The term "hypertonic" refers to a formulation with an osmotic pressure above that of human (i.e., greater than 350 mOsm/L).

The term "hydrogen-bonding" is a partially electrostatic attraction between a hydrogen (H) which is bound to a more electronegative atom such as nitrogen (N) or oxygen (O) and another adjacent atom bearing a lone pair of electrons. For example, when it is stated that the nitrogen acts as a "hydrogen bond donor" it means that a hydrogen (H) bound to a nitrogen (N) is donated by the nitrogen as it electrostatically attracted to or accepted by an adjacent atom bearing a lone pair of electrons such as an oxygen. Similarly, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. Sometimes the hydrogen bonded atoms are called out without explicitly stating the origin and presence of an intermediate hydrogen atom. The term "hydrogen bonding" is used wherever LigPlot+ software predicts a hydrogen bonding interaction using its algorithm and applied parameters of 3.35 Å for maximum distance between hydrogen bond donor and acceptor. Not all hydrogen bonds may actually be in place simultaneously; this is evident for atoms that are shown to form 4 putative hydrogen bonds, where however, at any given time only 3 hydrogen bonds are chemically possible. In general, although crystal structures such as the co-crystal structural information herein does not directly show or detect hydrogen bonding, the software used to describe the co-crystal does predict such H-bonding exists. Therefore, throughout the disclosure when a H-bond is present and described, it may be said to be "predicted" by software to be present.

The term ionic bonding includes a type of chemical bond that involves the electrostatic attraction between oppositely charged ions, and is the primary interaction occurring in ionic compounds.

The term "van der Waals" interaction includes weak, short-range electrostatic attractive forces between uncharged molecules, arising from the interaction of permanent or transient electric dipole moments. As determined by LigPlot+ software employing models derived from the corresponding crystallographic MASP-2 compound co-structures, such interactions include all contacts that are computed using non-bonded contact parameters between hydrophobic to any contacts for interactions with a maximum contact distance of 3.90 Å.

The term "π-π interaction" or "π-π stacking" interaction includes attractive, non-covalent interactions between aromatic rings that are oriented either roughly parallel or roughly perpendicular (such as in "edge-face" interactions) to each other, since they contain π-bonds.

Typically, the active site of serine proteases such as MASP-2 is shaped as a cleft where the polypeptide substrate or inhibitor binds. Schechter and Berger labeled amino acid residues from the N to C terminus of the polypeptide substrate as follows: Pi, . . . , P3, P2, P1, P1', P2', P3', . . . , Pj) and their respective binding sub-sites Si, . . .

, S3, S2, S1, S1', S2', S3', . . . , Sj. The cleavage is catalyzed between P1 and P1' (Schechter, I. & Berger, A. On the size of the active site in proteases. I. Papain. Biochem. Biophys. Res. Commun. 27 (1967)).

The term "binding site" is an area on the protein wherein a small molecule can interact with, such as a region on the surface of MASP-2. The binding site or region may not or only partially overlap with the active site, but nevertheless render the MASP-2 molecule less active or inactive.

The term "or" refers to an alternative and should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is equivalent to the group "selected from the group consisting of A and B."

The linking term "comprising" or "comprise" is not closed. For example, "a composition comprising A" must include at least the component A, but it may also include one or more other components (e.g., B; B and C; B, C, and D; and the like). The term "comprising" therefore should in general be construed as not excluding additional ingredients. For example, a claim to "a composition comprising A" would cover compositions that include A and B; A, B, and C; A, B, C, and D; A, B, C, D, and E; and the like.

The term "hypertonic" refers to a formulation with an osmotic pressure above that of human (i.e., greater than 350 mOsm/KglHhO).

The term "agent" refers to a compound or mixture of compounds that, when added to a composition, tend to produce an effect on the composition's properties. For example, a composition comprising a thickening agent is likely to be more viscous than an otherwise identical comparative composition that lacks the thickening agent.

A "synthetic" compound means a compound that is not naturally occurring and that has been synthesized by humans. Reference to a compound herein may be understood to include reference to synthetic compounds, unless the context indicates otherwise.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

At various places in the present specification, certain features of the compounds are disclosed in groups or in ranges. It is specifically intended that such a disclosure include each and every individual sub-combination of the members of such groups and ranges. For example, the terms "$C_{1-6}$ alkyl" and "$C_{1-6}$ alkyl" are specifically intended to individually disclose (without limitation) methyl, ethyl, $C_3$ alkyl, $C_4$ alkyl, $C_5$ alkyl, and $C_6$ alkyl.

The term "substituted" means that an atom or group of atoms formally replaces hydrogen as a "substituent" attached to another group. The term "substituted", unless otherwise indicated, refers to any level of substitution, e.g., mono-, di-, tri-, tetra-, penta-, or higher substitution, where such substitution is permitted (e.g., results in a stable compound). The substituents are independently selected, and substitution may be at any chemically accessible position. It is to be understood that substitution at a given atom is limited by valency. The phrase "optionally substituted" means substituted or unsubstituted. The term "substituted" means that at least hydrogen atom is replaced with a substituent. A single divalent substituent, e.g., oxo, can replace two hydrogen atoms.

The terms "$C_{n-m}$" and "$C_n$-$C_m$" where n and m are integers indicates a group that contains from n to m carbon atoms. Examples include $C_{1-4}$, $C_{1-6}$, and the like. The term is intended to expressly disclose every member in the range, i.e., $C_n$, $C_{n+1}$, $C_{n+2}$ . . . $C_{m-2}$, $C_{m-1}$, $C_{m-}$. For example, $C_{1-6}$ is intended to disclose $C_1$, $C_2$, $C_3$, $C_4$, $C_5$, and $C_6$. As used herein, "$C_{n-m}$" means the same as "$C_n$-$C_m$".

The term "n-membered," where n is an integer (e.g., 6-membered), typically describes the number of ring-forming atoms in a moiety where the number of ring-forming atoms is n. The term "n–m membered" wherein n and m are integers (e.g., 6-10 membered) describes a range where the number of ring forming atoms is from n to m. For example, piperidinyl is an example of a 6-membered heterocyclyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. In certain specific embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl. In some embodiments, alkyl is a $C_1$-$C_{12}$ alkyl, a $C_1$-$C_8$ alkyl, a $C_{1-6}$ alkyl, or $C_1$-$C_4$ alkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. In certain embodiments, an alkyl or alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_p R^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

"Alkynyl" refers to a straight-chain or branched hydrocarbon group corresponding to an alkyl group as defined above having one or more triple carbon-carbon bonds. An alkynyl group formally corresponds to an alkyne with one C—H bond replaced by the point of attachment of the alkyl group to the remainder of the compound. The term "$C_{n-m}$ alkynyl" and "$C_n$-$C_m$ alkynyl" refer to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms. Unless indicated otherwise, alkynyl groups are optionally substituted.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. In some embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

The term "hydroxyalkyl" refers to an alkyl group as defined above in which one or more of the hydrogen atoms has been replaced by a hydroxy group (i.e., —OH). The term "$C_{n-m}$ hydroxyalkyl" refers to a $C_{n-m}$ alkyl group having n to m carbon atoms and from at least one hydroxy group. In some embodiments, the hydroxyalkyl group comprises one hydroxy group. In certain aspects, the hydroxyalkyl group comprises two or more hydroxy groups (e.g., a "dihydroxyalkyl"), each on the same or a different carbon atom(s). In certain aspects, the hydroxyalkyl group has 1, 2, 3, 4, 5, 6, or more hydroxy groups. Examples may include, but are not limited to, hydroxymethyl, 2-hydroxyethyl, and 1-hydroxyethyl. In some embodiments, hydroxyalkyl is a $C_1$-$C_{12}$ hydroxyalkyl, a $C_1$-$C_8$ hydroxyalkyl, a $C_1$-$C_6$ hydroxyalkyl, or $C_1$-$C_4$ hydroxyalkyl.

"Aminylalkyl" refers to an alkyl group as defined above in which one or more hydrogen atoms have been replaced by an aminyl group (i.e., —$NR^{100}R^{101}$ wherein $R^{100}$ and $R^{101}$ are each independently hydrogen, alkyl, alkenyl, or alkynyl as defined herein). In some embodiments, the aminylalkyl comprises one aminyl group. In some embodiments, the aminyl group is —$NH_2$.

"Carboxyalkyl" refers to an alkyl group as defined above in which one or more hydrogen atoms have been replaced by a carboxy group (i.e., —C(O)OH). In some embodiments, the carboxyalkyl comprises one carboxy group. In some embodiments, carboxyalkyl is a $C_1$-$C_{12}$ carboxyalkyl, a $C_1$-$C_8$ carboxyalkyl, a $C_1$-$C_6$ carboxyalkyl, or $C_1$-$C_4$ carboxyalkyl.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, an aryl group may be optionally substituted by one or more substituents independently selected from the group consisting of alkyl, alkenyl, halo, haloalkyl, haloalkenyl, cyano, nitro, aryl, arylalkyl, cycloalkyl, cycloalkylalkyl, heterocyclyl, heterocyclylalkyl, heteroaryl, heteroarylalkyl, —$R^{101}$—$OR^{100}$, —$R^{101}OC(O)R^{100}$, —$R^{101}$, —$N(R^{100})_2$, —$R^{101}$, —$N(R^{100})$—$R^{103}$, —$OR^{100}$, —$R^{101}$, —$C(O)R^{100}$, —$R^{101}$, —$C(O)OR^{100}$, —$R^{101}$, —$C(O)N(R^{100})_2$, —$R^{101}$, —$N(R^{100})C(O)R^{102}$, —$R^{101}$, —$N(R^{100})C(O)R^{102}$, —$R^{101}$, —$N(R^{100})S(O)_tR^{102}$ (where p is 1 to 2), —$R^{101}$, —$N{=}C(OR^{100})R^{100}$, —$R^{101}$, —$S(O)_pOR^{102}$ (where p is 1 to 2), —$R^{101}$, —$S(O)_tR^{102}$ (where t is 0 to 2), and —$R^{101}$, —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain. In some embodiments an aryl group has the following structure:

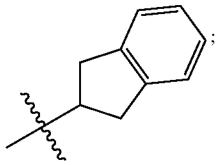
;
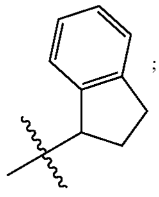
;
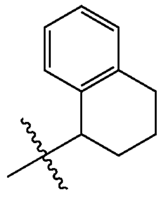
or
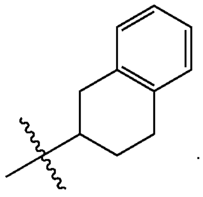
.

"Arylalkyl" or "aralkyl" refers to a group of formula -alkylene-aryl wherein the alkylene group and aryl groups are as defined herein, respectively. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is $C_{6-10}$ aryl-$C_{1-3}$ alkyl. In some embodiments, arylalkyl is phenyl-$C_{1-3}$ alkyl. Examples include, but are not limited to, benzyl, 1-phenylethyl, 4-methylbenzyl, and 1,1,-dimethyl-1-phenylmethyl. In some embodiments, arylalkyl is optionally substituted benzyl.

"Aryloxy" refers to a group with the formula —O-aryl wherein aryl is a group as defined above. In some embodiments, the aryloxy group is —O—$C_{6-10}$ aryl. In some embodiments, the aryloxy is a substituted or unsubstituted phenyloxy (i.e., —O—$C_6$ aryl).

"Arylalkoxy" refers to a group with the formula -alkoxy-aryl wherein alkoxy and aryl are groups as defined above, respectively. In some embodiments, arylalkoxy is $C_{6-10}$ aryl-$C_{1-3}$ alkoxy. In some embodiments, arylalkoxy is $C_{6-10}$ aryl-$C_{1-4}$ alkoxy. In some embodiments, arylalkoxy is $C_{6-10}$ aryl-$C_{1-3}$ alkoxy. In some embodiments, arylalkoxy is phenyl-$C_{1-3}$ alkoxy (e.g., methoxy).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. In some embodiments, a cycloalkyl group may be optionally substituted by one or more substituents independently selected from the group consisting of alkyl, alkenyl, halo, haloalkyl, haloalkenyl, cyano, nitro, oxo, aryl, arylalkyl, cycloalkyl, cycloalkylalkyl, heterocyclyl, heterocyclylalkyl, heteroaryl, heteroarylalkyl, —$R^{101}$, —$OR^{100}$, —$R^{101}$, —OC(O)—$R^{100}$, —$R^{101}$, —$N(R^{100})$—$R^{103}$, —$OR^{100}$, —$R^{101}$, —$N(R^{100})_2$, —$R^{101}$, —C(O)$R^{100}$, —$R^{101}$, —C(O)O$R^{100}$, —$R^{101}$, —C(O)$N(R^{100})_2$, —$R^{101}$, —$N(R^{100})$C(O)$R^{102}$, —$R^{101}$, —$N(R^{100})$C(O)$R^{102}$, —$R^{101}$, —$N(R^{100})S(O)_pR^{102}$ (where p is 1 to 2), —$R^{101}$, —N═C($OR^{100}$)$R^{100}$, —$R^{101}$, —$S(O)_pOR^{102}$ (where p is 1 to 2), —$R^{101}$, —$S(O)_tR^{102}$ (where t is 0 to 2), and —$R^{101}$, —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Cycloalkylalkyl" refers to a radical of the formula —$R^{100}R^{101}$ where $R^{100}$ is an alkylene chain as defined above and $R^{101}$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Alkoxy" refers to a radical group having the following formula "—O-alkyl," wherein the alkyl group is as defined herein above. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms. Unless indicated otherwise, alkoxy groups are optionally substituted.

"Alkoxyalkyl" refers to a radical having the following formula "-alkylene-O-alkyl," wherein the alkylene and alkyl groups are as defined herein above, respectively. In some embodiments, the alkoxyalkyl group comprises one —O-alkyl group. In some embodiments, the alkoxyalkyl group comprises two or more alkoxy groups. Examples may include, but are not limited to, methoxymethyl, ethoxymethyl, 3-ethoxyethyl, and 1-methoxyethyl. Unless indicated otherwise, alkoxyalkyl groups are optionally substituted.

"Oxo" refers to a═O group. For example, an oxo connected to a carbon atom forms a carbonyl group (i.e., C═O). Alternatively, when an oxo group is attached to a heteroatom, for example, a sulfoxide, sulfone group, an N-oxide group is formed.

"Sulfido" refers to a ═S group.

"Amino" refers to a —$NH_2$ group.

"Carbamyl" refers to a —C(O)$NH_2$ group.

"Carboxy" refers to a —C(O)OH group.

"Carbonyl" refers to a C(═O) group, which also may be written as C(O).

"Cyano" or "nitrile" refers to a —C≡N group, which also may be written as —CN.

"Nitro" refers to a —$NO_2$ group.

"Hydroxy" or "hydroxyl" refers to an —OH group.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

The term "haloalkoxy", employed alone or in combination with other terms, refers to a group of formula —O-haloalkyl, wherein the haloalkyl group is as defined above. Example haloalkoxy groups include trifluoromethoxy, difluoromethoxy, pentafluoroethoxy, and the like.

"Heterocyclyl" refers to a stable 3- to 18-membered non-aromatic ring radical which consists of two to twelve carbon atoms and from one to six heteroatoms selected from the group consisting of nitrogen, oxygen, and sulfur. Unless stated otherwise specifically in the specification, the heterocyclyl radical may be a monocyclic, bicyclic, tricyclic, or tetracyclic ring system, which may include fused, bridged, and spiro ring systems; and the nitrogen, carbon, or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, 1-azaspiro[3.3]heptan-1-yl, 5-azaspiro[2.3]hexan-5-yl, 2-oxa-6-azaspiro[3.3]heptan-6-yl, 1-oxa-6-azaspiro[3.4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. In certain embodiments, a heterocyclyl group may be optionally substituted by one or more substituents selected from the group consisting of alkyl, alkenyl, halo, haloalkyl, haloalkenyl, cyano, oxo, thioxo, nitro, aryl, arylalkyl, cycloalkyl, cycloalkylalkyl, heterocyclyl, heterocyclylalkyl, heteroaryl, heteroarylalkyl, —$R^{101}$, —$OR^{100}$, —$R^{101}$, —OC(O)—$R^{100}$, —$R^{101}$, —$N(R^{100})$—$R^{103}$, —$OR^{100}$, —$R^{101}$, —$N(R^{100})_2$, —$R^{101}$, —C(O)$R^{100}$, —$R^{101}$, —C(O)$R^{100}$, —$R^{101}$, —C(O)$N(R^{100})_2$, —$R^{101}$, —$N(R^{100})$C(O)$R^{102}$, —$R^{101}$, —$N(R^{100})$C(O)$R^{102}$, —$R^{101}$, —$N(R^{100})S(O)_pR^{102}$ (where p is 1 to 2), —$R^{101}$, —N═CO$R^{100}$)$R^{102}$, —$R^{101}$, —$S(O)_pOR^{102}$ (where p is 1 to 2), —$R^{101}$, —$S(O)_tR^{102}$ (where t is 0 to 2), and —$R^{101}$, —$S(O)_pN(R^{100})_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Heterocyclylalkyl" refers to a radical of the formula —$R^{100}R^{101}$ where $R^{100}$ is an alkylene chain as defined above and $R^{101}$ is a heterocyclyl radical as defined above, and if the heterocyclyl is a nitrogen-containing heterocyclyl, the heterocyclyl may be attached to the alkyl radical at the nitrogen atom. In some embodiments, the alkylene chain of the heterocyclylalkyl radical may be optionally substituted as defined above for an optionally substituted alkylene chain. In some embodiments, the heterocyclyl part of the heterocyclylalkyl radical may be optionally substituted as defined above for an optionally substituted heterocyclyl group.

"Heteroaryl" refers to a 4- to 14-membered ring system radical comprising hydrogen atoms, one to thirteen carbon atoms, one to six heteroatoms selected from the group consisting of nitrogen, oxygen, and sulfur, and at least one aromatic ring. For purposes of this disclosure, the heteroaryl radical may be a monocyclic, bicyclic, tricyclic, or tetracyclic ring system, which may include fused or bridged ring systems; and the nitrogen, carbon, or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). In certain embodiments, a heteroaryl group may be optionally substituted by one or more substituents selected from the group consisting of alkyl, alkenyl, halo, haloalkyl, haloalkenyl, cyano, oxo, thioxo, nitro, thioxo, aryl, arylalkyl, cycloalkyl, cycloalkylalkyl, heterocyclyl, heterocyclylalkyl, heteroaryl, heteroarylalkyl, —$R^{101}$, —$OR^{100}$, —$R^{101}$, —OC(O)—$R^{100}$, —$R^{101}$, —$N(R^{100})$—$R^{103}$, —$OR^{100}$, —$R^{101}$, —$N(R^{100})_2$, —$R^{101}$, —$C(O)R^{100}$, —$R^{101}$, —$C(O)OR^{100}$, —$R^{101}$, —$C(O)N(R^{100})_2$, —$R^{101}$, —$N(R^{100})C(O)R^{102}$, —$R^{101}$, —$N(R^{100})C(O)R^{100})C(O)R^{102}$, —$R^{101}$, —$N(R^{100})S(O)_pR^{102}$ (where p is 1 to 2), —$R^{101}$, —$N{=}C(OR^{100})R^{100}$, —$R^{101}$, —$S(O)_pOR^{102}$ (where p is 1 to 2), —$R^{101}$, —$S(O)_tR^{102}$ (where t is 0 to 2), and —$R^{101}$, —$S(O)_pN(R^{100})_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl, or heteroarylalkyl, and each $R^{103}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl. The term "heteroaryl" includes, e.g., the following structures:

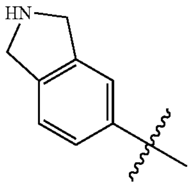
;
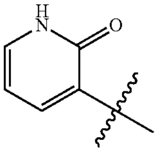
and
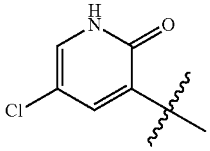
.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula $R^{100}R^{101}$ where $R^{100}$ is an alkylene chain as defined above and $R^{101}$ is a heteroaryl radical as defined above. When specifically stated in the specification, the heteroaryl part of the heteroarylalkyl radical may be optionally substituted as defined above for an optionally substituted heteroaryl group. In some specific embodiments, the alkylene chain part of the heteroarylalkyl radical may be optionally substituted as defined above for an optionally substituted alkylene chain.

The compounds and methods of the present disclosure are also meant to encompass all pharmaceutically acceptable compounds of Structures (I), (II) and (III) being isotopically-labelled by having one or more atoms replaced by an atom having a different atomic mass or mass number.

Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radio-labelled compounds could be useful to help determine or measure the effectiveness of the compounds, by characterizing, for example, the site or mode of action or binding affinity. Certain isotopically-labelled compounds of Structures (I), (II) or (III), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In one embodiment, the compounds of Structures (I), (II) or (III) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of Structures (I), (II) or (III) can generally be prepared by conventional techniques known to those skilled in the art or by processes analogous to those described in the Examples and Preparations as set out below using an appropriate isotopically-labeled reagent in place of the non-labeled reagent previously employed.

This disclosure is also meant to encompass the in vivo metabolic products of the disclosed compounds. Such products may result from, for example, the oxidation, reduction, hydrolysis, amidation, esterification, and the like of an administered compound, primarily due to enzymatic processes. Accordingly, this disclosure includes compounds produced by a process comprising contacting a compound of this disclosure with a mammal for a period of time sufficient to yield a metabolic product thereof. Such products are typically are identified by administering a radio-labelled compound in a detectable dose to an animal, such as rat, mouse, guinea pig, monkey, or to human, allowing sufficient time for metabolism to occur, and isolating its conversion products from the urine, blood, or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substituents on the functional group are also "optionally substituted" and so on, for the purposes of this disclosure, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, and caffeine.

Often crystallizations produce a solvate of the compound of the disclosure (e.g., a compound of Structure (I), (II) or (III)). As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents, or excipients therefor.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting the disease or condition's development;

(c) relieving (or ameliorating) the disease or condition, i.e., causing regression of the disease or condition; or (d) relieving (or ameliorating) the symptoms resulting from the disease or condition, e.g., without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more stereocenter and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres giving rise to geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes enantiomers, which refers to two stereoisomers whose molecules are non-superimposable mirror images of one another. See, e.g., Smith, M. B. and J. March, March's Advanced Organic Chemistry: Reactions, Mechanisms, and Structure, 6th edition (Wiley, 2007), for a detailed description of the structure and properties of enantiomers and stereoisomers.

A "tautomer" refers to a proton shift from one atom of a molecule to another atom of the same molecule. The present disclosure includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 14.0 software program. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

At certain places, the definitions or embodiments may refer to specific rings (e.g., an azetidine ring, a pyridine ring, etc.). Unless otherwise indicated, these rings can be attached to any ring member provided that the valency of the atom is not exceeded.

When any two groups or two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). Unless otherwise indicated, if two or more groups having the same definition are present, but the definition provides for alternatives, it should be understood that each occurrence of the same group is independently selected from the possible alternatives. For example, if two or more $R^a$ groups are present in a compound, and the definition of $R^a$ provides that $R^a$ can be A, B, or C, then it should be understood that each $R^a$ group present in the compound is independently chosen from A, B, and C, so that the $R^a$ groups present in the compound can be the same or different.

Compounds, and salts thereof, including pharmaceutically acceptable salts, can be found together with other substances such as water and solvents (e.g., hydrates and solvates) or can be isolated. When in the solid state, the compounds described herein, and salts thereof may occur in various forms and may, e.g., take the form of solvates, including hydrates. The compounds may be in any solid-state form, such as a polymorph or solvate, so unless clearly indicated otherwise, reference to compounds and salts thereof should be understood as encompassing any solid-state form of the compound.

In some embodiments, the compounds described herein or salts thereof, are substantially isolated. "Substantially isolated" means the compound is at least partially or substantially separated from the environment in which it was formed or detected. Partial separation can include, e.g., a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof.

The following abbreviations may be used herein and, unless otherwise noted, have the meanings indicated below:

ACN or MeCN (acetonitrile); chrom. (chromatography); $CH_2Cl_2$ (dichloromethane); DIAD (Diisopropyl azodicarboxylate); L (liter(s)); m- (meta); Ms (methanesulfonyl); NCS (N-chlorosuccinimide); NIS (N-iodosuccinimide);

Phth (Phthalimide); TPP (triphenylphosphine); and Tr (trityl). Other abbreviations may also be used and have the meanings that would be understood by the person having skill in the art.

II. Compounds

In certain aspects, the present disclosure provides a compound of Structure (I):

(I)

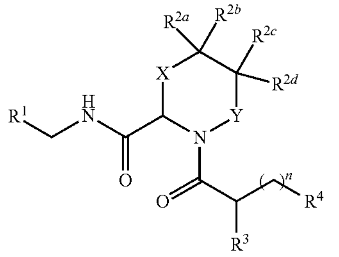

or a stereoisomer, tautomer, or pharmaceutically acceptable salt thereof, wherein:

X is a direct bond, —$CR^{2e}R^{2f}$, —, or —$CR^{2e}R^{2f}$, —$CR^{2g}R^{2h}$, —;

Y is a direct bond or —$CR^{2i}R^{2j}$, —;

$R^1$ is a substituted or unsubstituted aryl, substituted or unsubstituted heteroaryl, substituted or unsubstituted cycloalkyl, or a substituted or unsubstituted heterocyclyl;

$R^{2a}$, $R^{2b}$, $R^{2c}$, $R^{2d}$, $R^{2e}$, $R^{2f}$, $R^{2g}$, $R^{2h}$, $R^{2i}$, and $R^{2j}$ are each independently selected from the group consisting of hydrogen, halo, C(=O)$OR^5$, OC(=O)$R^5$, hydroxyalkyl, alkoxy, alkoxyalkyl, haloalkoxy, cyano, aminylalkyl, carboxyalkyl, $NR^5R^6$, C(=O)$NR^5R^6$, N($R^5$)C(=O)$R^6$, $NR^5$C(=O)$NR^6$, $S(O)_t$, $SR^5$, nitro, N($R^5$)C(O)$OR^6$, C(=$NR^5$)$NR^6R^7$, N($R^5$)C(=$NR^6$)$NR^7R^8$, S(O)$R^5$, S(O)$NR^5R^6$, $S(O)_2R^5$, N($R^5$)$S(O)_2R^6$, $S(O)_2NR^5R^6$, aryl, heteroaryl, heterocyclyl, cycloalkyl, and oxo, provided that at least one of $R^{2a}$, $R^{2b}$, $R^{2c}$, $R^{2d}$, $R^{2e}$, $R^{2f}$, $R^{2g}$, $R^{2h}$, $R^{2i}$, and $R^{2j}$ is not hydrogen;

$R^3$ is $NR^{3a}R^{3b}$;

$R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, or cycloalkyl; or $R^{3a}$ and $R^{3b}$, together with the nitrogen to which they are attached, form an optionally substituted 4-7 membered heteroaryl or an optionally substituted 4-7 membered heterocyclyl; or $R^{3a}$ and $R^4$ together with the nitrogen and carbon to which they are attached, respectively, form an optionally substituted 4-7 membered heterocyclyl, and $R^{3b}$ is hydrogen, alkyl, hydroxyalkyl, haloalkyl, alkoxyalkyl, heterocyclyl, heteroaryl, heterocyclylalkyl, heteroarylalkyl, cycloalkyl, $(CH_2)$C(=O)$OR^6$, or $(CH_2)_n$P(=O)$(OR^6)_2$;

$R^4$ is a substituted or unsubstituted aryl, a substituted or unsubstituted heteroaryl, a substituted or unsubstituted cycloalkyl, or a substituted or unsubstituted heterocyclyl when n is 2, 3, 4, 5, or 6; or $R^4$ is a substituted or unsubstituted monocyclic heteroaryl, or a substituted or unsubstituted heterocyclyl when n is 0 or 1; or $R^4$ and $R^{3a}$ together with the carbon and nitrogen to which they are attached, respectively, form an optionally substituted 4-7 membered heterocyclyl;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3.

In some embodiments, $R^1$ is a substituted or unsubstituted aryl. In certain embodiments, $R^1$ is a substituted or unsubstituted $C_6$-$C_{10}$ aryl. In some more specific embodiments, $R^1$ is a substituted or unsubstituted phenyl. In certain specific embodiments, $R^1$ is a substituted phenyl.

In some embodiments, $R^1$ is phenyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, C(O)$R^9$, C(O)$NR^9R^{10}$, C(O)$OR^9$, OC(O)$R^9$, OC(O)$OR^9$, OC(O)$NR^9R^{10}$, $NR^9R^{10}$, N($R^9$)C(O)$R^{10}$, N($R^9$)C(O)$NR^{10}R^{11}$, N($R^9$)C(O)$OR^{10}$, C(=$NR^9$)$NR^{10}R^{11}$, C(=$NOR^9$)$NR^{10}R^{11}$, C(=NOC(O)$R^9$)$NR^{10}R^{11}$, C(=$NR^9$)N($R^{10}$)C(O)$OR^{11}$, N($R^9$)C(=$NR^{10}$)$NR^{11}R^{12}$, S(O)$R^9$, S(O)$NR^9R^{10}$, $S(O)_2R^9$, N($R^9$)$S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some more specific embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, C(O)$R^{13}$, C(O)$NR^{13}R^{14}$, C(O)$OR^{13}$, OC(O)$R^{13}$, OC(O)$NR^{13}R^{14}$, $NR^{13}R^{14}$, $NR^{13}$C(O)$R^{14}$, $NR^{13}$C(O)$NR^{14}R^{15}$, $NR^{13}$C(O)$OR^{14}$, C(=$NR^{13}$)$NR^{14}R^{15}$, $NR^{13}$C(=$NR^{14}$)$NR^{15}R^{16}$, S(O)$R^{13}$, S(O)$NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^1$ is phenyl substituted with at least one substituent selected from the group consisting of $OR^9$, C(=$NR^9$)$NR^{10}R^{11}$, C(=$NOR^9$)$NR^{10}R^{11}$, C(=NOC(O)$R^9$)$NR^{10}R^{11}$, and C(=$NR^9$)$NR^{10}$C(O)$OR^{11}$. In certain more specific embodiments, $R^1$ is substituted with at least one substituent selected from the group consisting of C(=$NR^9$)$NR^{10}R^{11}$, C(=$NOR^9$)$NR^{10}R^{11}$, C(=NOC(O)$R^9$)$NR^{10}R^{11}$, and C(=$NR^9$)$NR^{10}$C(O)$R^{11}$. In some embodiments, $R^1$ is substituted with at least one C(=$NR^9$)$NR^{10}R^{11}$. In some specific embodiments, $R^1$ is substituted with at least one —C(=NH)$NH_2$.

In certain more specific embodiments, $R^1$ has one of the following structures:

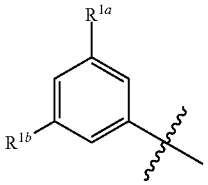 ; 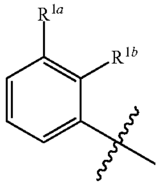 ;
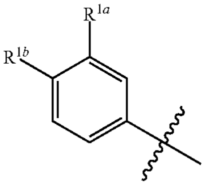 ; 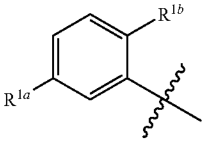 ;
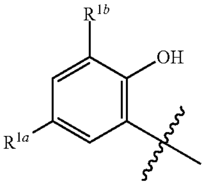 ; 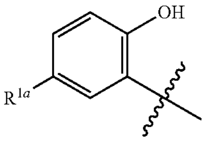 ;
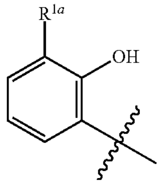 ; 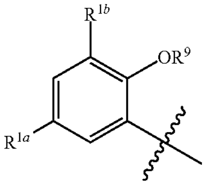 ;
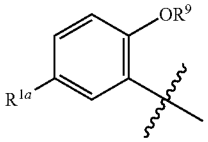 ; 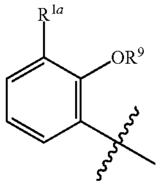 ;
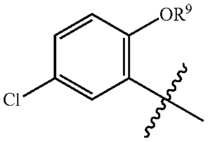 ; 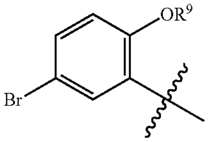 ;
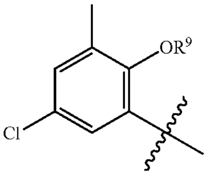 ; 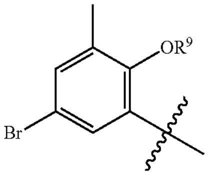 ;
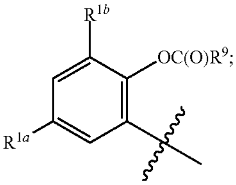 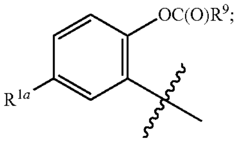
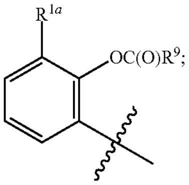 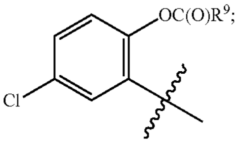
-continued
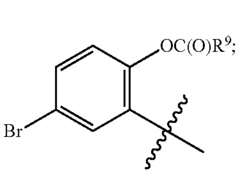 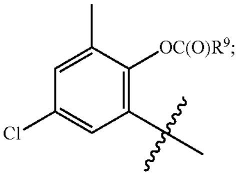
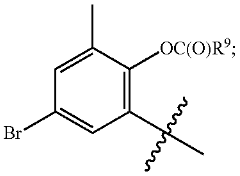 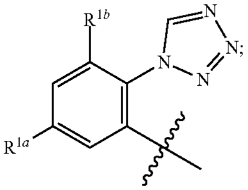
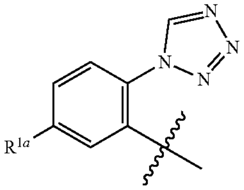 or 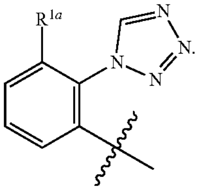
In still more specific embodiments, $R^1$ has one of the following structures:
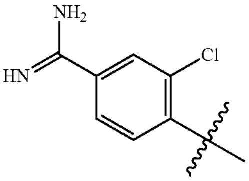 ;
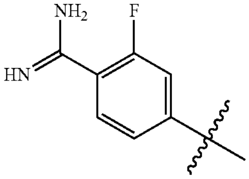 ;
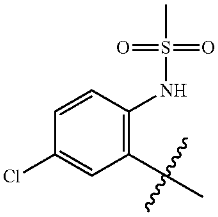 ; 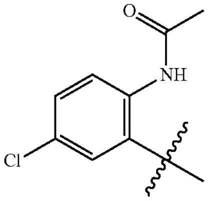 ;
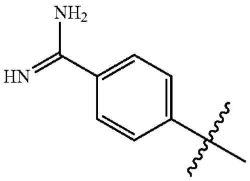 ; 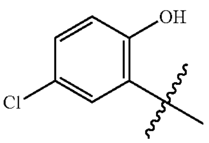 ;
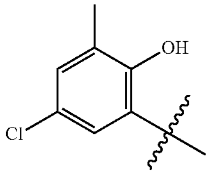 ; 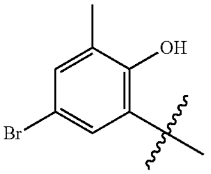 ;

-continued

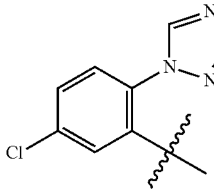

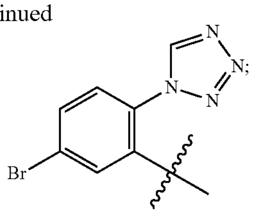

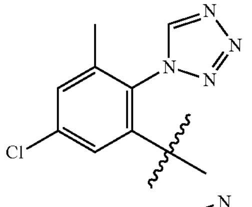

or

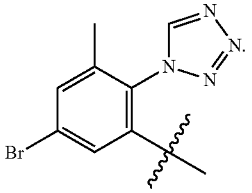

In some embodiments, $R^1$ has one of the following structures:

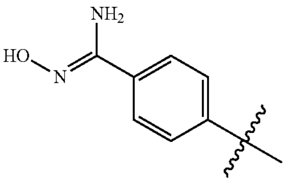

;

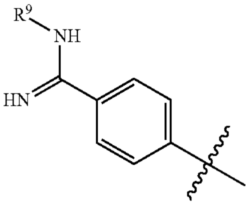

;

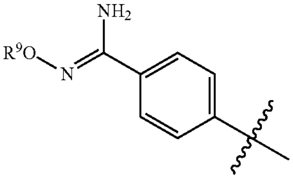

;

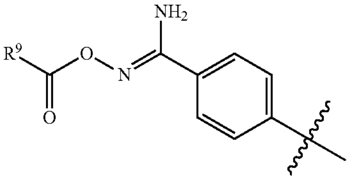

or

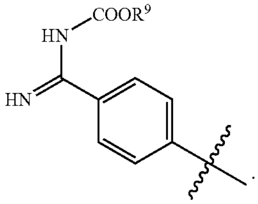

.

In some of the foregoing embodiments, $R^9$ is $C_{1-6}$ alkyl or $C_{1-6}$ haloalkyl. In certain more specific embodiments, $R^9$ is methyl. In some embodiments, $R^9$ is trifluoromethyl. In more embodiments, $R^1$ is an unsubstituted phenyl.

In certain other embodiments, $R^1$ is a substituted or unsubstituted heteroaryl. In more specific embodiments, $R^1$ is a substituted or unsubstituted 5-10 membered heteroaryl. In some more specific embodiments, $R^1$ is a substituted or unsubstituted pyridinyl, pyrrolopyridinyl, or benzoimidazolyl. In some embodiments, $R^1$ is a substituted or unsubstituted pyridin-3-yl, 1H-pyrrolo[2,3-b]pyridine-5-yl, 1H-pyrrolo[3,2-c]pyridine-2-yl, or 1H-benzo[d]imidazol-6-yl. In more specific embodiments, $R^1$ is pyridin-3-yl, 1H-pyrrolo[2,3-b]pyridine-5-yl, 1H-pyrrolo[3,2-c]pyridine-2-yl, or 1H-benzo[d]imidazol-6-yl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NOR^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl In certain specific embodiments, $R^1$ has one of the following structures:

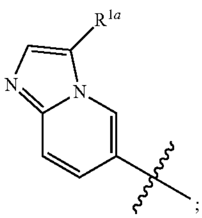

;

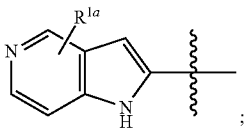

;

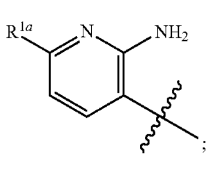

;

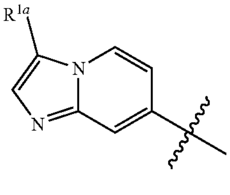

;

-continued
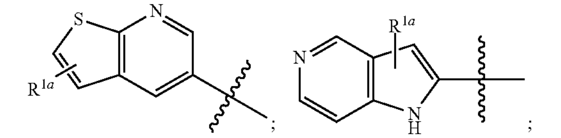
;
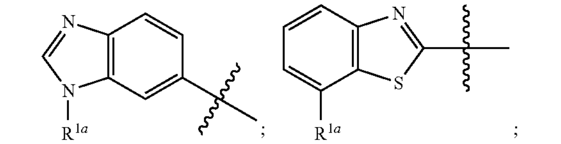
;
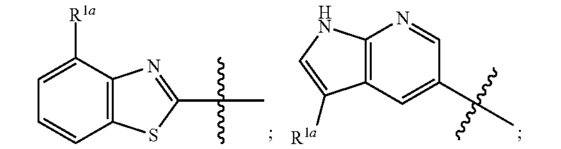
;
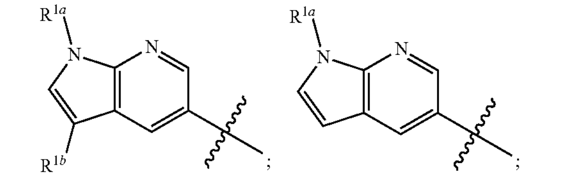
;
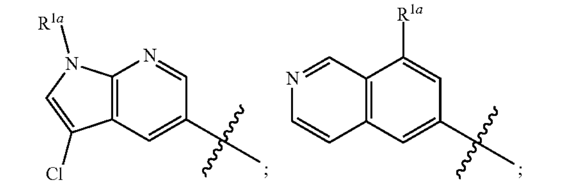
;
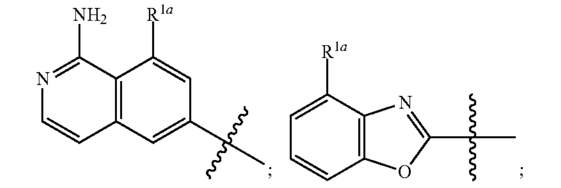
;
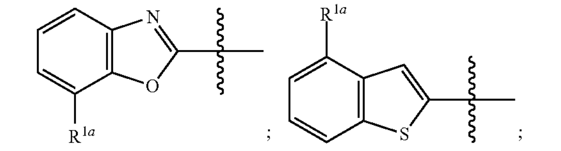
;
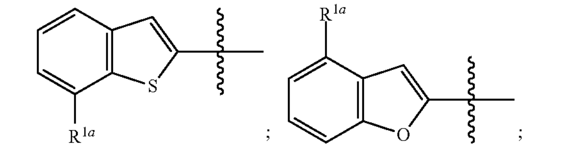
;
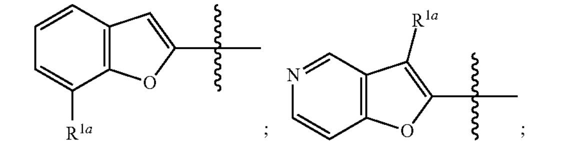
;
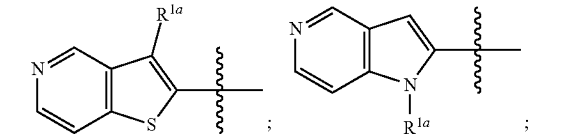
;
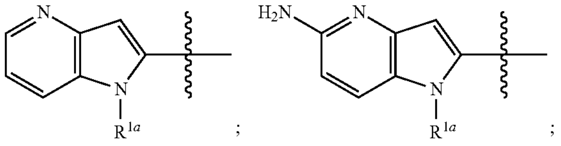
;
-continued
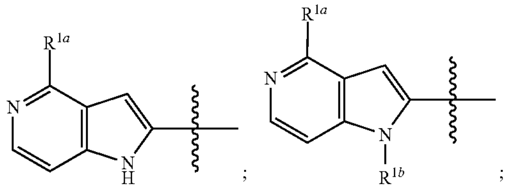
;
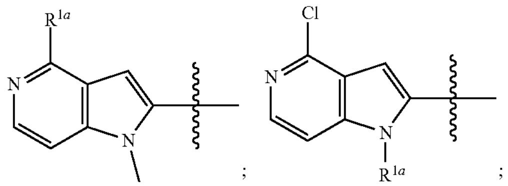
;
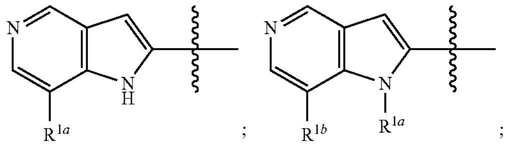
;
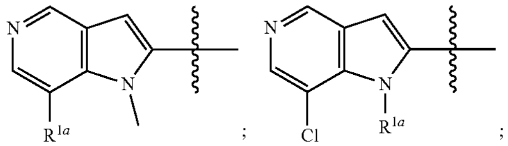
;
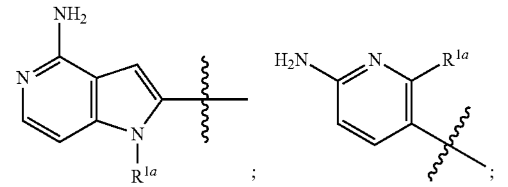
;
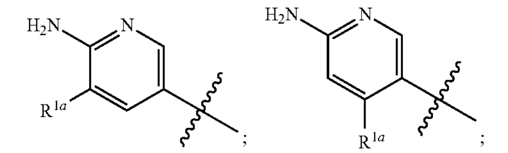
;
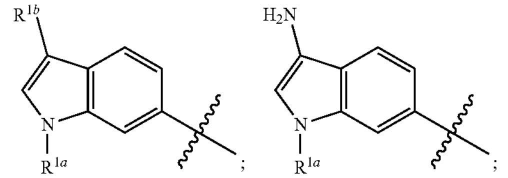
;
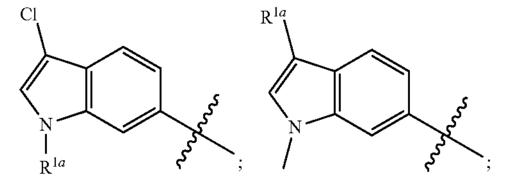
;
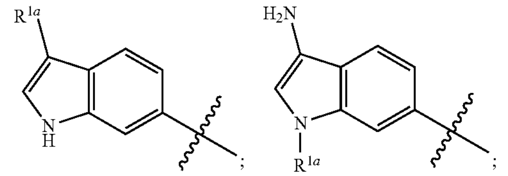
;
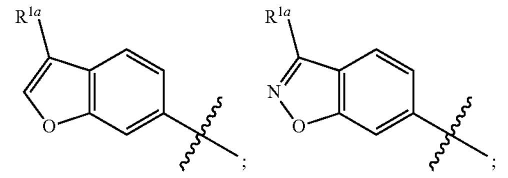
;

-continued
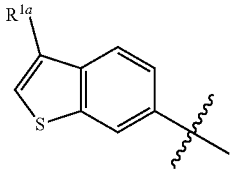 ;
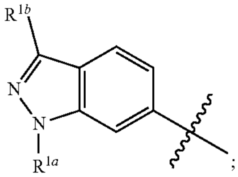 ;
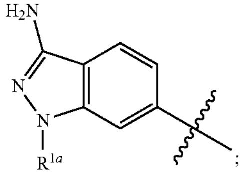 ;
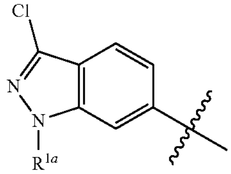 ;
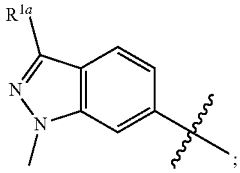 ;
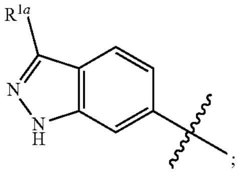 ;
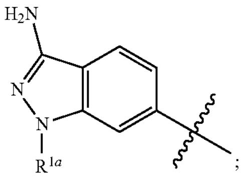 ;
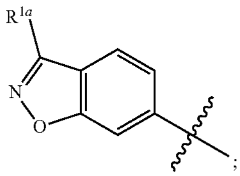 ;
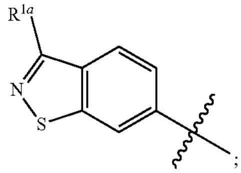 ;
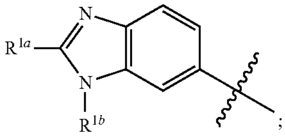 ;
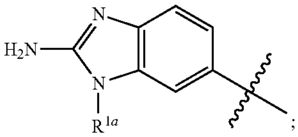 ;
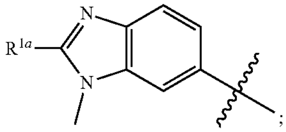 ;
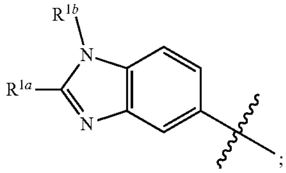 ;
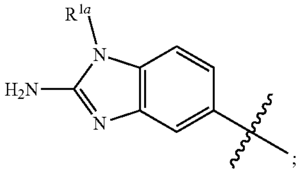 ;
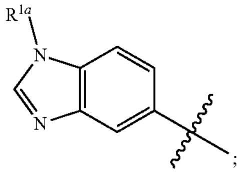 ;
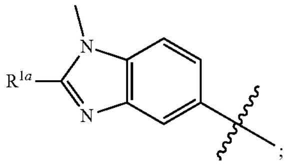 ;
-continued
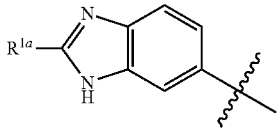 ;
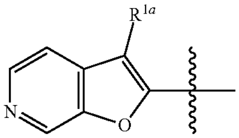 ;
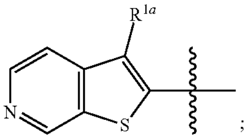 ;
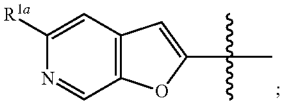 ;
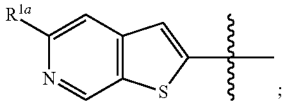 ;
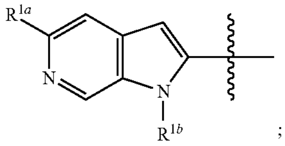 ;
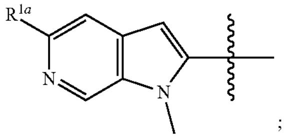 ;
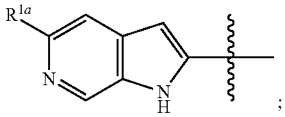 ;
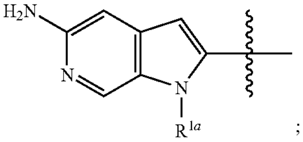 ;
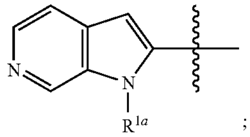 ;
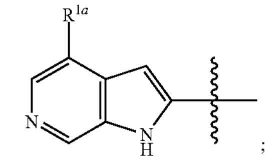 ;
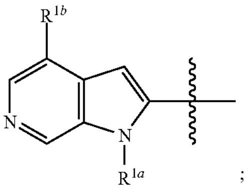 ;
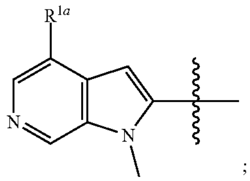 ;
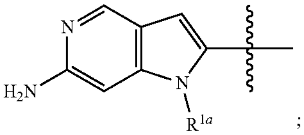 ;
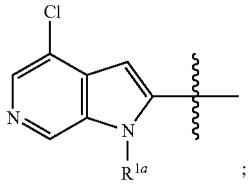 ;
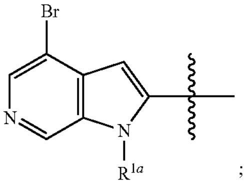 ;
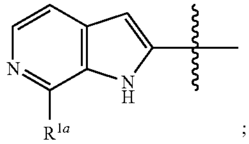 ;
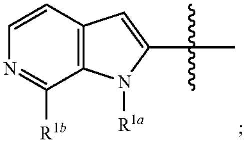 ;

-continued

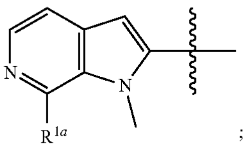
;
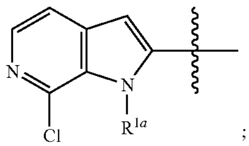
;
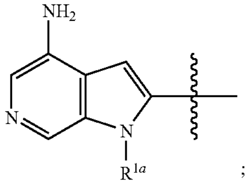
;
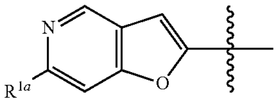
;
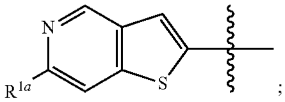
;
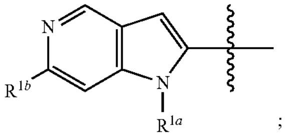
;
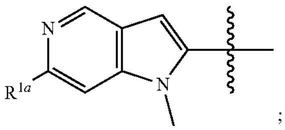
;
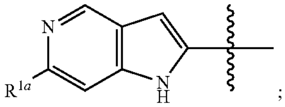
;
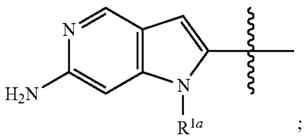
;
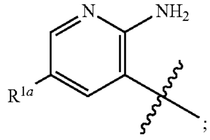
;
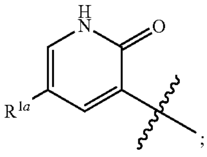
;
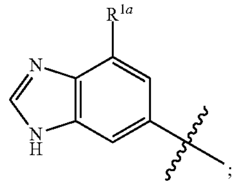
;
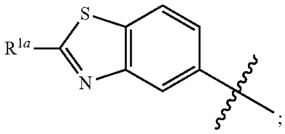
;
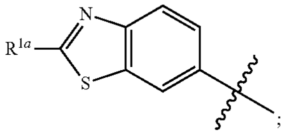
;
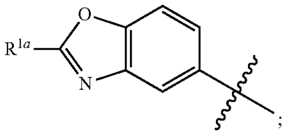
;
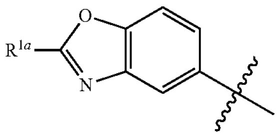
or -continued

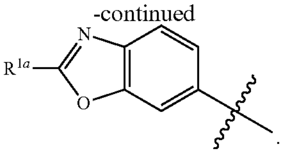
.

In some specific embodiments, $R^{1a}$ or $R^{1b}$ is independently $C_{1-6}$ alkyl, amino, $C(O)R^9$, $C(O)NR^9R^{10}$, $N(R^9)C(O)NR^{10}R^{11}$, $N(R^9)C(O)OR^{10}$, $OC(O)NR^9R^{10}$, or halo. In some embodiments, $R^{1a}$ or $R^{1b}$ is methyl or ethyl. In some specific embodiments, $R^{1a}$ or $R^{1b}$ is F, Cl, or Br. In certain embodiments, each $R^{1a}$ or $R^{1b}$ attached to nitrogen is $C_{1-6}$ alkyl, $C(O)R^9$, $C(O)NR^9R^{10}$, $N(R^9)C(O)NR^{10}R^{11}$, $N(R^9)C(O)OR^{10}$, or $OC(O)NR^9R^{10}$. In more specific embodiments, $R^{1a}$ or $R^{1b}$ is methyl or ethyl.

In some embodiments, $R^1$ has one of the following structures:

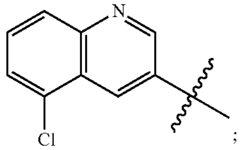
;
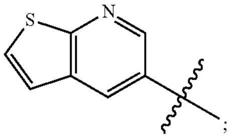
;
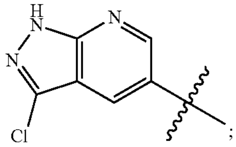
;
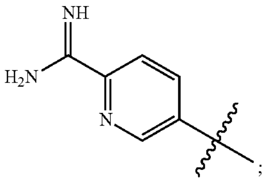
;
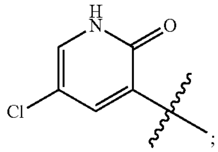
;
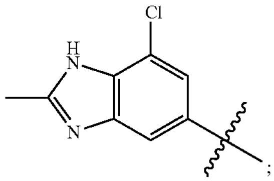
;
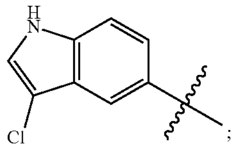
;
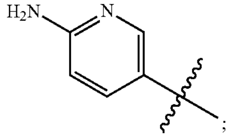
;
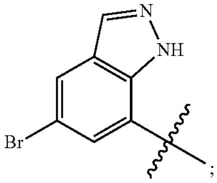
;
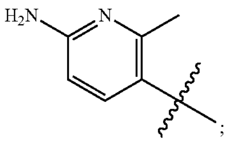
;
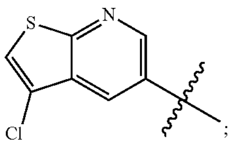
;
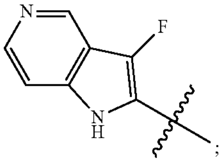
;
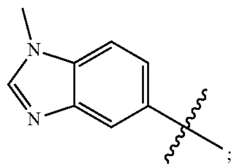
;
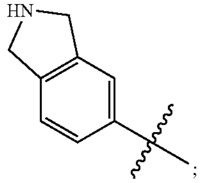
;

-continued
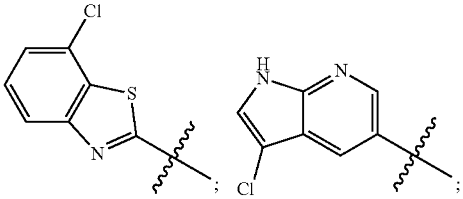
; ;
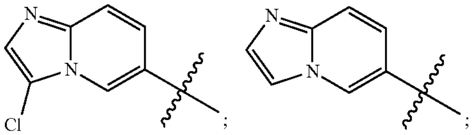
; ;
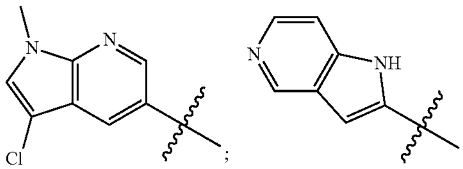
; ;
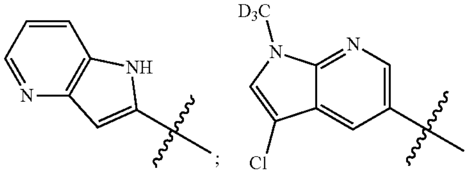
; or
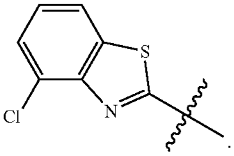
.
In certain embodiments, R[1] has one of the following structures:
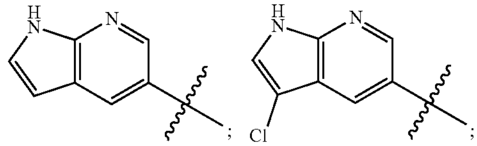
; ;
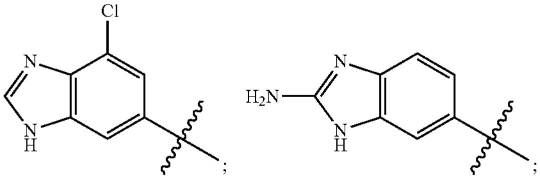
; ;
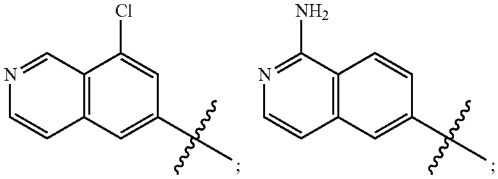
; ;
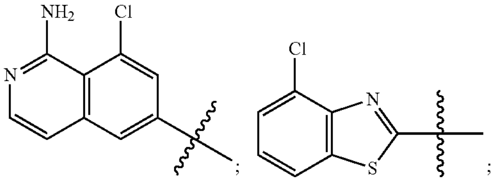
; ;
-continued
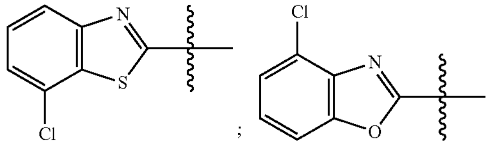
; ;
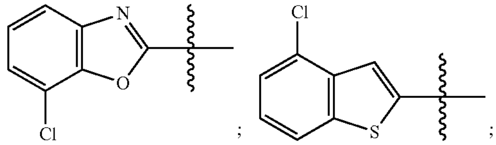
; ;
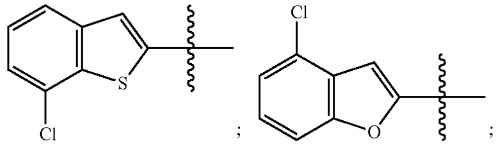
; ;
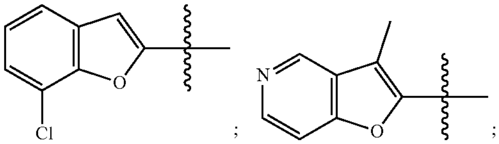
; ;
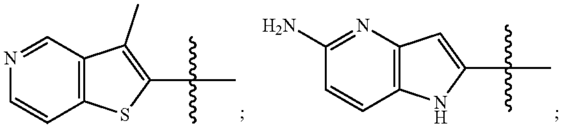
; ;
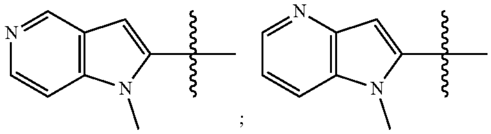
; ;
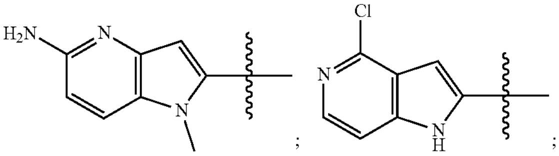
; ;
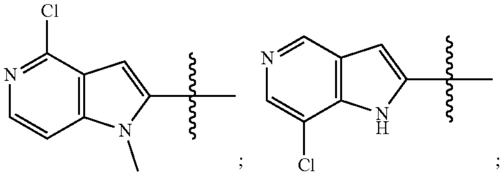
; ;
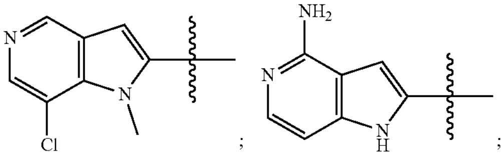
; ;
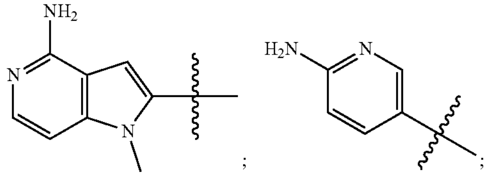
; ;
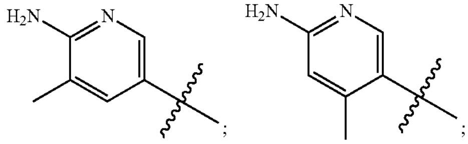
; ;

-continued
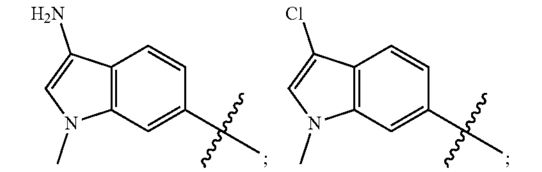;
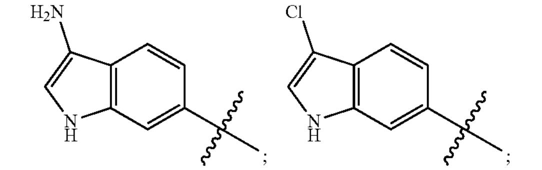;
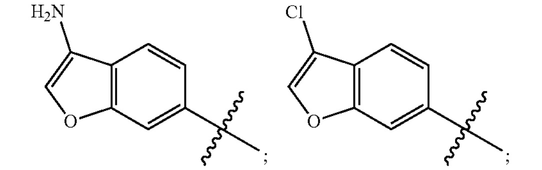;
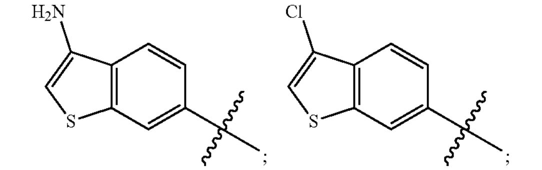;
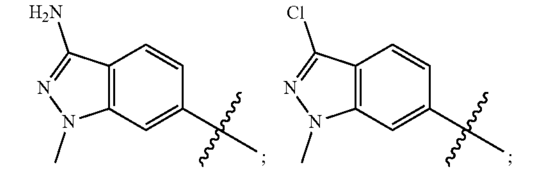;
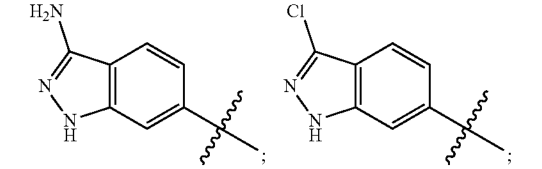;
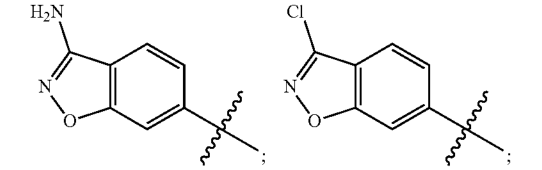;
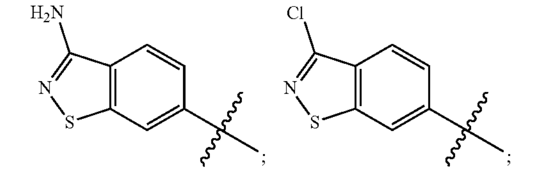;
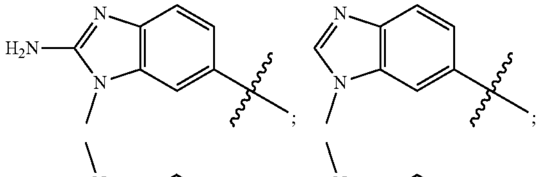;
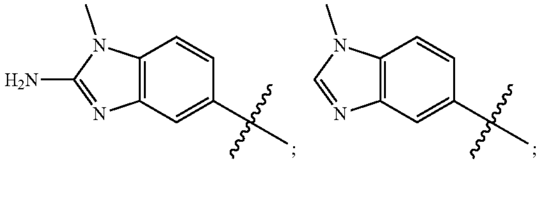;
-continued
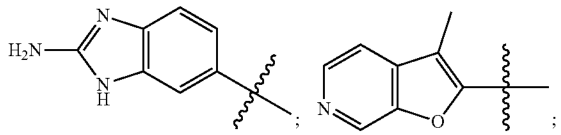;
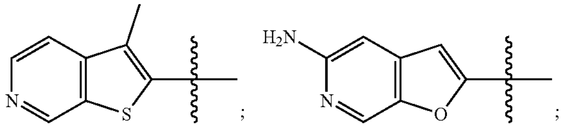;
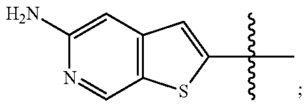;
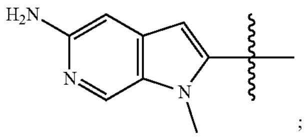;
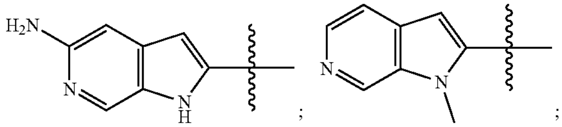;
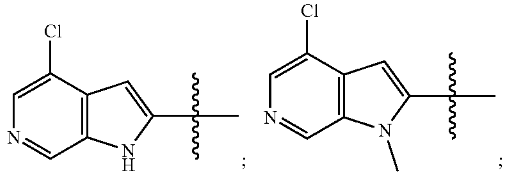;
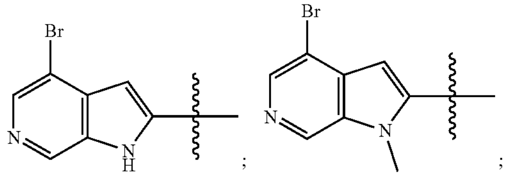;
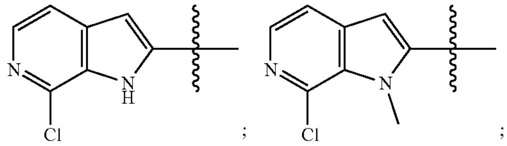;
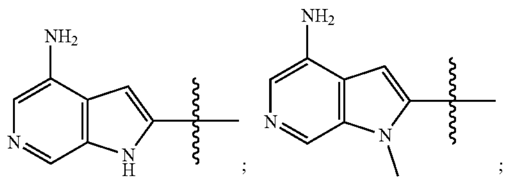;
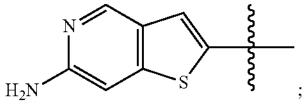;
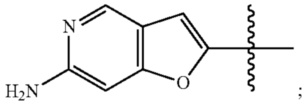;
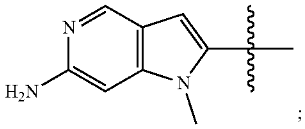;

-continued

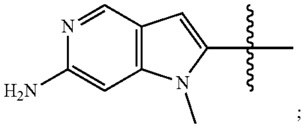 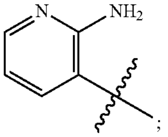 ;

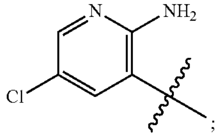 ; 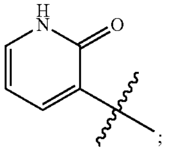 ;

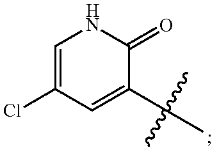 ; 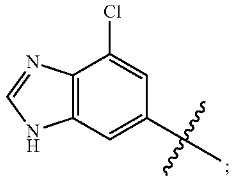 ;

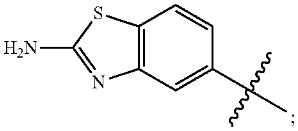 ;

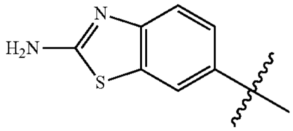 or

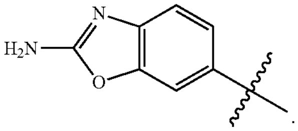 .

-continued

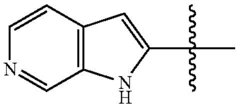 ; 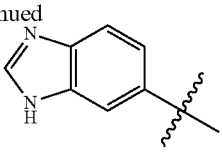 ;

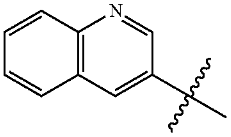 ; 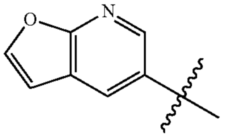 ;

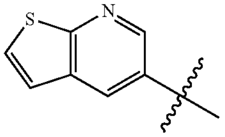 ; 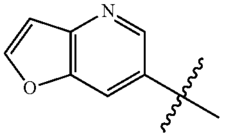 ;

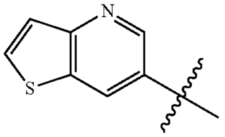 ; 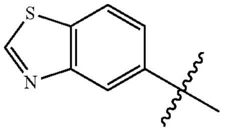 ;

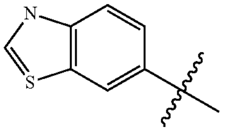 ; 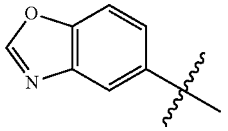 ; or

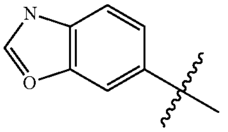 .

In certain embodiments, $R^1$ has one of the following structures:

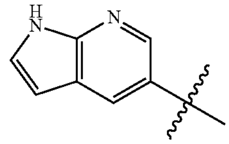 ; 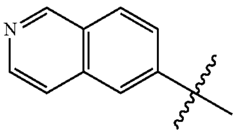 ;

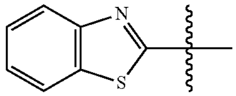 ; 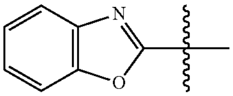 ;

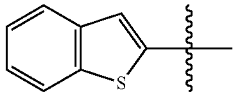 ; 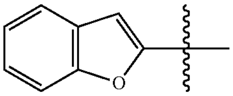 ;

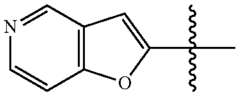 ; 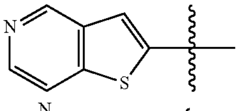 ;

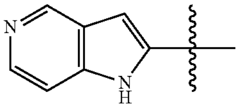 ; 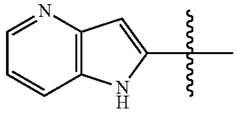 ;

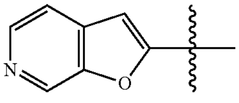 ; 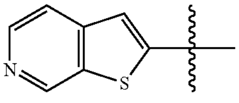 ;

In some embodiments, $R^1$ is a substituted or unsubstituted cycloalkyl. In certain embodiments, $R^1$ is a substituted or unsubstituted $C_{3-6}$ cycloalkyl. In some more specific embodiments, $R^1$ is a substituted $C_{3-6}$ cycloalkyl.

In some embodiments, $R^1$ is a $C_{3-6}$ cycloalkyl substituted with one or more of $R^{1a}$, $R^{1b}$, $R^{1c}$, $R^{1d}$, and $R^{1e}$ wherein $R^{1a}$, $R^{1b}$, $R^{1e}$, $R^{1d}$, and $R^{1e}$ are each independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments of the foregoing, $R^{1a}$, $R^{1b}$, $R^{1c}$, $R^{1d}$, or $R^{1e}$ is optionally substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{11}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is an unsubstituted a $C_{3-6}$ cycloalkyl. In certain embodiments, $R^1$ is a substituted or unsubstituted heterocyclyl. In certain specific embodiments, $R^1$ is a substituted or unsubstituted 4-10 membered heterocyclyl. In some embodiments, $R^1$ is a substituted 4-10 membered heterocyclyl.

In some embodiments, $R^1$ is a 4-10 membered heterocyclyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^1$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some of the foregoing embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is an unsubstituted 4-10 membered heterocyclyl.

In some embodiments, the compound has one of the following structures:

(IA)

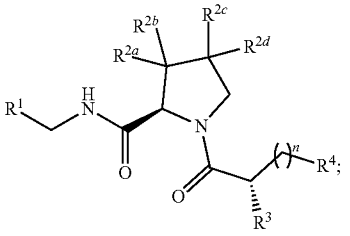

(IB)

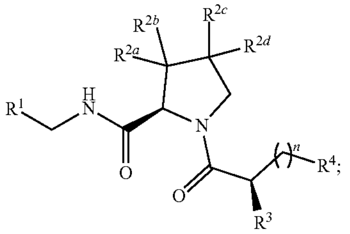

(IC)

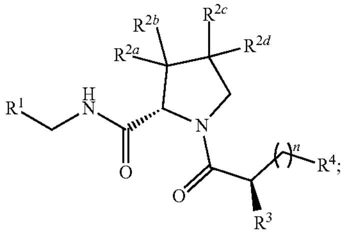

(ID)

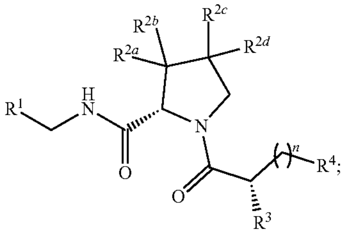

(IE)

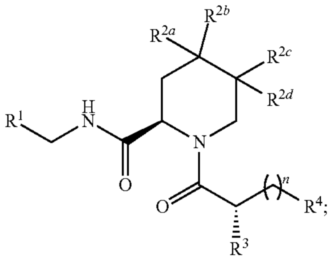

(IF)

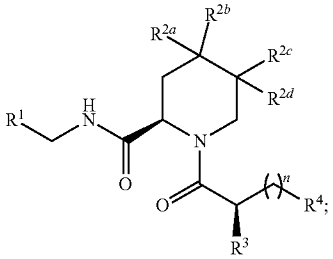

-continued (IG)

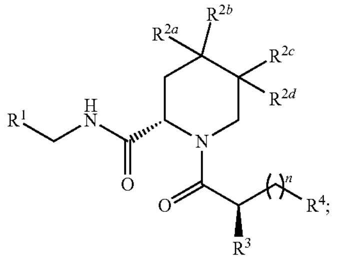

(IH)

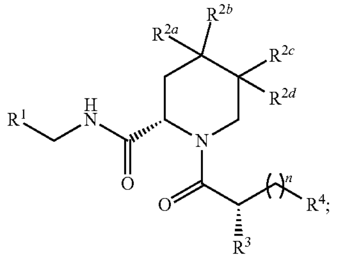

(IJ)

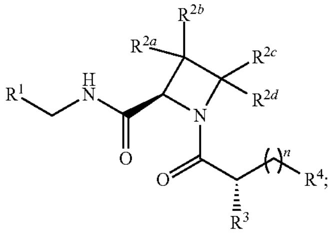

(IK)

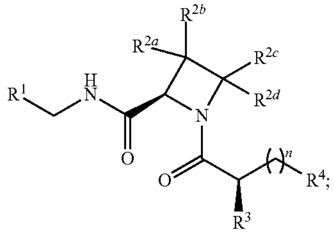

(IL)

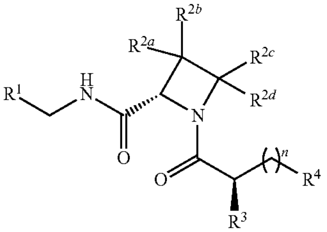

or (IM)

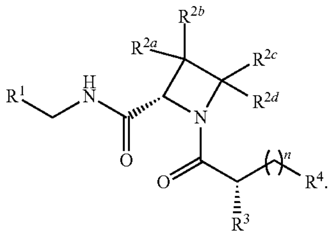

In some embodiments, at least one occurrence of $R^{2a}$, $R^{2b}$, $R^{2c}$, or $R^{2d}$ is alkoxy, alkoxyalkyl, cyano, C(=O)OR$^5$, OC(=O)R$^5$, C(=O)NR$^5$R$^6$, N(R$^5$)C(=O)R$^6$, aryl, heteroaryl, heterocyclyl, or C(=O)N(R$^5$)heterocyclyl, wherein $R^5$ and $R^6$ are, at each occurrence, independently hydrogen or $C_{1-6}$ alkyl. In some embodiments, $R^{2a}$ and $R^{2b}$ are both halo (e.g., fluoro).

In some more specific embodiments, X is $CH_2$, Y is a direct bond, $R^{2c}$ and $R^{2d}$ are both hydrogen, and $R^{2a}$ and $R^{2b}$ are both fluoro. In more specific embodiments, $R^{3b}$ is hydrogen and $R^{3a}$ and $R^4$ together with the nitrogen and carbon to which they are attached, respectively, form an optionally substituted 4-7 membered heterocyclyl (e.g., piperidinyl or pyrrolyl). In some more specific embodiments, the compound of Structure (I) has the following structure:

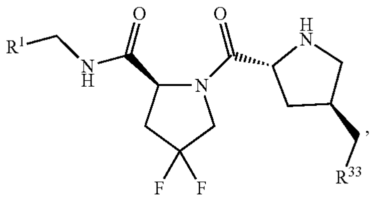

wherein:

$R^{33}$ is a substituted or unsubstituted aryl or a substituted or unsubstituted heteroaryl. In some embodiments, $R^{33}$ has the following structure:

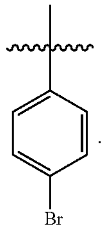

In certain embodiments, at least one occurrence of $R^{2a}$, $R^{2b}$, $R^{2c}$, or $R^{2d}$ is methoxy. In some embodiments, at least one of $R^{2a}$, $R^{2b}$, $R^{2c}$, and $R^{2d}$ is methoxymethyl. In certain embodiments, at least one of $R^{2a}$, $R^{2b}$, $R^{2c}$, and $R^{2d}$ is cyano. In some more specific embodiments, at least one of $R^{2a}$, $R^{2b}$, $R^{2c}$, and $R^{2d}$ is —C(=O)OH. In certain more specific embodiments, at least one of $R^{2a}$, $R^{2b}$, $R^{2c}$, and $R^{2d}$ is —C(=O)OCH$_3$ or —OC(=O)CH$_3$. In some embodiments, at least one of $R^{2a}$, $R^{2b}$, $R^{2c}$, and $R^{2d}$ is —C(=O)N(R')$_2$ or —NR'(C=O)alkyl wherein R' is, at each occurrence, independently a $C_{1-6}$ alkyl. In more specific embodiments, each occurrence of R' is methyl. In some embodiments, at least one of $R^{2a}$, $R^{2b}$, $R^{2c}$, and $R^{2d}$ is —C(=O)NR"heterocyclyl wherein R" is hydrogen or $C_{1-6}$ alkyl (e.g., methyl, ethyl, or isopropyl).

In some specific embodiments, at least one of $R^{2a}$, $R^{2b}$, $R^{2c}$, and $R^{2d}$ is a substituted or unsubstituted phenyl. In some embodiments, at least one of $R^{2a}$, $R^{2b}$, $R^{2c}$, and $R^{2d}$ is a substituted or unsubstituted heterocyclyl. In some embodiments, at least one of $R^{2a}$, $R^{2b}$, $R^{2c}$, and $R^{2d}$ is a substituted or unsubstituted heteroaryl (e.g., tetrazolyl, triazolyl, oxadiazolyl, imidazolidinyl, pyrazolyl, etc.). In some embodiments, $R^{2a}$ is heteroaryl or heterocyclyl. In some more specific embodiments, $R^{2c}$ is heteroaryl or heterocyclyl. In some embodiments, $R^{2a}$ is heterocyclyl. In some more specific embodiments, $R^{2c}$ is heterocyclyl. In certain specific embodiments, $R^{2a}$ is heteroaryl. In certain more specific embodiments, $R^{2c}$ is heteroaryl.

In some embodiments, at least one of $R^{2a}$, $R^{2b}$, $R^{2c}$, and $R^{2d}$ has one of the following structures:
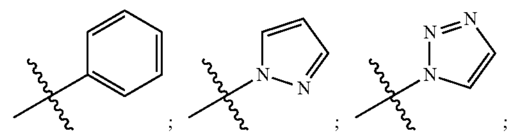
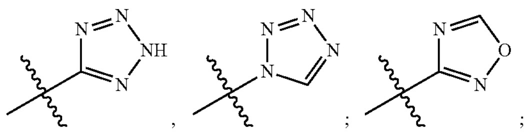
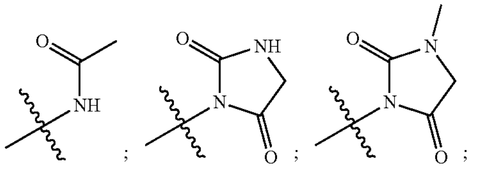
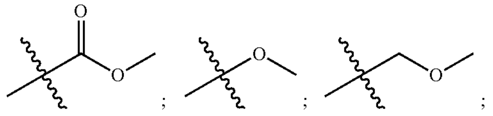
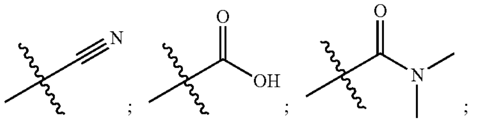
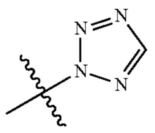
or
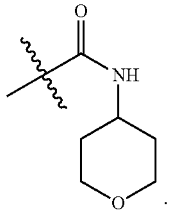
In more specific embodiments, at least one of $R^{2a}$, $R^{2b}$, $R^{2c}$, and $R^{2d}$ has one of the following structures:
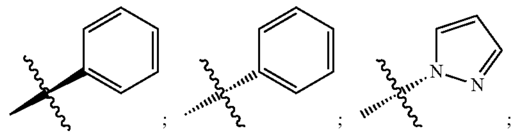
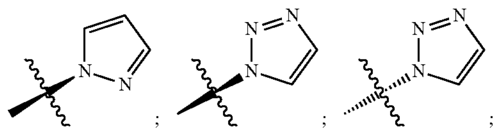
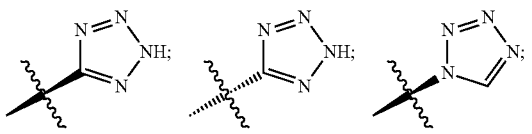
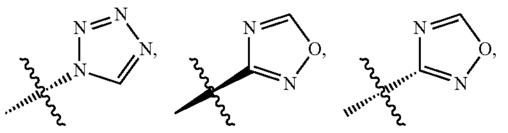
-continued
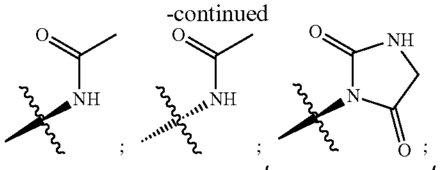
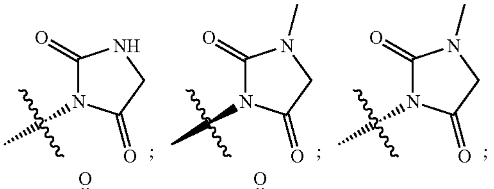
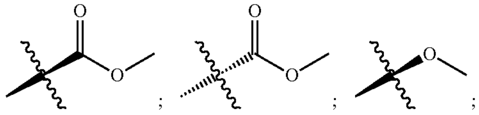
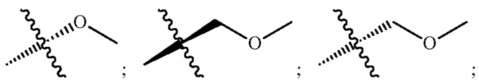
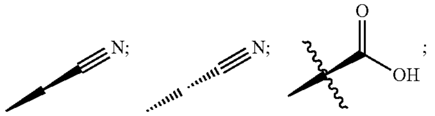
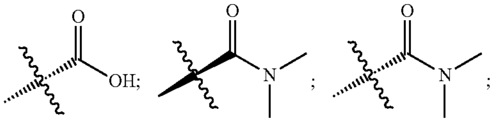
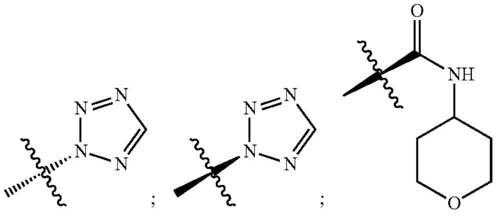
or
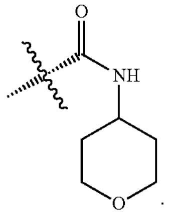
In some more specific embodiments, $R^3$ has one of the following structures:
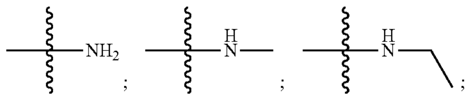
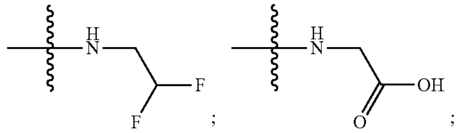
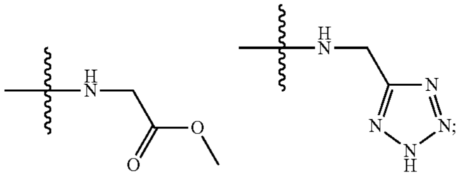

-continued

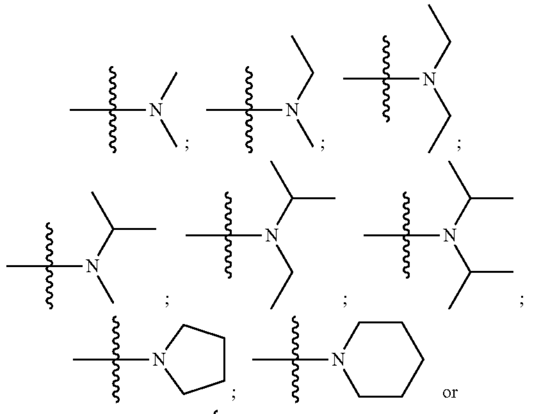

or

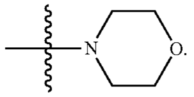

In certain embodiments, $R^3$ is $-NH_2$.

In some embodiments, n is 0. In certain embodiments, n is 1. In still other embodiments, n is 2. In some embodiments, n is 3, 4, 5, or 6.

In some embodiments, n is 2 and $R^4$ is a substituted or unsubstituted aryl. In some more specific embodiments, $R^4$ is a substituted aryl. In certain more specific embodiments, $R^4$ is substituted with a substituent selected from the group consisting of alkyl, halo (e.g., fluoro, chloro, bromo), haloalkyl, hydroxyl, amino, nitro, and combinations thereof. In some embodiments, $R^4$ is an unsubstituted aryl. In certain embodiments, $R^4$ has one of the following structures:

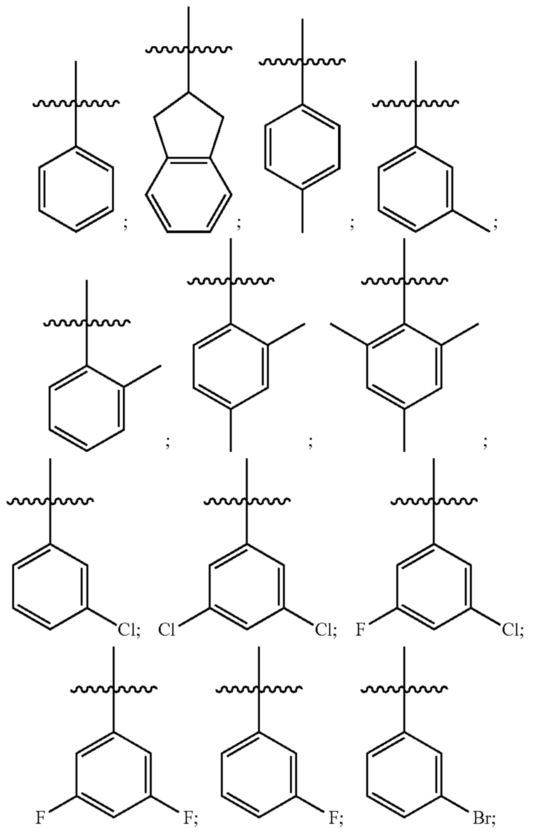

-continued

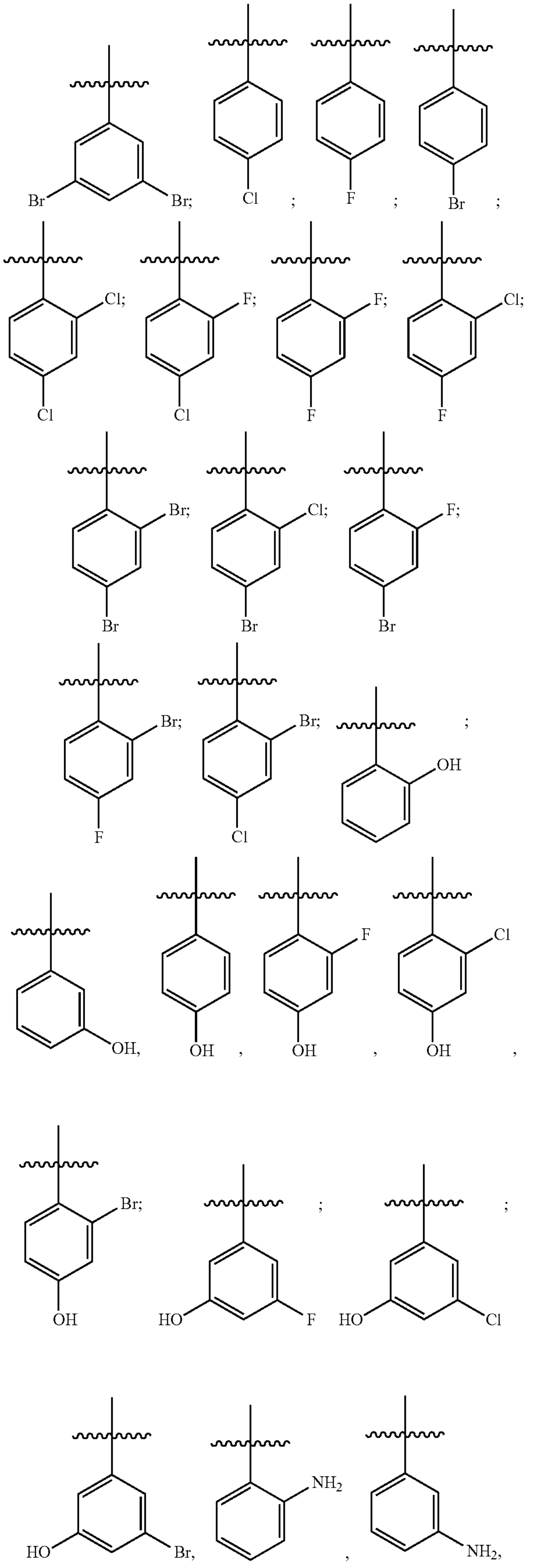

-continued
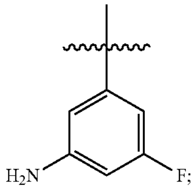 ;
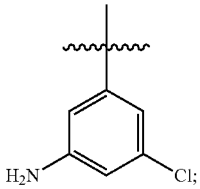 ;
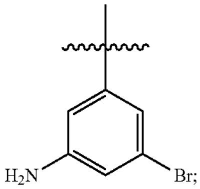 ;
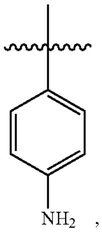 ,
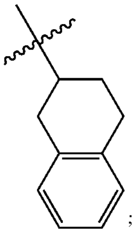 ;
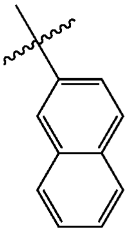 ;
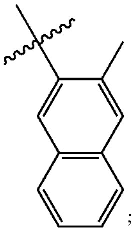 ;
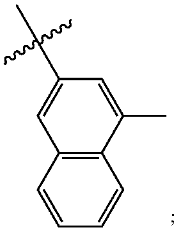 ;
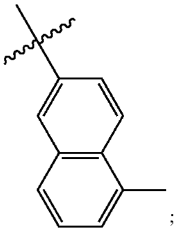 ;
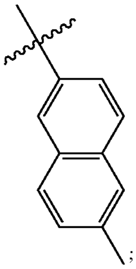 ;
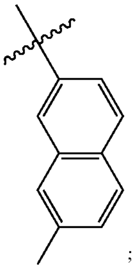 ;
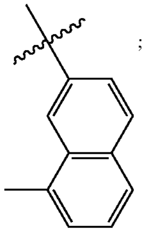 ;
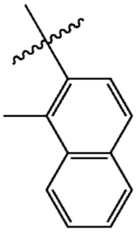 ;
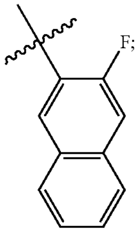 ;
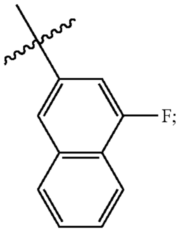 ;
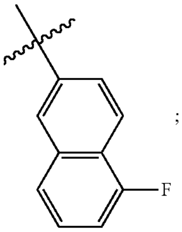 ;
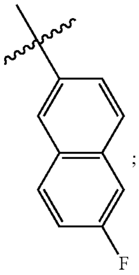 ;
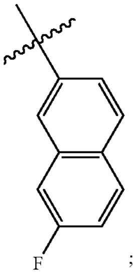 ;
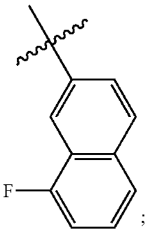 ;
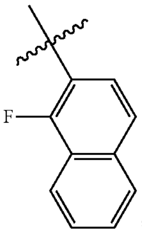 ;
-continued
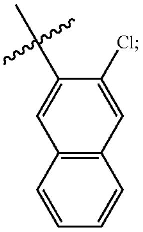 ;
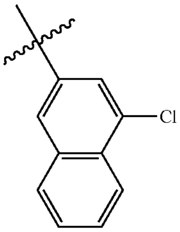 ;
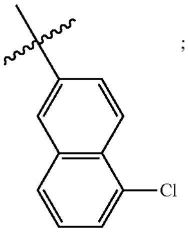 ;
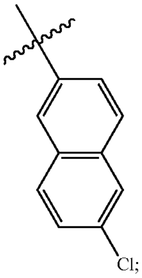 ;
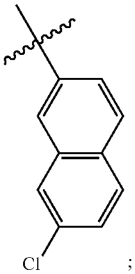 ;
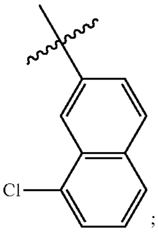 ;
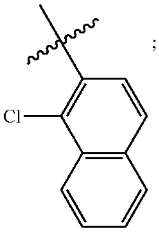 ;
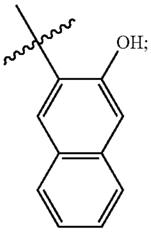 ;
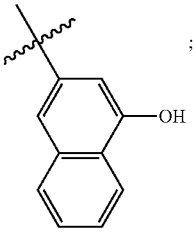 ;
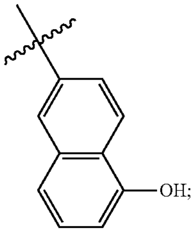 ;
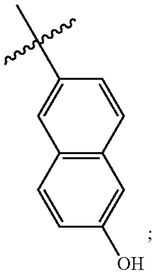 ;
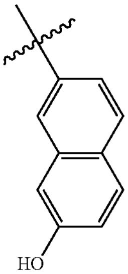 ;
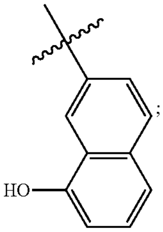 ;
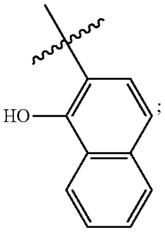 ;
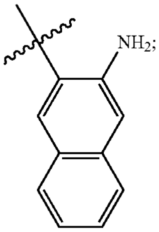 ;
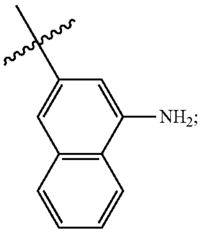 ;
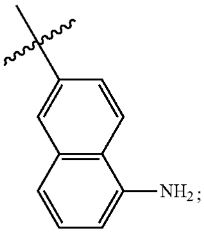 ;

-continued
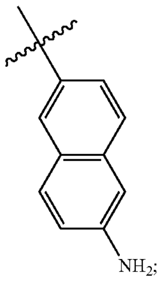;
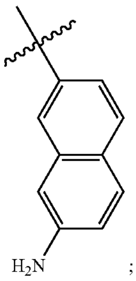;
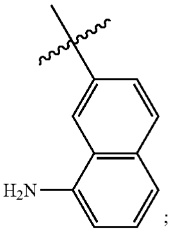;
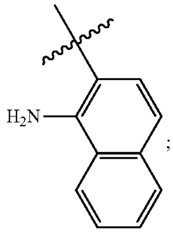;
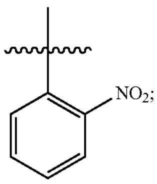;
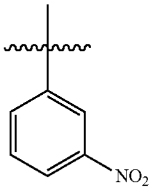
or
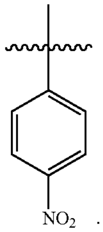.
In some more specific embodiments, $R^4$ has one of the following structures:
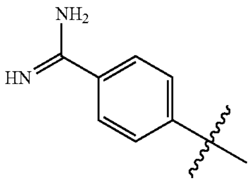;
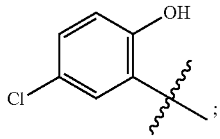;
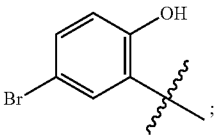;
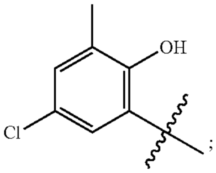;
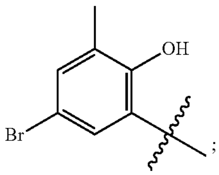;
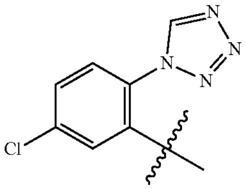;
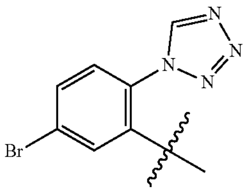;
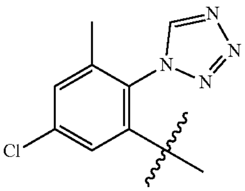
or
-continued
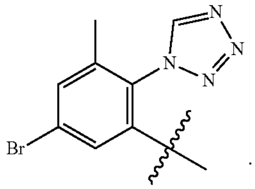.
In certain specific embodiments, n is 2 and $R^4$ is a substituted or unsubstituted heteroaryl. In some more specific embodiments, $R^4$ has one of the following structures:
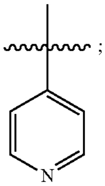;
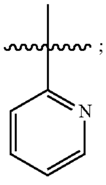;
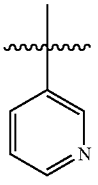;
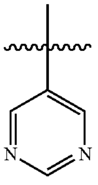;
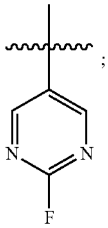;
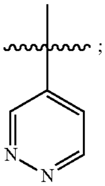;
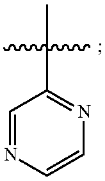;
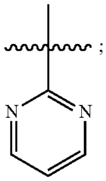;
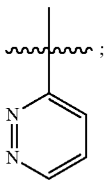;
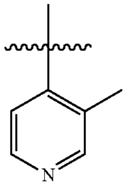;
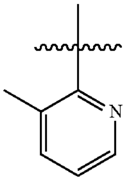;
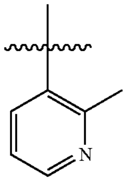;
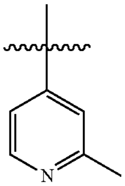;
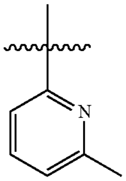;
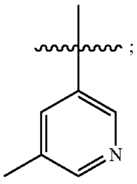;
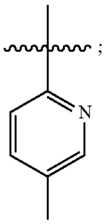;
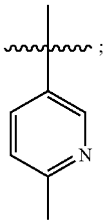;
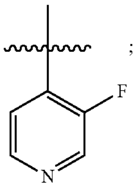;
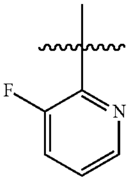;
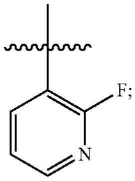;
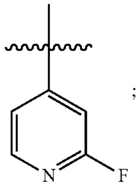;

-continued
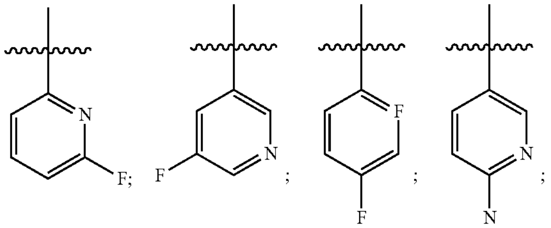
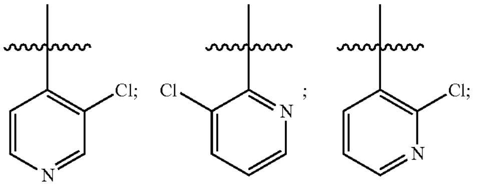
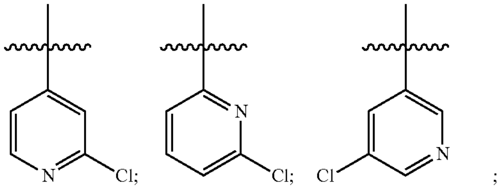
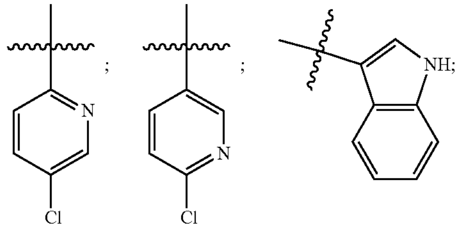
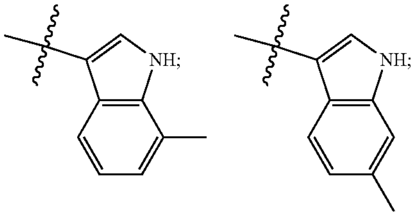
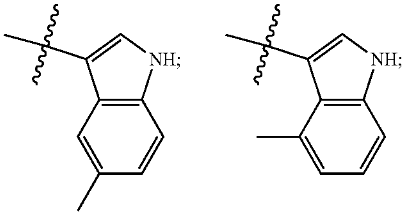
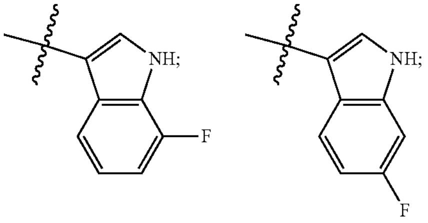
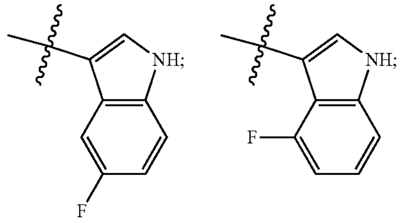
-continued
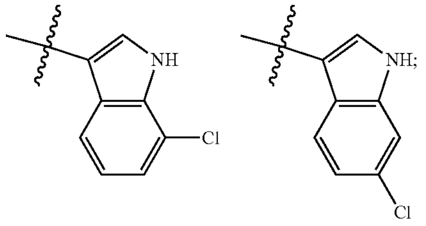
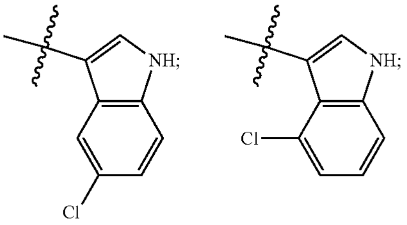
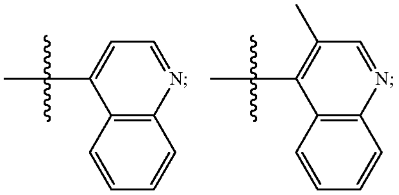
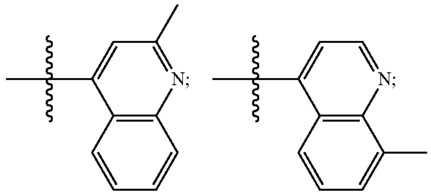
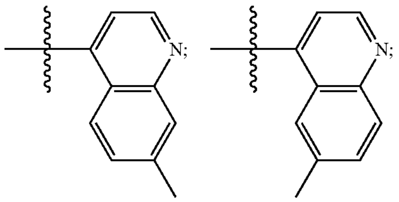
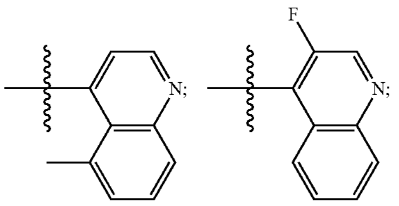
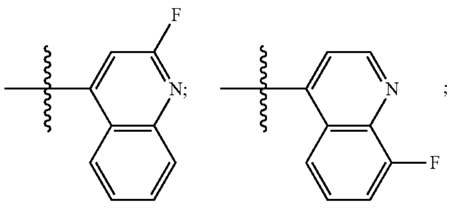
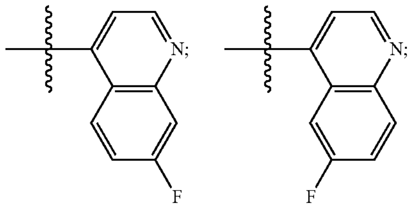

-continued
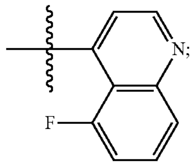;
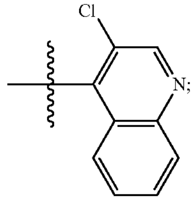;
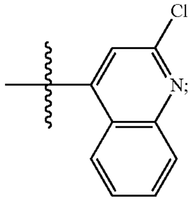;
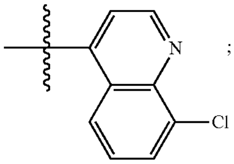;
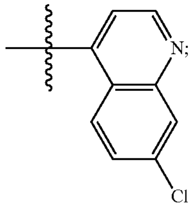;
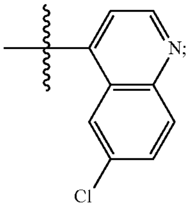;
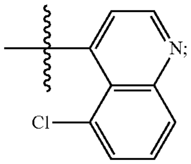;
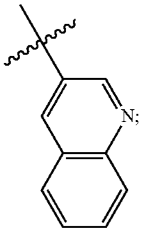;
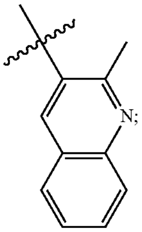;
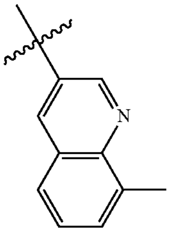;
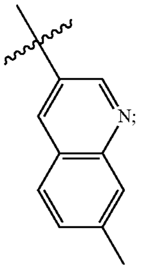;
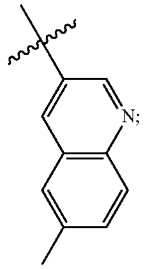;
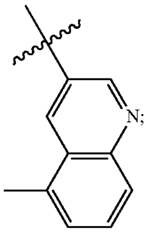;
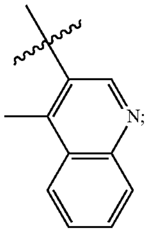;
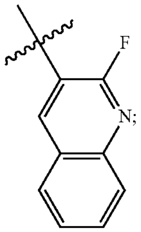;
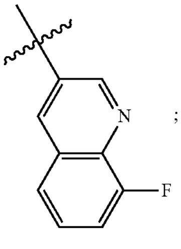;
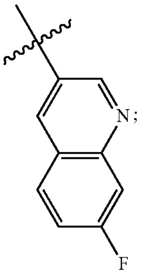;
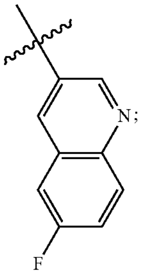;
-continued
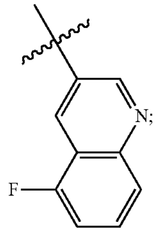;
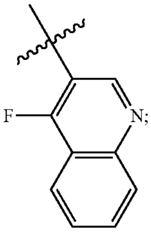;
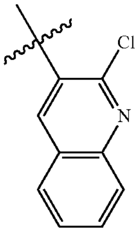;
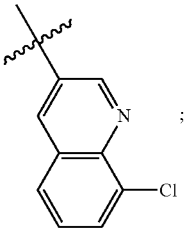;
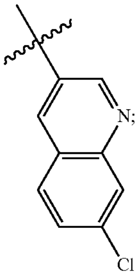;
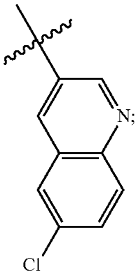;
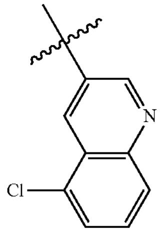
or
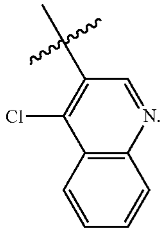.
In some embodiments, $R^4$ has one of the following structures:
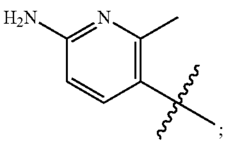;
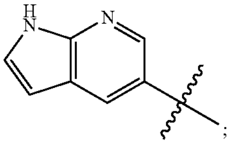;
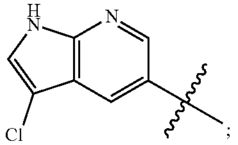;
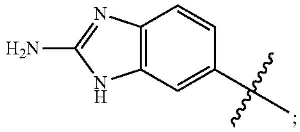;
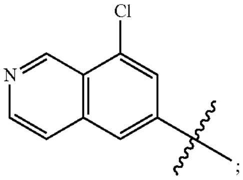;
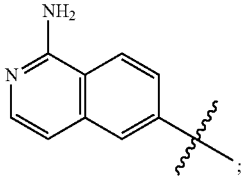;
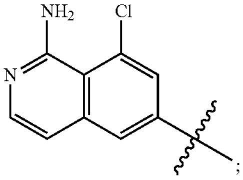;
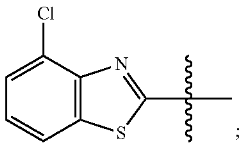;
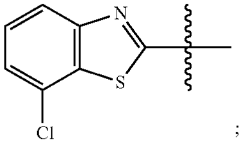;
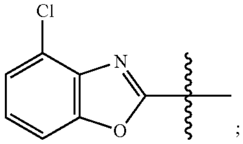;

-continued
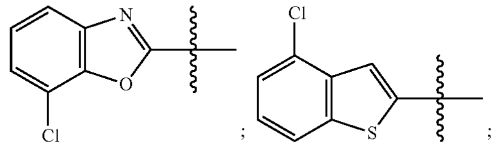
; ;
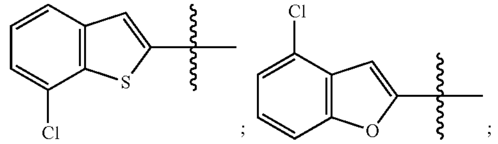
; ;
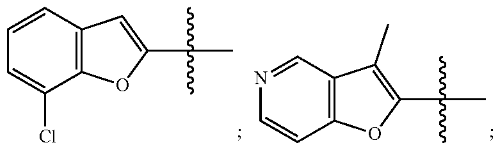
; ;
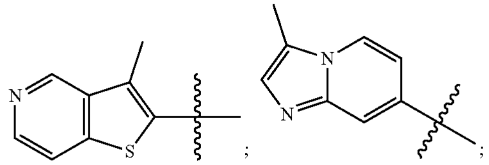
; ;
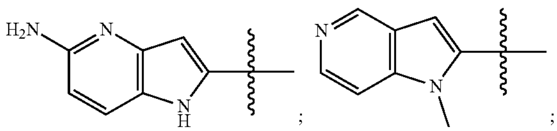
; ;
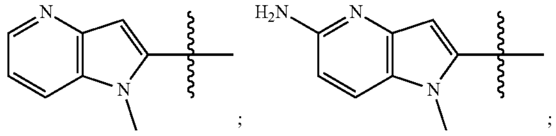
; ;
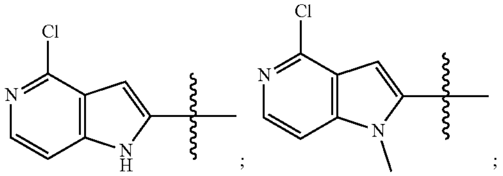
; ;
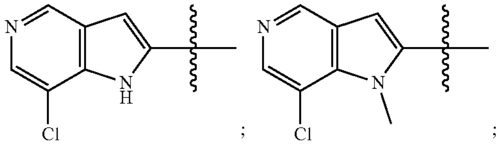
; ;
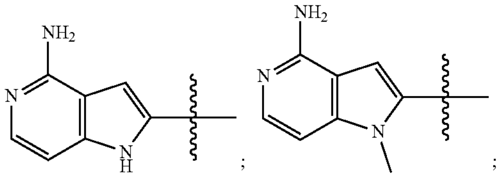
; ;
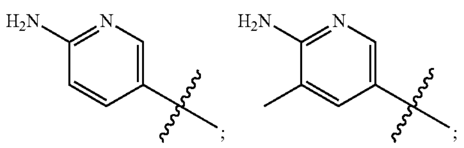
; ;
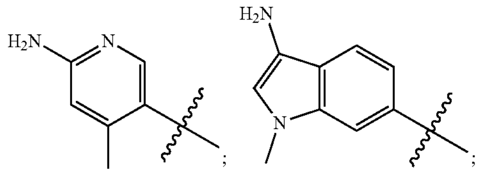
; ;
-continued
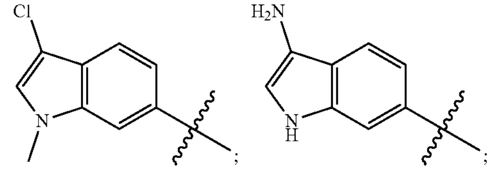
; ;
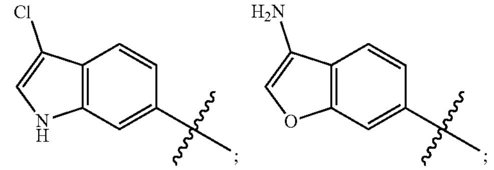
; ;
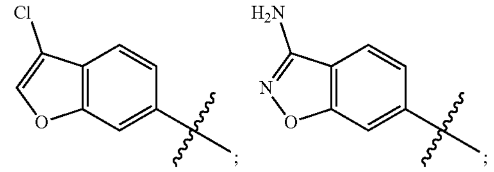
; ;
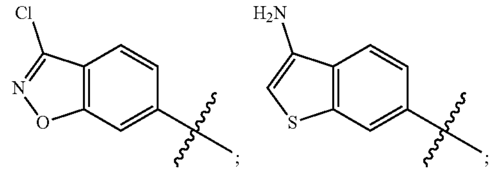
; ;
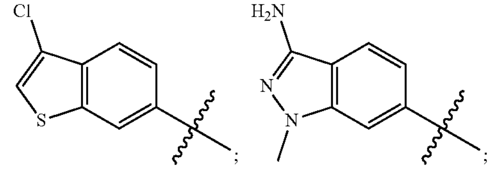
; ;
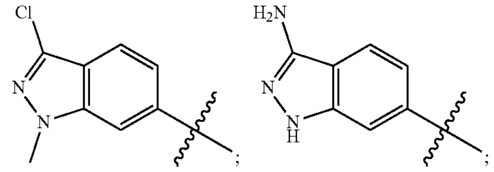
; ;
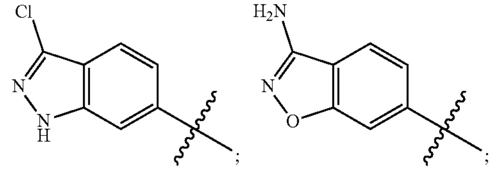
; ;
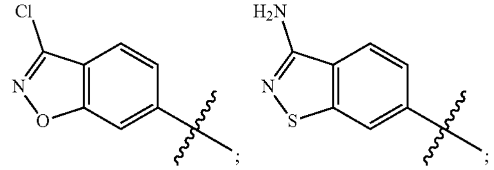
; ;
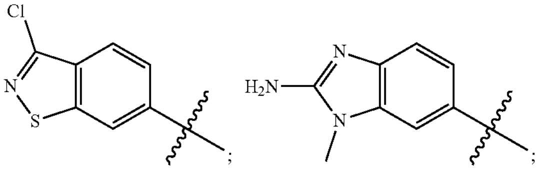
; ;
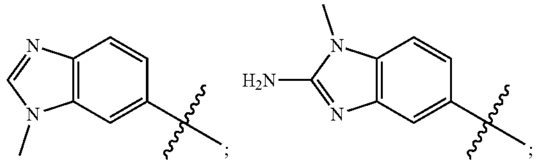
; ;

-continued
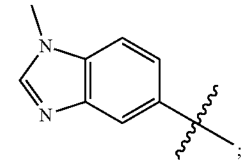
;
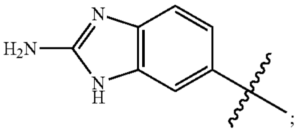
;
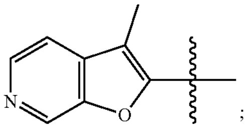
;
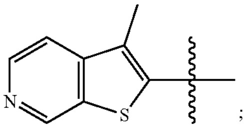
;
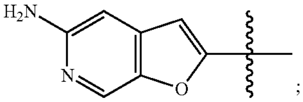
;
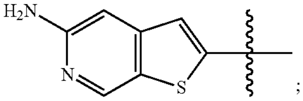
;
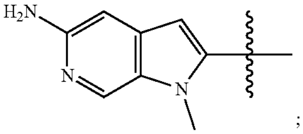
;
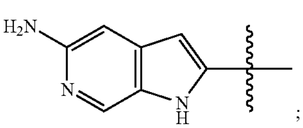
;
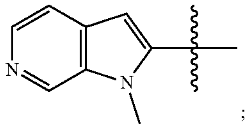
;
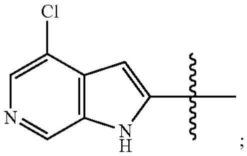
;
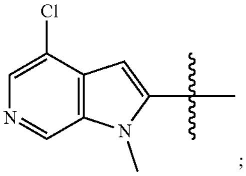
;
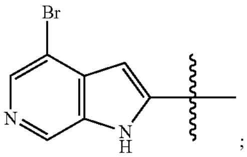
;
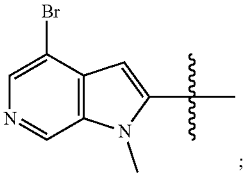
;
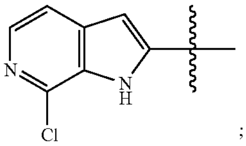
;
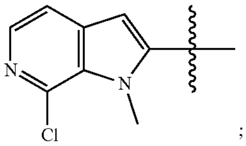
;
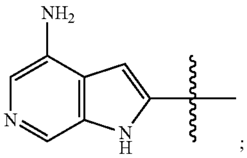
;
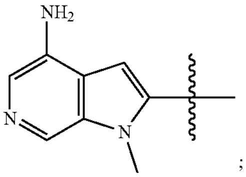
;
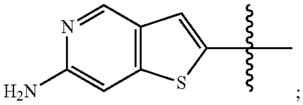
;
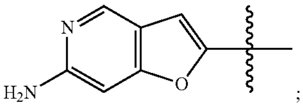
;
-continued
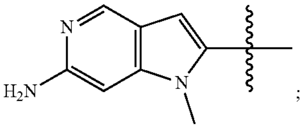
;
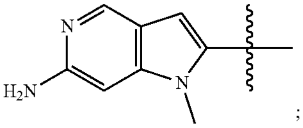
;
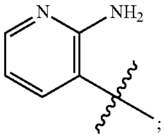
;
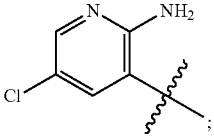
;
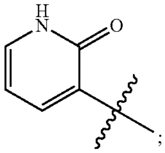
;
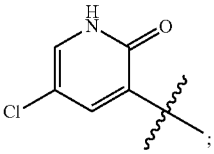
;
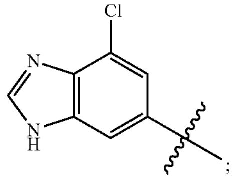
;
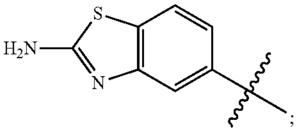
;
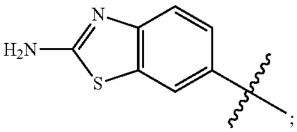
;
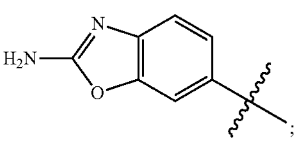
;
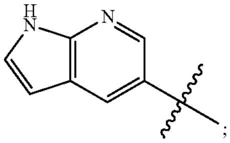
;
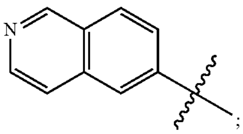
;
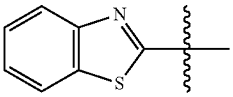
;
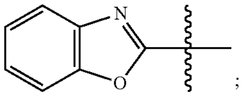
;
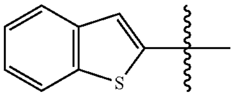
;
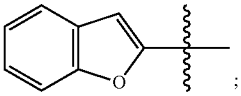
;
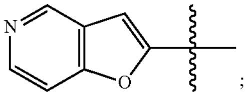
;
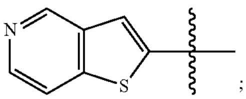
;
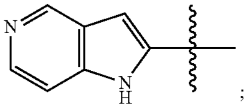
;
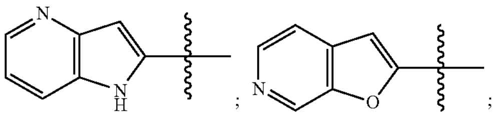
;
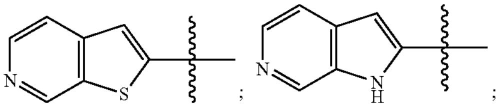
;

-continued
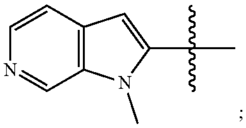 ; 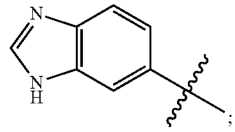 ;
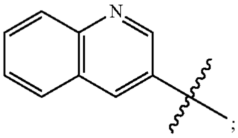 ; 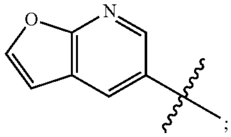 ;
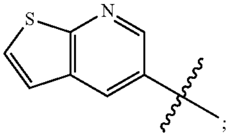 ; 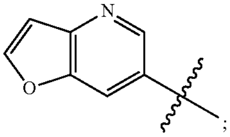 ;
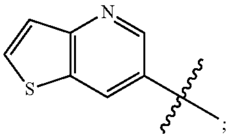 ; 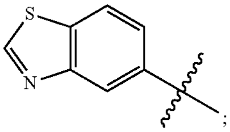 ;
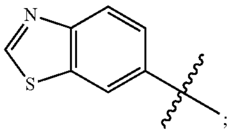 ; 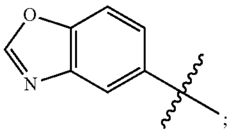 ; or
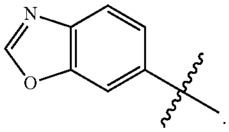 .
In some embodiments, $R^4$ has one of the following structures:
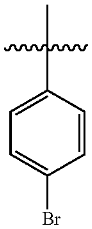 ; 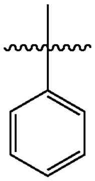 ; 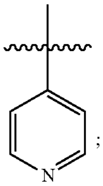 ; 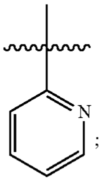 ; 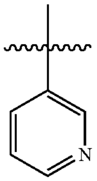 ;
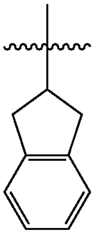 ; 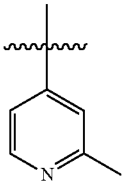 or 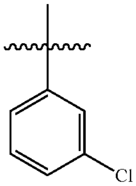 .
In certain related embodiments, n is 0 and $R^4$ has one of the following structures:
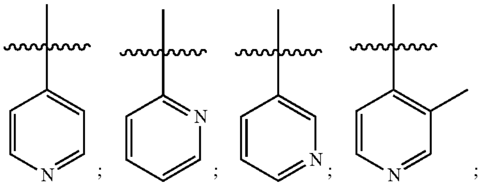
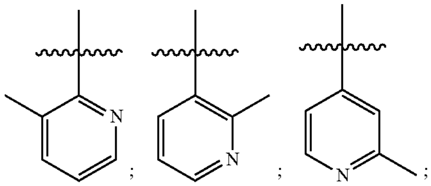
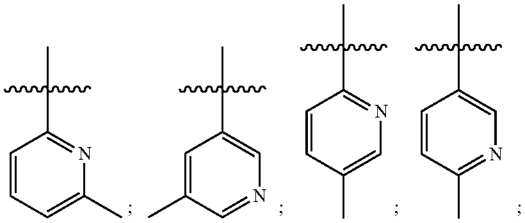
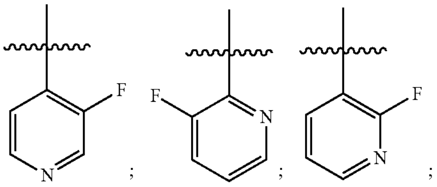
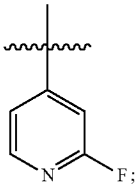
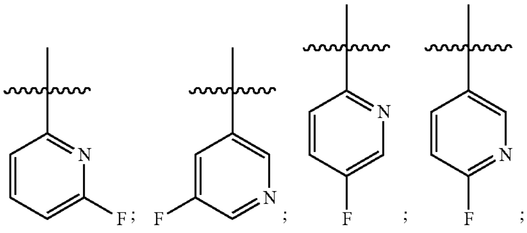
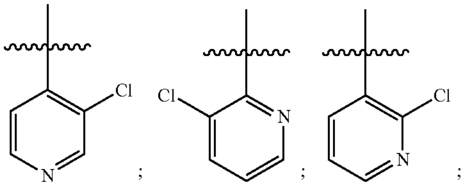
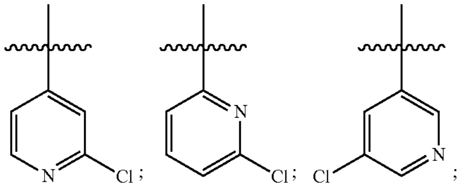

-continued

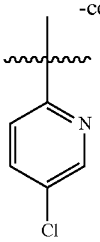 or 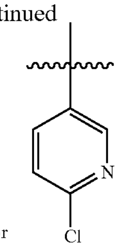 .

In some specific embodiments 4 has one of the following structures:

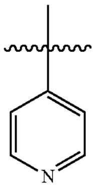 ; 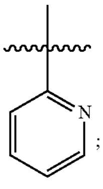 ; 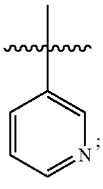 ; or 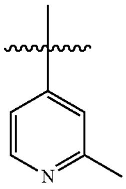 .

One embodiment provides a compound having the following Structure (II):

(II)

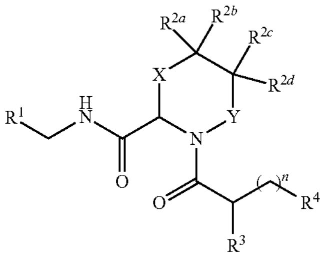

or a stereoisomer, tautomer, or pharmaceutically acceptable salt thereof, wherein:

X is a direct bond, —[C($R^{2e}$)$R^{2f}$]—, or —[C($R^{2e}$)$R^{2f}$]—[C($R^{2g}$)$R^{2h}$];

Y is a direct bond or —[C($R^{2i}$)$R^{2j}$];

$R^1$ is a substituted or unsubstituted aryl, substituted or unsubstituted heteroaryl, substituted or unsubstituted cycloalkyl, or a substituted or unsubstituted heterocyclyl;

$R^{2a}$, $R^{2b}$, $R^{2c}$, $R^{2d}$, $R^{2e}$, $R^{2f}$, $R^{2g}$, $R^{2h}$, $R^{2i}$, and $R^{2j}$ are each independently selected from the group consisting of hydrogen, halo, $OR^5$, C(═O)$OR^5$, OC(═O)$R^5$, hydroxyalkyl, alkoxy, alkoxyalkyl, haloalkoxy, cyano, aminylalkyl, carboxyalkyl, $NR^5R^6$, C(═O)$NR^5R^6$, N($R^5$)C(═O)$R^6$, $NR^5$C(═O)$NR^6$, $S(O)_t$, $SR^5$, nitro, N($R^5$)C(O)$OR^6$, C(═$NR^5$)$NR^6R^7$, N($R^5$)C(═$NR^6$)$NR^7R^8$, S(O)$R^5$, S(O)$NR^5R^6$, $S(O)_2R^5$, N($R^5$)$S(O)_2R^6$, $S(O)_2NR^5R^6$, aryl, heteroaryl, heterocyclyl, cycloalkyl, and oxo, provided that at least one of $R^{2a}$, $R^{2b}$, $R^{2c}$, $R^{2d}$, $R^{2e}$, $R^{2f}$, $R^{2g}$, $R^{2h}$, $R^{2i}$, and $R^{2j}$ is not hydrogen;

$R^3$ is $NR^{3a}R^{3b}$;

$R^{3a}$ and $R^{3b}$ are each independently hydrogen, alkyl, hydroxyalkyl, haloalkyl, alkoxyalkyl, —$CH_2$C(C═O)OH, —$CH_2$C(═O)Oalkyl, heterocyclyl, heteroaryl, heterocyclylalkyl, heteroarylalkyl, or cycloalkyl; or $R^{3a}$ and $R^{3b}$, together with the nitrogen to which they are attached, form an optionally substituted 4-7 membered heteroaryl or an optionally substituted 4-7 membered heterocyclyl;

$R^4$ is a substituted or unsubstituted aryl, a substituted or unsubstituted heteroaryl, a substituted or unsubstituted cycloalkyl, or a substituted or unsubstituted heterocyclyl when n is 2, 3, 4, 5, or 6; or $R^4$ is a substituted or unsubstituted monocyclic heteroaryl, or a substituted or unsubstituted heterocyclyl when n is 0 or 1;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3, provided that:

a) when one of $R^2$, $R^{2b}$, $R^{2c}$, $R^{2d}$, $R^{2e}$, $R^{2f}$, $R^{2g}$, $R^{2h}$, $R^{2i}$, and $R^{2j}$ is OH, $R^1$ does not have the following structure:

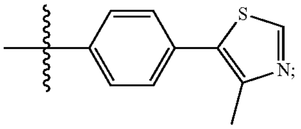 [SMILES: *c1ccc(-c2scnc2C)cc1]

b) when one of $R^{2a}$, $R^{2b}$, $R^{2c}$, $R^{2d}$, $R^{2e}$, $R^{2f}$, $R^{2g}$, and $R^{2h}$ is —OH, n is an integer from 2-6; and c) when one of $R^{2a}$, $R^{2b}$, $R^{2c}$, $R^{2d}$, $R^{2e}$, $R^{2f}$, $R^{2g}$, $R^{2h}$, $R^{2i}$, and $R^{2j}$ is an unsubstituted phenyl, neither $R^{3a}$ nor $R^{3b}$ has the following structure:

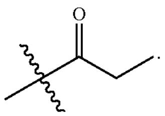 [SMILES: *C(=O)CC]

In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are alkyl. In some more embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are alkenyl. In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are arylalkyl. In certain embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are arylalkoxy. In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are cycloalkylalkoxy. In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are halo (e.g., fluoro). In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are hydroxyl. In some embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ are alkoxy. In certain specific embodiments, none of $R^{2a}$, $R^{2b}$, $R^{2c}$, $R^{2d}$, $R^{2e}$, $R^{2f}$, $R^{2g}$, $R^{2h}$, $R^{2i}$, or $R^{2j}$ have the following structure:

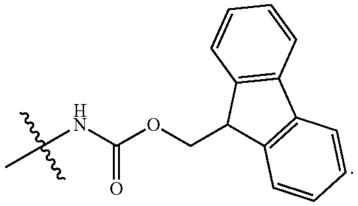 [SMILES: *NC(=O)OCC1c2ccccc2-c2ccccc21]

In still other embodiments, neither $R^{3a}$ nor $R^{3a}$ are carboxyalkyl. In some more embodiments, neither $R^{3a}$ nor $R^{3a}$ are arylalkylcarbonyl. In certain embodiments, neither $R^{3a}$ nor $R^{3a}$ are alkoxycarbonyl (e.g., Boc). In some embodiments, neither $R^{3a}$ nor $R^{3a}$ are heteroarylsulfo or alkylsulfo (e.g., —$S(O)_2CH_3$). In some embodiments, neither $R^{3a}$ nor $R^{3a}$ are arylalkoxycarbonyl (e.g., Fmoc).

In some embodiments, $R^1$ is a substituted or unsubstituted aryl. In certain embodiments, $R^1$ is a substituted or unsubstituted $C_6$-$C_{10}$ aryl. In some embodiments, $R^1$ is a substituted or unsubstituted phenyl. In certain embodiments, $R^1$ is a substituted phenyl. In some more specific embodiments, $R^1$ is phenyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some more specific embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{11}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain more specific embodiments, $R^1$ is phenyl substituted with at least one substituent selected from the group consisting of $OR^9$, $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In some embodiments, $R^1$ is substituted with at least one substituent selected from the group consisting of $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In some embodiments, $R^1$ is substituted with at least one $C(=NR^9)NR^{10}R^{11}$. In more specific embodiments, $R^1$ is substituted with at least one —$C(=NH)NH_2$. In still more specific embodiments, $R^1$ has one of the following structures:

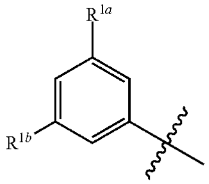
;
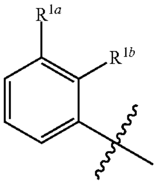
;
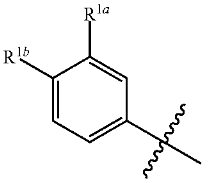
;
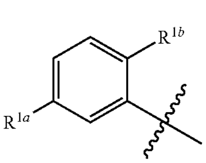
;
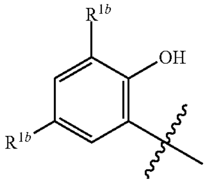
;
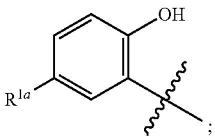
;
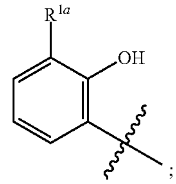
;
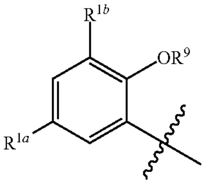
;
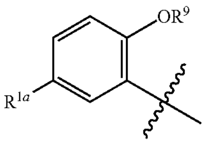
;
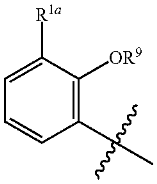
;
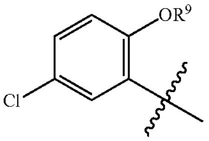
;
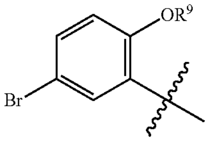
;
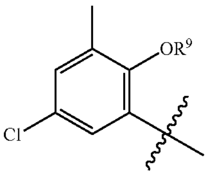
;
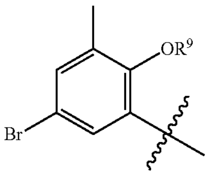
;
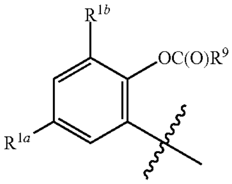
;
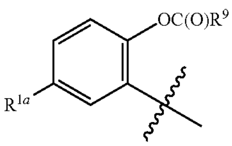
;
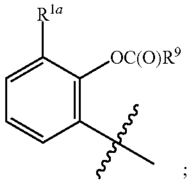
;
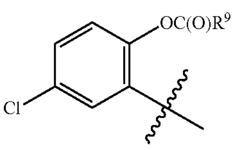
;

-continued
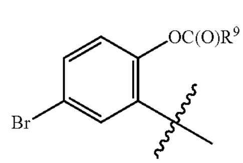
;
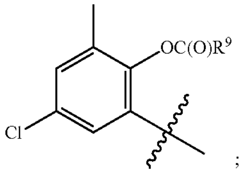
;
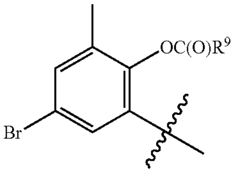
;
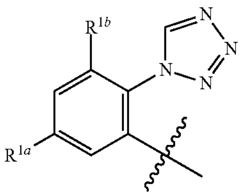
;
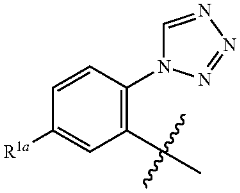
or
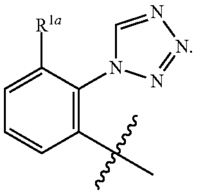
In some embodiments, $R^1$ has one of the following structures:
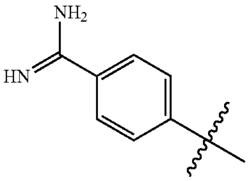
;
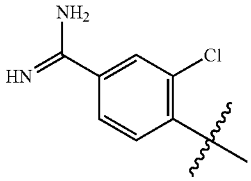
;
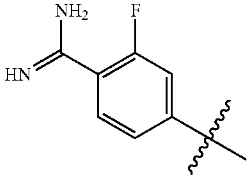
;
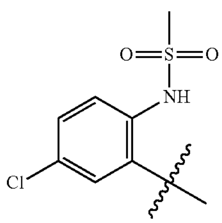
;
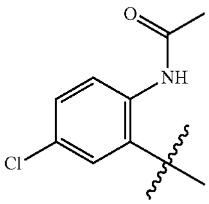
;
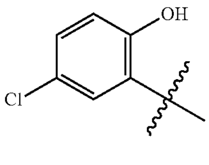
;
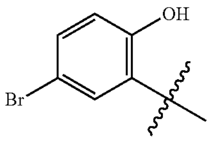
;
-continued
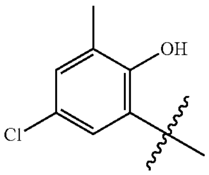
;
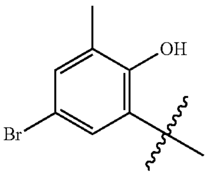
;
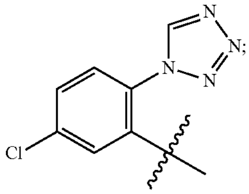
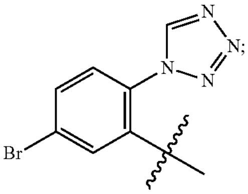
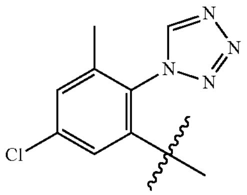
or
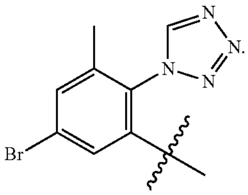
In certain specific embodiments, $R^1$ has one of the following structures:
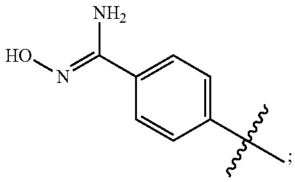
;
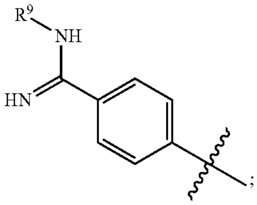
;
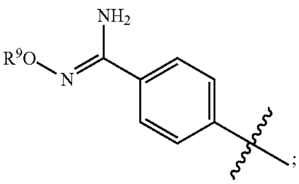
;
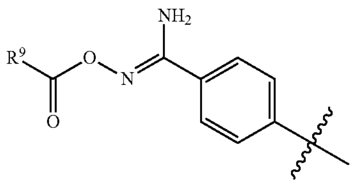
or -continued

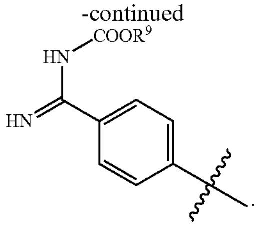

In some of the foregoing embodiments, $R^9$ is $C_{1-6}$ alkyl or $C_{1-6}$ haloalkyl. In more specific embodiments, $R^9$ is methyl. In certain embodiments, $R^9$ is trifluoromethyl. In some embodiments, $R^1$ is an unsubstituted phenyl.

In some embodiments, $R^1$ is a substituted or unsubstituted heteroaryl. In certain embodiments, $R^1$ is a substituted or unsubstituted 5-10 membered heteroaryl. In some embodiments, $R^1$ is a substituted or unsubstituted pyridinyl, pyrrolopyridinyl, or benzoimidazolyl. In some more specific embodiments, $R^1$ is a substituted or unsubstituted pyridin-3-yl, 1H-pyrrolo[2,3-b]pyridine-5-yl, 1H-pyrrolo[3,2-c]pyridine-2-yl, or 1H-benzo[d]imidazol-6-yl.

In some embodiments, $R^1$ is pyridin-3-yl, 1H-pyrrolo[2,3-b]pyridine-5-yl, or 1H-benzo[d]imidazol-6-yl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NOR^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In more specific embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some specific embodiments, $R^1$ has one of the following structures:

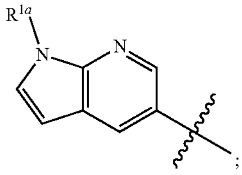 ; 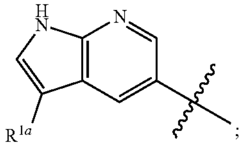 ;

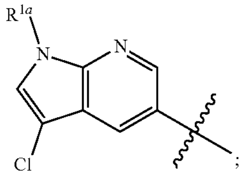 ; 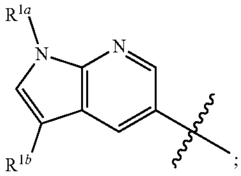 ;

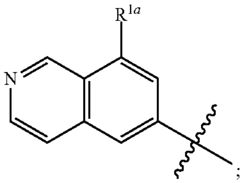 ; 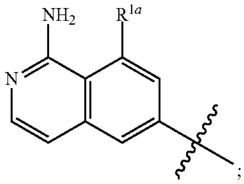 ;

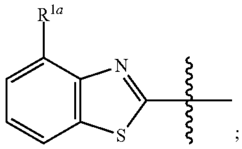 ; 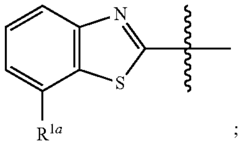 ;

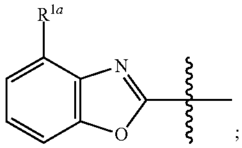 ; 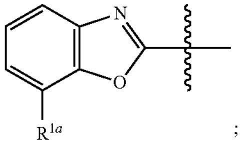 ;

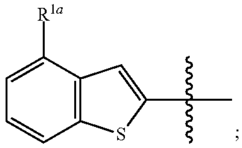 ; 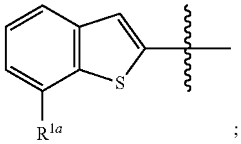 ;

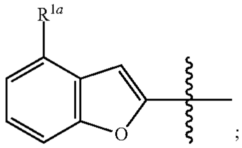 ; 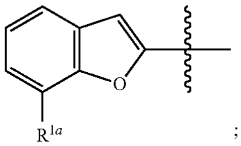 ;

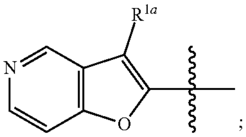 ; 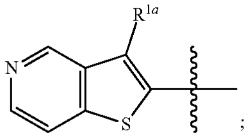 ;

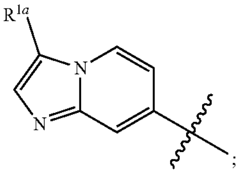 ; 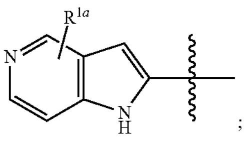 ;

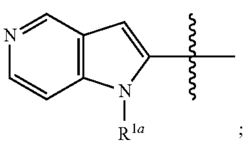 ; 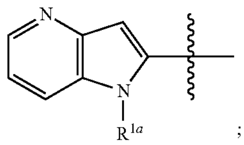 ;

-continued
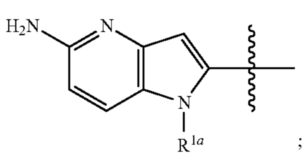;
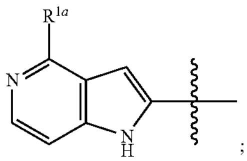;
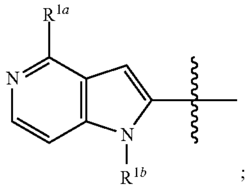;
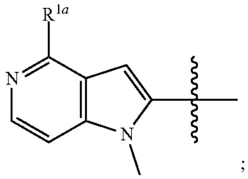;
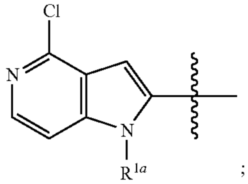;
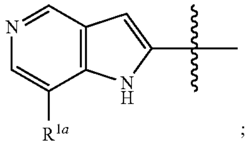;
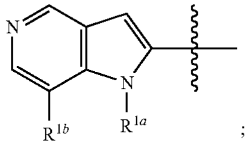;
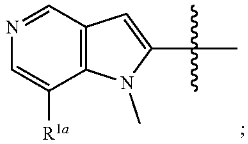;
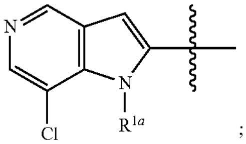;
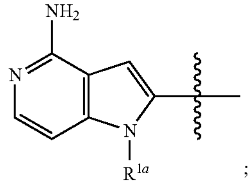;
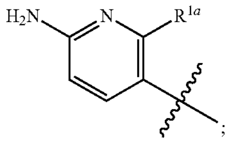;
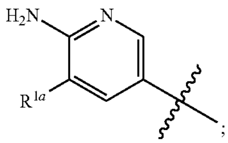;
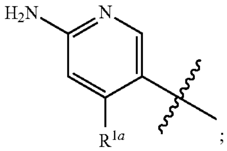;
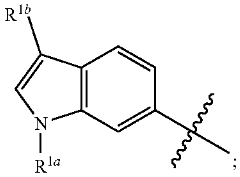;
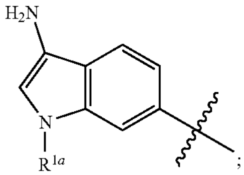;
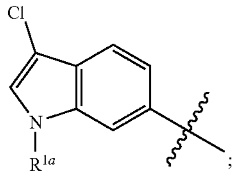;
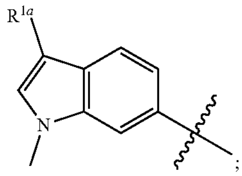;
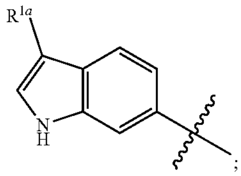;
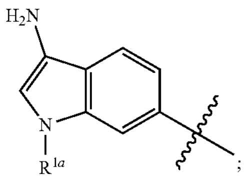;
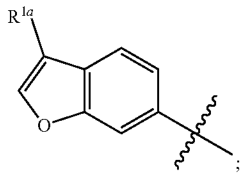;
-continued
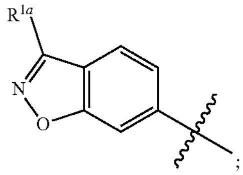;
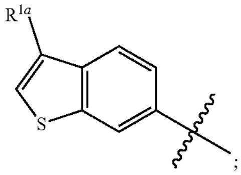;
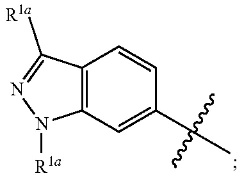;
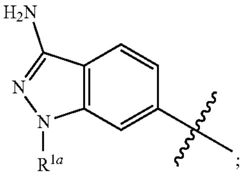;
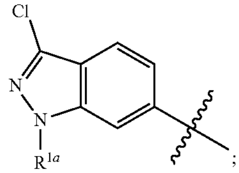;
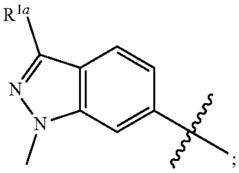;
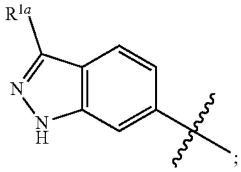;
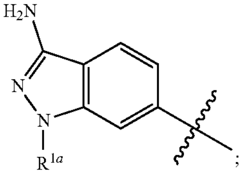;
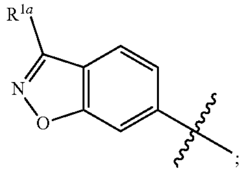;
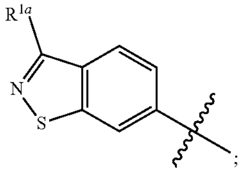;
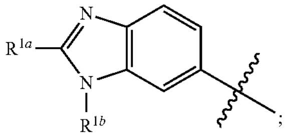;
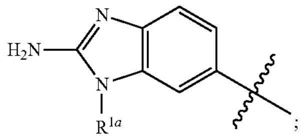;
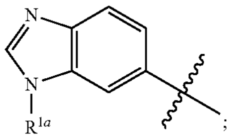;
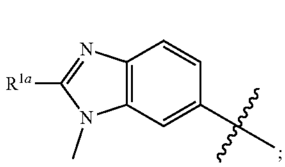;
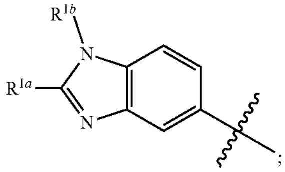;
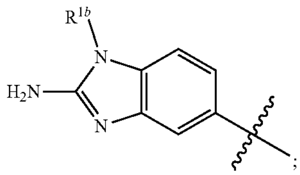;
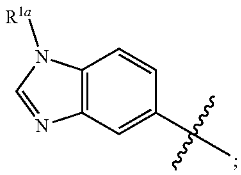;
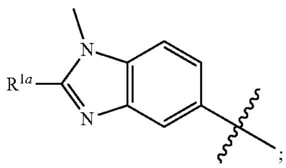;
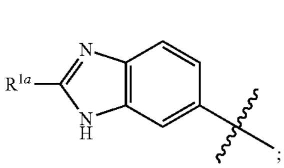;

-continued

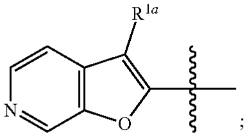 ; 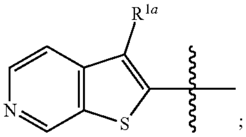 ;

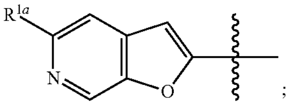 ;

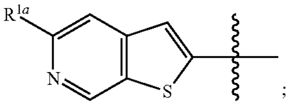 ;

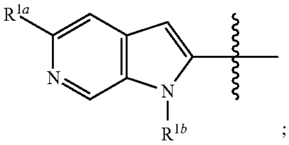 ;

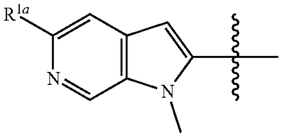 ;

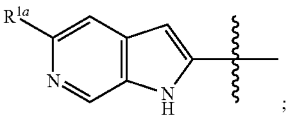 ;

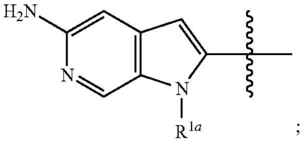 ; 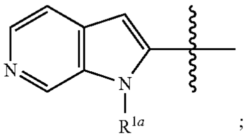 ;

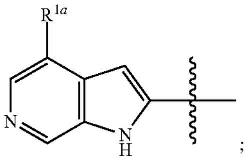 ; 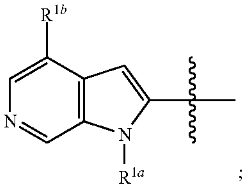 ;

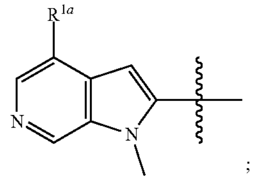 ; 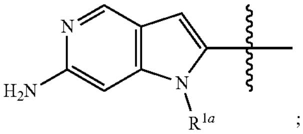 ;

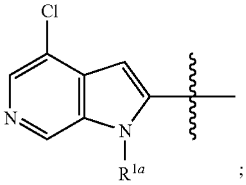 ; 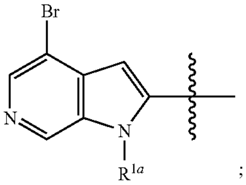 ;

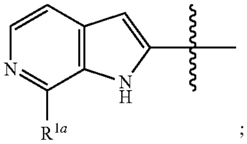 ; 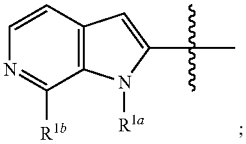 ;

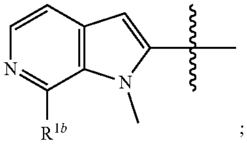 ; 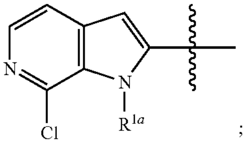 ;

-continued

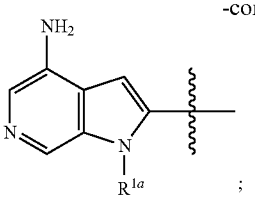 ; 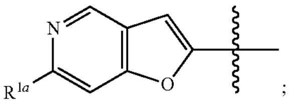 ;

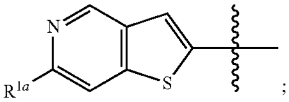 ;

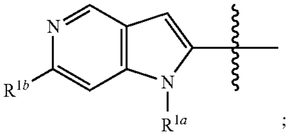 ;

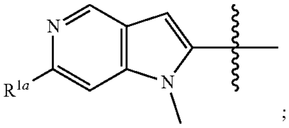 ;

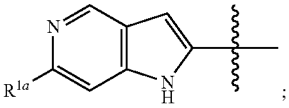 ;

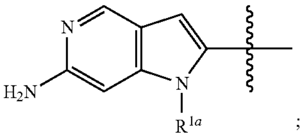 ; 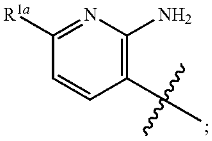 ;

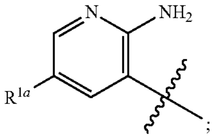 ; 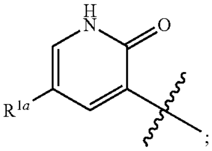 ;

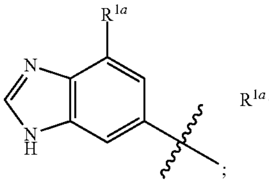 ; 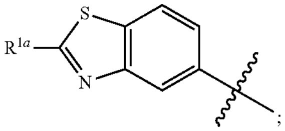 ;

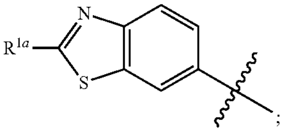 ; 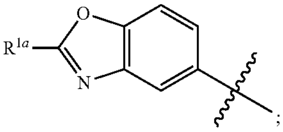 ;

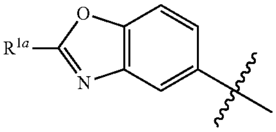 or

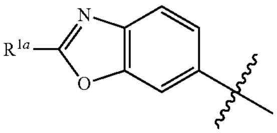 .

In some specific embodiments, $R^{1a}$ or $R^{1b}$ is independently $C_{1-6}$ alkyl, amino, $C(O)R^9$, $C(O)NR^9R^{10}$, $N(R^9)C(O)NR^{10}R^{11}$, $N(R^9)C(O)OR^{10}$, or $OC(O)NR^9R^{10}$, or halo. In more specific embodiments, $R^{1a}$ or $R^{1b}$ is methyl or ethyl. In other specific embodiments, $R^{1a}$ or $R^{1b}$ is F, Cl, or Br.

In some embodiments, each $R^{1a}$ or $R^{1b}$ attached to nitrogen is $C_{1-6}$ alkyl, $C(O)R^9$, $C(O)NR^9R^{10}$, $N(R^9)C(O)$ $NR^{10}R^{11}$, $N(R^9)C(O)OR^{10}$, or $OC(O)NR^9R^{10}$. In certain embodiments, $R^{1a}$ or $R^{1b}$ is methyl or ethyl.
In some embodiments, $R^1$ has one of the following structures:
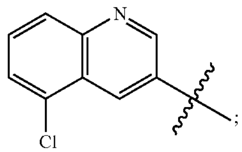
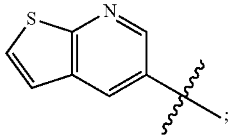
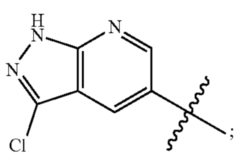
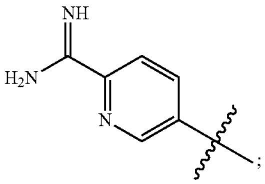
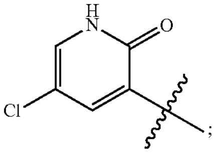
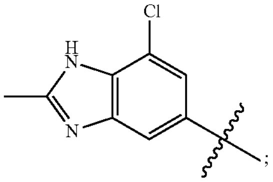
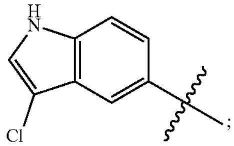
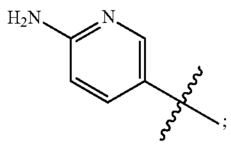
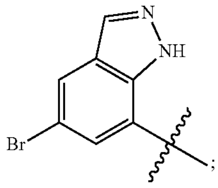
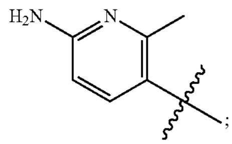
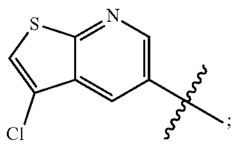
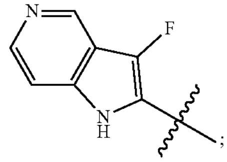
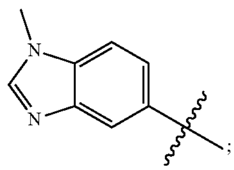
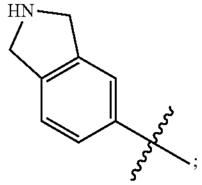
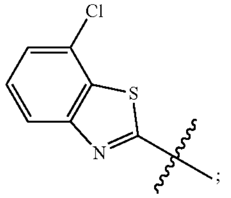
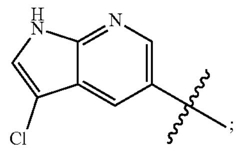
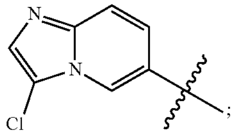
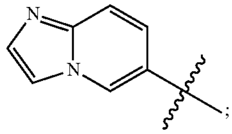
-continued
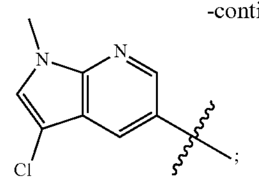
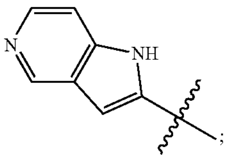
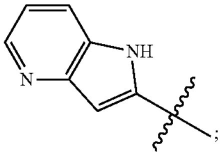
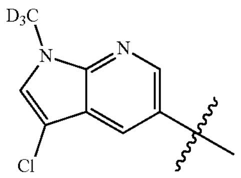
or
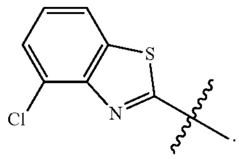
In some specific embodiments, $R^1$ has one of the following structures:
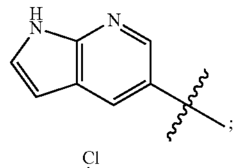
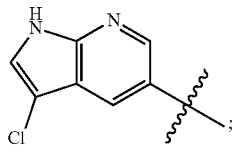
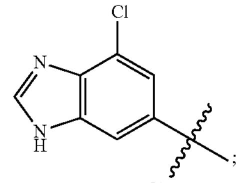
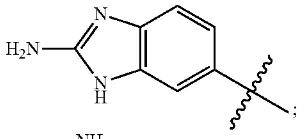
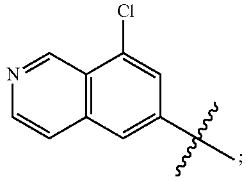
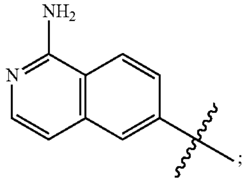
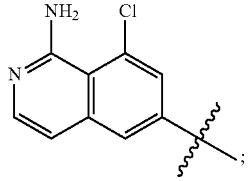
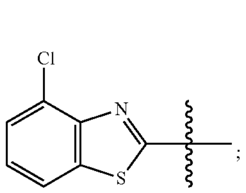
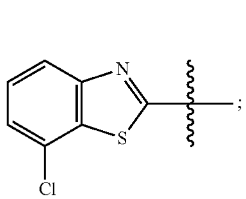
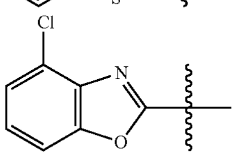
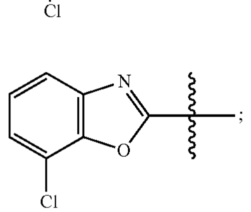
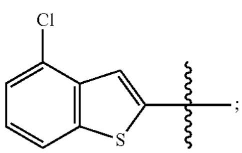

-continued
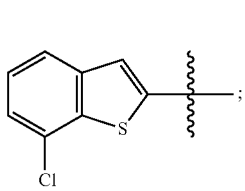;
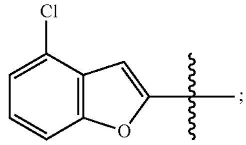;
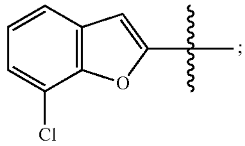;
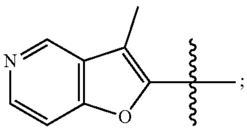;
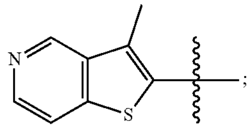;
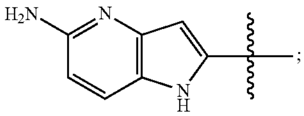;
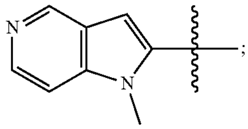;
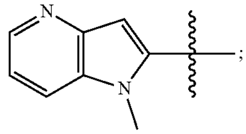;
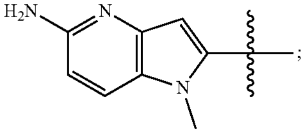;
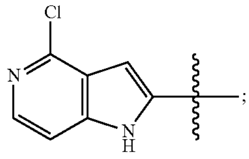;
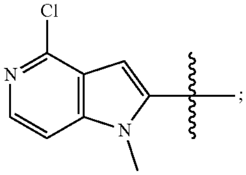;
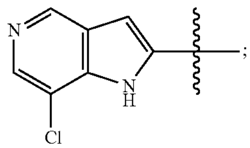;
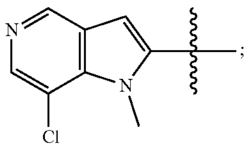;
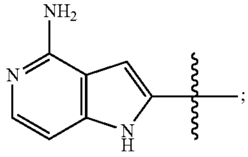;
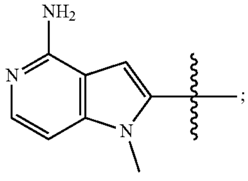;
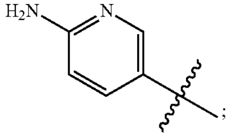;
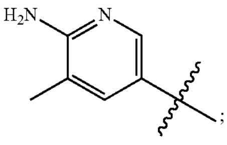;
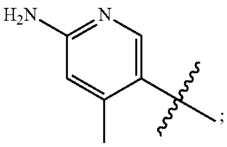;
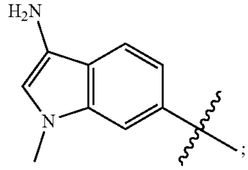;
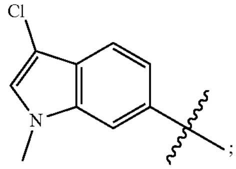;
-continued
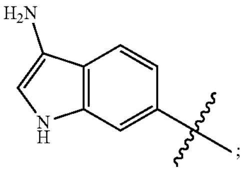;
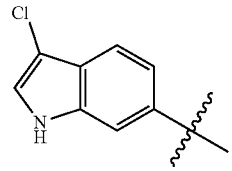;
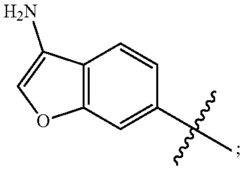;
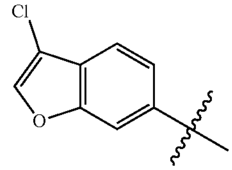;
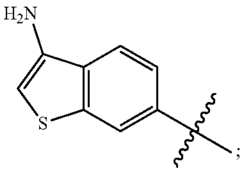;
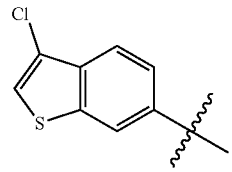;
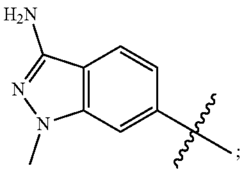;
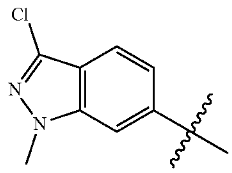;
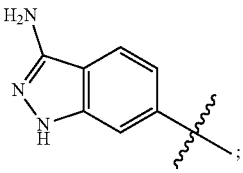;
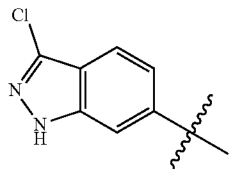;
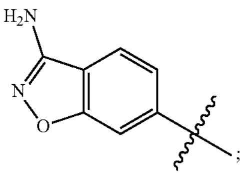;
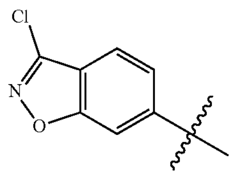;
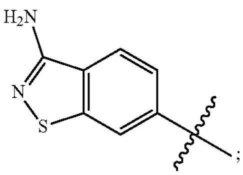;
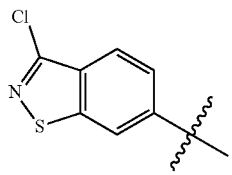;
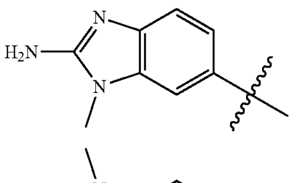;
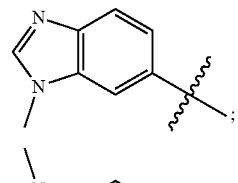;
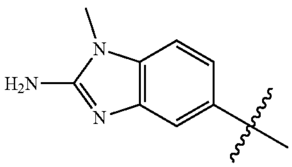;
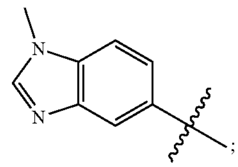;
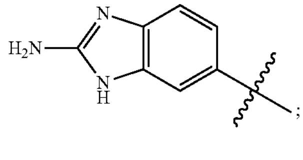;
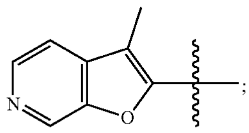;

-continued
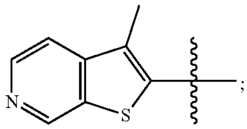 ; 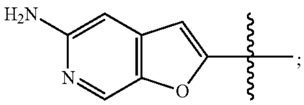 ;
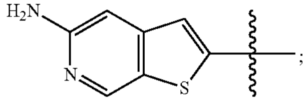 ;
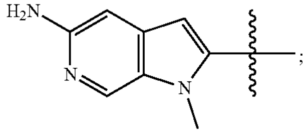 ;
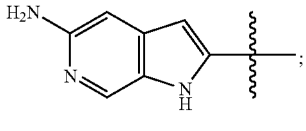 ; 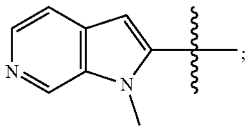 ;
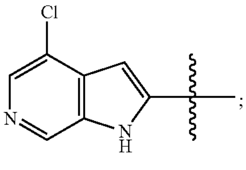 ; 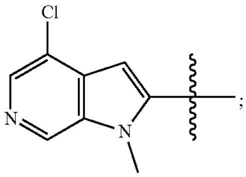 ;
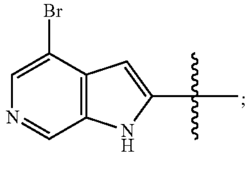 ; 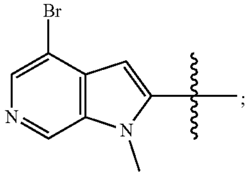 ;
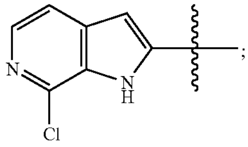 ; 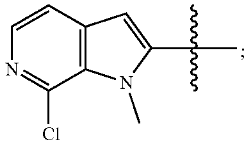 ;
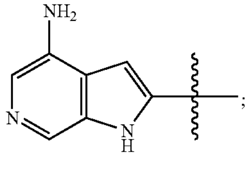 ; 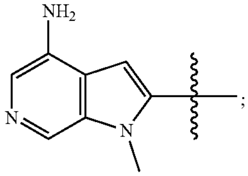 ;
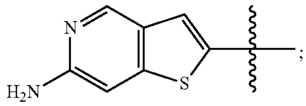 ;
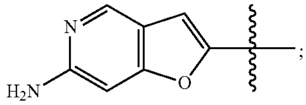 ;
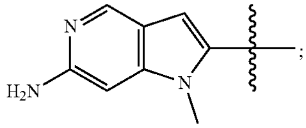 ;
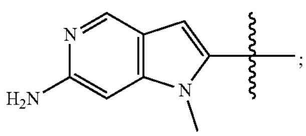 ; 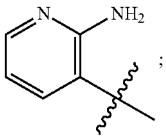 ;
-continued
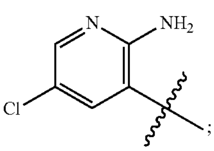 ; 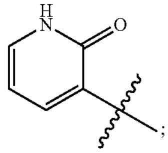 ;
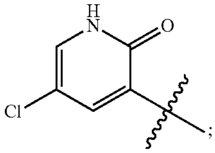 ; 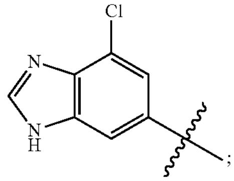 ;
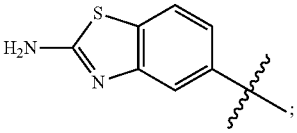 ;
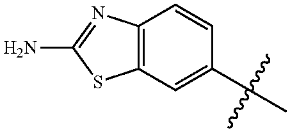 or
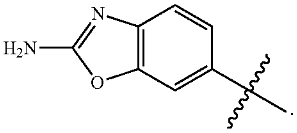 .
In some embodiments, $R^1$ has one of the following structures:
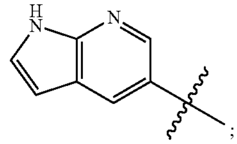 ; 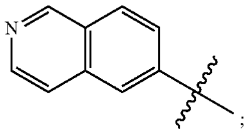 ;
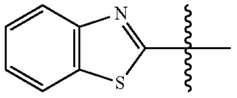 ; 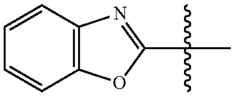 ;
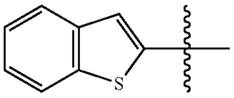 ; 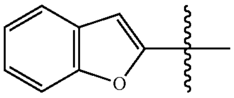 ;
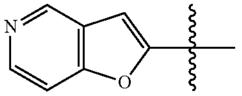 ; 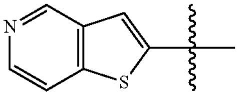 ;
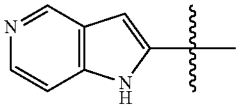 ; 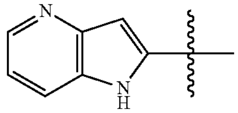 ;
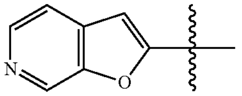 ; 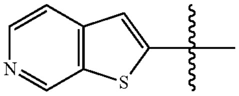 ;
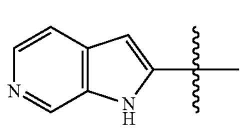 ; 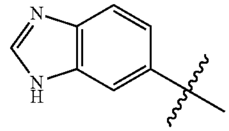 ;

-continued

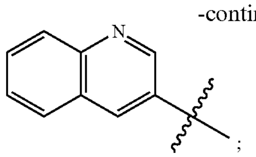
;
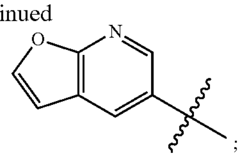
;
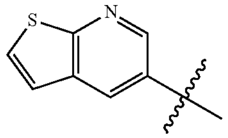
;
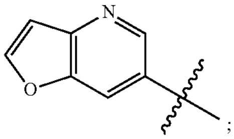
;
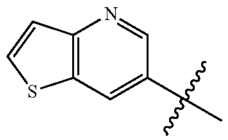
;
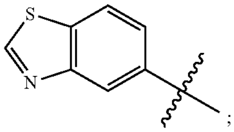
;
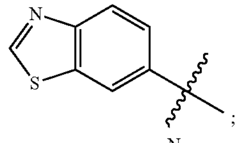
;
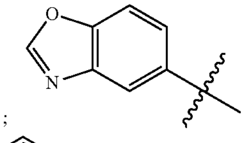
; or
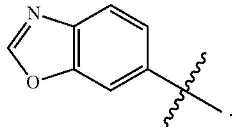
.

In some embodiments, $R^1$ is a substituted or unsubstituted cycloalkyl. In certain specific embodiments, $R^1$ is a substituted or unsubstituted $C_{3-6}$ cycloalkyl. In some embodiments, $R^1$ is a substituted $C_{3-6}$ cycloalkyl.

In some more specific embodiments, $R^1$ is a $C_{3-6}$ cycloalkyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^1$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some more specific embodiments, $R^{1a}$, $R^{1b}$, $R^{1c}$, $R^{1d}$, or $R^{1e}$ is optionally substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is an unsubstituted a $C_{3-6}$ cycloalkyl.

In some embodiments, $R^1$ is a substituted or unsubstituted heterocyclyl. In certain embodiments, $R^1$ is a substituted or unsubstituted 4-10 membered heterocyclyl. In some more specific embodiments, $R^1$ is a substituted 4-10 membered heterocyclyl.

In some embodiments, $R^1$ is a 4-10 membered heterocyclyl substituted with one or more of $R^{1a}$, $R^{1b}$, $R^1$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In more specific embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is an unsubstituted 4-10 membered heterocyclyl.

In certain embodiments, the compound has one of the following structures:

(IIA)

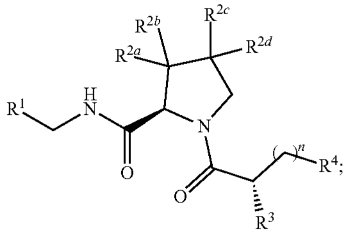
;

-continued (IIB)

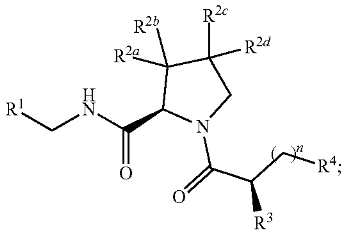

(IIC)

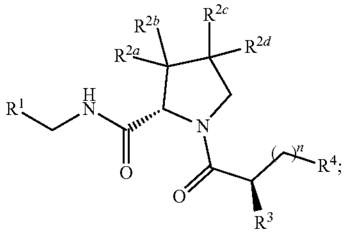

(IID)

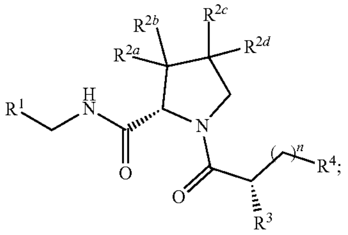

(IIE)

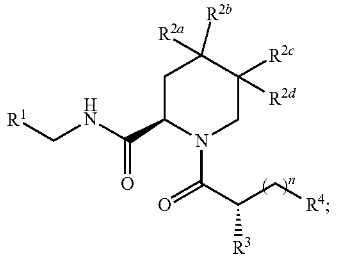

(IIF)

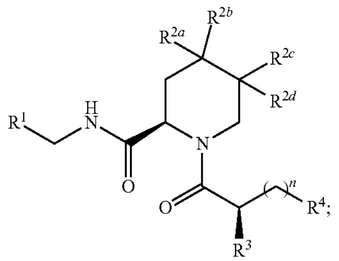

(IIG)

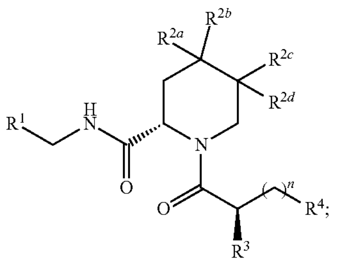

-continued (IIH)

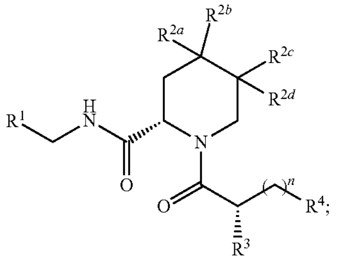

(IIJ)

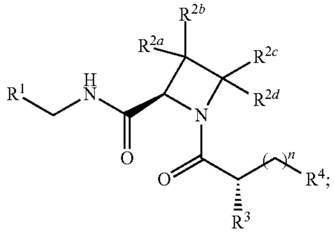

(IIK)

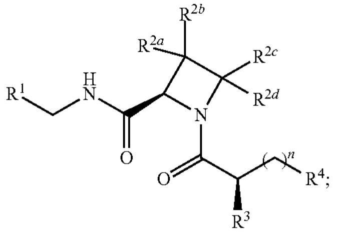

(IIL)

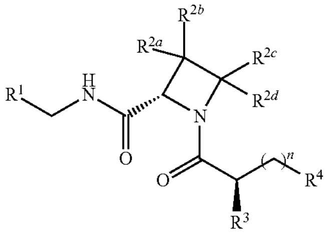

or (IIM)

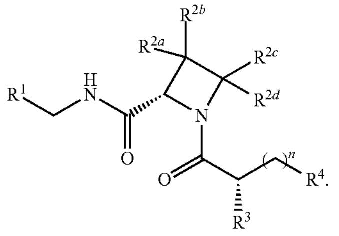

In some embodiments, at least one occurrence of $R^{2a}$, $R^{2b}$, $R^{2c}$, or $R^{2d}$ is alkoxy, alkoxyalkyl, cyano, C(═O)$OR^5$, OC(═O)$R^5$, C(═O)$NR^5R^6$, N($R^5$)C(═O)$R^6$, aryl, heteroaryl, heterocyclyl, or C(═O)N($R^5$)heterocyclyl, wherein $R^5$ and $R^6$ are, at each occurrence, independently hydrogen or $C_{1-6}$ alkyl. In certain embodiments, at least one occurrence of $R^{2a}$, $R^{2b}$, $R^{2c}$, or $R^{2d}$ is methoxy. In some embodiments, at least one occurrence of $R^{2a}$, $R^{2b}$, $R^{2c}$, or $R^{2d}$ is methoxymethyl. In certain embodiments, at least one occurrence of $R^{2a}$, $R^{2b}$, $R^{2e}$, or $R^{2d}$ is cyano. In some embodiments, at least one occurrence of $R^{2a}$, $R^{2b}$, $R^{2c}$, or $R^{2d}$ is —C(═O)OH. In certain embodiments, at least one occurrence of $R^{2a}$, $R^{2b}$, $R^2$, or $R^{2d}$ is —C(═O)$OCH_3$ or —OC(═O)$CH_3$. In some more specific embodiments, at least one occurrence of $R^{2a}$, $R^{2b}$, $R^{2c}$, or $R^{2d}$ is —C(═O)N(R')$_2$ or —NR'(C═O)alkyl wherein R' is, at each occurrence, independently a $C_{1-6}$ alkyl (e.g., methyl, ethyl, or isopropyl). In some of the foregoing embodiments, each occurrence of R' is methyl. In certain embodiments, at least one occurrence of $R^{2a}$, $R^{2b}$, $R^{2c}$, or $R^{2d}$ is —C(=O)NR"heterocyclyl wherein R" is hydrogen or $C_{1-6}$ alkyl (e.g., methyl, ethyl, or isopropyl).

In some embodiments, at least one occurrence of $R^{2a}$, $R^{2b}$, $R^{2c}$, or $R^{2d}$ is a substituted or unsubstituted phenyl. In certain embodiments, at least one occurrence of $R^{2a}$, $R^{2b}$, $R^{2c}$, or $R^{2d}$ is a substituted or unsubstituted heterocyclyl. In some embodiments, at least one occurrence of $R^{2a}$, $R^{2b}$, $R^{2c}$, or $R^{2d}$ is a substituted or unsubstituted heteroaryl.

In some embodiments, at least one occurrence of $R^{2a}$, $R^{2b}$, $R^{2c}$, or $R^{2d}$ has one of the following structures:

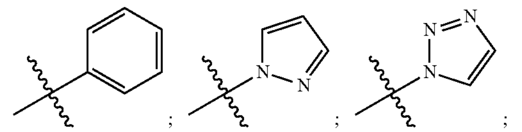
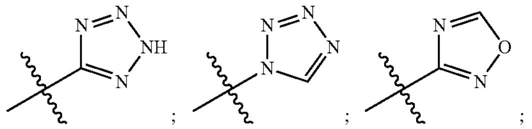
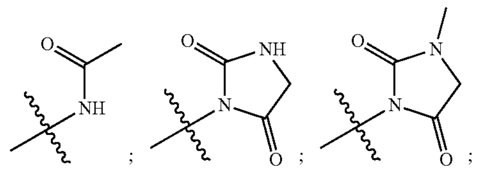
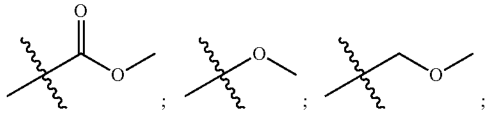
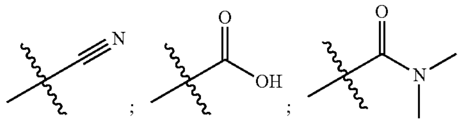
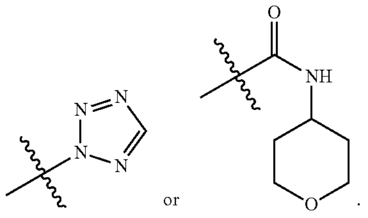

In some embodiments, at least one occurrence of $R^{2a}$, $R^{2b}$, $R^{2c}$, or $R^{2d}$ has one of the following structures:

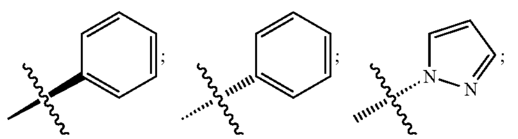
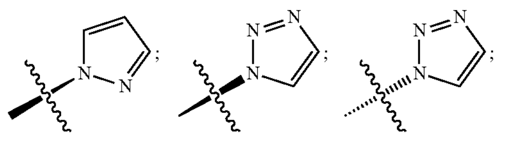

-continued

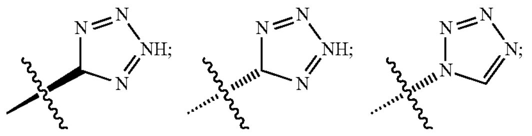
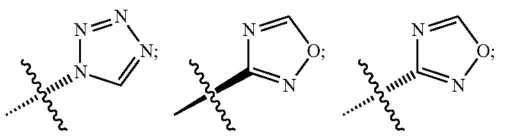
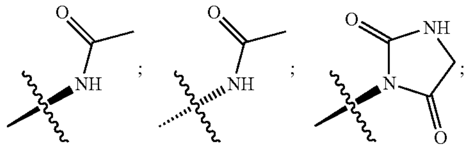
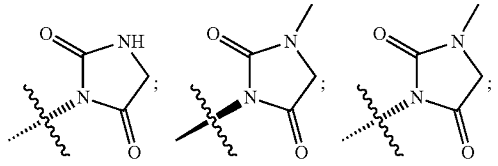
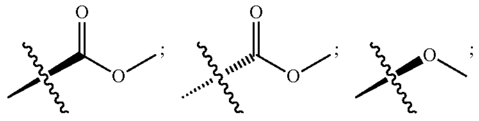
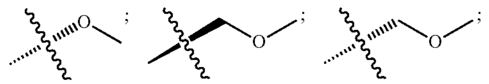
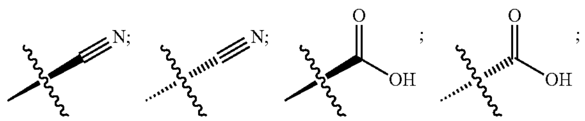
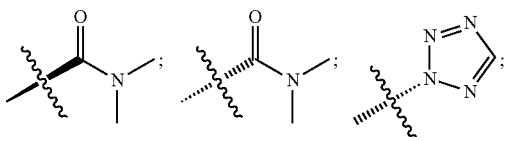
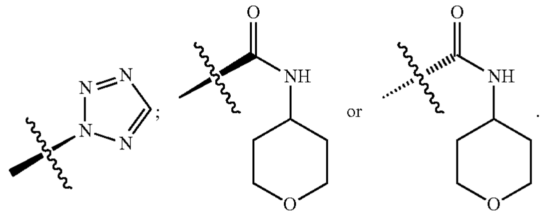

In some embodiments, $R^3$ has one of the following structures:

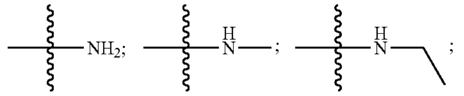
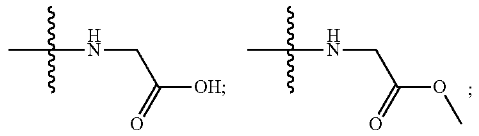

-continued
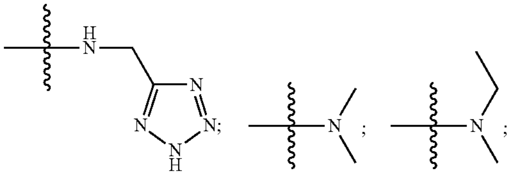
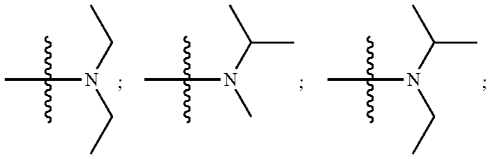
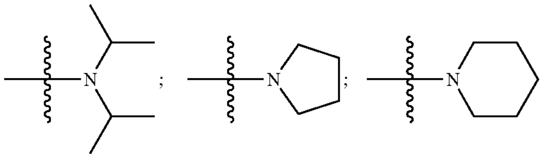
or
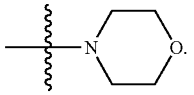
In some embodiments, $R^3$ is —$NH_2$. In certain embodiments, n is 0. In some other embodiments, n is 1. In certain other embodiments, n is 2. In still other embodiments, n is 3, 4, 5, or 6.
In some more specific embodiments, n is 2 and $R^4$ is a substituted or unsubstituted aryl. In certain more specific embodiments, $R^4$ has one of the following structures:
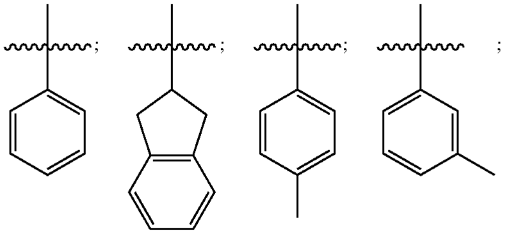
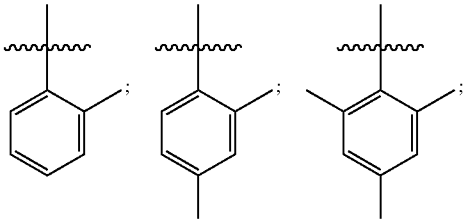
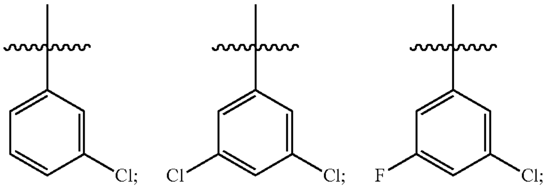
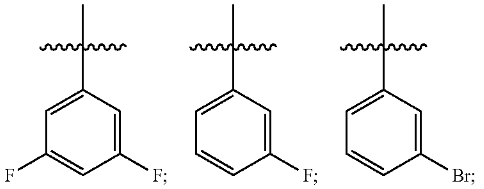
-continued
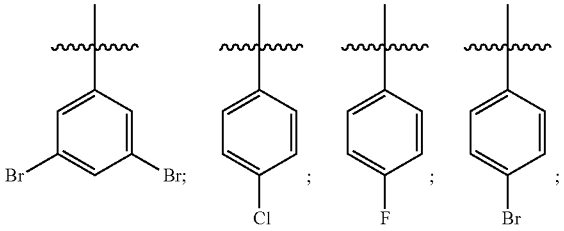
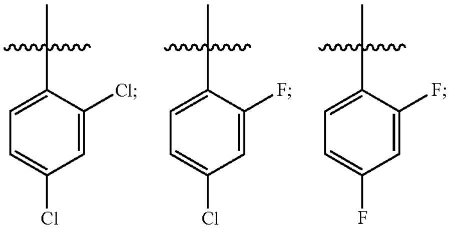
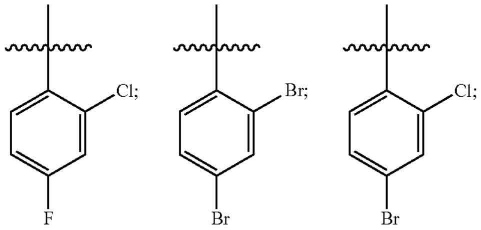
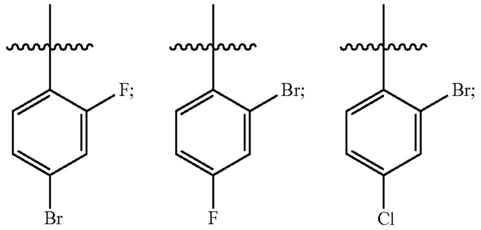
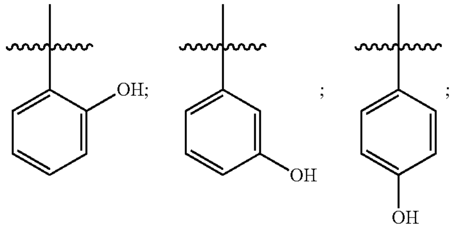
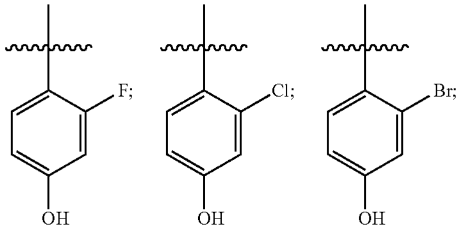
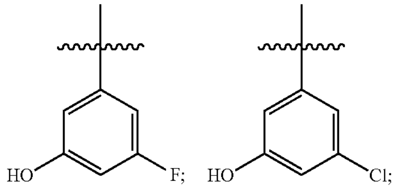

-continued
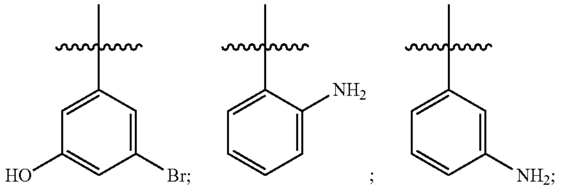
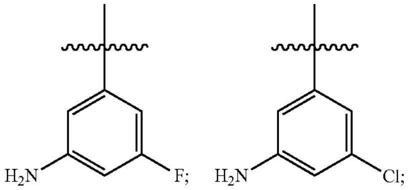
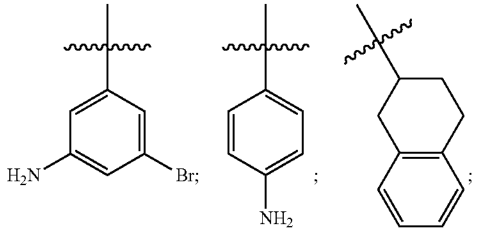
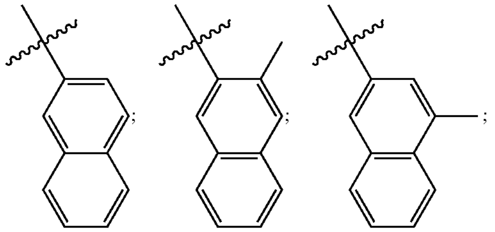
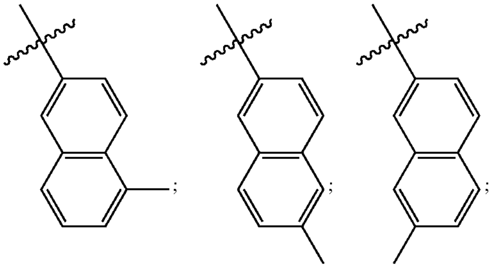
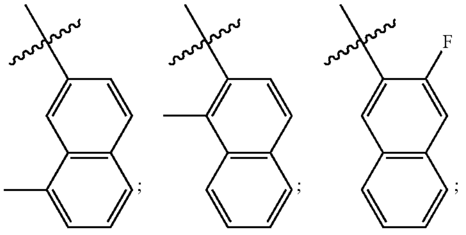
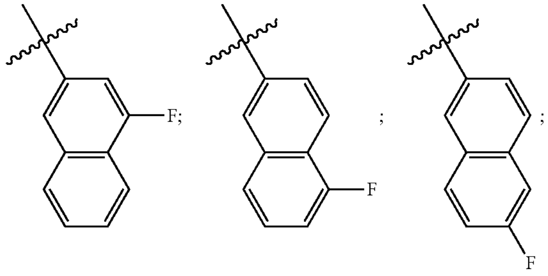
-continued
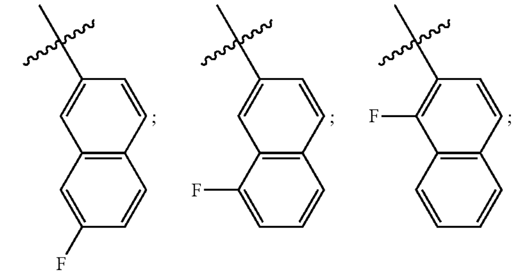
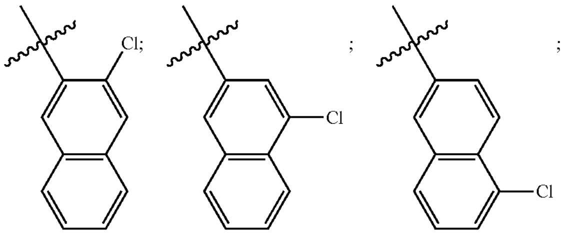
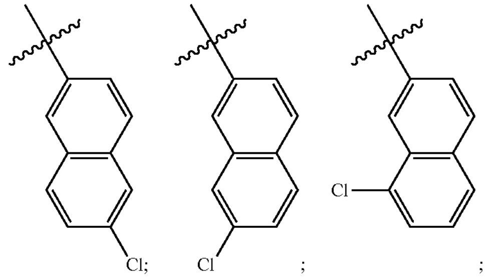
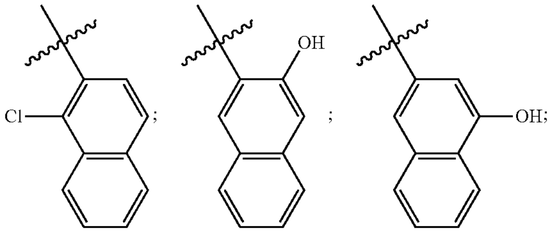
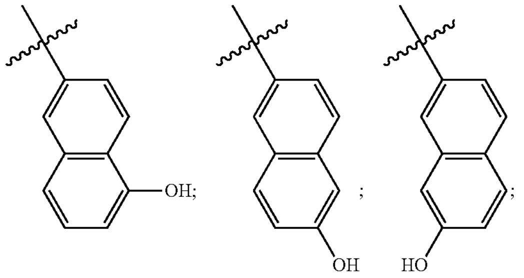
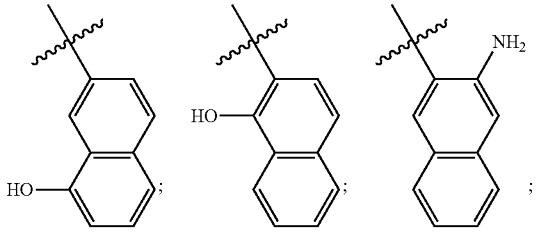

-continued
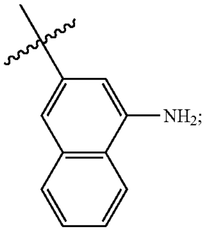
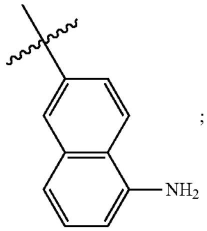
;
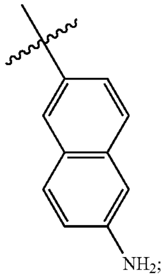
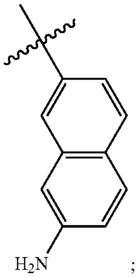
;
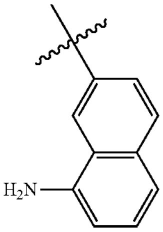
or
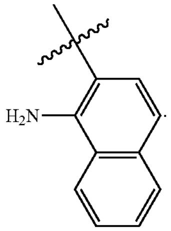
.
In certain embodiments, $R^4$ has one of the following structures:
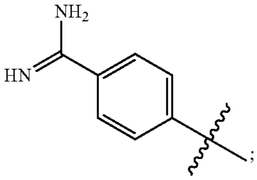
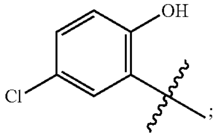
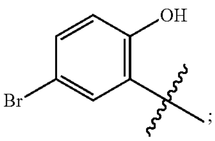
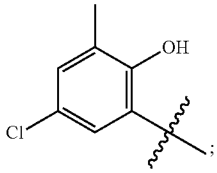
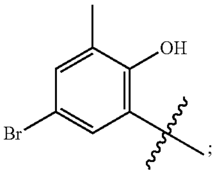
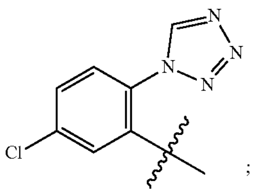
;
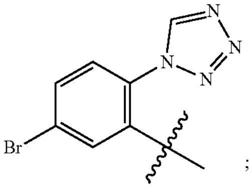
;
-continued
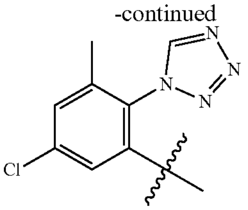
or
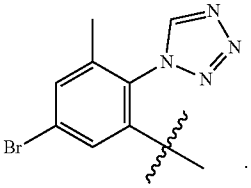
.
In some embodiments, n is 2 and $R^4$ is a substituted or unsubstituted heteroaryl. In some more specific embodiments, $R^4$ has one of the following structures:
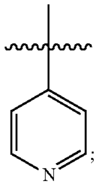
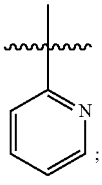
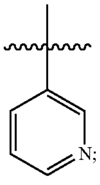
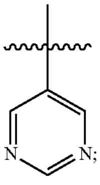
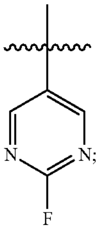
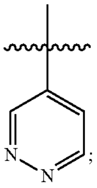
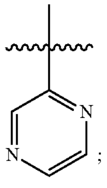
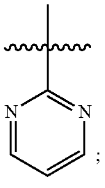
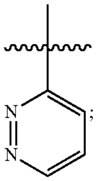
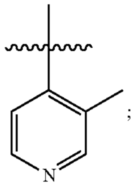
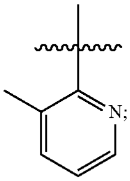
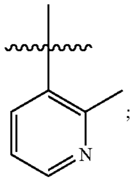
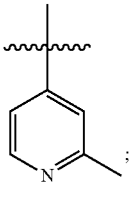
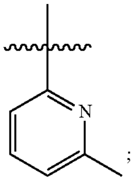
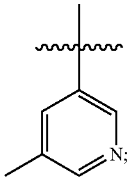
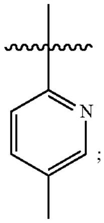
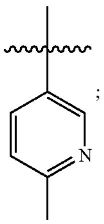
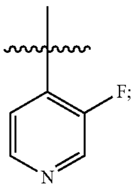
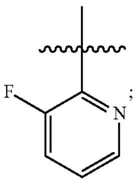
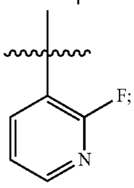

-continued
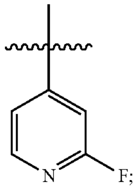
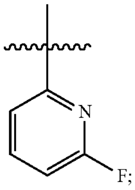
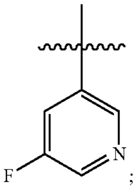
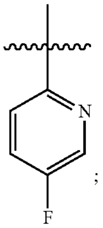
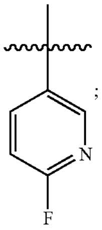
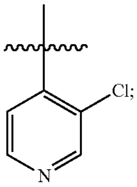
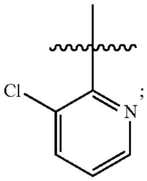
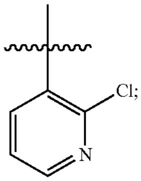
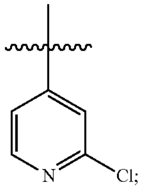
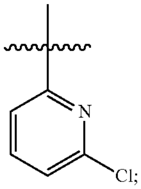
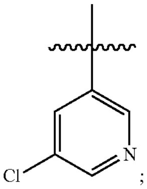
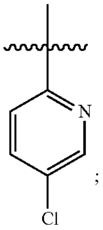
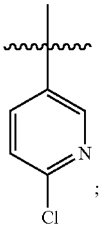
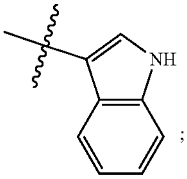
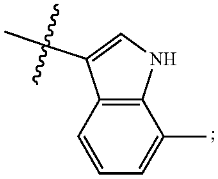
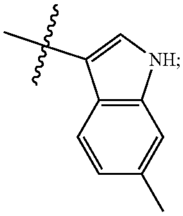
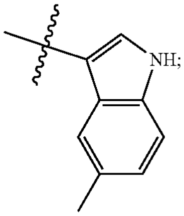
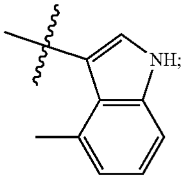
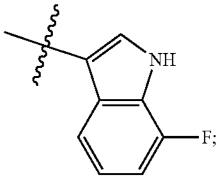
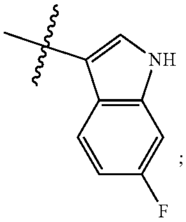
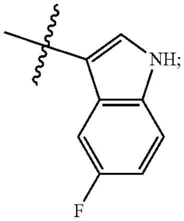
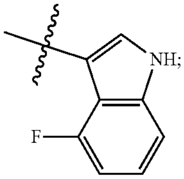
-continued
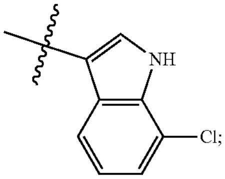
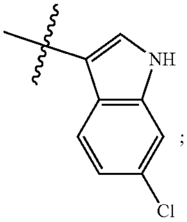
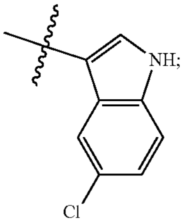
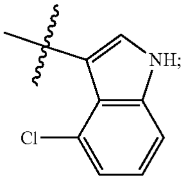
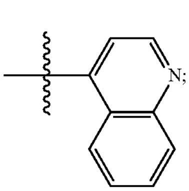
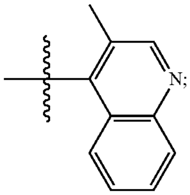
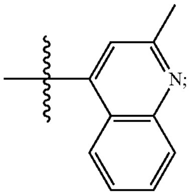
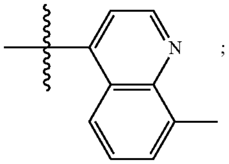
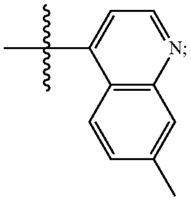
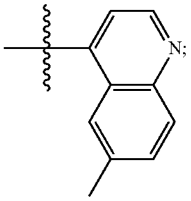
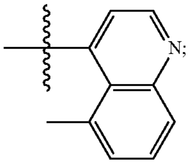
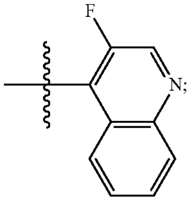
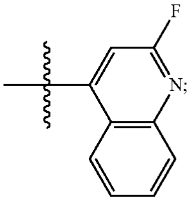
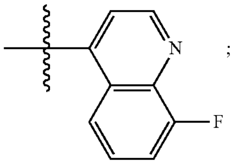
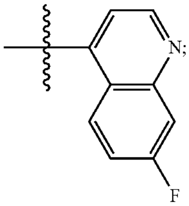
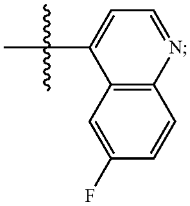

-continued
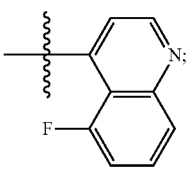 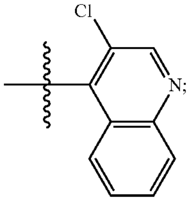
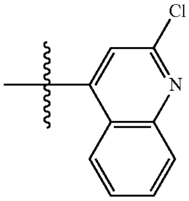 ; 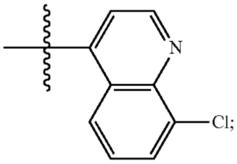
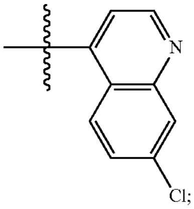 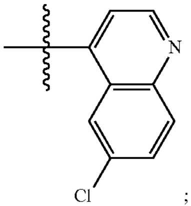 ;
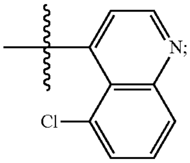 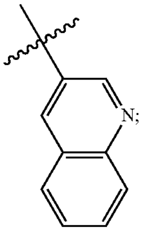 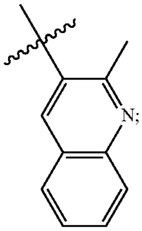
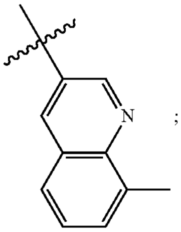 ; 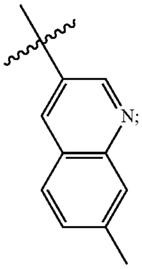 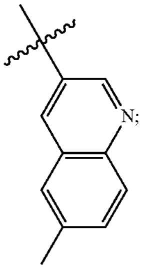
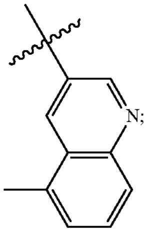 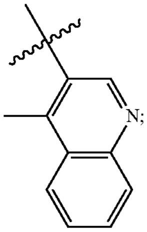 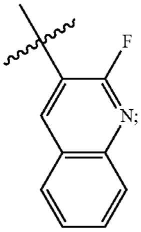
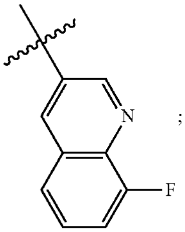 ; 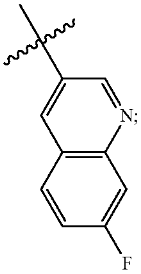 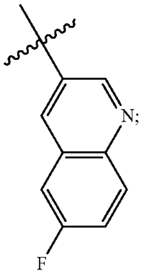
-continued
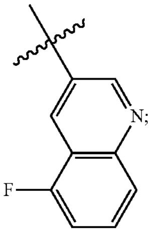 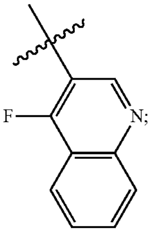 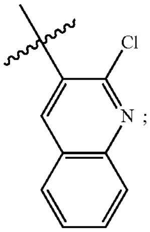
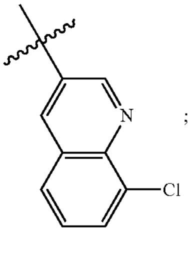 ; 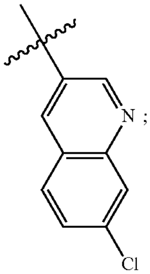 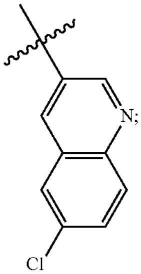
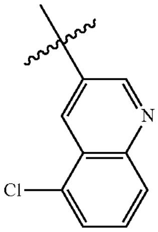 or 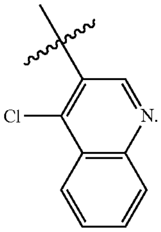
In some embodiments, $R^4$ has one of the following structures:
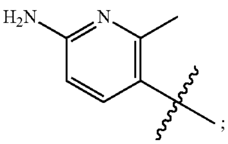 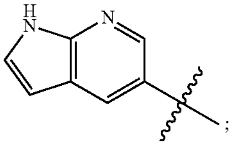
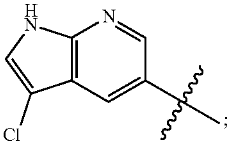 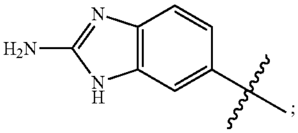
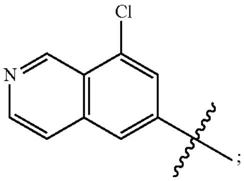 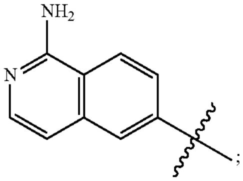
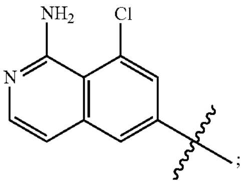 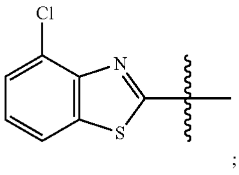 ;
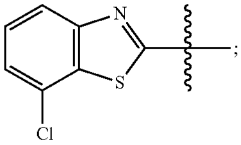 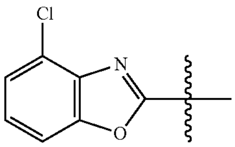

-continued
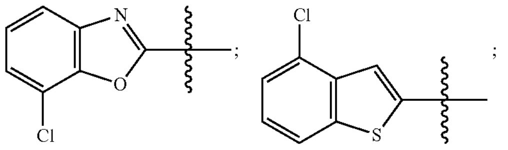
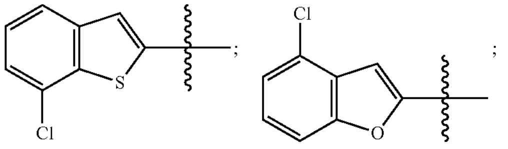
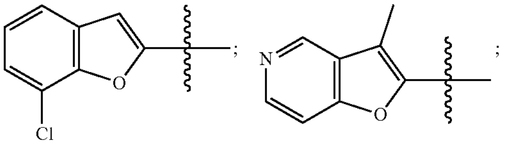
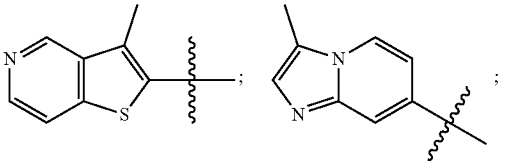
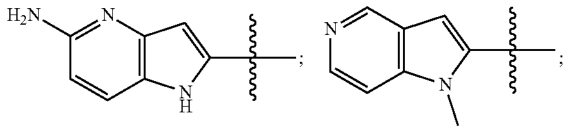
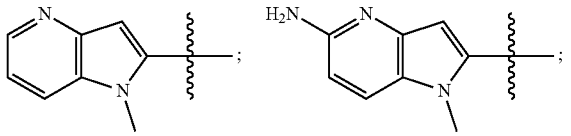
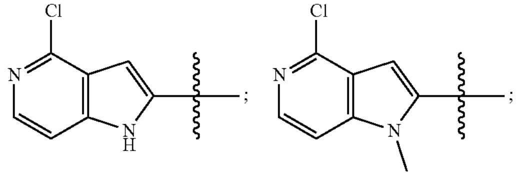
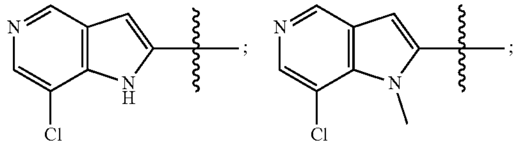
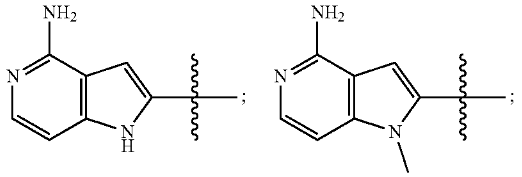
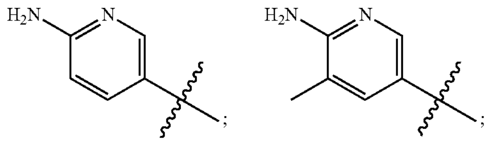
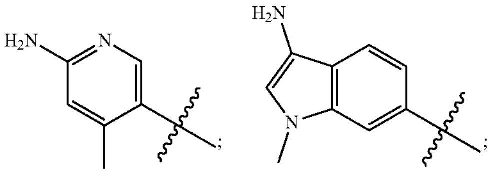
-continued
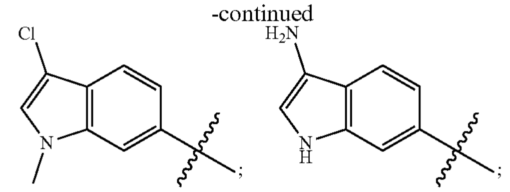
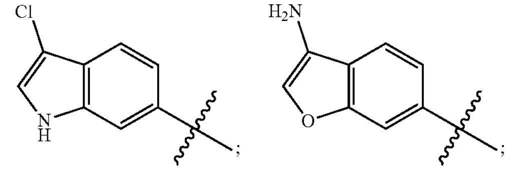
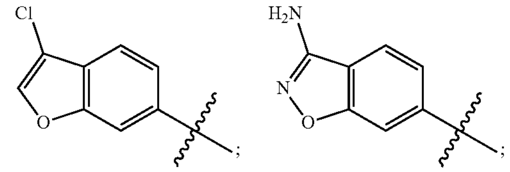
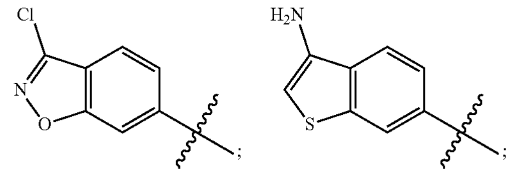
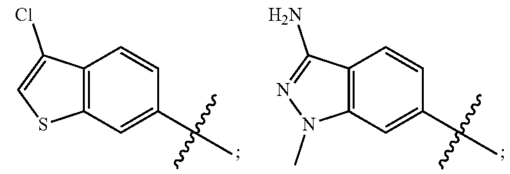
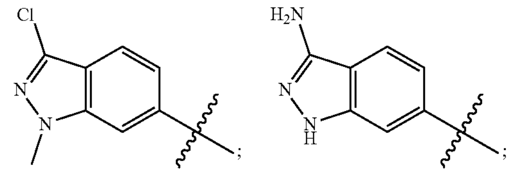
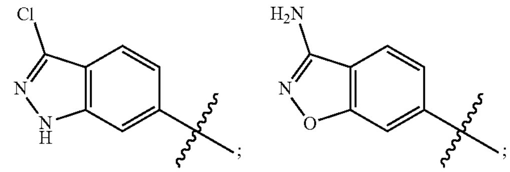
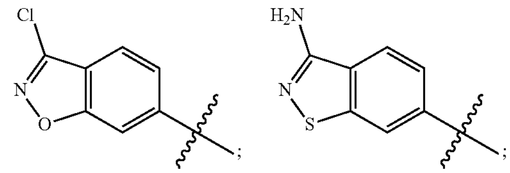
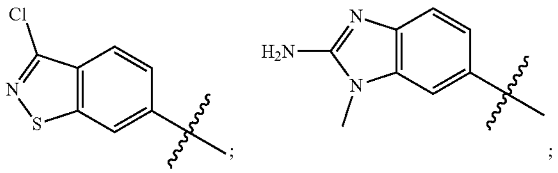
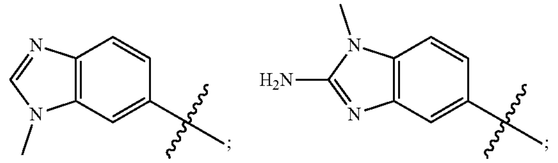

-continued
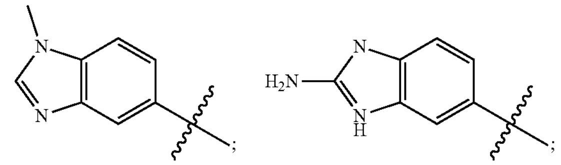
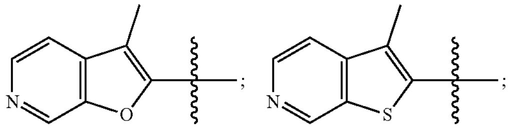
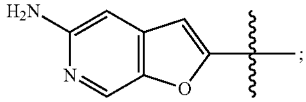
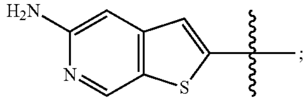
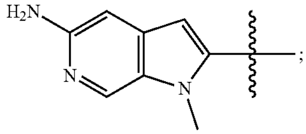
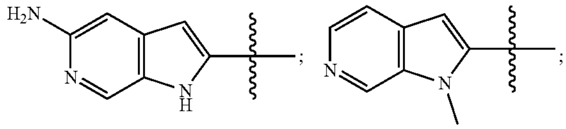
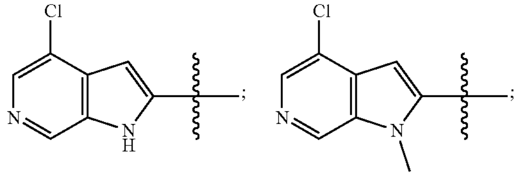
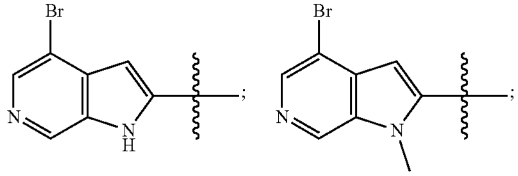
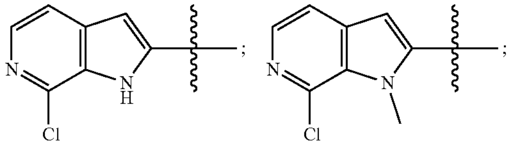
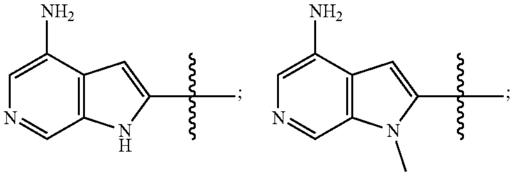
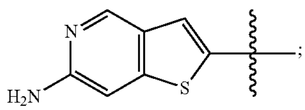
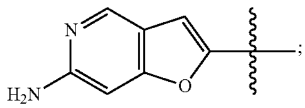
-continued
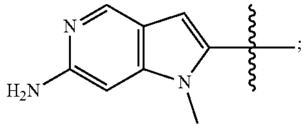
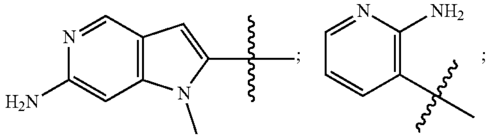
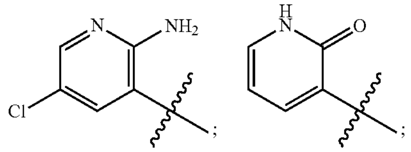
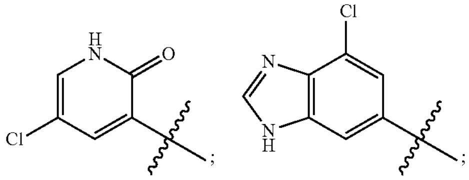
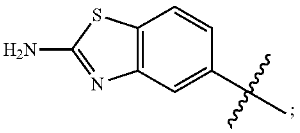
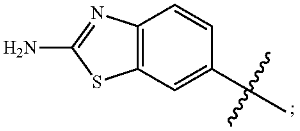
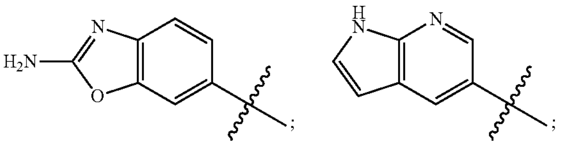
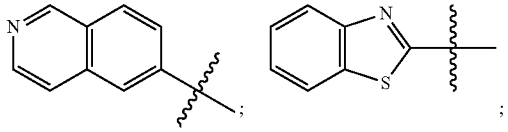
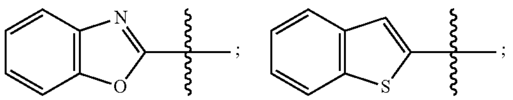
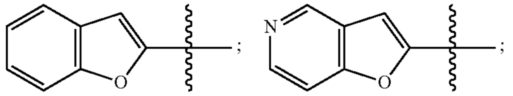
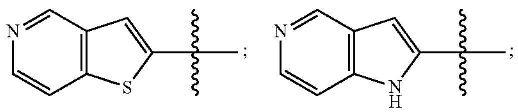
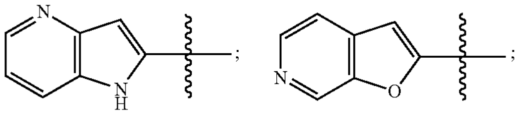
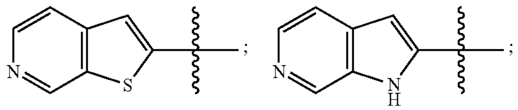

-continued
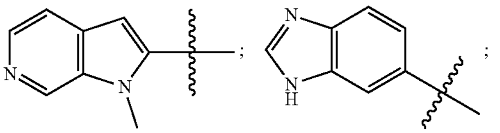
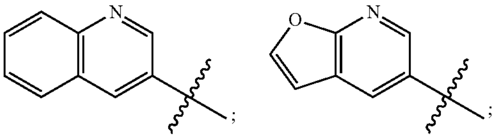
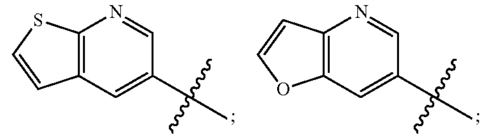
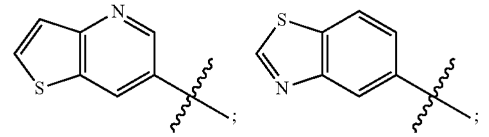
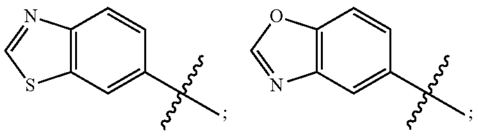
or
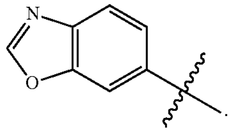
In certain specific embodiments, $R^4$ has one of the following structures:
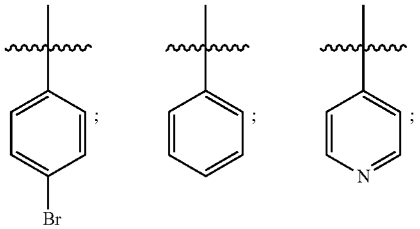
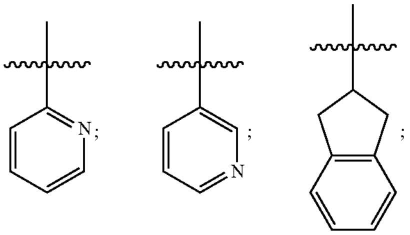
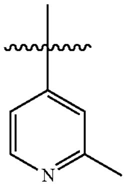
or
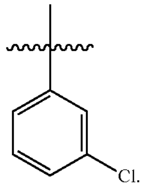
In some embodiments, n is 0 and $R^4$ has one of the following structures:
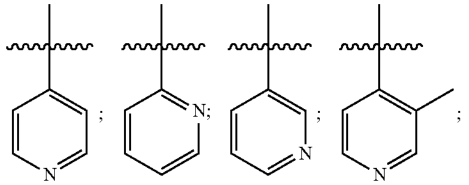
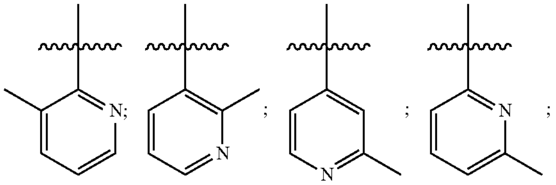
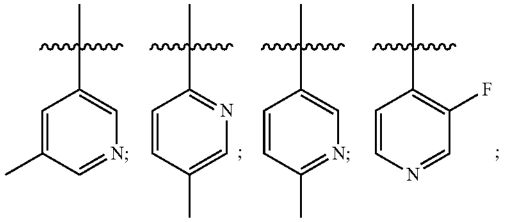
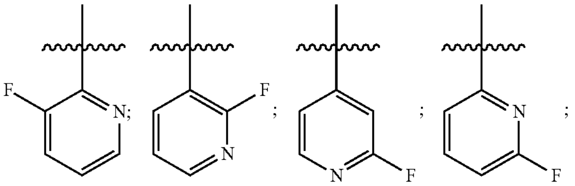
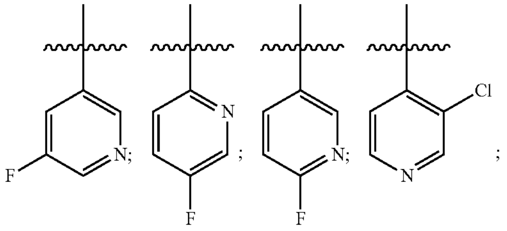
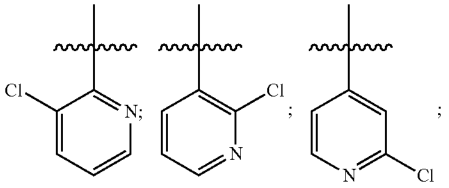
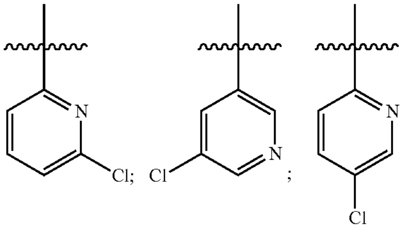
or
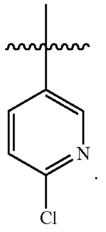

In some specific embodiments, $R^4$ has one of the following structures:

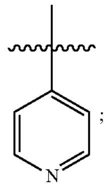
;
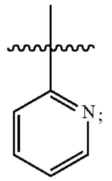

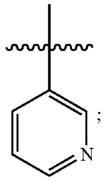
; or
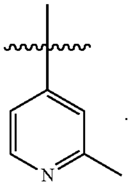
.

Another embodiment provides a compound having the following Structure (III):

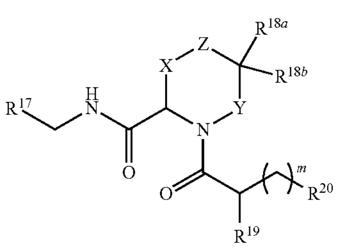
(III)

or a stereoisomer, tautomer, or pharmaceutically acceptable salt thereof, wherein:

X is a direct bond, —$CR^{2e}R^{2f}$, or —$CR^{2e}R^{2f}$, —$CR^{2g}R^{2h}$;

Y is a direct bond or —$CR^{2i}R^{2j}$, —;

Z is O or S;

$R^{17}$ is a substituted or unsubstituted aryl, substituted or unsubstituted heteroaryl, substituted or unsubstituted cycloalkyl, or a substituted or unsubstituted heterocyclyl;

$R^{18a}$, $R^{18b}$, $R^{18c}$, $R^{18d}$, $R^{18e}$, $R^{18f}$, $R^{18g}$, $R^{18h}$, $R^{18i}$, and $R^{18j}$ are each independently selected from the group consisting of hydrogen, halo, —$OR^{21}$, $C(=O)OR^{21}$, $OC(=O)R^{21}$, hydroxyalkyl, alkoxy, alkoxyalkyl, haloalkoxy, cyano, aminylalkyl, carboxyalkyl, $NR^{21}R^{22}$, $C(=O)NR^{21}R^{22}$, $N(R^{21})C(=O)R^{22}$, $NR^{21}C(=O)NR^{22}$, $S(O)_t$, $SR^{21}$, nitro, $N(R^{21})C(O)OR^{22}$, $C(=NR^{21})NR^{22}R^{23}$, $N(R^{21})C(=NR^{22})NR^{23}R^{24}$, $S(O)R^{21}$, $S(O)NR^{21}R^{22}$, $S(O)_2R^{21}$, $N(R^{21})S(O)_2R^{22}$, $S(O)_2NR^{21}R^{22}$, aryl, heteroaryl, heterocyclyl, cycloalkyl, and oxo, provided that at least one of $R^{18a}$, $R^{18b}$, $R^{18c}$, $R^{18d}$, $R^{18e}$, $R^{18f}$, $R^{18g}$, $R^{18h}$, $R^{18i}$, and $R^{18j}$ is not hydrogen;

$R^{19}$ is $NR^{19a}R^{19b}$;

$R^{19a}$ and $R^{19b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^5$, or $(CH_2)_nP(=O)(OR^5)_2$; or $R^{19a}$ and $R^{19b}$, together with the nitrogen to which they are attached, form an optionally substituted 4-7 membered heteroaryl or an optionally substituted 4-7 membered heterocyclyl;

$R^{2c}$ is a substituted or unsubstituted aryl, a substituted or unsubstituted heteroaryl, a substituted or unsubstituted cycloalkyl, or a substituted or unsubstituted heterocyclyl;

$R^{21}$, $R^{22}$, $R^{23}$, and $R^{24}$ are, at each occurrence, independently hydrogen, alkyl, hydroxyalkyl, haloalkyl, alkoxyalkyl, carboxyalkyl, heterocyclyl, heteroaryl, or cycloalkyl;

m is an integer from 0-6; and t is an integer from 1-3.

In some embodiments, $R^{17}$ has one of the following structures:

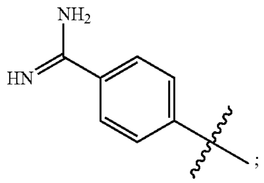
;
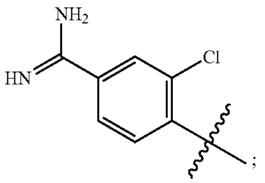
;
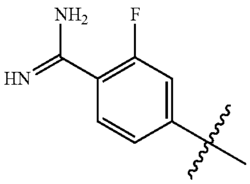
;
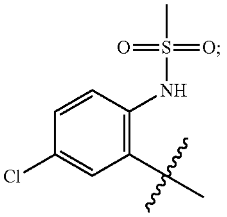

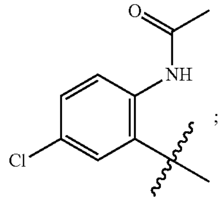
;
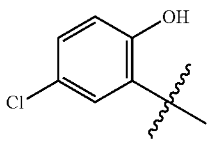
;
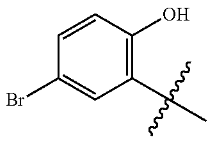
;
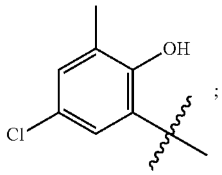
;
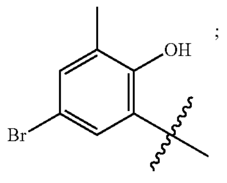
;
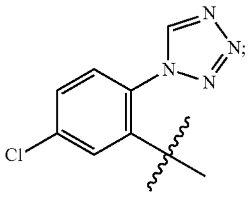

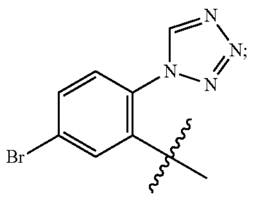

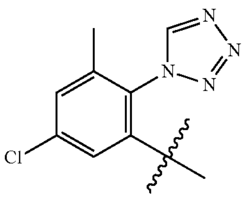
or
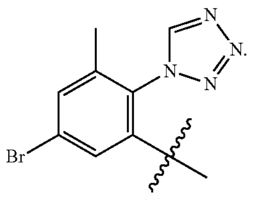

In some embodiments, $R^{17}$ has one of the following structures:
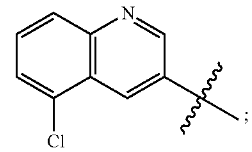 ;
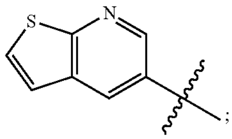 ;
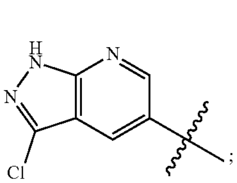 ;
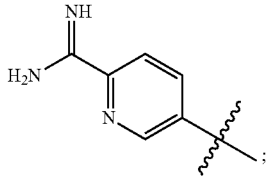 ;
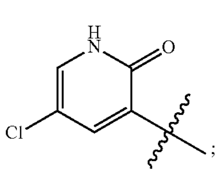 ;
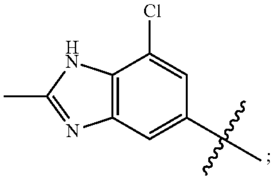 ;
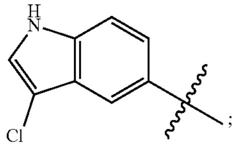 ;
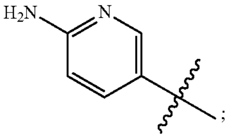 ;
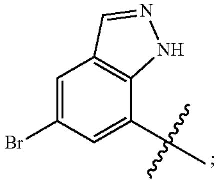 ;
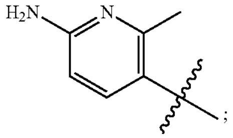 ;
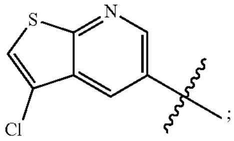 ;
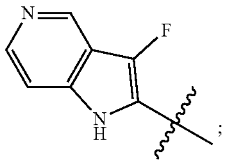 ;
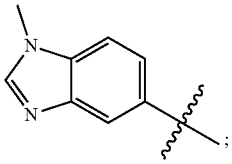 ;
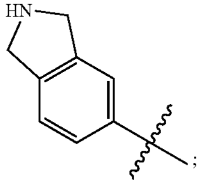 ;
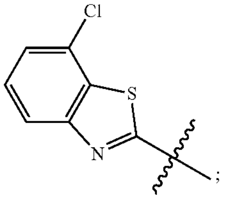 ;
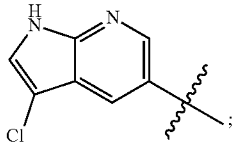 ;
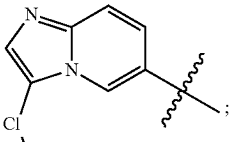 ;
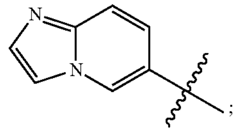 ;
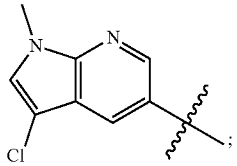 ;
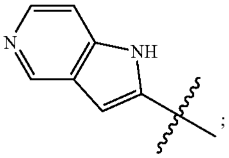 ;
-continued
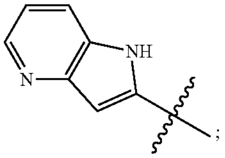 ;
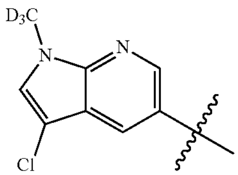 or
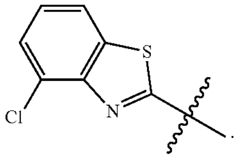 .
In certain embodiments, $R^{17}$ is an unsubstituted phenyl. In some more specific embodiments, $R^{17}$ has one of the following structures:
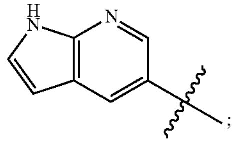 ;
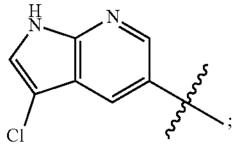 ;
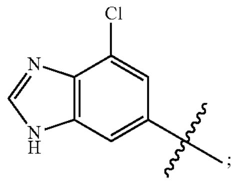 ;
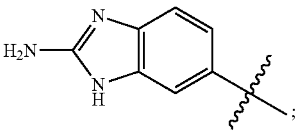 ;
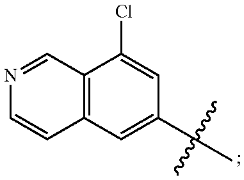 ;
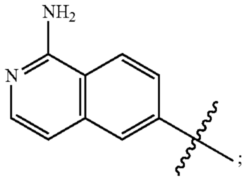 ;
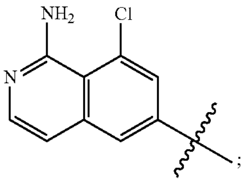 ;
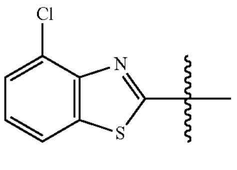 ;
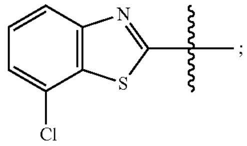 ;
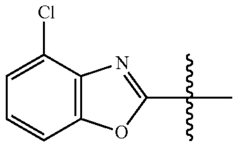
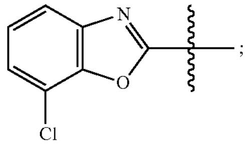 ;
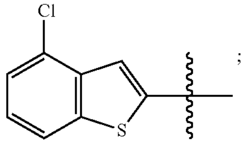 ;
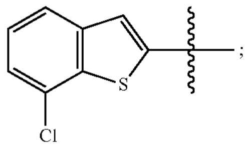 ;
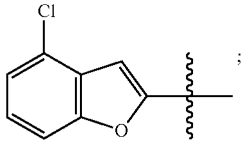 ;

-continued
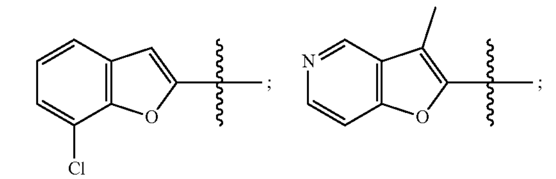
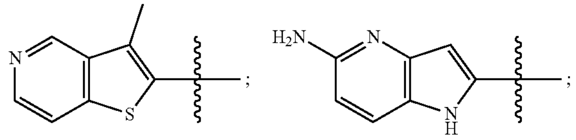
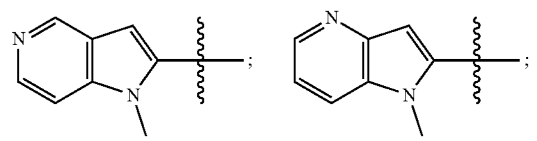
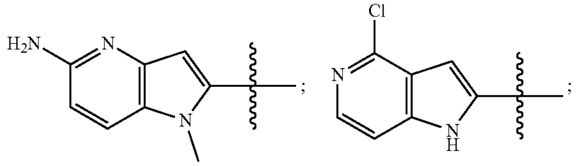
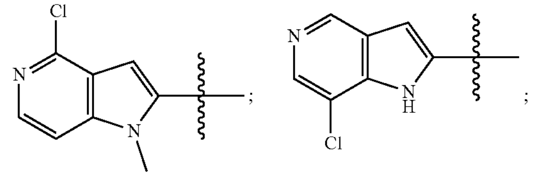
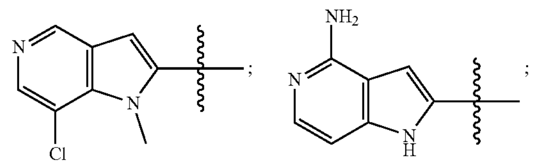
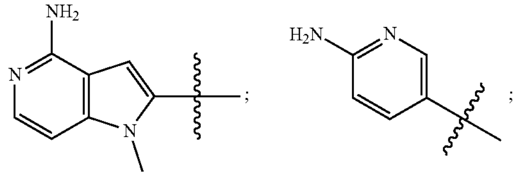
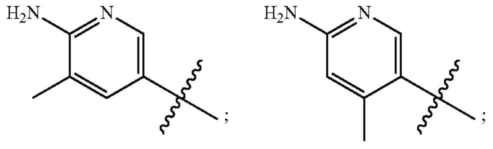
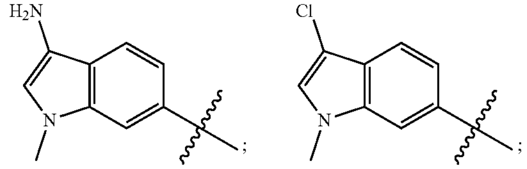
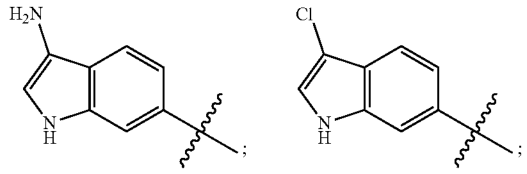
-continued
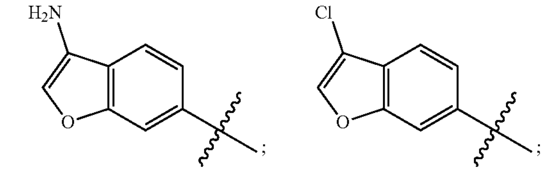
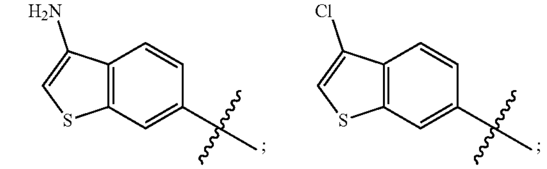
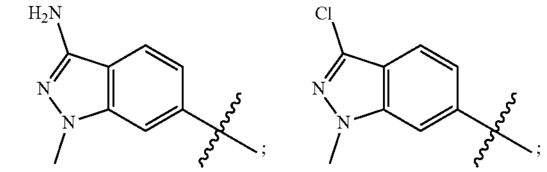
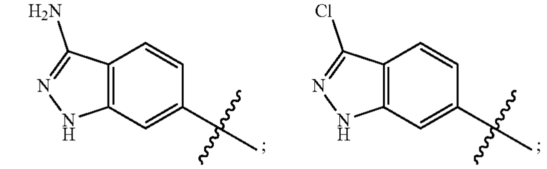
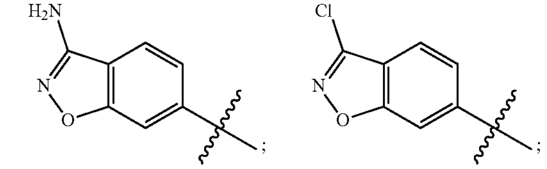
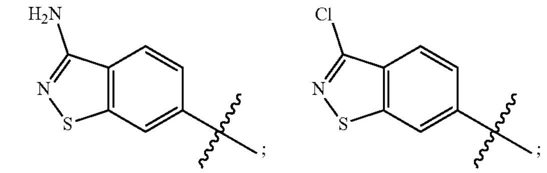
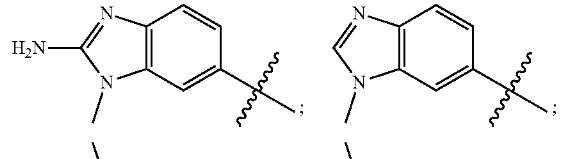
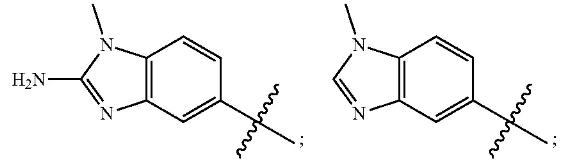
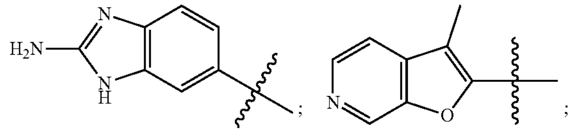
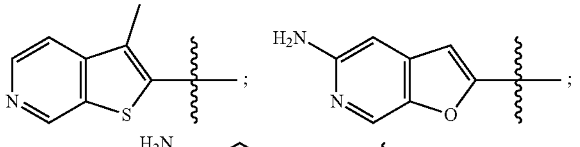
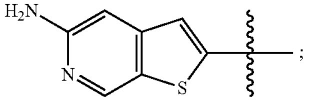

-continued
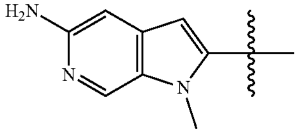;
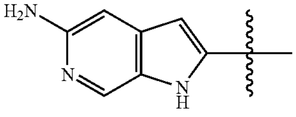; 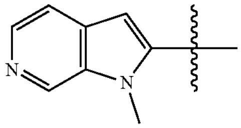;
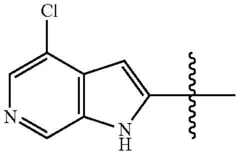; 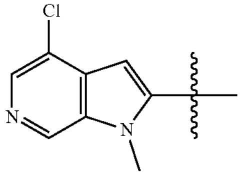;
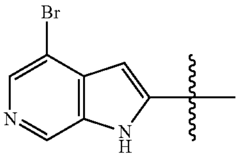; 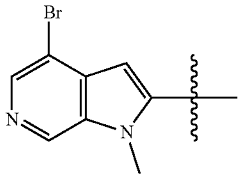;
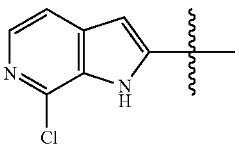; 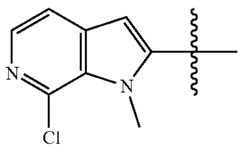;
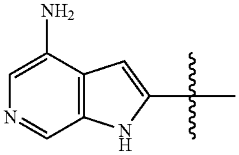; 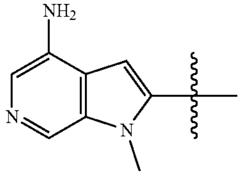;
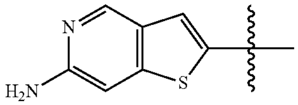;
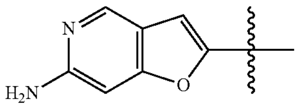;
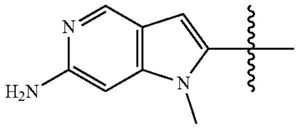;
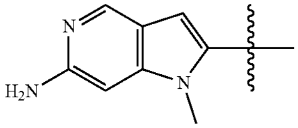; 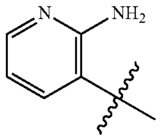;
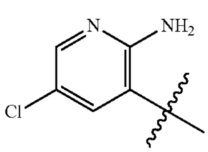; 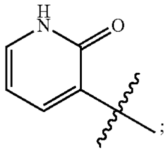;
-continued
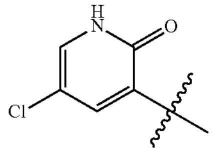; 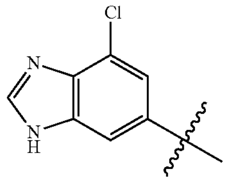;
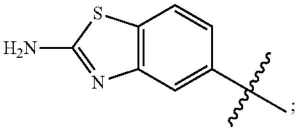;
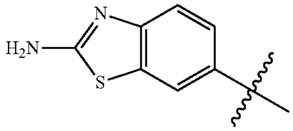 or
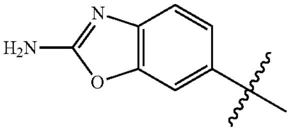.
In some more specific embodiments, $R^{17}$ has one of the following structures:
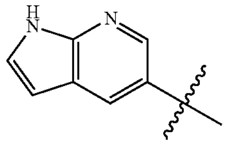; 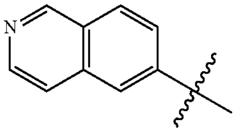;
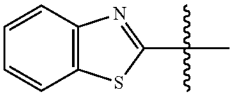; 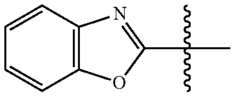;
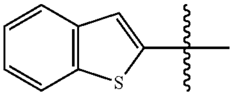; 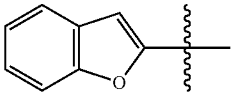;
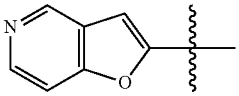; 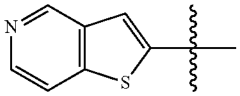;
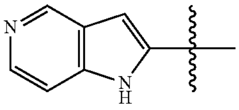; 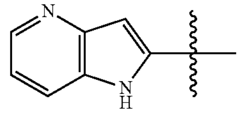;
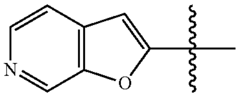; 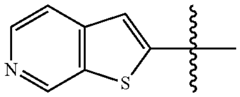;
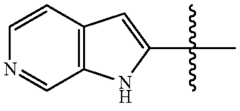; 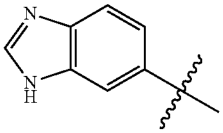;
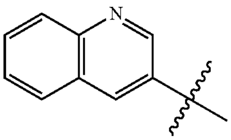; 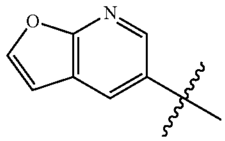;

-continued

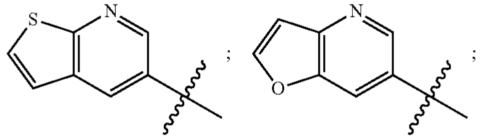

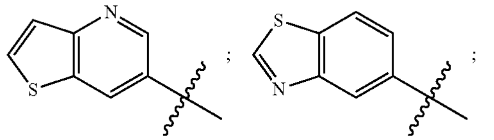

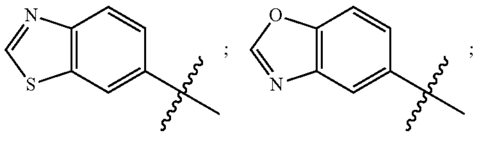

or

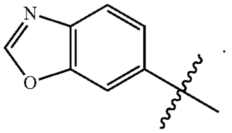

In some embodiments, at least one of $R^{18a}$ and $R^{18b}$ is alkoxy, alkoxyalkyl, cyano, C(═O)OR$^{21}$, OC(═O)R$^{21}$, C(═O)NR$^{21}$R$^{22}$, N(R$^{21}$)C(═O)R$^{22}$, aryl, heteroaryl, heterocyclyl, or C(═O)N(R$^{21}$)heterocyclyl, wherein $R^{21}$ and $R^{22}$ are, at each occurrence, independently hydrogen or $C_{1-6}$ alkyl. In certain more specific embodiments, at least one of $R^{18a}$ and $R^{18b}$ has one of the following structures:

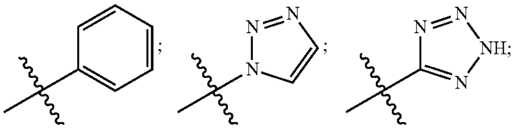

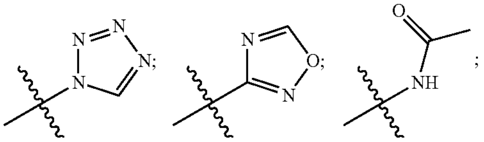

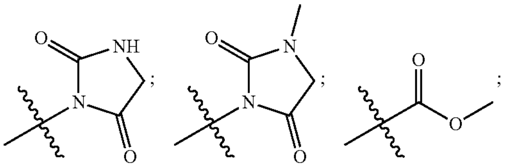

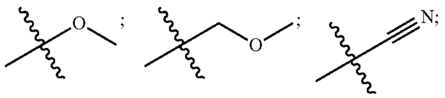

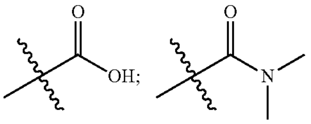

or

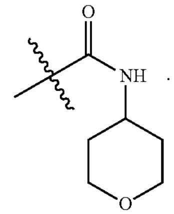

In some embodiments, $R^{19}$ has one of the following structures:

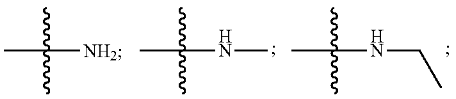

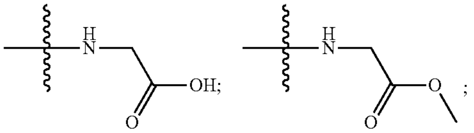

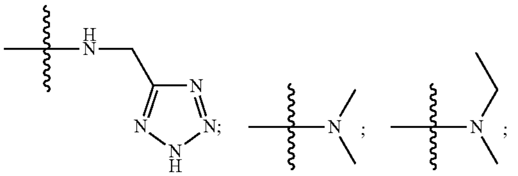

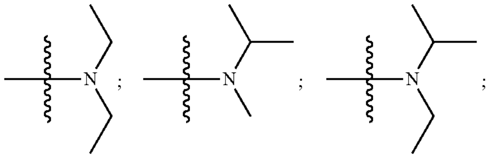

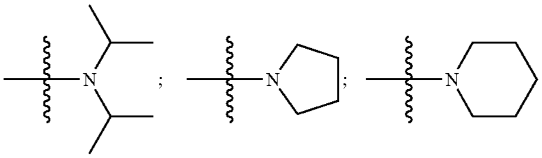

or

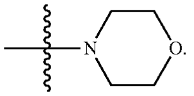

In certain embodiments, $R^{2c}$ has one of the following structures:

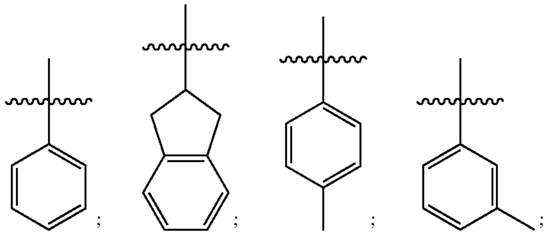

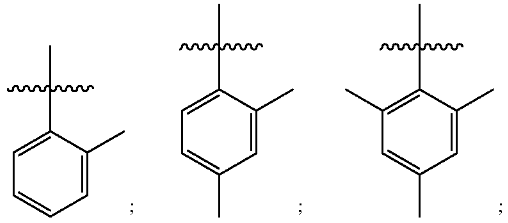

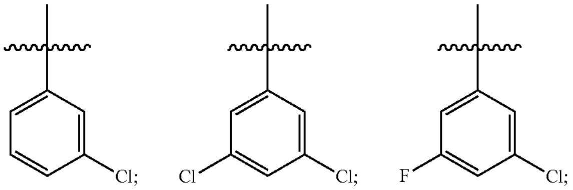

-continued
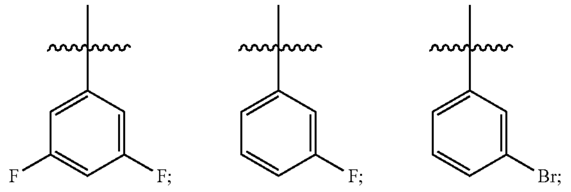
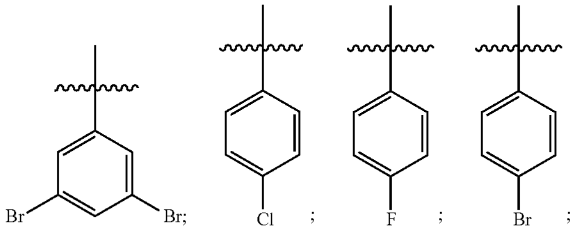
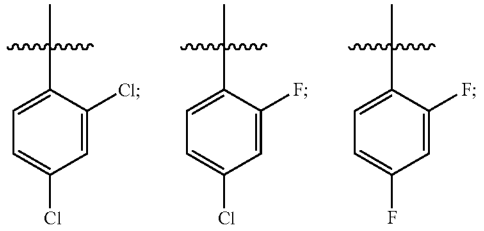
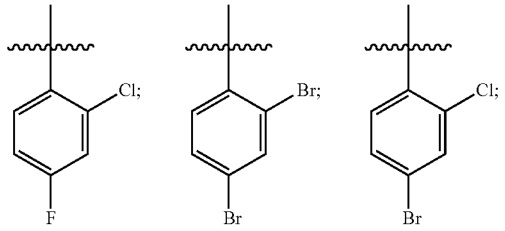
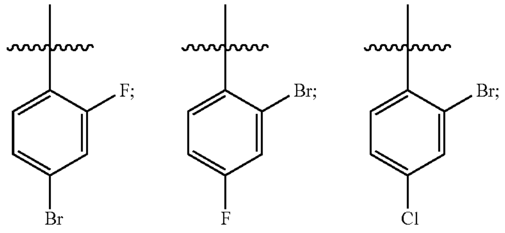
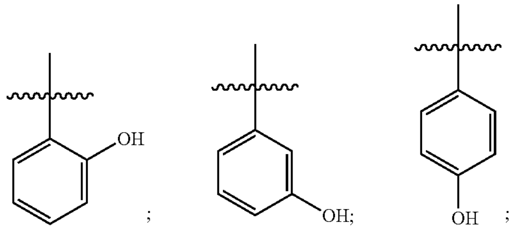
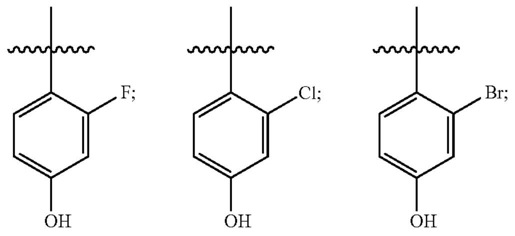
-continued
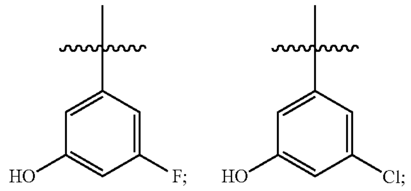
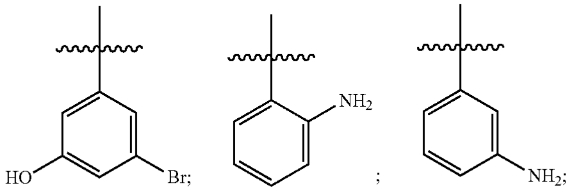
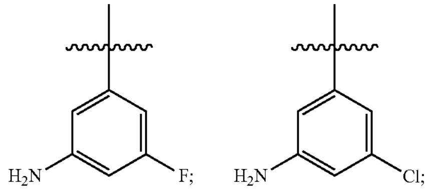
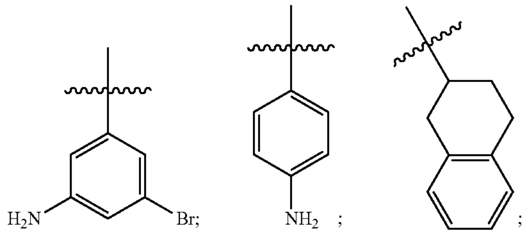
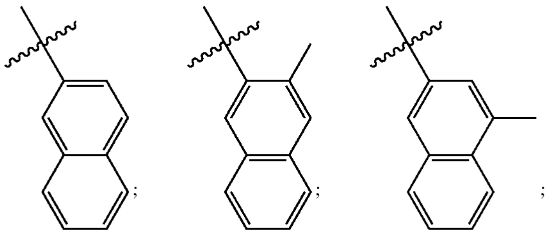
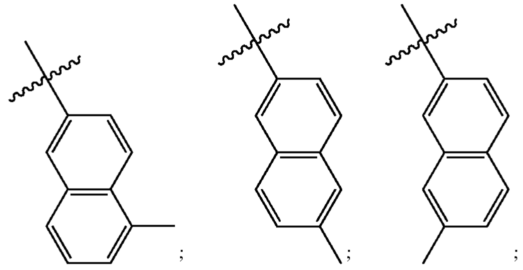
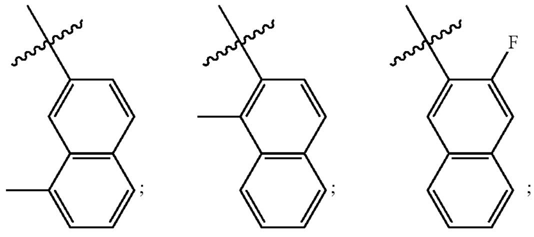

-continued
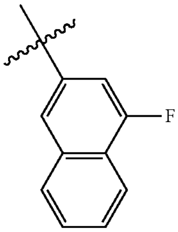
;
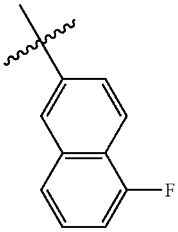
;
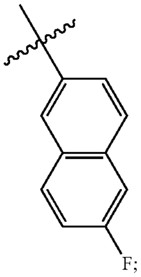
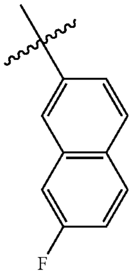
;
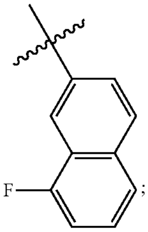
;
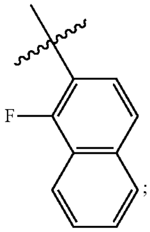
;
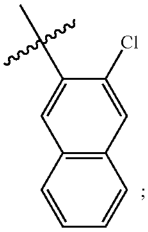
;
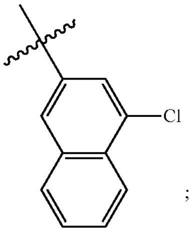
;
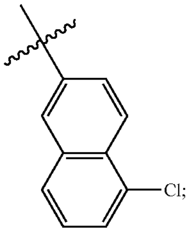
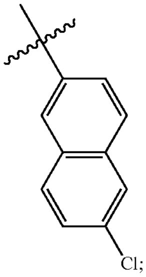
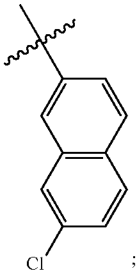
;
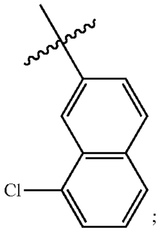
;
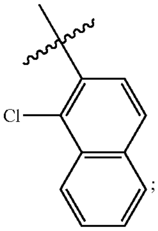
;
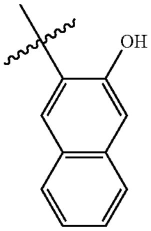
;
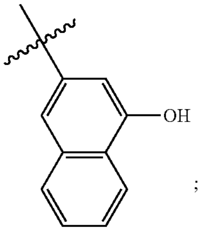
;
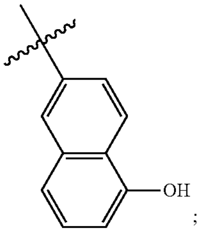
;
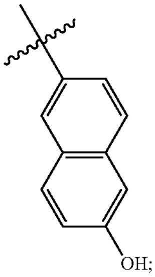
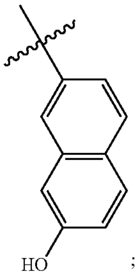
;
-continued
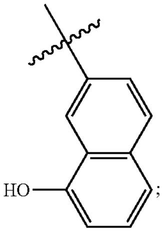
;
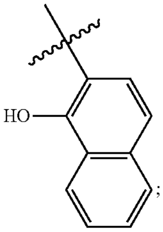
;
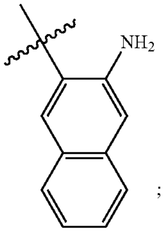
;
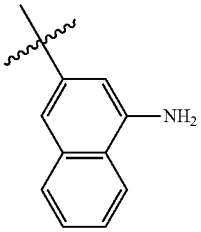
;
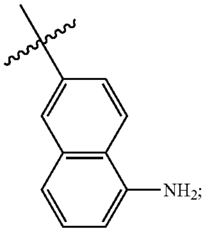
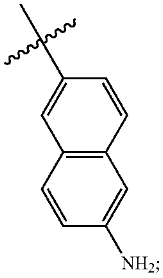
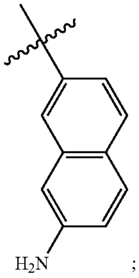
;
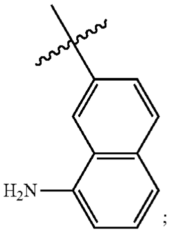
;
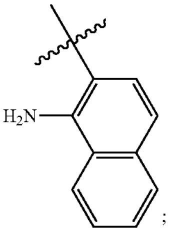
;
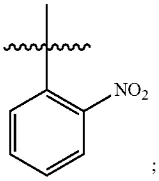
;
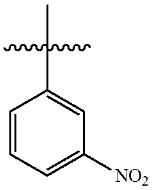
or
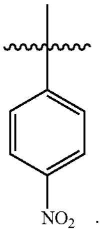
.
In some embodiments, $R^{2c}$ has one of the structures:
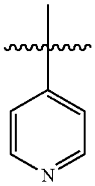
;
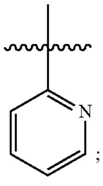
;
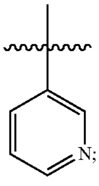
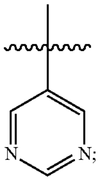

-continued
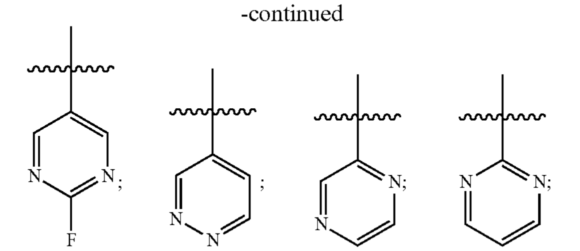
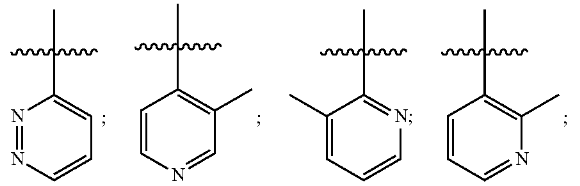
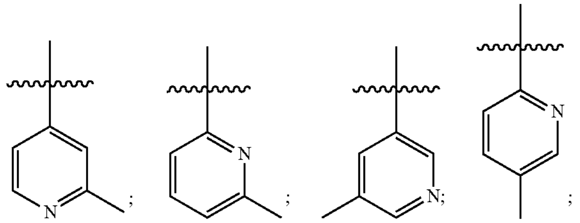
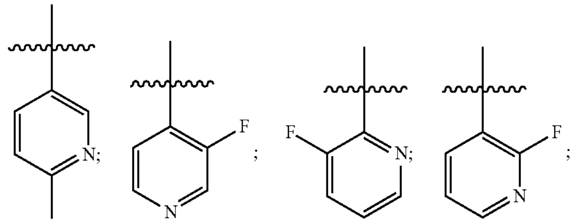
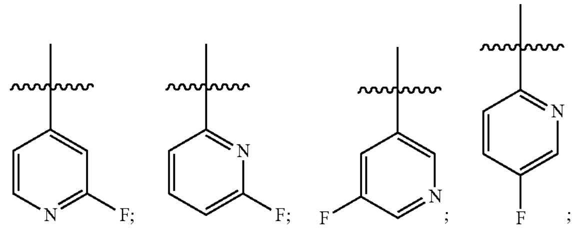
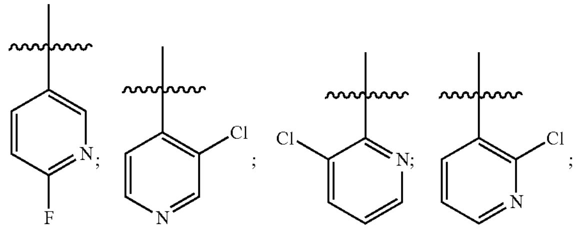
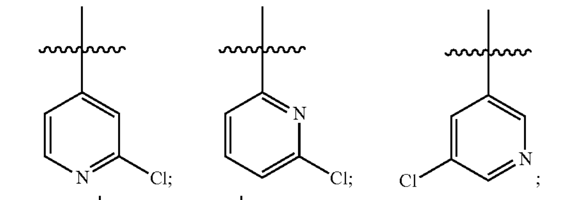
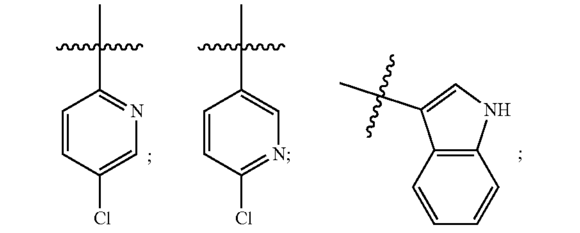
-continued
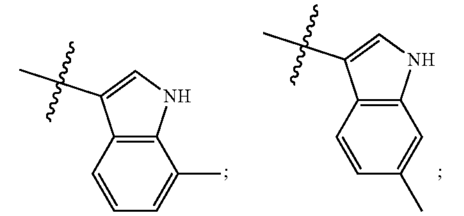
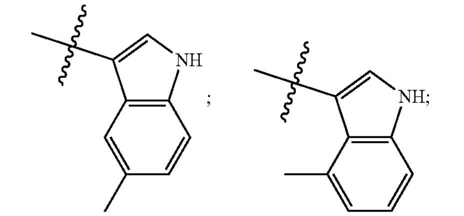
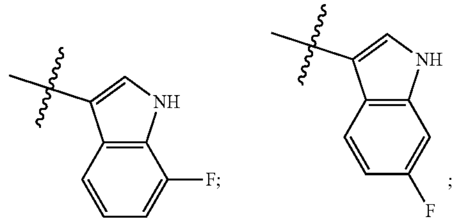
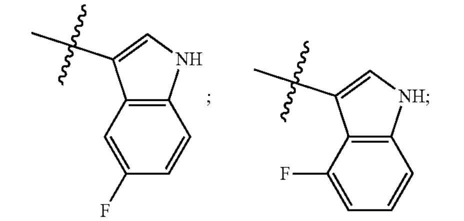
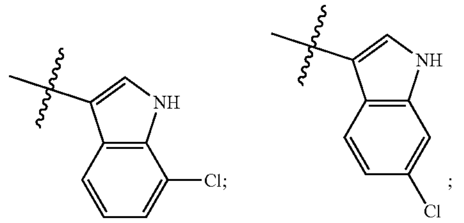
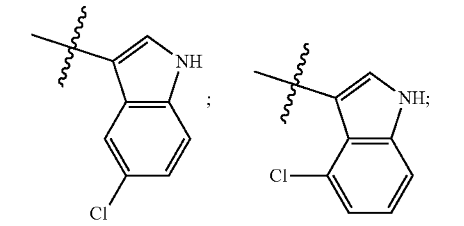
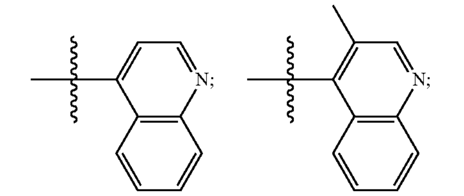
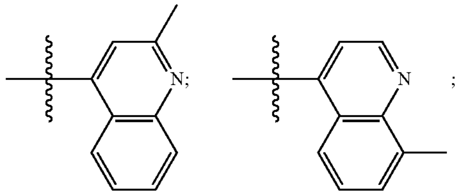

-continued
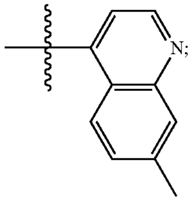
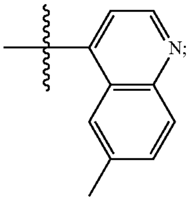
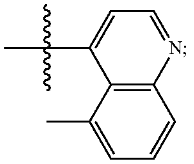
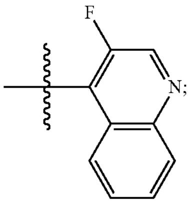
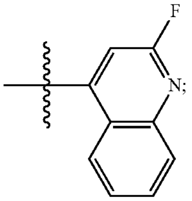
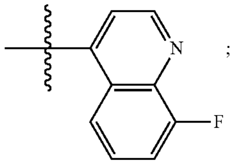
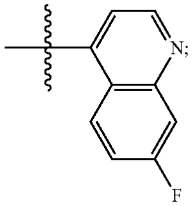
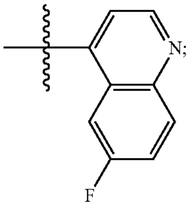
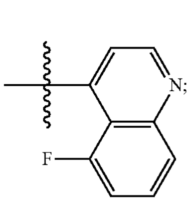
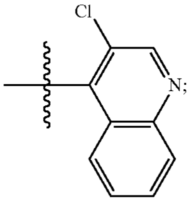
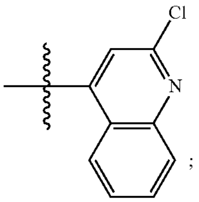
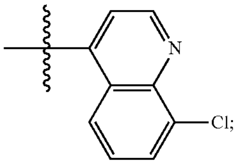
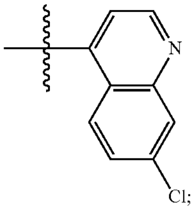
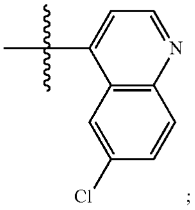
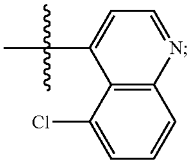
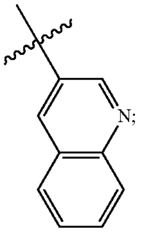
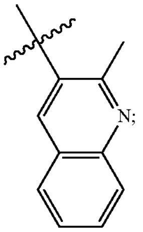
-continued
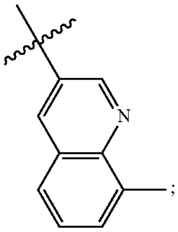
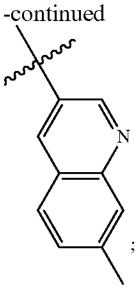
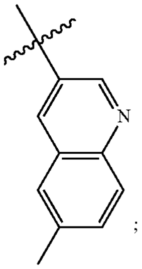
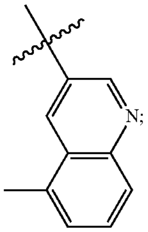
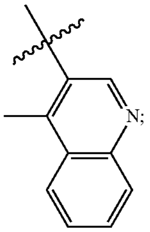
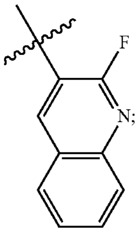
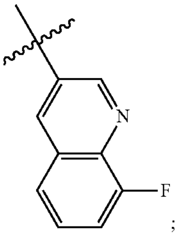
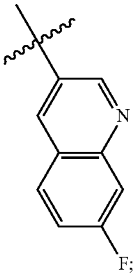
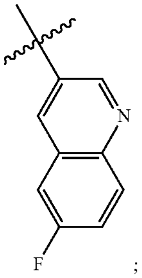
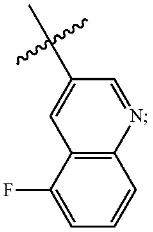
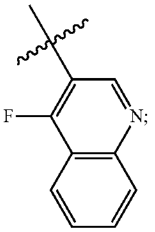
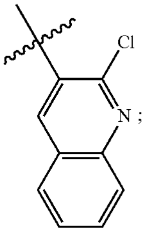
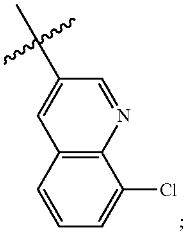
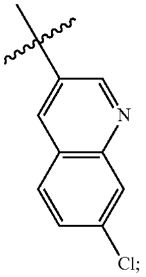
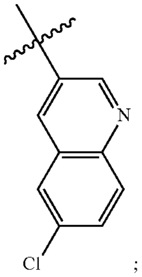
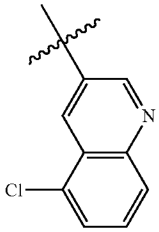
or
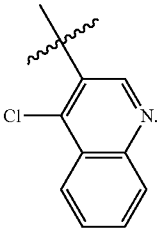

In some embodiments, $R^{2c}$ has one of the following structures:
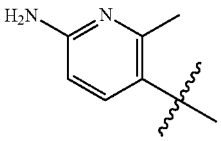 ; 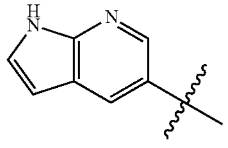 ;
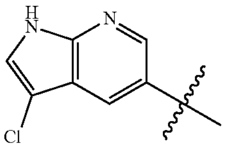 ; 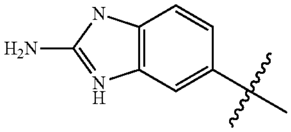 ;
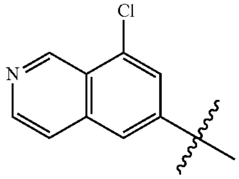 ; 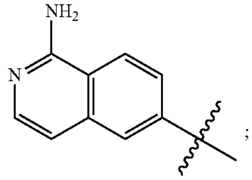 ;
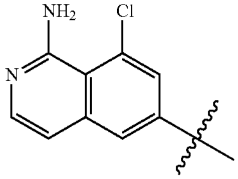 ; 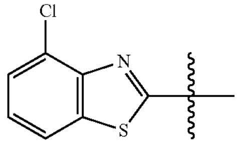 ;
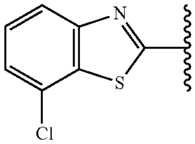 ; 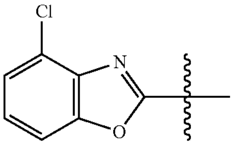 ;
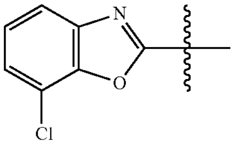 ; 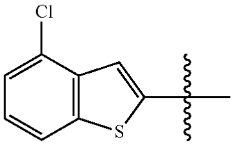 ;
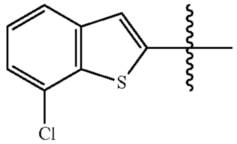 ; 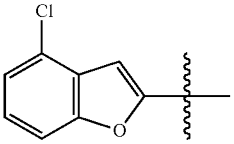 ;
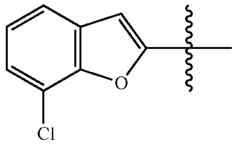 ; 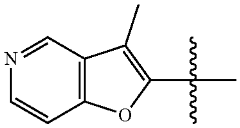 ;
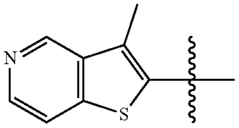 ; 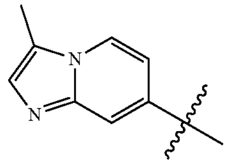 ;
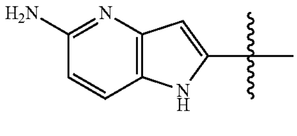 ; 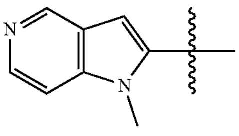 ;
-continued
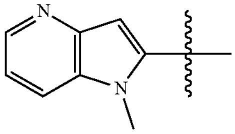 ; 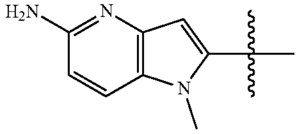 ;
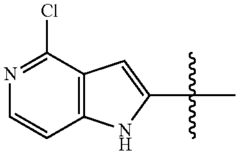 ; 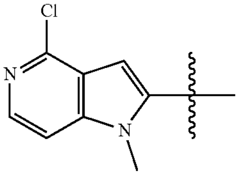 ;
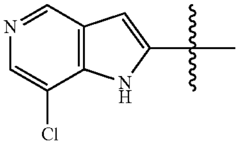 ; 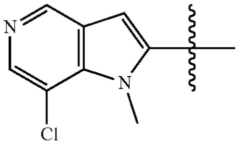 ;
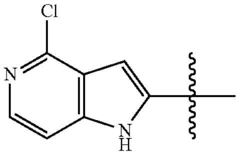 ; 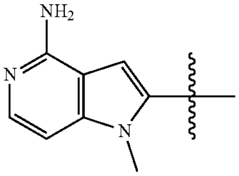 ;
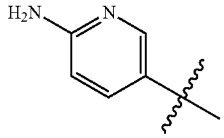 ; 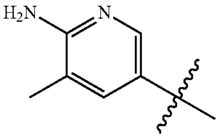 ;
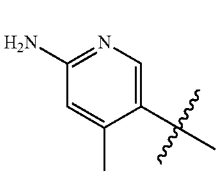 ; 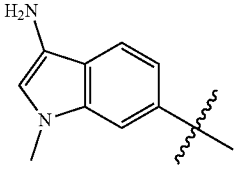 ;
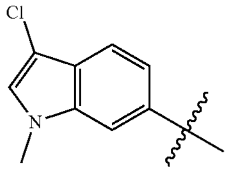 ; 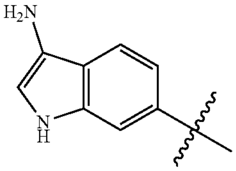 ;
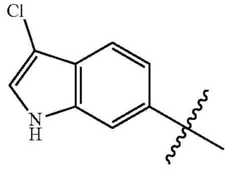 ; 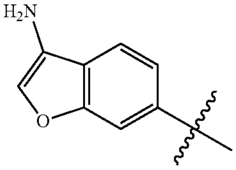 ;
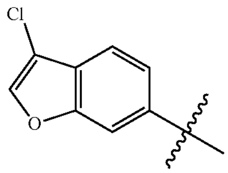 ; 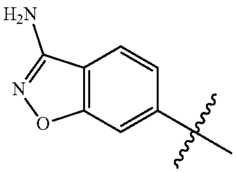 ;
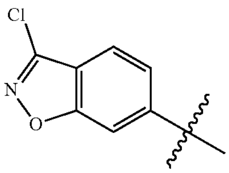 ; 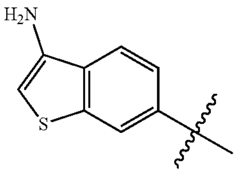 ;

-continued
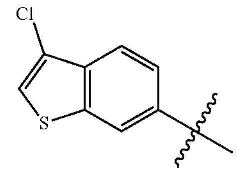
;
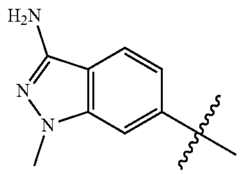
;
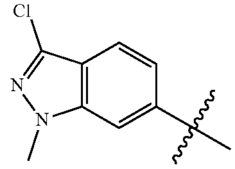
;
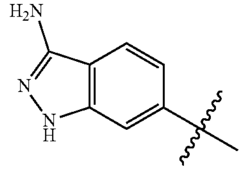
;
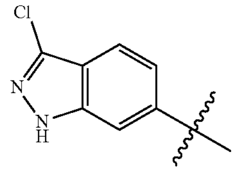
;
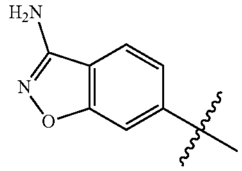
;
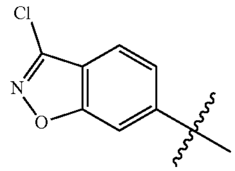
;
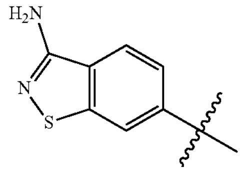
;
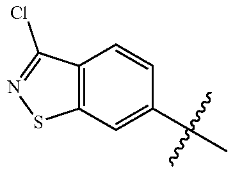
;
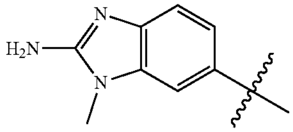
;
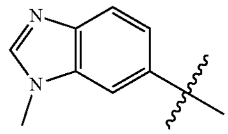
;
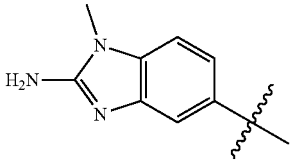
;
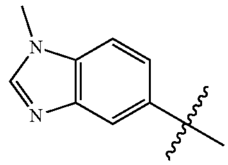
;
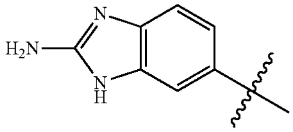
;
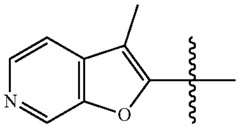
;
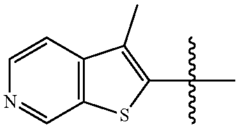
;
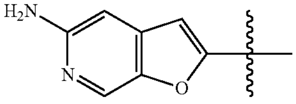
;
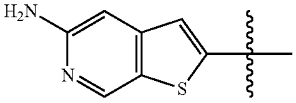
;
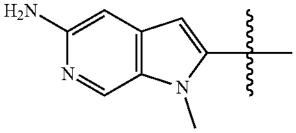
;
-continued
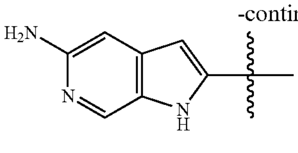
;
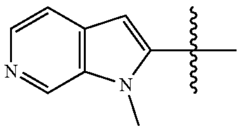
;
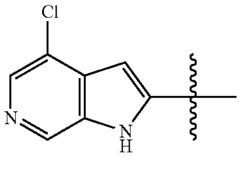
;
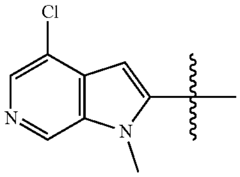
;
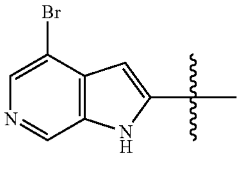
;
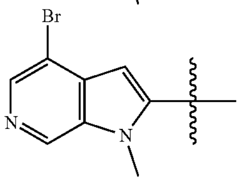
;
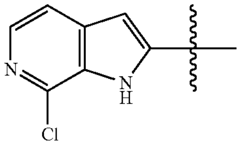
;
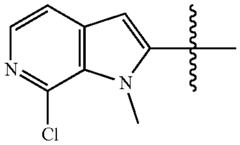
;
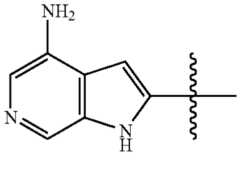
;
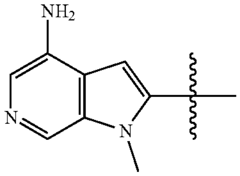
;
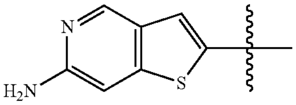
;
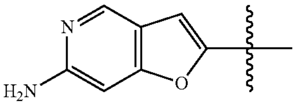
;
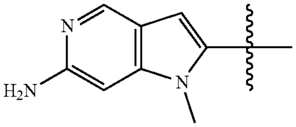
;
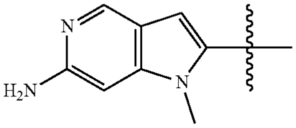
;
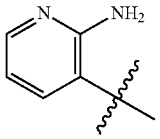
;
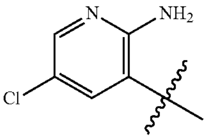
;
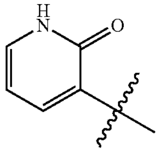
;
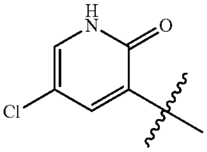
;
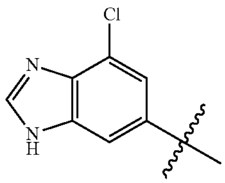
;
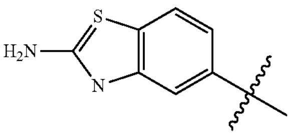
;

-continued

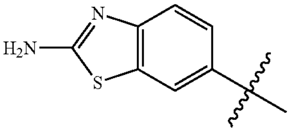
;

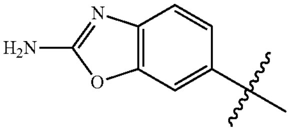
;
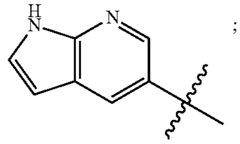
;

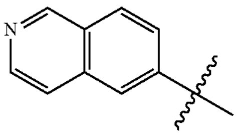
;
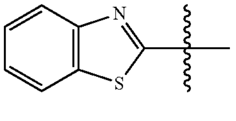
;

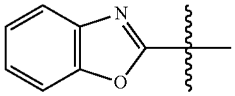
;
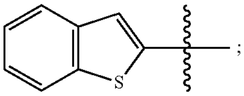
;

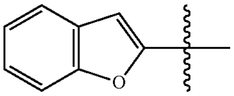
;
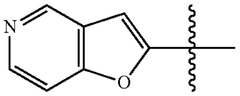
;

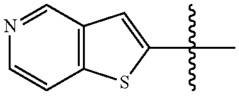
;
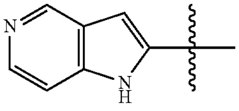
;

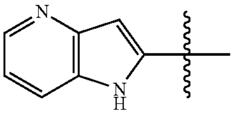
;
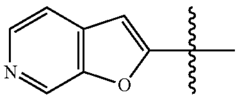
;

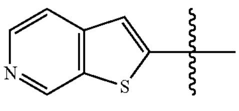
;
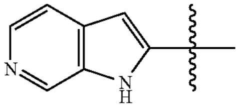
;

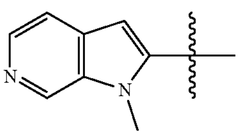
;
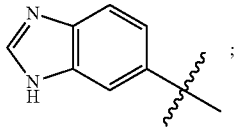
;

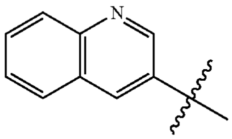
;
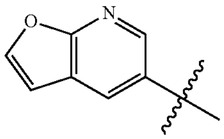
;

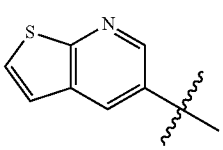
;
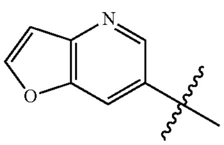
;

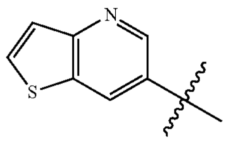
;

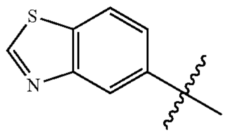
;

-continued

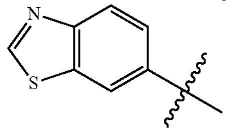
;
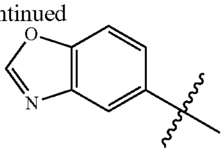
; or

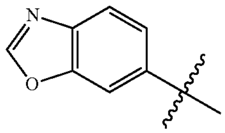
.

Another embodiment provides a compound having the following Structure (III)

(III)

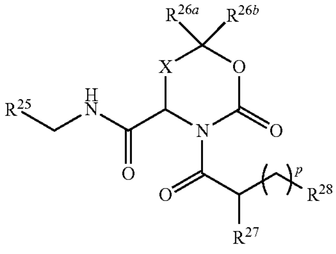

or a stereoisomer, tautomer, or pharmaceutically acceptable salt thereof, wherein:

X is a direct bond or —$CR^{26c}R^{26d}$, —;

$R^{25}$ is a substituted or unsubstituted aryl, substituted or unsubstituted heteroaryl, substituted or unsubstituted cycloalkyl, or a substituted or unsubstituted heterocyclyl;

$R^{26a}$, $R^{26b}$, $R^{26c}$, and $R^{26d}$ are each independently selected from the group consisting of hydrogen, halo, —$OR^{29}$, $C(=O)OR^{29}$, $OC(=O)R^{29}$, hydroxyalkyl, alkoxy, alkoxyalkyl, haloalkoxy, cyano, aminylalkyl, carboxyalkyl, $NR^{29}R^{30}$, $C(=O)NR^{29}R^{30}$, $N(R^{29})C(=O)R^{30}$, $NR^{29}C(=O)NR^{30}$, $S(O)_t$, $SR^{29}$, nitro, $N(R^{29})C(O)OR^{30}$, $C(=NR^{29})NR^{30}R^{31}$, $N(R^{29})C(=NR^{30})NR^{31}R^{32}$, $S(O)R^{29}$, $S(O)NR^{29}R^{30}$, $S(O)_2R^{30}$, $N(R^{29})S(O)_2R^{30}$, $S(O)_2NR^{29}R^{30}$, aryl, heteroaryl, heterocyclyl, cycloalkyl, and oxo, provided that at least one of $R^{26a}$, $R^{26b}$, $R^{26c}$, and $R^{26d}$ is not hydrogen;

$R^{27}$ is $NR^{27a}R^{27b}$;

$R^{27a}$ and $R^{27b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)$, $C(=O)OR^{29}$, or $(CH_2)_nP(=O)(OR^{29})_2$; or $R^{27a}$ and $R^{27b}$, together with the nitrogen to which they are attached, form an optionally substituted 4-7 membered heteroaryl or an optionally substituted 4-7 membered heterocyclyl;

$R^{28}$ is a substituted or unsubstituted aryl, a substituted or unsubstituted heteroaryl, a substituted or unsubstituted cycloalkyl, or a substituted or unsubstituted heterocyclyl;

$R^{29}$, $R^{30}$, $R^{31}$, and $R^{32}$ are, at each occurrence, independently hydrogen, alkyl, hydroxyalkyl, haloalkyl, alkoxyalkyl, carboxyalkyl, heterocyclyl, heteroaryl, or cycloalkyl;

p is an integer from 0-6; and t is an integer from 1-3.

In some embodiments, $R^{25}$ has one of the following structures:

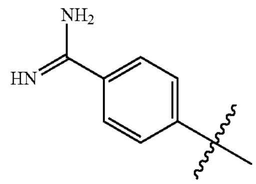
;
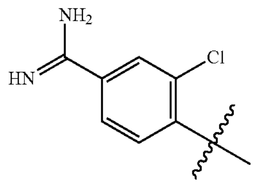
;
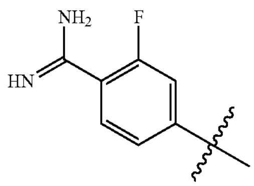
;
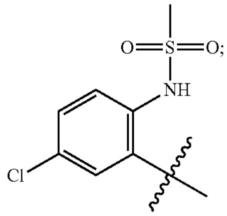
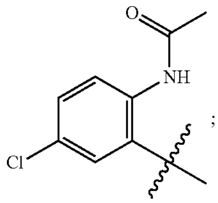
;
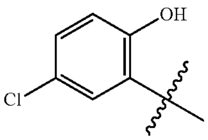
;
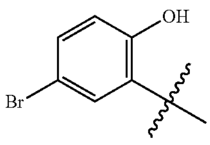
;
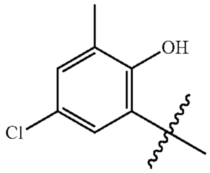
;
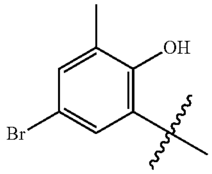
;
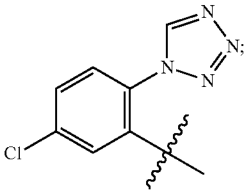
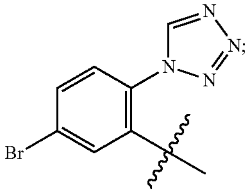
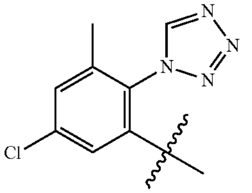
or
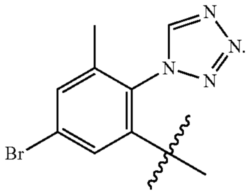
In some embodiments, $R^{25}$ is an unsubstituted phenyl.
In some more specific embodiments, $R^{25}$ has one of the following structures:
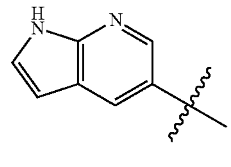
;
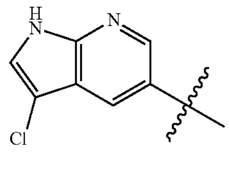
;
-continued
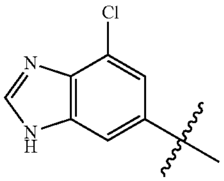
;
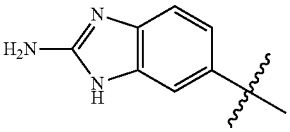
;
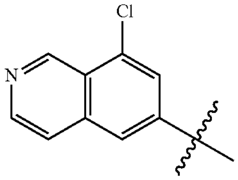
;
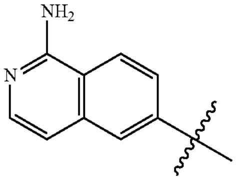
;
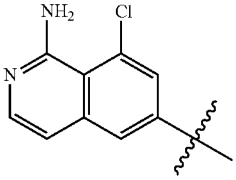
;
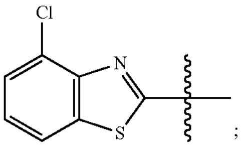
;
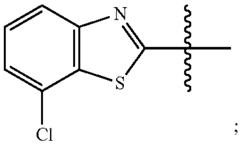
;
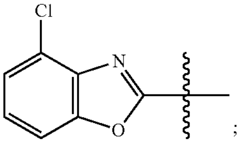
;
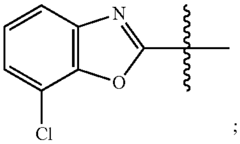
;
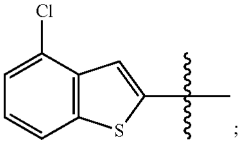
;
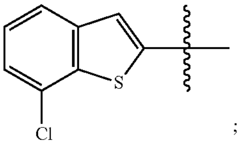
;
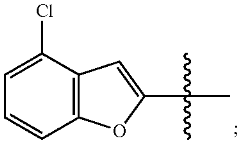
;
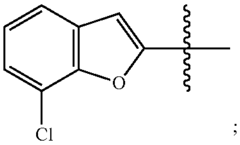
;
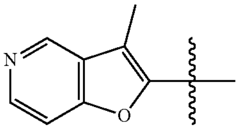
;
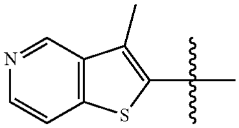
;
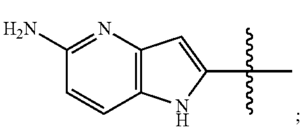
;
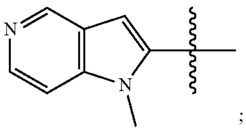
;
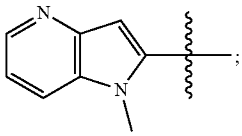
;
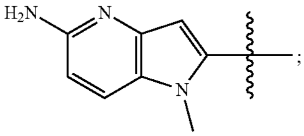
;
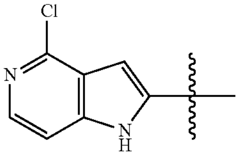
;
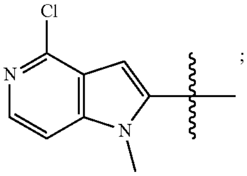
;

-continued
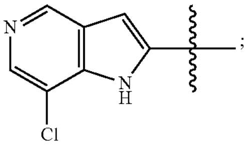 ; 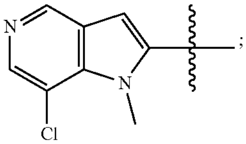 ;
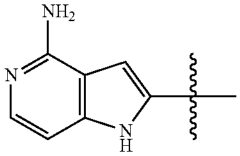 ; 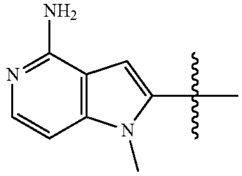 ;
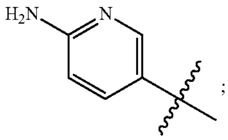 ; 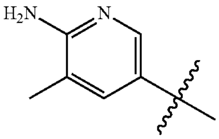 ;
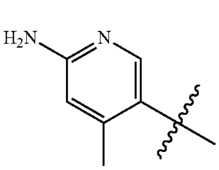 ; 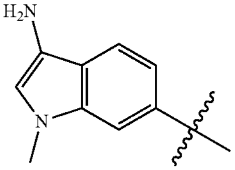 ;
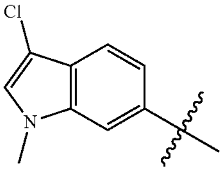 ; 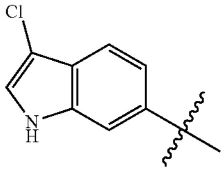 ;
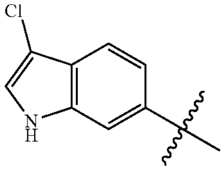 ; 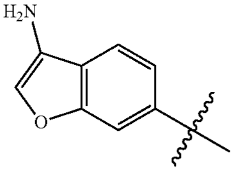 ;
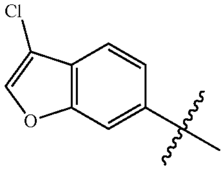 ; 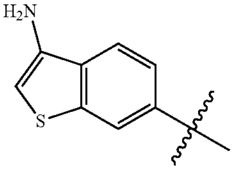 ;
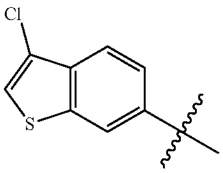 ; 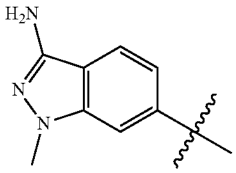 ;
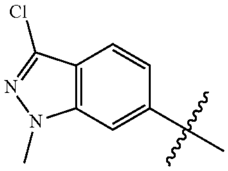 ; 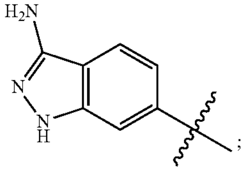 ;
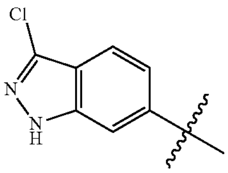 ; 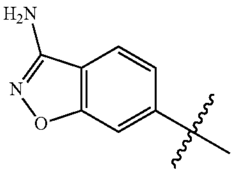 ;
-continued
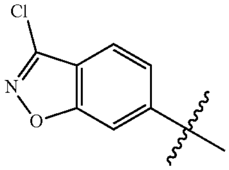 ; 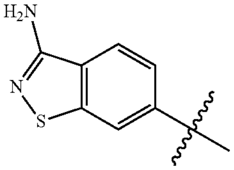 ;
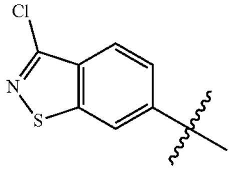 ; 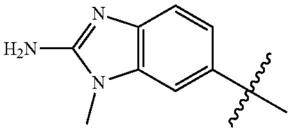 ;
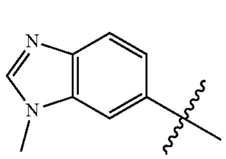 ; 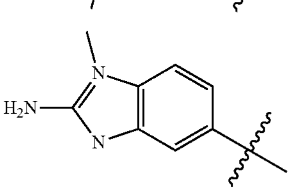 ;
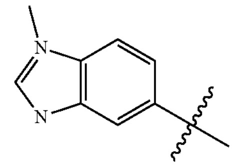 ; 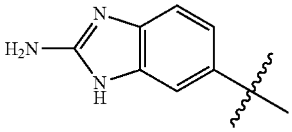 ;
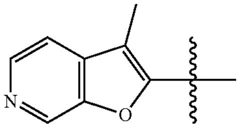 ; 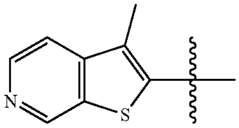 ;
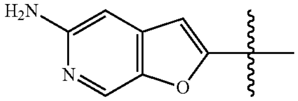 ;
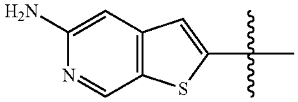 ;
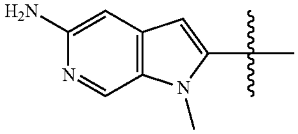 ;
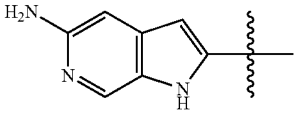 ; 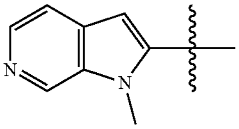 ;
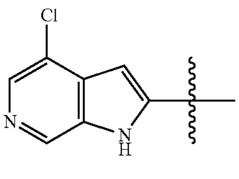 ; 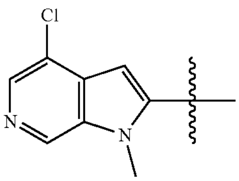 ;
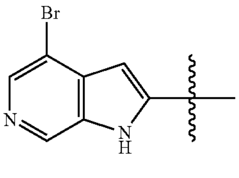 ; 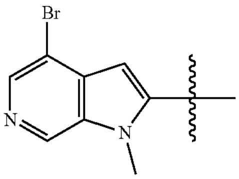 ;

-continued
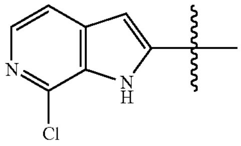 ; 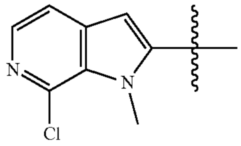 ;
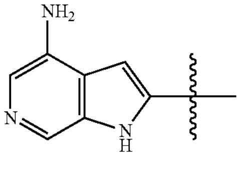 ; 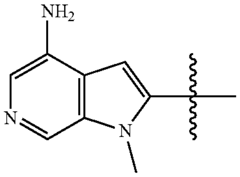 ;
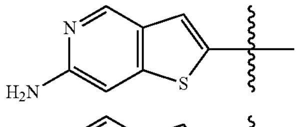 ;
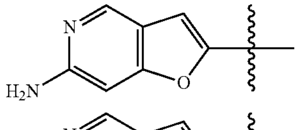 ;
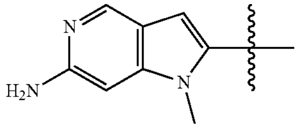 ;
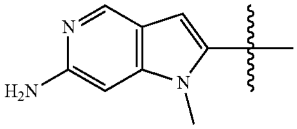 ; 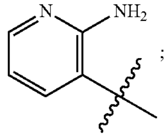 ;
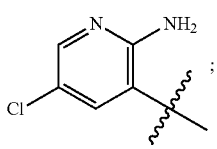 ; 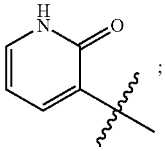 ;
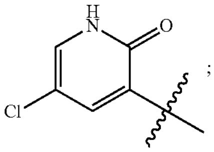 ; 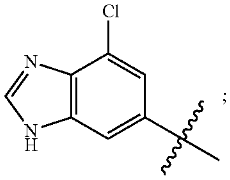 ;
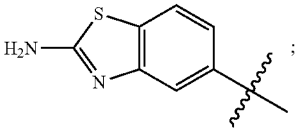 ;
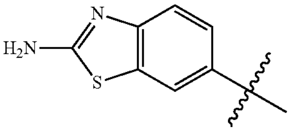 or
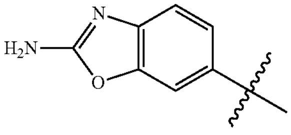 .
In some embodiments, $R^{25}$ has one of the following structures:
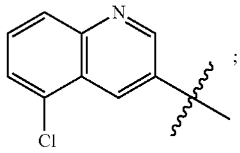 ; 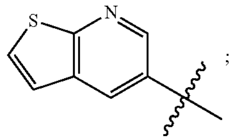 ;
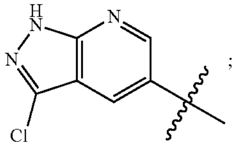 ; 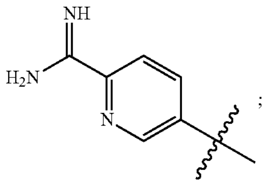 ;
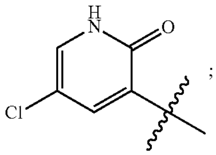 ; 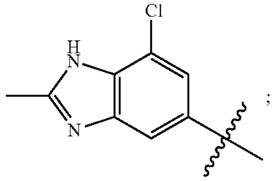 ;
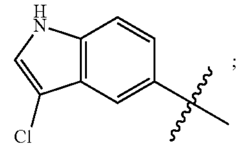 ; 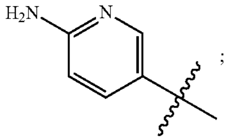 ;
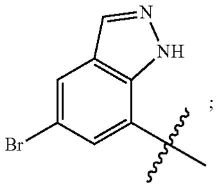 ; 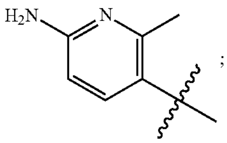 ;
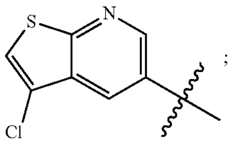 ; 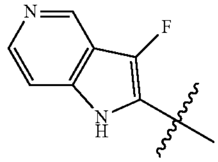 ;
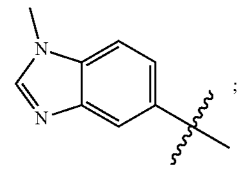 ; 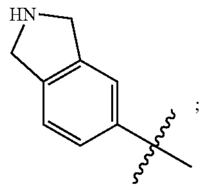 ;
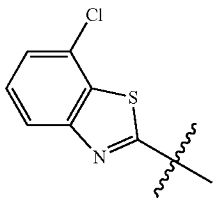 ; 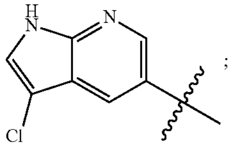 ;
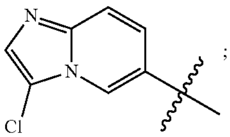 ; 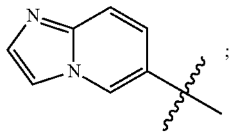 ;
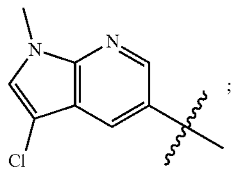 ; 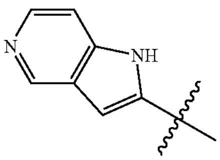 ;

-continued

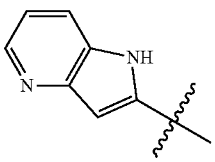 ; 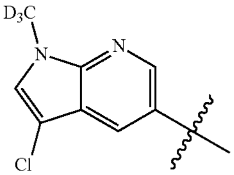 or

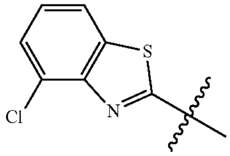 .

In some embodiments, $R^{25}$ has one of the following structures:

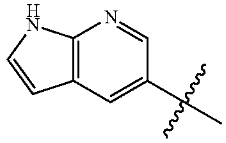 ; 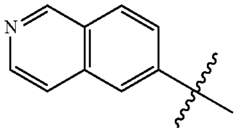 ;

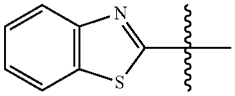 ; 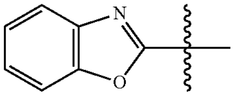 ;

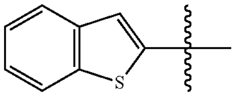 ; 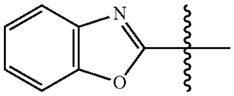 ;

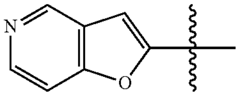 ; 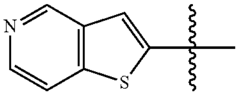 ;

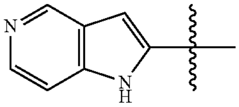 ; 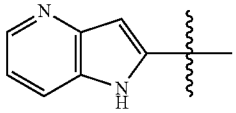 ;

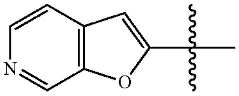 ; 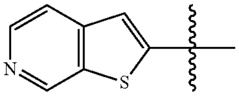 ;

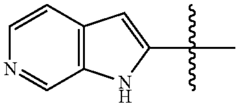 ; 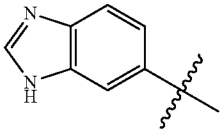 ;

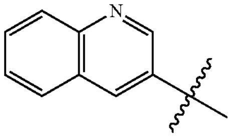 ; 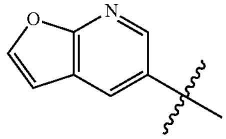 ;

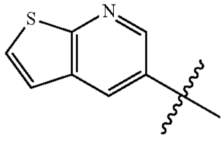 ; 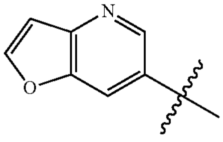 ;

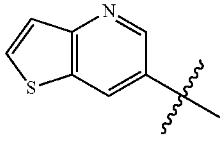 ; 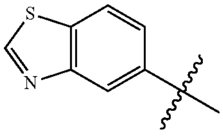 ;

-continued

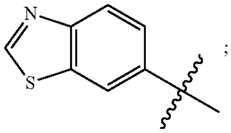 ; 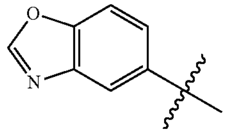 ; or

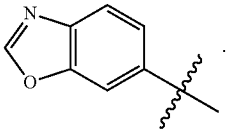 .

In certain embodiments, at least one of $R^{26a}$ and $R^{26b}$ is alkoxy, alkoxyalkyl, cyano, C(═O)OR$^{29}$, OC(═O)R$^{29}$, C(═O)NR$^{29}$R$^{30}$, N(R$^{29}$)C(═O)R$^{30}$, aryl, heteroaryl, heterocyclyl, or C(═O)N(R$^{29}$)heterocyclyl, wherein $R^{29}$ and $R^{30}$ are, at each occurrence, independently hydrogen or $C_{1-6}$ alkyl. In more specific embodiments, at least one occurrence of $R^{26a}$ or $R^{26b}$ has one of the following structures:

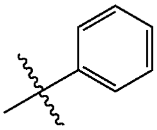 ; 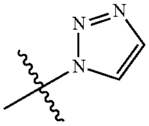 ; 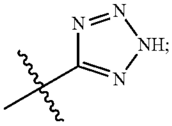

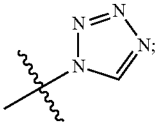 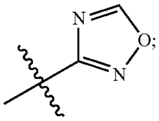 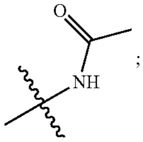 ;

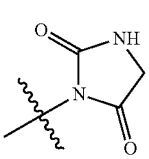 ; 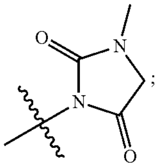 ; 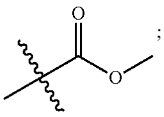 ;

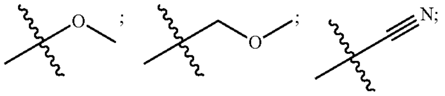

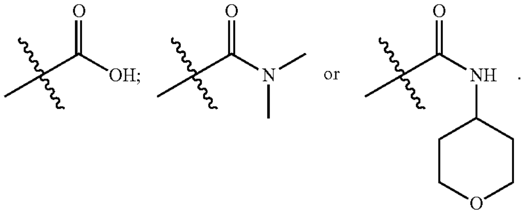

In certain embodiments, $R^{27}$ has one of the following structures:

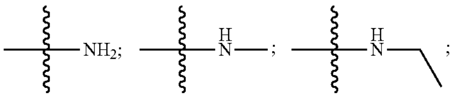

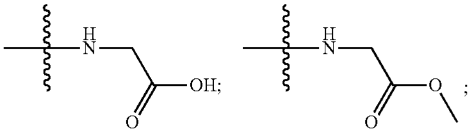

-continued
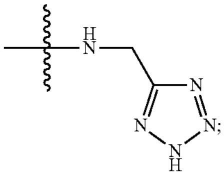 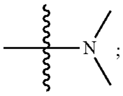 ; 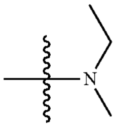 ;
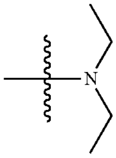 ; 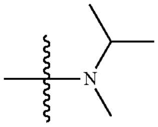 ; 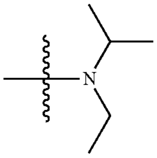 ;
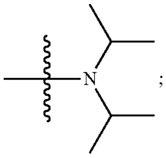 ; 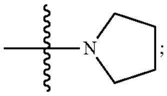 ; 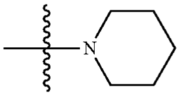 or
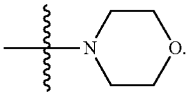
In some embodiments, $R^{28}$ has one of the following structures:
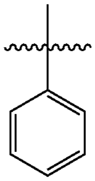 ; 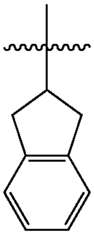 ; 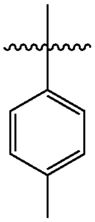 ; 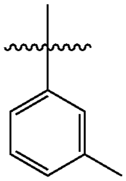 ;
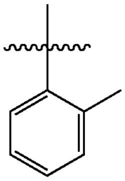 ; 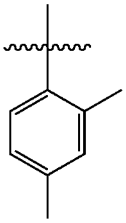 ; 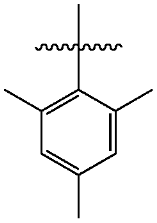 ;
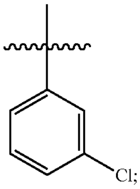 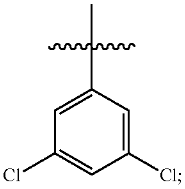 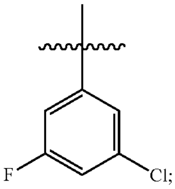
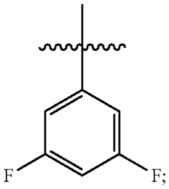 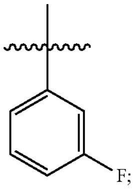 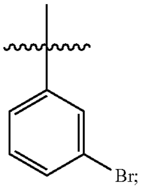
-continued
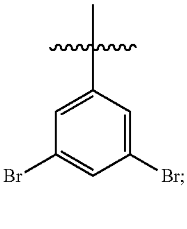 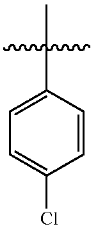 ; 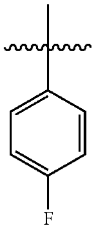 ; 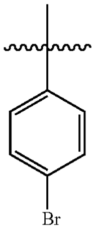 ;
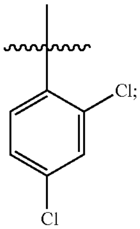 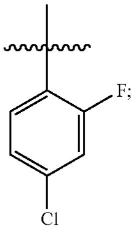 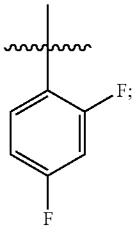
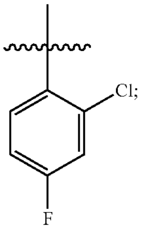 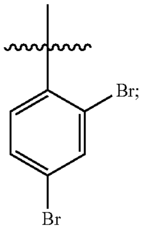 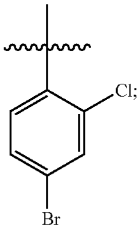
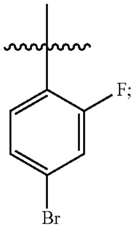 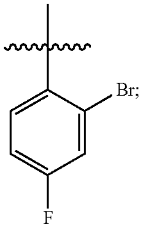 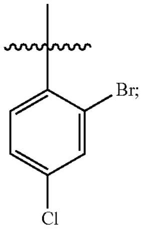
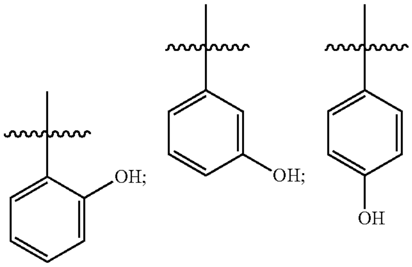 ;
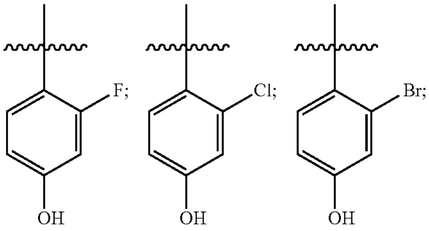
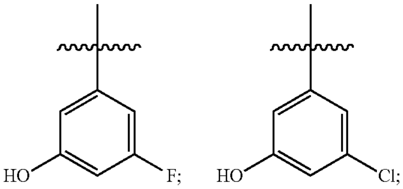

-continued
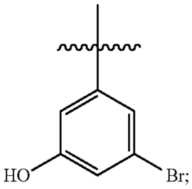
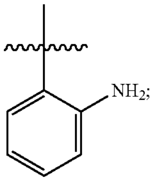
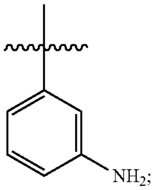
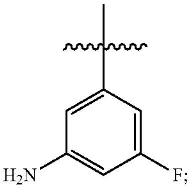
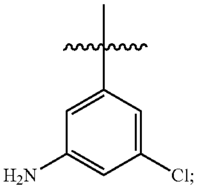
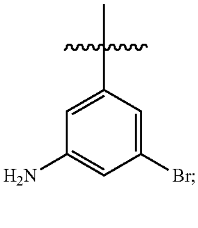
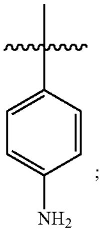
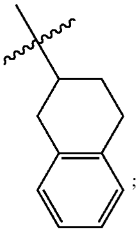
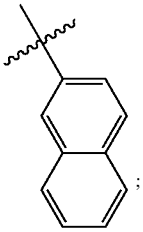
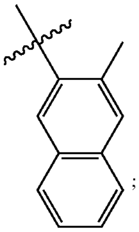
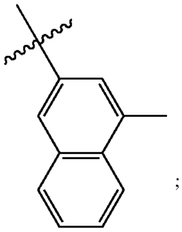
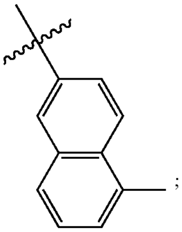
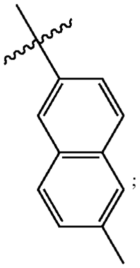
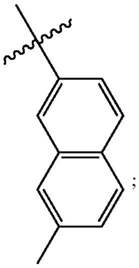
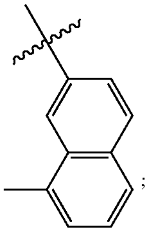
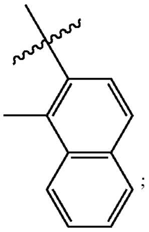
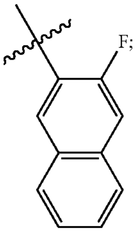
-continued
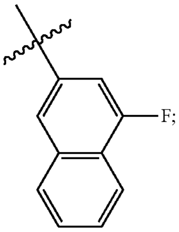
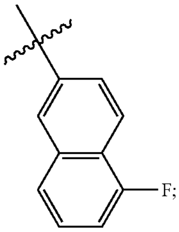
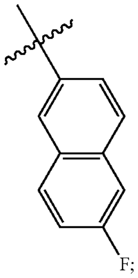
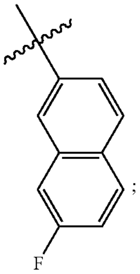
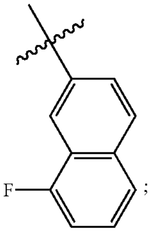
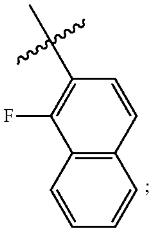
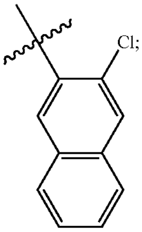
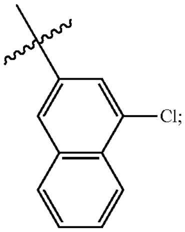
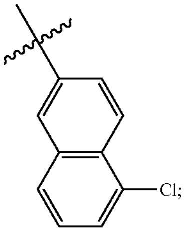
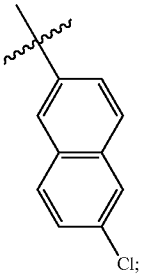
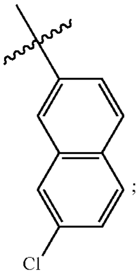
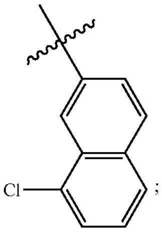
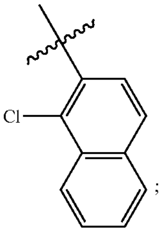

-continued
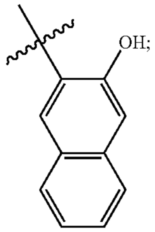
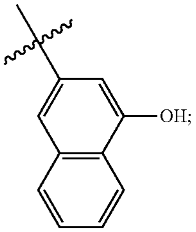 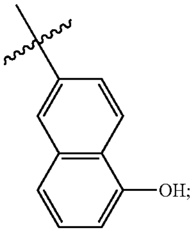 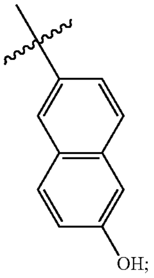
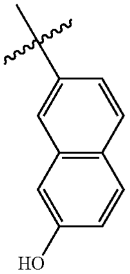 ; 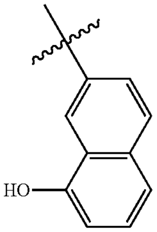 ; 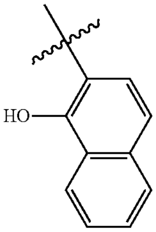 ;
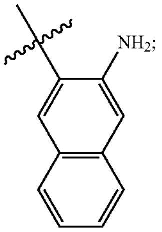
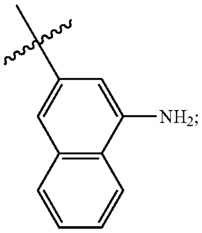 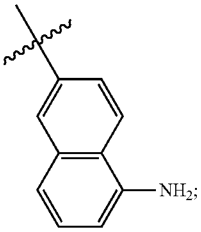
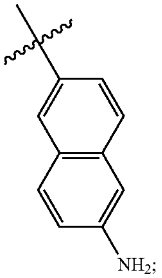
-continued
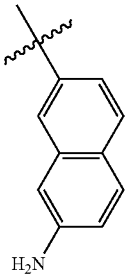 ; 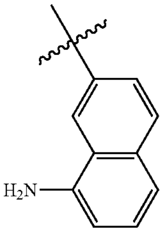 ; 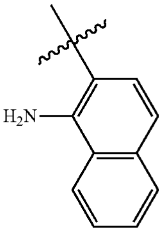 ;
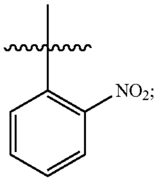 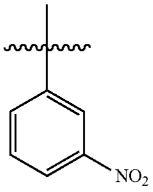 or 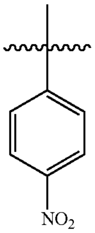 .
In some embodiments, $R^{28}$ has one of the following structures:
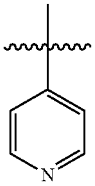 ; 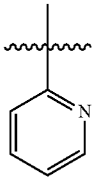 ; 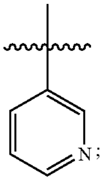 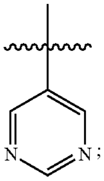 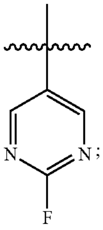
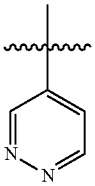 ; 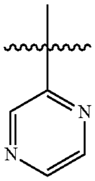 ; 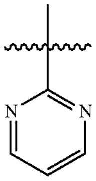 ; 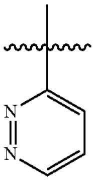 ; 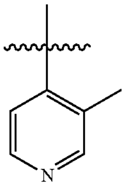 ;
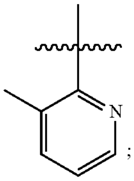 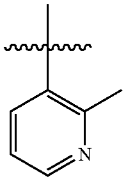 ; 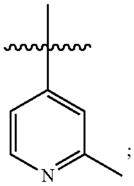 ; 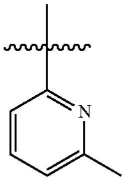 ;
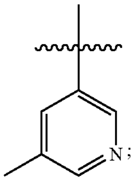 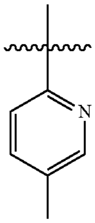 ; 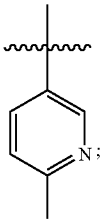 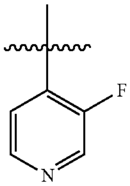 ;
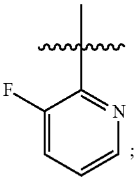 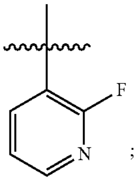 ; 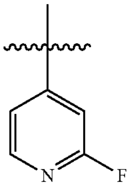 ; 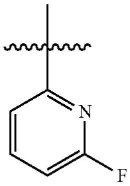 ;

-continued
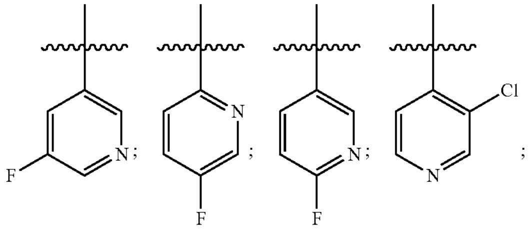
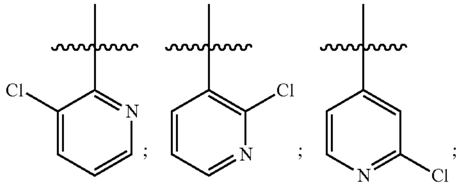
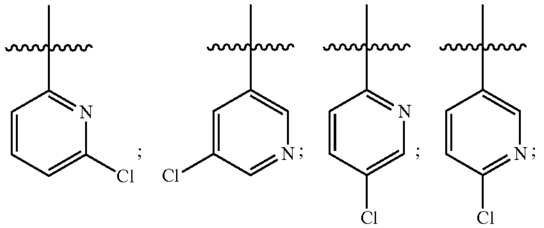
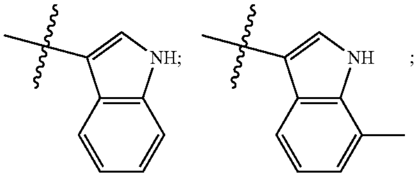
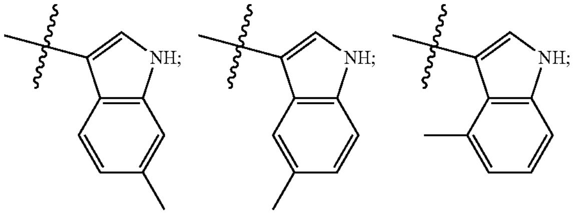
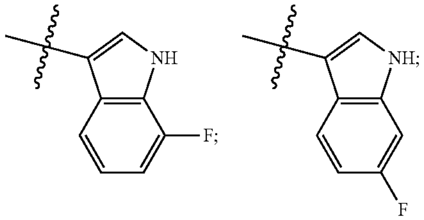
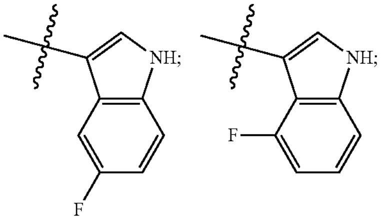
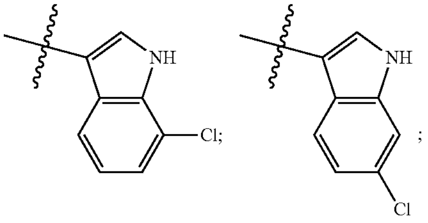
-continued
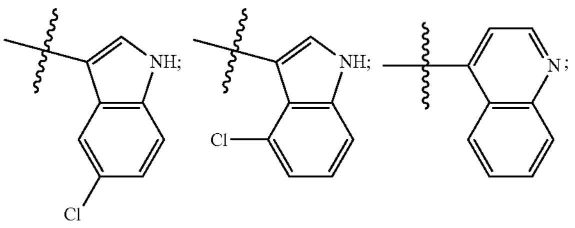
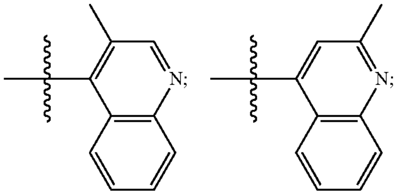
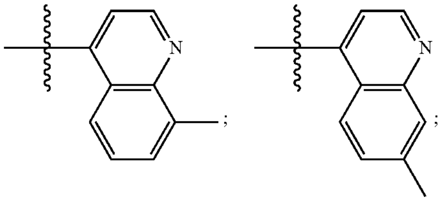
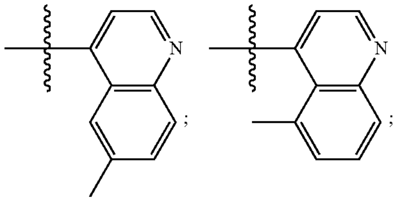
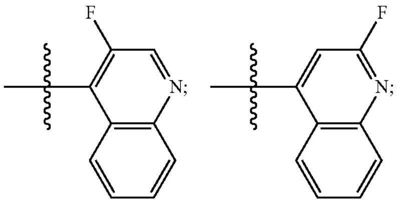
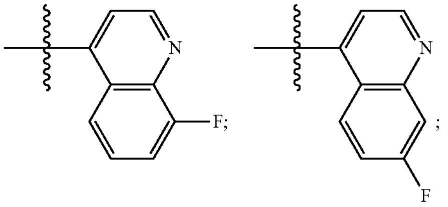
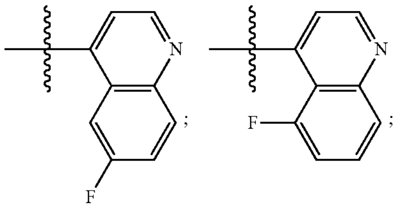
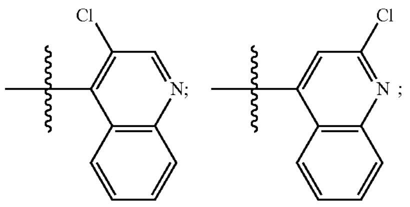

-continued
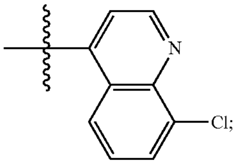
;
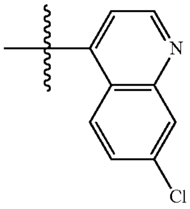
;
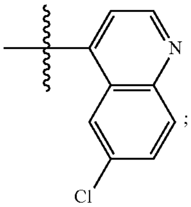
;
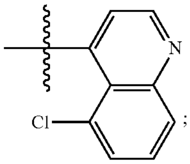
;
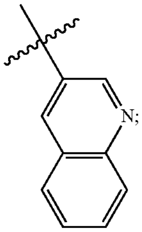
;
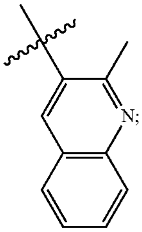
;
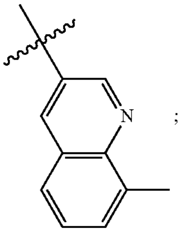
;
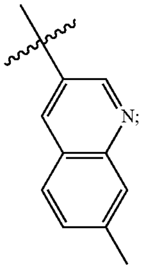
;
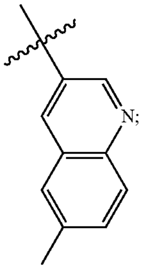
;
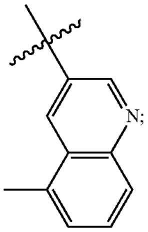
;
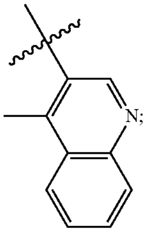
;
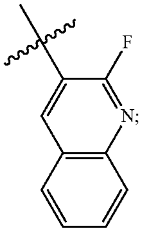
;
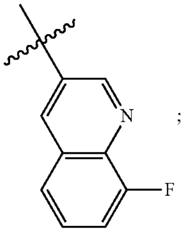
;
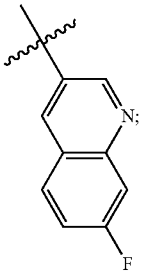
;
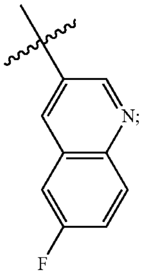
;
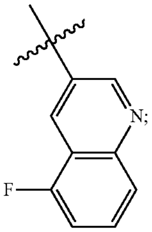
;
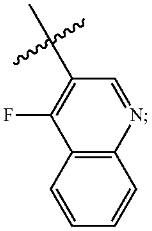
;
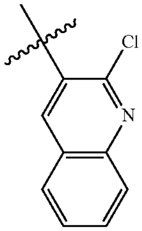
;
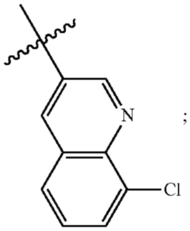
;
-continued
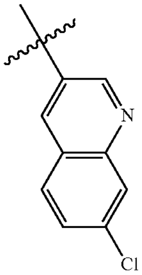
;
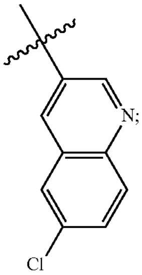
;
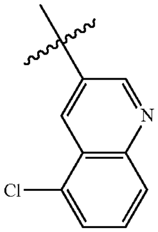
or
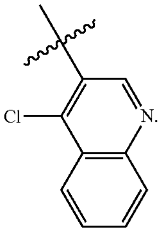
.
In certain embodiments, $R^{28}$ has one of the following structures:
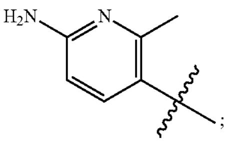
;
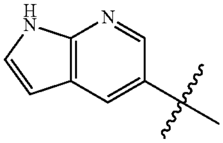
;
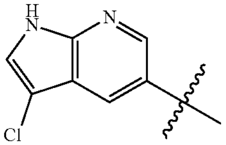
;
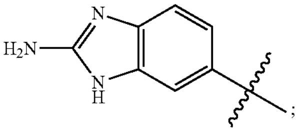
;
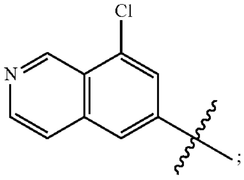
;
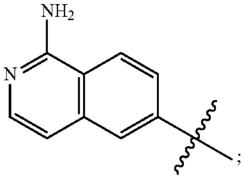
;
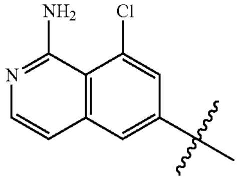
;
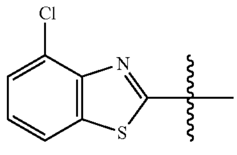
;
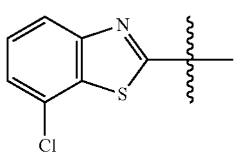
;
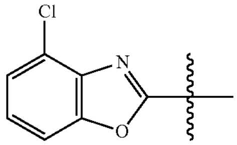
;
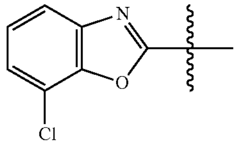
;
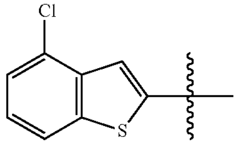
;

-continued
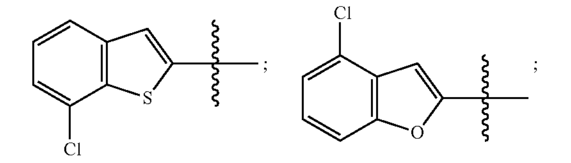
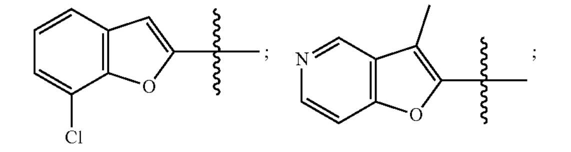
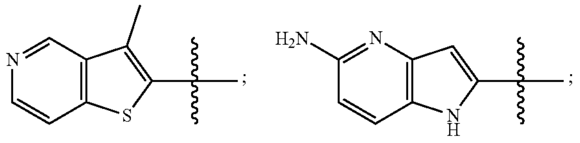
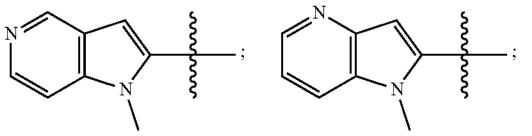
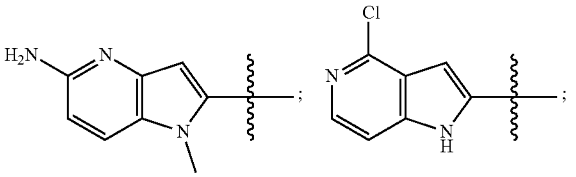
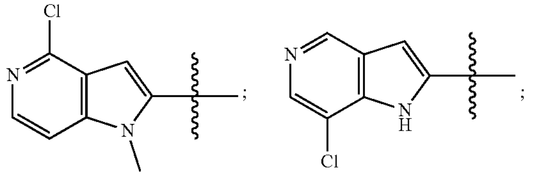
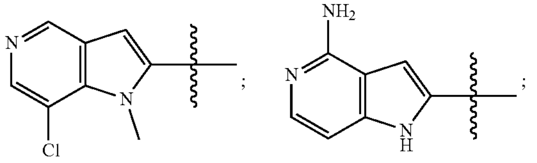
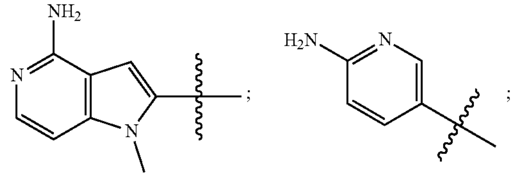
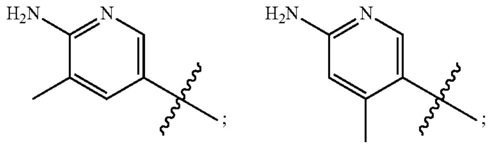
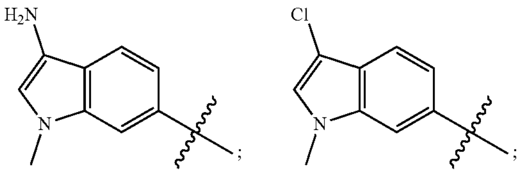
-continued
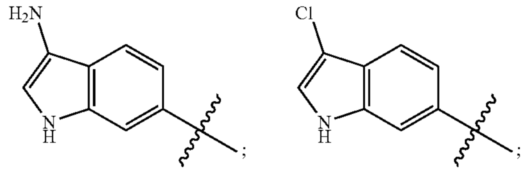
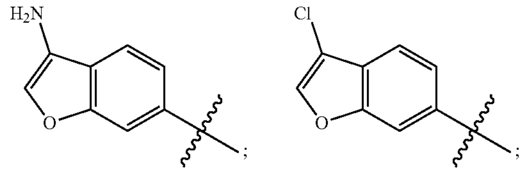
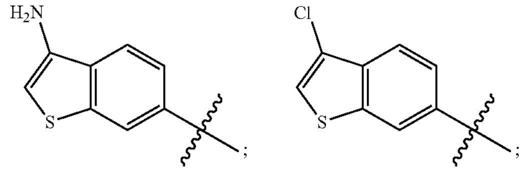
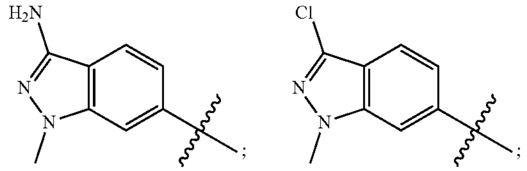
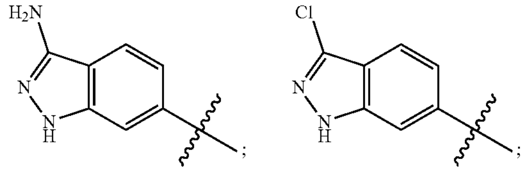
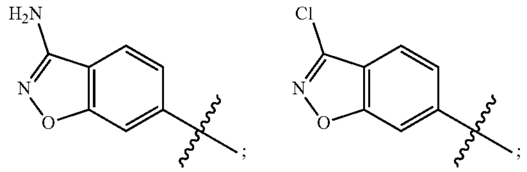
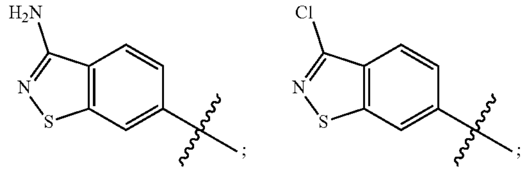
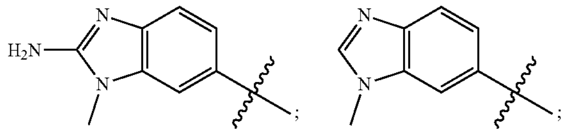
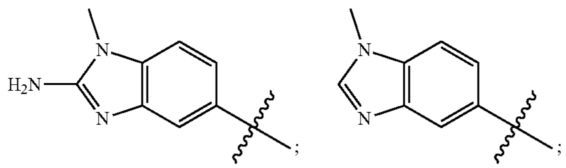
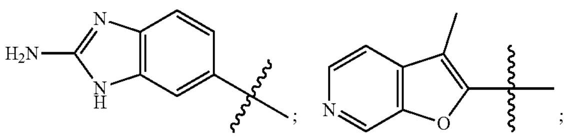

-continued
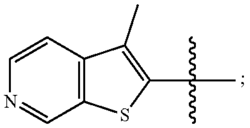 ; 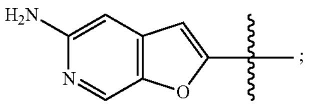 ;
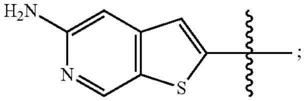 ;
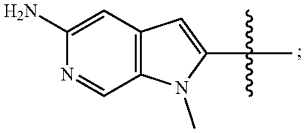 ;
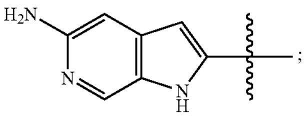 ; 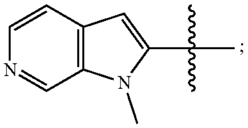 ;
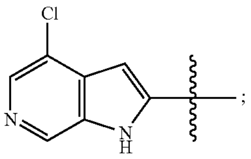 ; 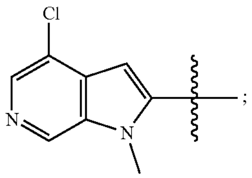 ;
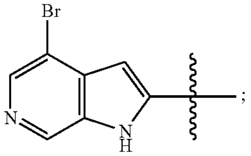 ; 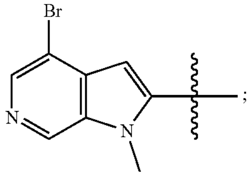 ;
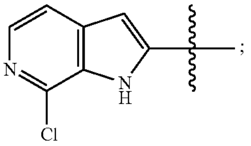 ; 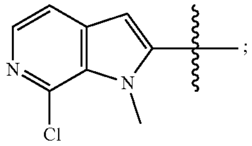 ;
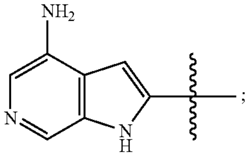 ; 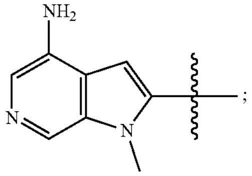 ;
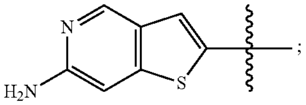 ;
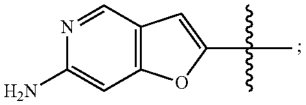 ;
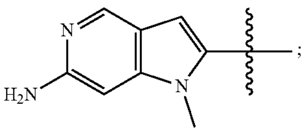 ;
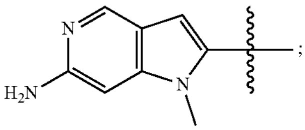 ; 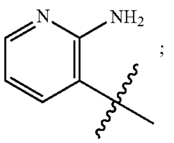 ;
-continued
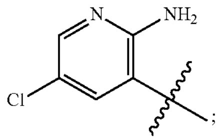 ; 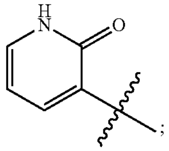 ;
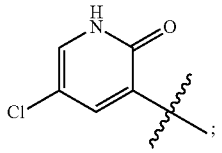 ; 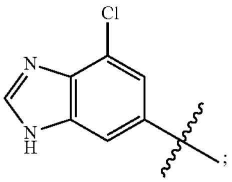 ;
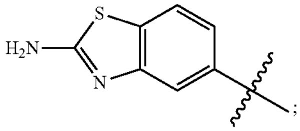 ;
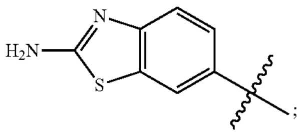 ;
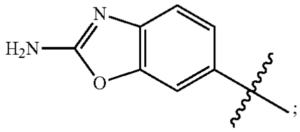 ;
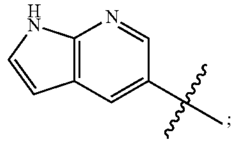 ; 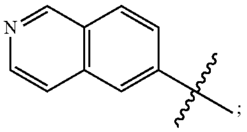 ;
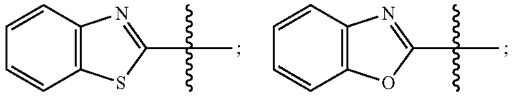 ;
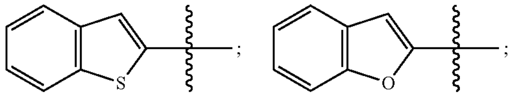 ;
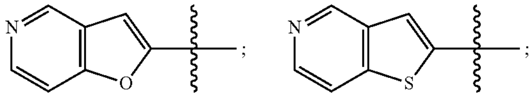 ;
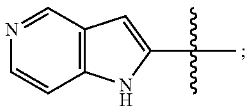 ; 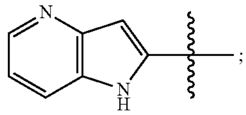 ;
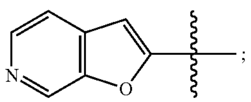 ; 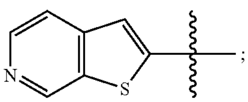 ;
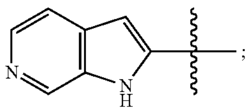 ; 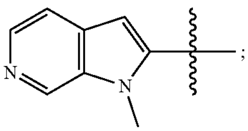 ;
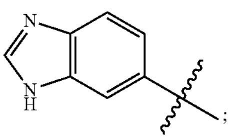 ; 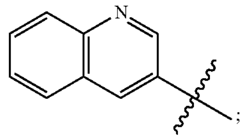 ;

-continued

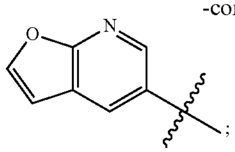;
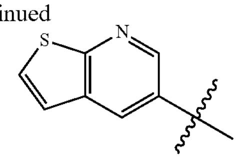;
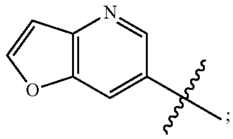;
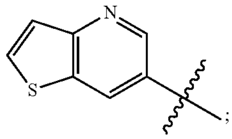;
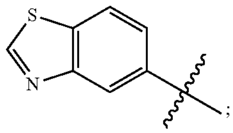;
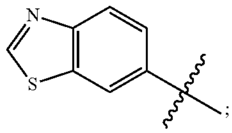;
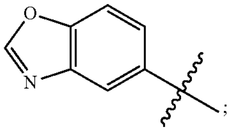; or
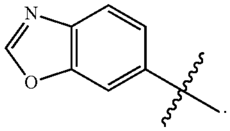.

In some embodiments, the compounds of Structure (I), (II) or (III), and embodiments thereof, can be in the form of a salt such as a pharmaceutically acceptable salt.

The compounds of Structure (I), (II) or (III), and embodiments thereof, are useful as inhibitors of MASP-2 and for therapeutic use. The compounds of Structure (I), (II) or (III), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Structure (I), (II) or (III), or an embodiment thereof, optionally in the form of a salt.

In some embodiments the compound Structure (I), (II) or (III) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Structure (I), (II) or (III) set forth in the Examples, including the compounds listed in Table 1, (e.g., compounds with selectivity for MASP-2 over thrombin). In certain aspects, one or more of the variables defining the compounds of Structure (I), (II) or (III) is selected from the corresponding substituents in the compounds of Structure (I), (II) or (III) in the Examples including the compounds listed in Table 1, preferably, those of the compounds with selectivity for MASP-2 over thrombin.

In certain aspects, the disclosure sets forth a stereochemically pure enantiomer or diastereomer (e.g., an optically active compound with one or more stereocenter(s)). Unless specifically indicated otherwise, for any compound with one or more stereocenters is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

Certain embodiments provide a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain embodiments provide a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., “Prodrugs of Benzamide,” Prodrugs 2007, 191-222; Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

III. Synthesis

Compounds described herein, including salts thereof, can be prepared using known organic synthesis techniques and can be synthesized according to any of numerous possible synthetic routes, such as those illustrated in the Examples below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent’s freezing temperature to the solvent’s boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March’s Advanced Organic Chemistry: Reactions, Mechanisms, and Structure, 6th Ed. (Wiley, 2007); Petursson et al., “Protecting Groups in Carbohydrate Chemistry,” *J. Chem. Educ.*, 1997, 74(11), 1297; and Wuts et al., Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high-performance liquid chromatography (HPLC) or thin layer chromatography (TLC).

The particular synthetic methods used in the Examples provide general guidance in connection with preparing the compounds of the disclosure. One skilled in the art would understand that the preparations can be modified or optimized using general knowledge of organic chemistry to prepare various compounds within the scope of the present disclosure.

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the disclosure may be synthesized and that a broad repertoire of synthetic organic reactions is available to be potentially employed in synthesizing compounds of the disclosure. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry*, Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II* (Pergamon Press, 1996); Smith et al., *March's Advanced Organic Chemistry: Reactions, Mechanisms, and Structure,* 6th Ed. (Wiley, 2007); Trost et al. (Ed.), *Comprehensive Organic Synthesis* (Pergamon Press, 1991).

IV. Methods of Treatment

In another aspect, the present disclosure provides a method of treating a patient suffering from, or at risk for developing a MASP-2-associated disease or disorder such as a MASP-2-dependent complement-associated disease or disorder comprising administering a small molecule inhibitor of MASP-2.

The compound can be any small molecule inhibitor of MASP-2. In some embodiments, the compound can be a small molecule inhibitor of MASP-2 that binds to the serine protease domain of MASP-2. In some embodiments, the compound can be a small molecule inhibitor such as a synthetic small molecule inhibitor of MASP-2. In some embodiments, the compound can be a small molecule inhibitor of MASP-2 that binds to the catalytic, substrate-binding region of MASP-2. In some embodiments, the compound selectively inhibits MASP-2 relative to thrombin. For example, in some embodiments, the compound is a compound of Structure (I), (II) or (III) as described in any of the foregoing embodiments.

As described in U.S. Pat. Nos. 7,919,094; 8,840,893; 8,652,477; 8,951,522, 9,011,860, 9,475,885, 9,644,035, U.S. Patent Application Publication Nos. US 2013/0344073, US 2013/0266560, US 2015/0166675, US 2017/0137537, US 2017/0166660, US 2017/0189525, US 2017/0267781, US 2017/0283508, US 2017/0253667, US 2018/0105604, and PCT Publication Nos. WO 2018/045054, WO 2019/036460 and U.S. patent application Ser. No. 62/688,611 (each of which is assigned to Omeros Corporation, the assignee of the instant application, each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or over-activation of the complement system can lead to serious disease, such as thrombotic microangiopathies (TMAs, including aHUS, TTP and HUS) in which endothelial damage as well as fibrin and platelet-rich thrombi in the microvasculature lead to organ damage. The lectin pathway plays a dominant role in activating complement in settings of endothelial cell stress or injury and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

Accordingly, in some embodiments, the method comprises administering to a patient suffering from or at risk for developing a MASP-2-dependent complement-associated disease or disorder an amount of a compound of the disclosure in an amount sufficient to inhibit MASP-2 dependent complement activation in the mammalian subject to thereby treat the disease or disorder. In some embodiments, the method can further comprise, prior to administering a compound of the disclosure to the patient, determining that the patient is afflicted with the lectin complement-associated disease or disorder.

In some embodiments, the MASP-2-dependent complement-associated disease or disorder is selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease, diffuse alveolar hemorrhage, or similar, as well as combinations thereof.

In some embodiments, the MASP-2-dependent complement-associated disease or disorder is a thrombotic microangiopathy (TMA) including thrombotic thrombocytopenic purpura (TTP), refractory TTP, Upshaw-Schulman Syndrome (USS), hemolytic uremic syndrome (HUS), atypical hemolytic syndrome (aHUS), non-Factor H-dependent atypical hemolytic syndrome, aHUS secondary to an infection, plasma therapy-resistant aHUS, a TMA secondary to cancer, a TMA secondary to chemotherapy, a TMA secondary to transplantation, or a TMA associated with hematopoietic stem cell transplant.

In some embodiments, the method comprises administering to a patient suffering from or at risk for developing graft-versus-host disease (GVHD), including acute GVHD, chronic GVHD or steroid-resistant GVHD an amount of a compound of the disclosure in an amount sufficient to inhibit MASP-2 dependent complement activation in the mammalian subject to thereby treat the disease or disorder. In some embodiments, the subject suffering from or at risk for developing GVHD has previously undergone, is undergoing, or will undergo a hematopoietic stem cell transplant.

In some embodiments, the method comprises administering to a patient suffering from, or at risk for developing diffuse alveolar hemorrhage (DAH) an amount of a compound of the disclosure in an amount sufficient to inhibit MASP-2 dependent complement activation in the mammalian subject to thereby treat the disease or disorder. In some embodiments, the subject suffering from, or at risk for developing DAH has previously undergone, is undergoing, or will undergo a hematopoietic stem cell transplant.

In some embodiments, the method comprises administering to a patient suffering from, or at risk for developing veno-occlusive disease (VOD) an amount of a compound of the disclosure in an amount sufficient to inhibit MASP-2 dependent complement activation in the mammalian subject to thereby treat the disease or disorder. In some embodiments, the subject suffering from, or at risk for developing VOD has previously undergone, is undergoing, or will undergo a hematopoietic stem cell transplant.

In some embodiments, the method comprises administering to a patient suffering from, or at risk for developing idiopathic pneumonia syndrome (IPS) an amount of a compound of the disclosure in an amount sufficient to inhibit MASP-2 dependent complement activation in the mammalian subject to thereby treat the disease or disorder. In some embodiments, the subject suffering from, or at risk for developing IPS has previously undergone, is undergoing, or will undergo a hematopoietic stem cell transplant.

In some embodiments, the method comprises administering to a patient suffering from, or at risk for developing capillary leak syndrome (CLS) an amount of a compound of the disclosure in an amount sufficient to inhibit MASP-2 dependent complement activation in the mammalian subject to thereby treat the disease or disorder. In some embodiments, the subject suffering from, or at risk for developing CLS has previously undergone, is undergoing, or will undergo a hematopoietic stem cell transplant.

In some embodiments, the method comprises administering to a patient suffering from, or at risk for developing engraftment syndrome (ES) an amount of a compound of the disclosure in an amount sufficient to inhibit MASP-2 dependent complement activation in the mammalian subject to thereby treat the disease or disorder. In some embodiments, the subject suffering from, or at risk for developing ES has previously undergone, is undergoing, or will undergo a hematopoietic stem cell transplant.

In some embodiments, the method comprises administering to a patient suffering from, or at risk for developing fluid overload (FO) an amount of a compound of the disclosure in an amount sufficient to inhibit MASP-2 dependent complement activation in the mammalian subject to thereby treat the disease or disorder. In some embodiments, the subject suffering from, or at risk for developing FO has previously undergone, is undergoing, or will undergo a hematopoietic stem cell transplant.

In some embodiments, the method comprises administering to a patient suffering from any of the above-referenced diseases or conditions an amount of a compound as disclosed in PCT Application No. PCT/US19/34225, which is hereby incorporated in its entirety.

In some embodiments, the MASP-2-dependent complement-associated disease or disorder is a renal condition including mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis, IgA nephropathy, and the like, as well as combinations thereof.

In some embodiments, the MASP-2-dependent complement-associated disease or disorder is renal fibrosis (e.g., tubulointerstitial fibrosis) and/or proteinuria in a subject suffering from or at risk for developing chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to, nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin), opiates (e.g., heroin), or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial Mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjogren's syndrome and post-infections glomerulonepthritis.

In some embodiments, the MASP-2-dependent complement-associated disease or disorder is an inflammatory reaction resulting from tissue or solid organ transplantation, including allotransplantation or xenotransplantation of whole organs (e.g., kidney, heart, liver, pancreas, lung, cornea, and the like) or tissue grafts (e.g., valves, tendons, bone marrow, and the like).

In some embodiments, the MASP-2-dependent complement-associated disorder is an ischemia reperfusion injury (I/R), including myocardial I/R, gastrointestinal I/R, renal I/R, and I/R following an aortic aneurism repair, I/R associated with cardiopulmonary bypass, cerebral I/R, stroke, organ transplant or reattachment of severed or traumatized limbs or digits; revascularization to transplants and/or replants, and hemodynamic resuscitation following shock, surgical procedures, or similar, as well as combinations thereof.

In some embodiments, the MASP-2-dependent complement-associated disease or disorder is a complication associated with non-obese diabetes (Type-1 diabetes or Insulin-dependent diabetes mellitus) and/or complications associated with Type-1 or Type-2 (adult onset) diabetes including diabetic angiopathy, diabetic neuropathy, diabetic retinopathy, diabetic macular edema, and the like, as well as combinations thereof.

In some embodiments, the MASP-2-dependent complement-associated disease or disorder is a cardiovascular disease or disorder, including Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); venous gas embolus (VGE); and inhibition of restenosis following stent placement, rotational atherectomy, percutaneous transluminal coronary angioplasty (PTCA), and the like as well as combinations thereof.

In some embodiments, the MASP-2-dependent complement-associated disease or disorder is an inflammatory gastrointestinal disorder, including pancreatitis, diverticulitis and bowel disorders including Crohn's disease, ulcerative colitis, irritable bowel syndrome, inflammatory bowel disease (IBD), or similar, as well as combinations thereof.

In some embodiments, the MASP-2-dependent complement-associated disease or disorder is a pulmonary disorder, including acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression, emphysema, and the like, as well as combinations thereof.

In some embodiments, the MASP-2-dependent complement-associated disease or disorder is an extracorporeal exposure-triggered inflammatory reaction and the method comprises treating a subject undergoing an extracorporeal circulation procedure. In some embodiments, the extracorporeal circulation procedure includes hemodialysis, plasmapheresis, leukopheresis, extracorporeal membrane oxygenation (ECMO), heparin-induced extracorporeal membrane oxygenation LDL precipitation (HELP), cardiopulmonary bypass (CPB), and the like.

In some embodiments, the MASP-2-dependent complement-associated disease or disorder is selected from inflammatory or non-inflammatory arthritides and other musculoskeletal disorders, e.g., osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy, systemic lupus erythematosus (SLE), or similar, as well as combinations thereof.

In some embodiments, the MASP-2-dependent complement-associated disease or disorder is a skin disorder; for example, psoriasis, autoimmune bullous dermatoses, eosinophilic spongiosis, bullous pemphigoid, epidermolysis bullosa acquisita, atopic dermatitis, herpes gestationis, and other skin disorders. In some embodiments, the MASP-2-dependent complement-associated disease or disorder is a thermal burn, chemical burn, or combinations thereof, including capillary leakage caused thereby.

In some embodiments, the MASP-2-dependent complement-associated disease or disorder is a peripheral nervous system (PNS) and/or central nervous system (CNS) disorder or injury including multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, demyelination, meningitis, or similar, as well as combinations thereof.

In some embodiments, the MASP-2-dependent complement-associated disease or disorder is sepsis or a condition resulting from sepsis including severe sepsis, septic shock, acute respiratory distress syndrome resulting from sepsis, hemolytic anemia, systemic inflammatory response syndrome, hemorrhagic shock, or the like, as well as combinations thereof.

In some embodiments, the MASP-2-dependent complement-associated disease or disorder is a urogenital disorder including painful bladder disease, sensory bladder disease, chronic abacterial cystitis and interstitial cystitis, male and female infertility, placental dysfunction and miscarriage, pre-eclampsia, or similar, as well as combinations thereof.

In some embodiments, the MASP-2-dependent complement-associated disease or disorder is an inflammatory reaction in a subject being treated with chemotherapeutics and/or radiation therapy, including for the treatment of cancerous conditions.

In some embodiments, the MASP-2-dependent complement-associated disease or disorder is an angiogenesis-dependent cancer, including a solid tumor(s), blood borne tumor(s), high-risk carcinoid tumors, tumor metastases, and the like, including combinations thereof.

In some embodiments, the MASP-2-dependent complement-associated disease or disorder is an angiogenesis-dependent benign tumor, including hemangiomas, acoustic neuromas, neurofibromas, trachomas, carcinoid tumors, pyogenic granulomas, or similar, as well as combinations thereof.

In some embodiments, the MASP-2-dependent complement-associated disease or disorder is an endocrine disorder including Hashimoto's thyroiditis, stress, anxiety, other potential hormonal disorders involving regulated release of prolactin, growth or insulin-like growth factor, adrenocorticotropin from the pituitary, or similar, as well as combinations thereof.

In some embodiments, the MASP-2-dependent complement-associated disease or disorder is an ophthalmic disease or disorder including age-related macular degeneration, glaucoma, endophthalmitis, and the like, as well as combinations thereof.

In some embodiments, the MASP-2-dependent complement-associated disease or disorder is an ocular angiogenic disease or condition including age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica, rubeosis, or similar, as well as combinations thereof.

In some embodiments, the MASP-2-dependent complement-associated disease or disorder is disseminated intravascular coagulation (DIC) or other complement mediated coagulation disorder, including DIC secondary to sepsis, severe trauma, including neurological trauma (e.g., acute head injury; see Kumura et al, *Acta Neurochirurgica* 55:23-28 (1987), infection (e.g., bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the MASP-2-dependent complement-associated disease or disorder is selected from the group consisting of acute radiation syndrome, dense deposit disease, Degos Disease, Catastrophic Antiphospholipid Syndrome (CAPS), Behcet's disease, cryoglobulinemia, paroxysmal nocturnal hemoglobinuria (PNH), cold agglutinin disease, and combinations thereof.

In some embodiments, the MASP-2-dependent complement-associated disease or disorder is selected from the group consisting of aHUS, HSCT-TMA, IgAN, Lupus Nephritis (LN), and combinations thereof.

In some embodiments, the method comprises administering to a patient suffering from, or at risk for developing a disease, disorder or condition associated with fibrin-induced activation of the complement system and the associated activation of the coagulation and/or contact systems an amount of a compound according to any one of the foregoing embodiments (e.g., a compound of Structure (I), (II) or (III)) in an amount sufficient to inhibit MASP-2 dependent complement activation in the mammalian subject to thereby treat the disease or disorder. In some embodiments, the subject is suffering from, or at risk of developing, a disease, disorder or condition associated with complement-related inflammation, excessive coagulation or contact system activation initiated by fibrin or activated platelets. In some embodiments, the subject is suffering from a disease or disorder selected from the group consisting of arterial thrombosis, venous thrombosis, deep vein thrombosis, post-surgical thrombosis, restenosis following coronary artery bypass graft and/or an interventional cardiovascular procedure (e.g., angioplasty or stent placement), atherosclerosis, plaque rupture, plaque instability, restenosis, hypotension, acute respiratory distress syndrome (ARDS), systemic inflammatory response syndrome (SIRS), disseminated intravascular coagulation (DIC), veno-occlusive disease (VOD), thrombotic microangiopathy, lupus nephritis, superficial thrombophlebitis, Factor V Leiden mutation, ischemic/reperfusion injury, human immunodeficiency virus (HIV) infection, undergoing hormone-replacement therapy (HRT), Alzheimer's disease and/or suffering from a hypercoagulable state.

In some embodiments, the subject is suffering from, or at risk for developing an acquired hypercoagulable state due to at least one or more of the following: undergoing therapy with a drug selected from the group consisting of 5-FU, GM-CSF, cisplatin, heparin, COX-2 inhibitor, contrast media, corticosteroids and antipsychotics; venous stasis (immobilization, surgery, etc.), antiphospholipid syndrome, cancer (promyelocytic leukemia, lung, breast, prostate, pancreas, stomach and colon tumors), tissue injury due to trauma or surgery, presence of a catheter in a central vein, acquired deficiency of a protein involved in clot formation (e.g., protein C), paroxysmal nocturnal hemoglobinuria (PNH), elevated levels of homocysteine, heart failure, presence of a mechanical valve, pulmonary hypertension with in situ thrombosis, atrial fibrillation, heparin-induced thrombocytopenia (HIT), heparin-induced thrombocytopenia and thrombosis (HITT), Kawasaki disease with in situ thrombus, Takayasu arteritis with in situ thrombus, thrombophilia of metastatic cancer, elevated Factor VIII levels, pregnancy, inflammatory bowel disease (IBD), or due to a genetic defect that causes or increases the risk of developing, a hypercoagulable state, such as a genetic defect selected from the group consisting of a Prothrombin 20210 gene mutation, an MTHFR mutation, a deficiency of protein C, a deficiency of protein S, a deficiency of protein A, a deficiency of protein Z, an antithrombin deficiency, and a genetic disorder producing thrombophilia.

In some embodiments, the subject is suffering from, or at risk for developing, a disease or disorder that is amenable to treatment with a kallikrein inhibitor. In some embodiments, the subject is suffering from, or at risk for developing a disease or disorder amenable to treatment with a kallikrein inhibitor is selected from the group consisting of hereditary angioedema, diabetic macular edema and bleeding during cardiopulmonary bypass. In some embodiments, the subject is suffering from, or at risk for developing, a disease or disorder that is amenable to treatment with a thrombin inhibitor, such as arterial thrombosis, venous thrombosis, pulmonary embolism, atrial fibrillation, heparin-induced thrombocytopenia, conversion from one anticoagulant to another, or off-label use for extracorporeal circuit patency of continuous renal replacement therapy (CRRT) in critically ill patients with HIT (maintenance).

In some embodiments, the subject has previously experienced, is currently suffering from, or is at risk for developing atrial fibrillation and the MASP-2 inhibitory compound (e.g., a compound of Structure (I), (II) or (III)) is administered in an amount sufficient to reduce the risk of stroke in said subject. In some embodiments, the subject is suffering from, or at risk for developing, a disease or disorder that is amenable to treatment with a factor XII inhibitor, such as deep vein thrombosis (both primary prophylaxis and extended therapy), pulmonary embolism, nonvalvular atrial fibrillation, prevention of recurrent ischemia after acute coronary syndrome in subjects with or without atrial fibrillation, end-stage renal disease, cerebral ischemia, angina, or to reduce or prevent clotting associated with medical devices (e.g., valves, small caliber grafts, etc.) and/or extracorporeal circuits.

In some embodiments, the subject has previously experienced, is currently suffering from, or is at risk for developing nonvalvular atrial fibrillation and the MASP-2 inhibitory compound (e.g., a compound of Structure (I), (II) or (III)) is administered in an amount sufficient to reduce the risk of stroke and/or embolism in said subject. In some embodiments, the subject has an acquired disease or disorder that increases the propensity for thromboembolism, such as a disease or disorder selected from the group consisting of atherosclerosis, antiphospholipid antibodies, cancer (e.g., promyelocytic leukemia, lung, breast, prostate, pancreatic, stomach and colon), hyperhomocysteinemia, infection, tissue injury, venous stasis (such as due to surgery, orthopedic or paralytic immobilization, heart failure, pregnancy, or obesity) and a subject taking oral contraceptives that contain estrogen.

In some embodiments, the subject is in need of anticoagulant therapy and the MASP-2 inhibitory compound (e.g., a compound of Structure (I), (II) or (III)) is used as a replacement for standard anticoagulant therapy (e.g., Warfarin). In some embodiments, the subject has a condition that normally prohibits standard anticoagulant therapy, such as CNS amyloid angiopathy. In some embodiments of the method, the MASP-2 inhibitory compound is administered as a bridging agent perioperatively in a subject otherwise on standard anticoagulation therapy. In some embodiments, the subject has sickle cell disease which is a vaso-occlusive disorder involving activation of platelets.

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane cofactor CD46 as well as complement factor H-related protein 1 (CFHR1) and complement factor H-related protein 3 (CFHR3). (Zipfel, P. F., et al., PloS Genetics 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10]. In: Pagon R A, Bird T D, Dolan C R, et al., editors. GeneReviews™, Seattle (WA): University of Washington, Seattle.

Hematopoietic stem cell transplant-associated TMA (HSCT-TMA) is a life-threatening complication that is triggered by endothelial injury. The kidney is the most commonly affected organ, though HSCT-TMA can be a multisystem disease that also involves the lung, bowel, heart, and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., Biol Blood Marrow Transplant, 11(8):571-5, 2005).

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., NEnglJ Med 36S(25): 2402-4, 2013). Clinical markers such as impaired kidney function, sustained hypertension, and heavy proteinuria (over 1 g per day) are associated with poor prognosis (Goto M et al., Nephrol Dial Transplant 24(10):3068-74, 2009; Berthoux F. et al., J Am Soc Nephrol 22(4):752-61, 2011). Proteinuria is the strongest prognostic factor independent of other risk factors in multiple large observational studies and prospective trials (Coppo R. et al., J Nephrol 18(5):503-12, 2005; Reich H. N., et al., J Am Soc Nephrol 18(12):3177-83, 2007). It is estimated that 15-20% of patients reach ESRD within 10 years of disease onset if left untreated (D'Amico G., Am J Kidney Dis 36(2):227-37, 2000). The diagnostic hallmark of IgAN is the predominance of IgA deposits, alone or with IgG, IgM, or both, in the glomerular mesangium.

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, 10th Ed, Lippincott Williams & Wilkins: pages 792-9, 2012) with a prevalence of 20-70 per 100,000 people in the U.S. Lupus nephritis often presents in patients with other symptoms of active SLE, including fatigue, fever, rash, arthritis, serositis, or central nervous system disease (Pisetsky D. S. et al., Med Clin North Am 81(1): 113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

V. Compositions, Dosage, and Administration

The compounds as described herein (e.g., a compound of Structure (I), (II) or (III)) can be administered in a manner compatible with the dosage formulation, and in such amount as will be effective or suitable for treatment. The quantity to be administered depends on a variety of factors including, e.g., the age, body weight, physical activity, and diet of the individual, and the desired effect. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied by a physician and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or liquid forms, preferably in unit dosage forms suitable for simple administration of precise dosages.

As used herein, the term "unit dosage form" refers to physically discrete units suitable as unitary dosages for humans and other mammals, each unit containing a predetermined quantity of an active agent calculated to produce the desired onset, tolerability, and/or efficacious effects, in association with a suitable pharmaceutical excipient (e.g., an ampoule). In addition, more concentrated dosage forms may be prepared, from which the more dilute unit dosage forms may then be produced.

The compounds described herein (e.g., a compound of Structure (I), (II) or (III)) can be administered to a subject in need of treatment using methods known in the art, such as by oral administration or by injection. The injection can be, e.g., subcutaneous, intravenous, intraperitoneal, or intramuscular. As described herein, parenteral formulations can be prepared in dosage unit form for ease of administration and uniformity of dosage. As used herein the term "unit dosage form" refers to physically discrete units suited as unitary dosages for the subject to be treated; each unit containing a predetermined quantity of active compound calculated to produce the desired therapeutic effect.

The pharmaceutical compositions of the present application comprise a therapeutically effective amount of a compound of the present disclosure ((e.g., a compound of Structure (I), (II) or (III)) formulated together with one or more pharmaceutically acceptable carriers or excipient. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations include, for example, sterile injectable aqueous or oleaginous suspensions formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound as disclosed in the foregoing embodiments (e.g., a compound of Structure (I), (II) or (III)) include ointments, pastes, creams, lotions, gels, powders, solutions, sprays, inhalants, or patches. For example, the active component may be ad-mixed under sterile conditions with a pharmaceutically acceptable carrier or excipient and any needed preservatives or buffers as may be required.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound according to any one of the foregoing embodiments, in such amounts and for such time as is necessary to achieve the desired result. As is well understood in the medical arts a therapeutically effective amount of a compound will be at a reasonable benefit/risk ratio applicable to any medical treatment.

In general, compounds (e.g., compounds of Structure (I), (II) or (III)) will be administered in therapeutically effective amounts via any of the usual and acceptable modes known in the art, either singly or in combination with one or more other therapeutic agents. A therapeutically effective amount may vary widely depending on the severity of the disease, the age and relative health of the subject, the potency of the compound used and other factors.

In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 250 mg, about 5 mg to about 150 mg, about 5 mg to about 100 mg, about 10 mg to about 75 mg, about 10 mg to about 50 mg, such as 10, 20, 30, 40, or about 50 mg, conveniently administered, e.g., in divided doses up to four times a day or in retard form. Suitable unit dosage forms for oral administration comprise from ca. 1 to 60 mg active ingredient.

In certain embodiments, a therapeutic amount or dose of the compound (e.g., compounds of Structure (I), (II) or (III)) may range from about 0.1 mg/kg to about 500 mg/kg, alternatively from about 1 mg/kg to about 50 mg/kg. In general, treatment regimens according to the present application comprise administration to a patient in need of such treatment from about 10 mg to about 1000 mg of the compound(s) per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds (e.g., compounds of Structure (I), (II) or (III)) and compositions thereof will be decided by an attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combination, e.g., a kit, comprising:

a) a first agent which is a compound of the application as disclosed herein, in free form or in pharmaceutically acceptable salt form, and b) at least one co-agent. The kit can comprise instructions for its administration.

Methods for preparing such dosage forms are known to those skilled in the art (see, e.g., REMINGTON'S PHARMACEUTICAL *SCIENCES,* 18th ED., Mack Publishing Co., Easton, PA (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, 18th ED., Mack Publishing Co., Easton, PA (1990)).

General Methods

The following examples are provided by way of illustration only and not by way of limitation. Those of skill will readily recognize a variety of noncritical parameters which could be changed or modified to yield essentially similar results.

If not otherwise stated, chromatography refers to flash chromatography conducted on silica gel. Amine column refers to flash chromatography conducted on Redisep Rf Gold high performance amine column.

HPLC purification was performed on a Waters preparative reverse phase HPLC system with the combination of UV/MS detectors (254 nm and 280 nm) and XBridge Prep (19×50 mm) $C_{18}$ 10 μM OBD column. Eluents were a mixture of water and acetonitrile (with 0.05% trifluoroacetic acid). Flow rate was typically 50 mL/min with a linear gradient of water in acetonitrile from 5-95% in 8 minutes. The injection volume was from 0.2 to 1 mL with maximum 20 mg per load.

Abbreviations

μ micro
° C. degrees Celsius
Ac acetyl
anhyd anhydrous
aq aqueous
atm atmosphere(s)
Bn benzyl
Boc tert-butoxycarbonyl
Bu butyl
calcd calculated
Cbz benzyloxycarbonyl
CPME cyclopentyl methyl ether
concd concentrated
conc concentration
DCC N, N'-dicyclohexylcarbodiimide
DIEA N,N-diisopropylethylamine
DMAP 4-(N,N-dimethylamino)pyridine
DMF dimethylformamide
DMSO dimethylsulfoxide
EDC N-(3-dimethylaminopropyl)-N'-ethylcarbodiimide hydrochloride
equiv equivalent
ES electrospray
Et ethyl
$Et_2O$ diethyl ether
g gram(s)
h hour(s)
HATU N-[(Dimethylamino)-1H-1,2,3-triazolo-[4,5-b]pyridin-1-ylmethylene]-N-methylmethanaminium hexafluorophosphate N-oxide
HBTU N,N,N',N'-Tetramethyl-O-(1H-benzotriazol-1-yl) uronium hexafluorophosphate, O-(Benzotriazol-1-yl)-
HPLC high-performance liquid chromatography/high-performance liquid chromatography
HOBt 1-hydroxybenzotriazole hydrate
iPrOH iso-propanol
L liter(s)
LiOH lithium hydroxide
m milli
M molar
MeCN acetonitrile
min minute(s)
mL milliliter
mol mole; molecular (as in mol wt)
MS mass spectrometry
MW molecular weight
NBS N-bromosuccinimide
NHS N-hydroxysuccinimide
NMM 4-methylmorpholine
NMR nuclear magnetic resonance
ortho
obsd observed
p para
Ph phenyl
ppt precipitate
Pr propyl
psi pounds per square inch
temp temperature
TFA trifluoroacetic acid
THF tetrahydrofuran Example 1

Preparation of Methyl (3R,5S)-1-((R)-2-amino-4-phenylbutanoyl)-5-((4-carbamimidoylbenzyl)carbamoyl)pyrrolidine-3-carboxylate ditrifluoroacetate (Compound I-1)

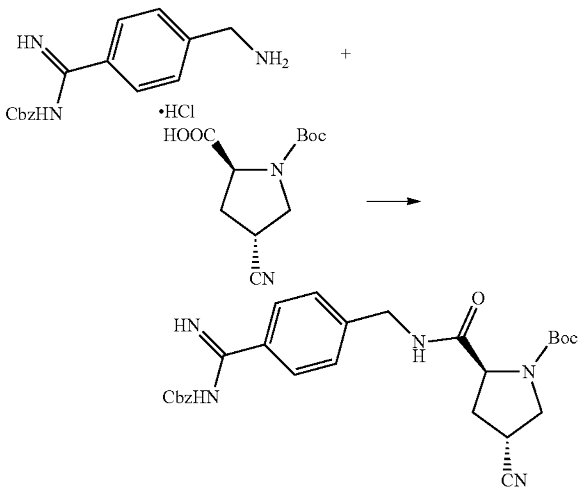

Step 1: To 1-(tert-butyl) 2-methyl (2S,4R)-4-cyanopyrrolidine-1,2-dicarboxylate (90 mg, 0.38 mmol, 1 eq.) and N-hydroxysuccinamide (48 mg, 0.42 mmol, 1.1 eq.) in dichloromethane (3.8 mL, 0.1M), was added DCC (93 mg, 0.38 mmol, 1.1 eq.). After 1 h stirring, benzyl ((4-(aminomethyl)phenyl)(imino)methyl)carbamate hydrochloride (120 mg, 0.38 mmol, 1 eq.) suspended in saturated sodium bicarbonate (3.8 mL, 0.1 M) was added to the solution. The mixture was allowed to stir for another hour, after which, the layers were partitioned and the organic was run through a 0.45 micron filter and concentrated. The resulting residue was purified on a silica column using EtOAc/Heptane to yield tert-butyl (2S,4R)-2-((4-(N-((benzyloxy)carbonyl)carbamimidoyl)benzyl)carbamoyl)-4-cyanopyrrolidine-1-carboxylate (180 mg, 95%) as an off-white film.

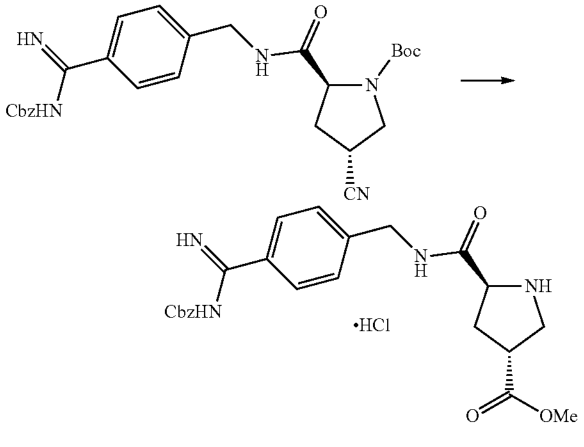

Step 2: To a solution of tert-butyl (2S,4R)-2-((4-(N-((benzyloxy)carbonyl)carbamimidoyl)benzyl)carbamoyl)-4-cyanopyrrolidine-1-carboxylate (180 mg, 0.36 mmol, 1 eq.) in methanol (1.8 mL, 0.2M), was added HCl in dioxane (4M, 1.8 mL, 0.2M) and the reaction mixture was stirred until reaction was complete as monitored by LCMS. The reaction mixture was then concentrated in vacuo to afford methyl (3R,5S)-5-((4-(N-((benzyloxy)carbonyl)carbamimidoyl)benzyl)carbamoyl)pyrrolidine-3-carboxylate hydrochloride as a clear film which was carried forward without further purification.

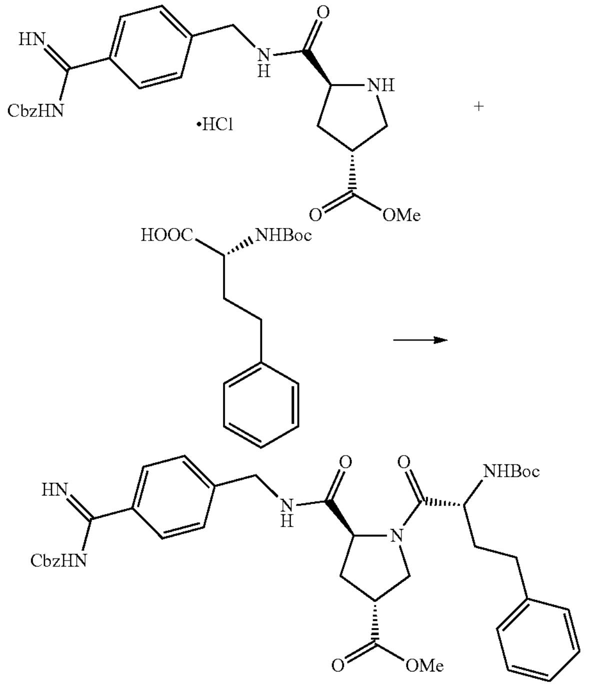

Step 3: To a solution of methyl (3R,5S)-5-((4-(N-((benzyloxy)carbonyl)carbamimidoyl)benzyl)carbamoyl)pyrrolidine-3-carboxylate hydrochloride (0.36 mmol, 1 eq.) and D-homophenylalanine (121 mg, 0.43 mmol, 1.2 eq.), in anhydrous N,N-dimethylformamide (7.2 mL, 0.05M) was added DIEA (250 μL, 1.2 mmol, 4 eq.) followed by hydroxybenzotriazole (60 mg, 0.43 mmol, 1.2 eq.) and 1-ethyl-3-(3-dimethylaminopropyl)carbodiimide (83 mg, 0.43 mmol, 1.2 eq.). After stirring overnight, reaction mixture was diluted with ethyl acetate then extracted with saturated ammonium chloride, followed by saturated sodium bicarbonate, then water (2 times), then brine. The organic layer was then concentrated and purified on a silica column using EtOAc/Heptane to afford methyl (3R,5S)-5-((4-(N-((benzyloxy)carbonyl)carbamimidoyl)benzyl)carbamoyl)-1-((R)-2-((tert-butoxycarbonyl)amino)-4-phenylbutanoyl)pyrrolidine-3-carboxylate (34 mg, 13%).

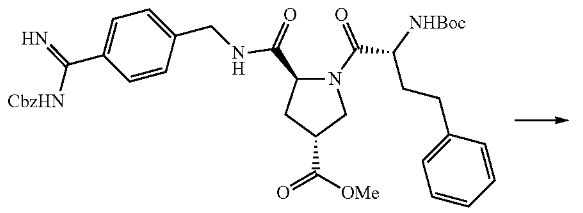

-continued

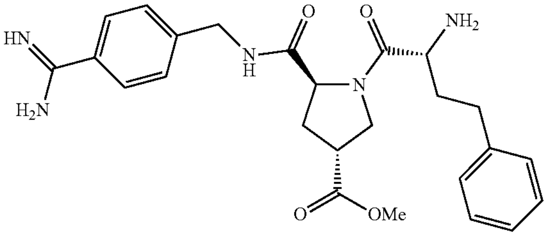

•2TFA

Step 4: To a solution of methyl (3R,5S)-5-((4-(N-((benzyloxy)carbonyl)carbamimidoyl)benzyl)carbamoyl)-1-((R)-2-((tert-butoxycarbonyl)amino)-4-phenylbutanoyl)pyrrolidine-3-carboxylate (30 mg, 0.04 mmol, 1 eq.) in dichloromethane (100 μL, 0.2M) was added trifluoroacetic acid (40 μL, 0.45 mmol, 20 eq.). After stirring for 3 h reaction was complete as monitored by LCMS and the reaction mixture was concentrated to dryness and dissolved in anhydrous methanol (200 μL, 0.1M) to which 10% palladium on carbon (5 mg, 15 wt %) was added and the reaction mixture was sparged with argon for 10 minutes, followed by hydrogen for 10 minutes. The reaction mixture was left under a balloon of hydrogen for approximately 30 mins until reaction completion which was monitored by LCMS. The reaction mixture then sparged with argon for 10 minutes and filtered over celite. The filtrate was then concentrated in vacuo to afford methyl (3R,5S)-1-((R)-2-amino-4-phenylbutanoyl)-5-((4-carbamimidoylbenzyl)carbamoyl)pyrrolidine-3-carboxylate ditrifluoroacetate (27.1 mg, 98% over 2 steps) as a solid white powder following lyophilization.

Example 2

Preparation of (2S,4S)-1-((R)-2-amino-4-phenylbutanoyl)-N-(4-carbamimidoylbenzyl)-4-(methoxymethyl)pyrrolidine-2-carboxamide dihydrochloride (Compound I-2)

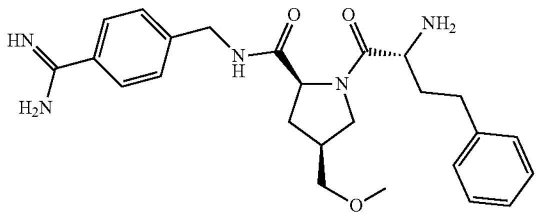

•2HCl (2S,4S)-1-((R)-2-amino-4-phenylbutanoyl)-N-(4-carbamimidoylbenzyl)-4-(methoxymethyl)pyrrolidine-2-carboxamide dihydrochloride was synthesized according to the procedures for Example 1 except that in Step 4, the Boc group was deprotected with HCl in isopropanol with anhydrous methanol as the solvent.

Example 3

Preparation of (2S,4R)-1-((R)-2-amino-4-phenylbutanoyl)-N-(4-carbamimidoylbenzyl)-4-phenylpyrrolidine-2-carboxamide dihydrochloride (Compound I-3)

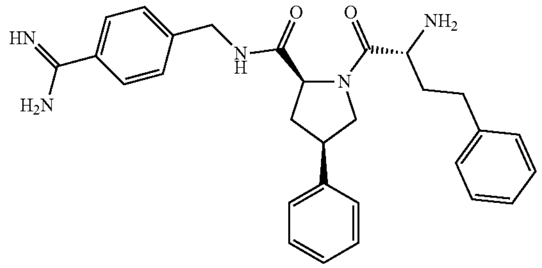 [SMILES: N=C(N)c1ccc(CNC(=O)[C@@H]2C[C@H](c3ccccc3)CN2C(=O)[C@H](N)CCc2ccccc2)cc1]

(2S,4R)-1-((R)-2-amino-4-phenylbutanoyl)-N-(4-carbamimidoylbenzyl)-4-phenylpyrrolidine-2-carboxamide dihydrochloride was synthesized according to the procedures for Example 2.

Example 4

Preparation of ((R)-1-((2S,4R)-2-((4-carbamimidoylbenzyl)carbamoyl)-4-phenylpyrrolidin-1-yl)-1-oxo-4-phenylbutan-2-yl)glycine (Compound I-4)

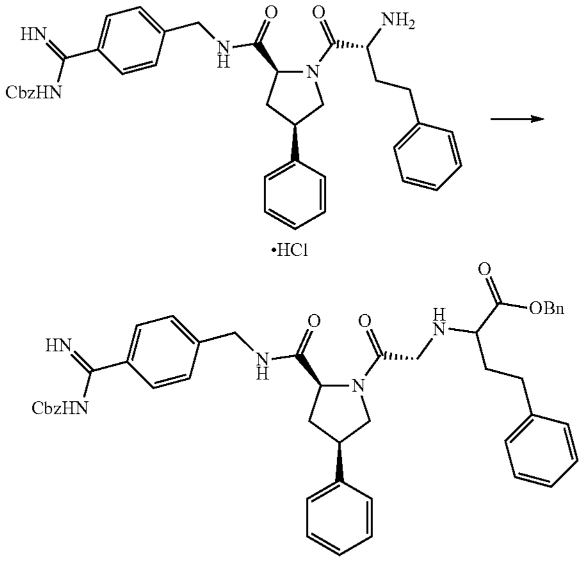

Step 1: To a solution of benzyl ((4-(((2S,4R)-1-((R)-2-amino-4-phenylbutanoyl)-4-phenylpyrrolidine-2-carboxamido)methyl)phenyl)(imino)methyl)carbamate hydrochloride (114 mg, 0.17 mmol, 1 eq.) in anhydrous acetonitrile (1.1 mL, 0.16M), DIEA (120 μL, 1.5M) was added followed by benzyl bromoacetate (35 μL, 0.22 mmol, 1.3 eq.). The reaction mixture was stirred for 16 h, at which point additional benzyl bromoacetate (35 μL, 0.22 mmol, 1.3 eq.) was added and the reaction was stirred for a further 24 h. The reaction mixture was then diluted with ethyl acetate and washed four times with water, then one time with brine. The organic layer was concentrated and purified on an amine column using EtOAc/Heptane to afford benzyl ((R)-1-((2S, 4R)-2-((4-(N-((benzyloxy)carbonyl)carbamimidoyl)benzyl) carbamoyl)-4-phenylpyrrolidin-1-yl)-1-oxo-4-phenylbutan-2-yl)glycinate (43 mg, 32%).

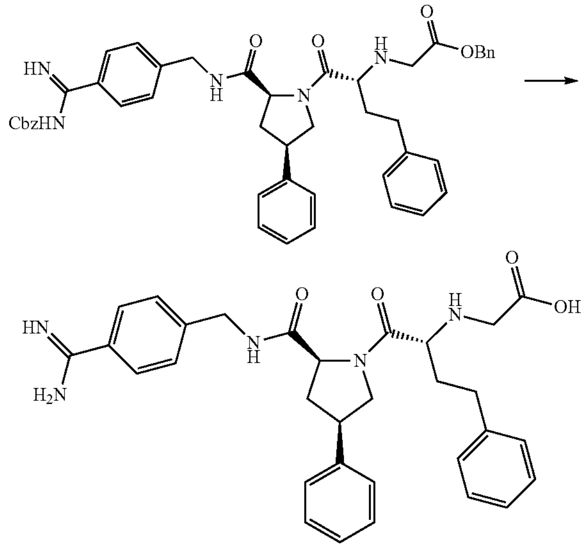

Step 2: To a solution of benzyl ((R)-1-((2S,4R)-2-((4-(N-((benzyloxy)carbonyl)carbamimidoyl)benzyl)carbamoyl)-4-phenylpyrrolidin-1-yl)-1-oxo-4-phenylbutan-2-yl)glycinate (43 mg, 0.056 mmol, 1 eq.) in anhydrous methanol (560 µL, 0.1M) was added 10% palladium on carbon (20 mg, 50 wt %) and the reaction mixture was sparged with argon for 10 minutes, followed by hydrogen for 10 minutes. The reaction mixture was left under a balloon of hydrogen for approximately 2 hr until reaction completion which was monitored by LCMS. The reaction mixture then sparged with argon for 10 minutes and filtered over Celite. The filtrate was then concentrated in vacuo to afford ((R)-1-((2S, 4R)-2-((4-carbamimidoylbenzyl)carbamoyl)-4-phenylpyrrolidin-1-yl)-1-oxo-4-phenylbutan-2-yl)glycine (22.4 mg, 74%) as a solid white powder following lyophilization.

Example 5

Preparation of (2S,4S)-1-((R)-2-amino-4-phenylbutanoyl)-N-(4-carbamimidoylbenzyl)-4-phenylpyrrolidine-2-carboxamide dihydrochloride (Compound I-11)

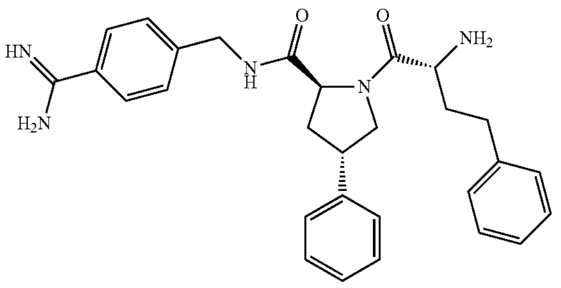 [SMILES: N=C(N)c1ccc(CNC(=O)[C@@H]2C[C@@H](c3ccccc3)CN2C(=O)[C@H](N)CCc2ccccc2)cc1]

(2S,4S)-1-((R)-2-amino-4-phenylbutanoyl)-N-(4-carbamimidoylbenzyl)-4-phenylpyrrolidine-2-carboxamide dihydrochloride was synthesized according to the procedures for Example 2.

Example 6

Preparation of (2S)-1-((R)-2-Amino-4-Phenylbutanoyl)-N-(4-Carbamimidoylbenzyl)-4-Phenylpyrrolidine-2-Carboxamide Dihydrochloride (Compounds I-22 and I-23

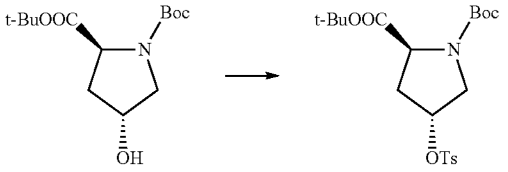

Step 1: To di-tert-butyl (2S,4R)-4-hydroxypyrrolidine-1,2-dicarboxylate (500 mg, 1.7 mmol, 1 eq.) and triethylamine (840 µL, 6 mmol, 3 eq.) in dichloromethane (8 mL, 0.25M), was added DMAP (24 mg, 0.2 mmol, 0.1 eq.) followed by tosyl chloride (460 mg, 2.4 mmol, 1.2 eq.). After 16 h stirring, the mixture was further diluted with dichloromethane, washed twice with 1N HCl, followed by 1N NaOH 2 times then by brine. The organic layer was dried over sodium sulfate, concentrated under vacuum and the resulting residue purified on a silica column using EtOAc/Heptane to yield di-tert-butyl (2S,4R)-4-(tosyloxy)pyrrolidine-1,2-dicarboxylate (690 mg, 90%) as a white solid.

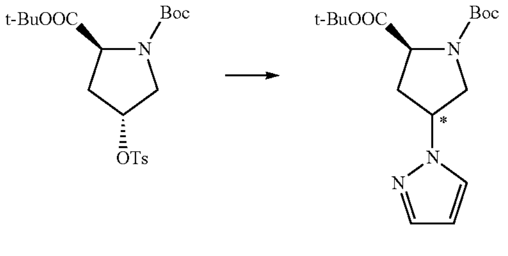

Step 2: A mixture consisting of di-tert-butyl (2S,4R)-4-(tosyloxy)pyrrolidine-1,2-dicarboxylate (100 mg, 0.23 mmol, 1 eq.), 1H-pyrazole (30 mg, 0.46 mmol, 2 eq.) and cesium carbonate (98 mg, 0.3 mmol, 1.5 eq.) in N,N-dimethylformamide (1 mL, 0.2M) was sealed and heated to 60° C. After stirring for 16 h, the mixture was partitioned between ethyl acetate and saturated ammonium chloride. The organic layer was further washed with water followed by brine then dried over sodium sulfate and concentrated. The resulting residue was purified on a silica column using EtOAc/Heptane to yield di-tert-butyl (2S)-4-(1H-pyrazol-1-yl)pyrrolidine-1,2-dicarboxylate (41.1 mg, 53%) as a white solid.

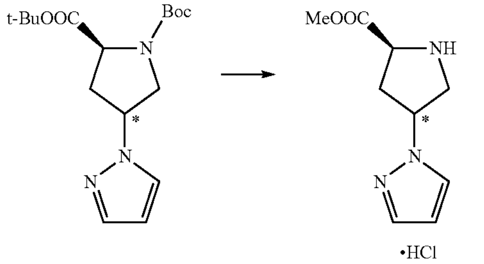

Step 3: To a solution of di-tert-butyl (2S)-4-(1H-pyrazol-1-yl)pyrrolidine-1,2-dicarboxylate (41 mg, 0.12 mmol, 1 eq.) in methanol (2.4 mL, 0.05M) was added hydrochloric acid in dioxane (4N solution, 300 μL, 0.4 mmol, 20 eq.). After stirring for 16 h, the reaction was incomplete, so additional hydrochloric acid in dioxane (4N solution, 300 μL, 0.4 mmol, 20 eq.) was added and the reaction mixture was heated to 40° C. After 3d the reaction mixture was concentrated in vacuo and carried to the next step without further purification.

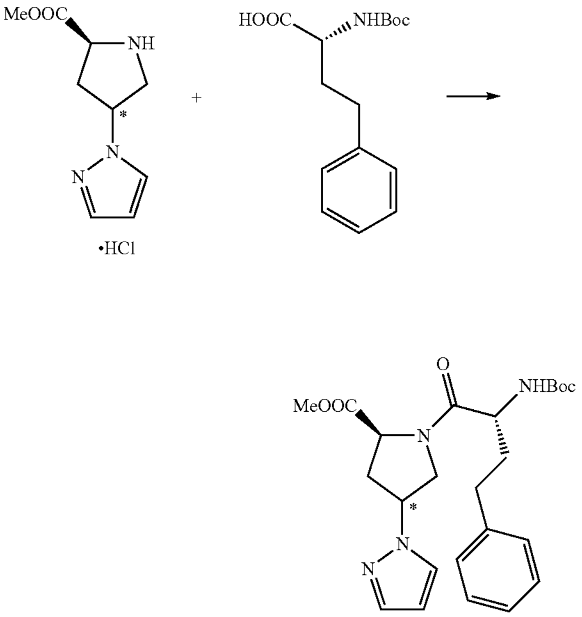

Step 4: To a solution of methyl (2S)-4-(1H-pyrazol-1-yl) pyrrolidine-2-carboxylate hydrochloride (0.12 mmol, 1 eq.) and D-homophenylalanine (40 mg, 0.14 mmol, 1.2 eq.), in anhydrous N,N-dimethylformamide (1.2 mL, 0.05M) was added DIEA (84 μL, 0.48 mmol, 4 eq.) followed by hydroxybenzotriazole (20 mg, 0.14 mmol, 1.2 eq.) and 1-ethyl-3-(3-dimethylaminopropyl)carbodiimide (28 mg, 0.14 mmol, 1.2 eq.). After stirring overnight, the reaction mixture was diluted with ethyl acetate. The resulting solution was washed with saturated ammonium chloride, followed by saturated sodium bicarbonate, water then brine. The organic layer was concentrated and the resulting residue purified on a silica column using EtOAc/Heptane to afford methyl (2S)-1-((R)-2-((tert-butoxycarbonyl)amino)-4-phenylbutanoyl)-4-(1H-pyrazol-1-yl)pyrrolidine-2-carboxylate (34 mg, 58%).

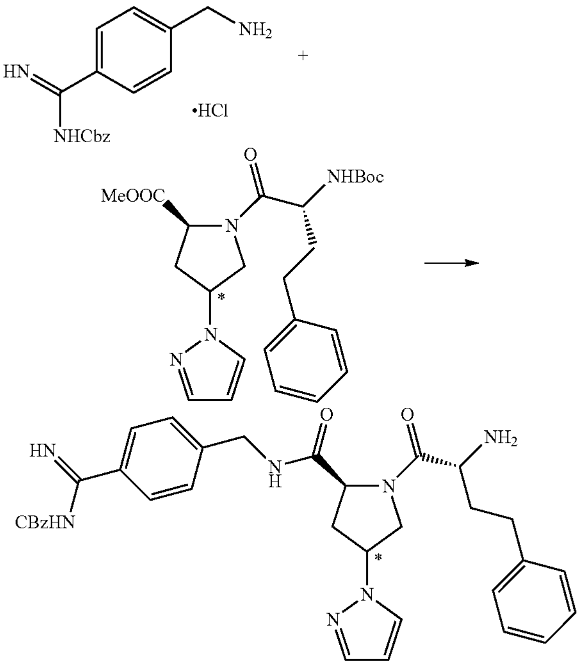

Step 5: Methyl (2S)-1-((R)-2-((tert-butoxycarbonyl) amino)-4-phenylbutanoyl)-4-(1H-pyrazol-1-yl)pyrrolidine-2-carboxylate was saponified using THF, $H_2O$, and LiOH and stirring at room temperature; the reaction mixture was conc'd to remove THF and to the aqueous solution was added 10% $KHSO_4$ solution. The resulting ppt collected via vacuum filtration and washed with hexanes. To the product of saponification, (2S)-1-((R)-2-((tert-butoxycarbonyl) amino)-4-phenylbutanoyl)-4-(1H-pyrazol-1-yl)pyrrolidine-2-carboxylic acid (0.07 mmol), benzyl ((4-(aminomethyl) phenyl)(imino)methyl)carbamate hydrochloride (29 mg, 0.09 mmol), was added DIEA (50 μL, 0.28 mmol) and DMF (540 μL). After cooling the reaction mixture to 0° C., HBTU (35 mg, 0.12 mmol) was added in a single portion and the reaction was left to stir at RT until completion. The mixture was concentrated and purified by silica column using EtOAc/Heptane which produced two crude products, one which was dissolved in ethyl acetate and washed with 0.1N HCl to afford an isomer of benzyl ((4-(((2S)-1-((R)-2-amino-4-phenylbutanoyl)-4-(1H-pyrazol-1-yl)pyrrolidine-2-carboxamido)methyl)phenyl)(imino)methyl)carbamate (8.5 mg, 13%). The other crude material was purified on a second column using MeOH/dichloromethane to afford the another isomer of benzyl ((4-(((2S)-1-((R)-2-amino-4-phenylbutanoyl)-4-(1H-pyrazol-1-yl)pyrrolidine-2-carboxamido)methyl)phenyl)(imino)methyl)carbamate (9.8 mg, 15%).

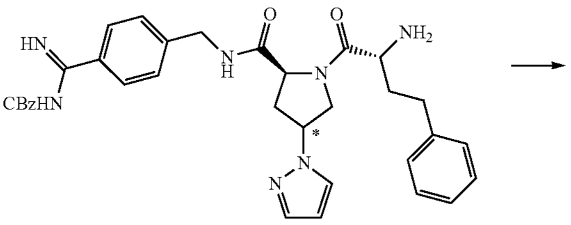

-continued

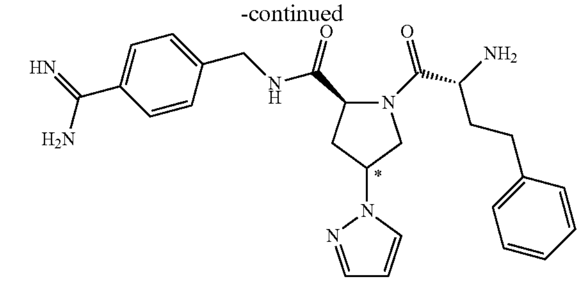

•2 HCl

Step 6: Each isomer of benzyl ((4-(((2S)-1-((R)-2-amino-4-phenylbutanoyl)-4-(1H-pyrazol-1-yl)pyrrolidine-2-carboxamido)methyl)phenyl)(imino)methyl)carbamate was deprotected using Step 4 of Example 1 except that the Boc group was deprotected with HCl in isopropanol with anhydrous methanol as the solvent to afford the title compounds.

Example 7

Preparation of (2S,4S)—N-((1H-pyrrolo[3,2-c]pyridin-2-yl)methyl)-1-((R)-2-amino-4-phenylbutanoyl)-4-(methoxymethyl)pyrrolidine-2-carboxamide ditrifluoroacetate (Compound I-24)

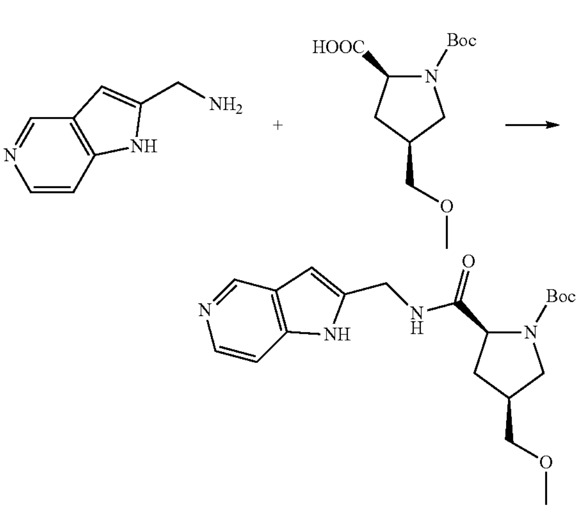

Step 1: Tert-butyl (2S,4S)-2-(((1H-pyrrolo[3,2-c]pyridin-2-yl)methyl)carbamoyl)-4-(methoxymethyl)pyrrolidine-1-carboxylate was prepared using the conditions in Step 5 of Example 6.

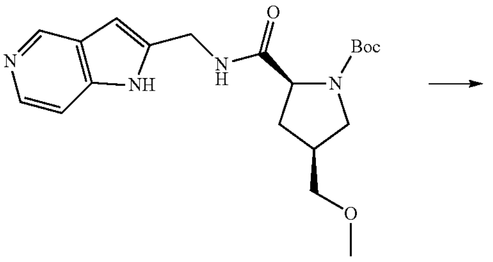

-continued

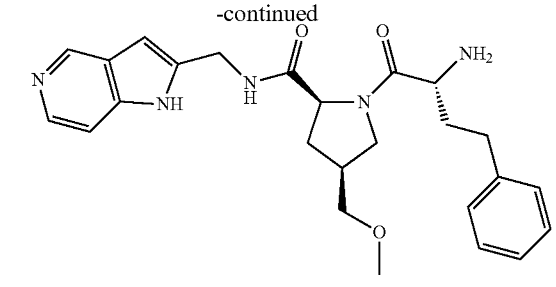

•2 TFA

Step 2: (2S,4S)—N-((1H-pyrrolo[3,2-c]pyridin-2-yl)methyl)-1-((R)-2-amino-4-phenylbutanoyl)-4-(methoxymethyl)pyrrolidine-2-carboxamide ditrifluoroacetate was prepared using the conditions in Step 2-4 of Example 1 except TFA/dichloromethane was used to deprotect the Boc group and no hydrogenation was performed in Step 4.

Example 8

Preparation of (2S,4S)—N-((1H-pyrrolo[3,2-c]pyridin-2-yl)methyl)-1-((R)-2-amino-4-phenylbutanoyl)-4-cyanopyrrolidine-2-carboxamide ditrifluoroacetate (Compound I-25)

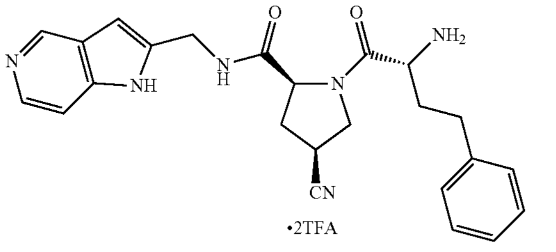 [SMILES: N#C[C@H]1C[C@@H](C(=O)NCc2cc3cnccc3[nH]2)N(C(=O)[C@H](N)CCc2ccccc2)C1]

•2TFA (2S,4S)—N-((1H-pyrrolo[3,2-c]pyridin-2-yl)methyl)-1-((R)-2-amino-4-phenylbutanoyl)-4-cyanopyrrolidine-2-carboxamide ditrifluoroacetate was synthesized according to the procedures for Example 1 except the hydrogenation deprotection was not required and TFA/dichloromethane was used to deprotect the Boc group.

Example 9

Preparation of (2S,4S)-1-((R)-2-amino-4-phenylbutanoyl)-N-(4-carbamimidoylbenzyl)-4-cyanopyrrolidine-2-carboxamide ditrifluoroacetate (Compound I-6)

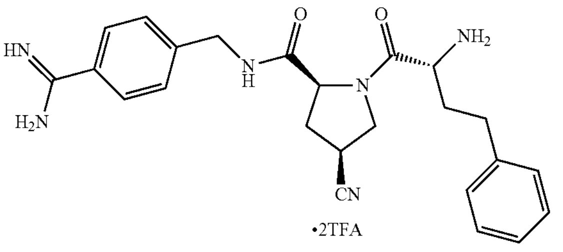 [SMILES: N#C[C@H]1C[C@@H](C(=O)NCc2ccc(C(=N)N)cc2)N(C(=O)[C@H](N)CCc2ccccc2)C1]

•2TFA (2S,4S)-1-((R)-2-amino-4-phenylbutanoyl)-N-(4-carbamimidoylbenzyl)-4-cyanopyrrolidine-2-carboxamide ditrifluoroacetate was synthesized according to the procedures for Example 1 except TFA/dichloromethane was used to deprotect the Boc group.

Table 1 lists compounds of the Examples described above, as well as additional compounds that may be prepared according to methods analogous to those described for the compounds above and other methods known to a person having skill in the art. In some embodiments, the compound is a compound in Table 1.

TABLE 1

Exemplary compounds

| Cmp No. | Structure | Salt | Exact Observed Mass (ES+; M + H) | Exact Calc. Mass |
|---|---|---|---|---|
| I-1 | 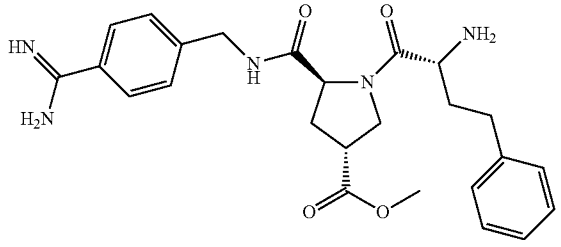 [SMILES: COC(=O)[C@@H]1C[C@@H](C(=O)NCc2ccc(C(=N)N)cc2)N(C(=O)[C@H](N)CCc2ccccc2)C1] | 2TFA | 466.44 | 465.24 |
| I-2 | 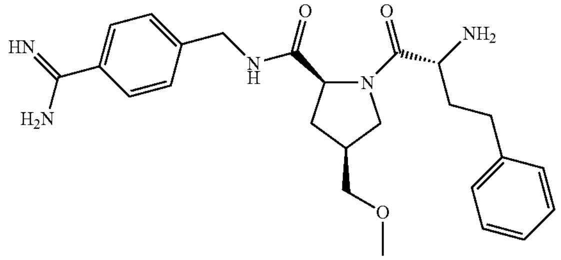 [SMILES: COC[C@H]1C[C@@H](C(=O)NCc2ccc(C(=N)N)cc2)N(C(=O)[C@H](N)CCc2ccccc2)C1] | 2HCl | 452.46 | 451.26 |
| I-3 | 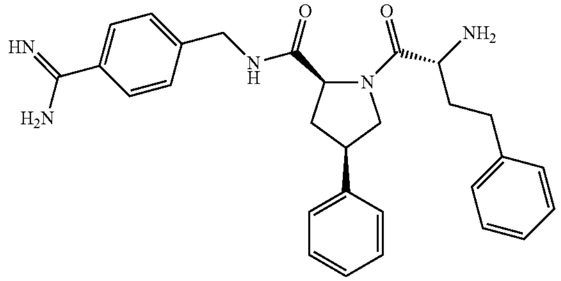 | 2HCl | 484.56 | 483.26 |
| I-4 | 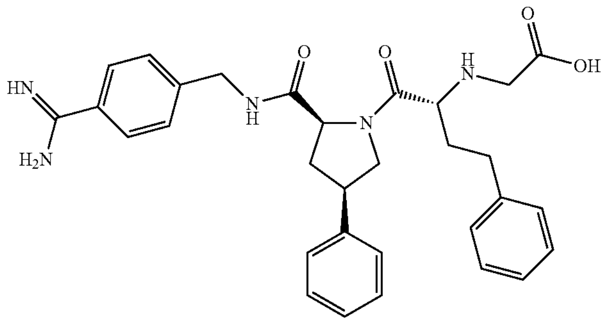 [SMILES: N=C(N)c1ccc(CNC(=O)[C@@H]2C[C@H](c3ccccc3)CN2C(=O)[C@@H](CCc2ccccc2)NCC(=O)O)cc1] | — | 542.47 | 541.64 |

TABLE 1-continued
| Exemplary compounds | | | | |
|---|---|---|---|---|
| Cmp No. | Structure | Salt | Exact Observed Mass (ES+; M + H) | Exact Calc. Mass |
| I-5 | 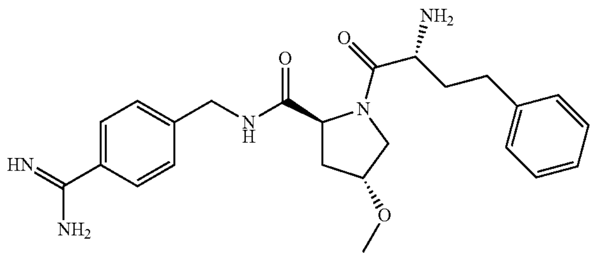 [SMILES: CO[C@@H]1C[C@@H](C(=O)NCc2ccc(C(=N)N)cc2)N(C(=O)[C@H](N)CCc2ccccc2)C1] | — | — | — |
| I-6 | 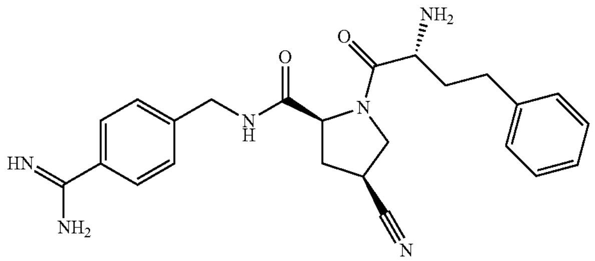 [SMILES: N#C[C@H]1C[C@@H](C(=O)NCc2ccc(C(=N)N)cc2)N(C(=O)[C@H](N)CCc2ccccc2)C1] | 2TFA | 433.0 | 432.23 |
| I-7 | 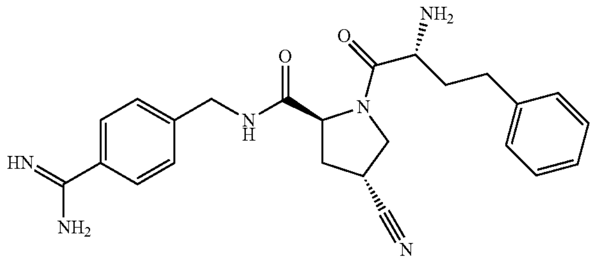 [SMILES: N#C[C@@H]1C[C@@H](C(=O)NCc2ccc(C(=N)N)cc2)N(C(=O)[C@H](N)CCc2ccccc2)C1] | — | — | — |
| I-8 | 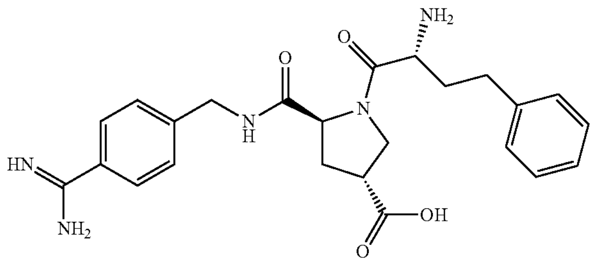 [SMILES: N=C(N)c1ccc(CNC(=O)[C@@H]2C[C@@H](C(=O)O)CN2C(=O)[C@H](N)CCc2ccccc2)cc1] | — | — | — |
| I-9 | 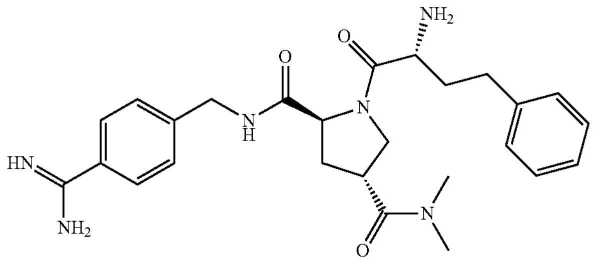 [SMILES: CN(C)C(=O)[C@@H]1C[C@@H](C(=O)NCc2ccc(C(=N)N)cc2)N(C(=O)[C@H](N)CCc2ccccc2)C1] | — | — | — |

TABLE 1-continued
| Exemplary compounds | | | | |
| --- | --- | --- | --- | --- |
| Cmp No. | Structure | Salt | Exact Observed Mass (ES+; M + H) | Exact Calc. Mass |
| I-10 | 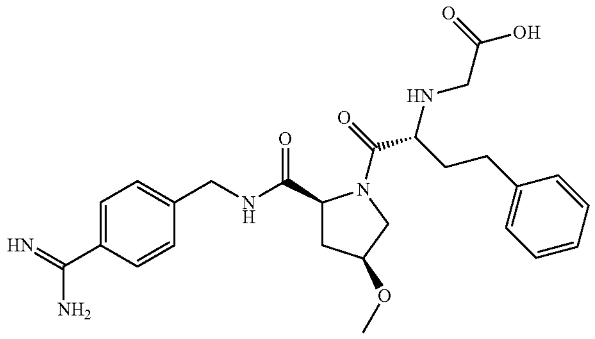 [SMILES: CO[C@H]1C[C@@H](C(=O)NCc2ccc(C(=N)N)cc2)N(C(=O)[C@@H](CCc2ccccc2)NCC(=O)O)C1] | — | — | — |
| I-11 | 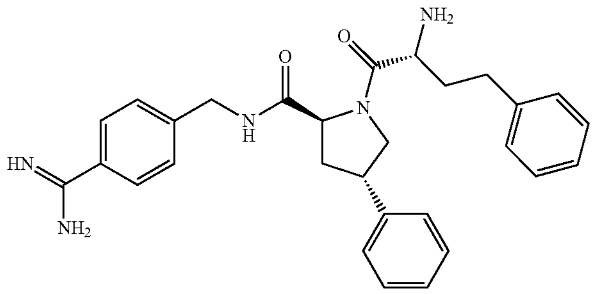 [SMILES: N=C(N)c1ccc(CNC(=O)[C@@H]2C[C@@H](c3ccccc3)CN2C(=O)[C@H](N)CCc2ccccc2)cc1] | 2HCl | 482.3 (M − H) | 483.26 |
| I-12 | 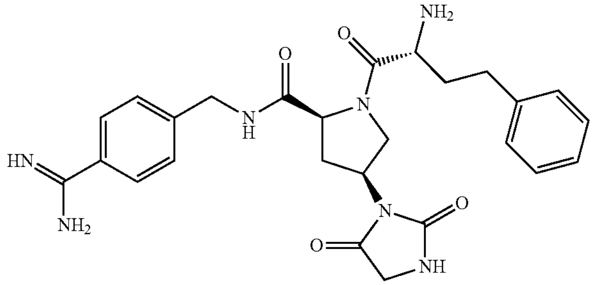 [SMILES: N=C(N)c1ccc(CNC(=O)[C@@H]2C[C@H](N3C(=O)CNC3=O)CN2C(=O)[C@H](N)CCc2ccccc2)cc1] | — | — | — |
| I-13 | 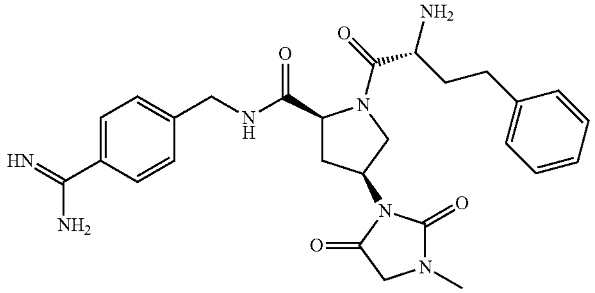 [SMILES: CN1CC(=O)N([C@H]2C[C@@H](C(=O)NCc3ccc(C(=N)N)cc3)N(C(=O)[C@H](N)CCc3ccccc3)C2)C1=O] | — | — | — |

TABLE 1-continued
| Exemplary compounds | | | | |
|---|---|---|---|---|
| Cmp No. | Structure | Salt | Exact Observed Mass (ES+; M + H) | Exact Calc. Mass |
| I-14 | 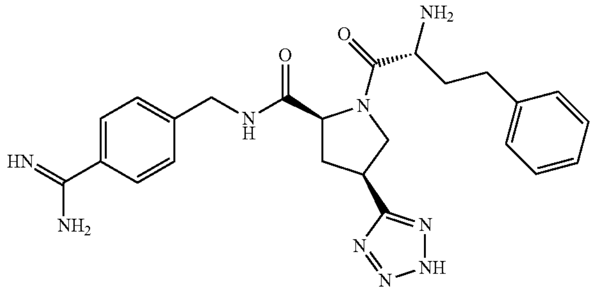 [SMILES: N=C(N)c1ccc(CNC(=O)[C@@H]2C[C@H](c3nn[nH]n3)CN2C(=O)[C@H](N)CCc2ccccc2)cc1] | — | — | — |
| I-15 | 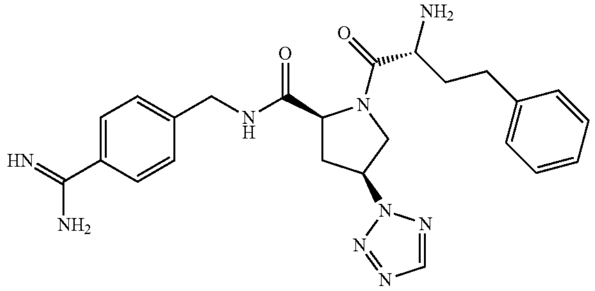 [SMILES: N=C(N)c1ccc(CNC(=O)[C@@H]2C[C@H](n3ncnn3)CN2C(=O)[C@H](N)CCc2ccccc2)cc1] | — | — | — |
| I-16 | 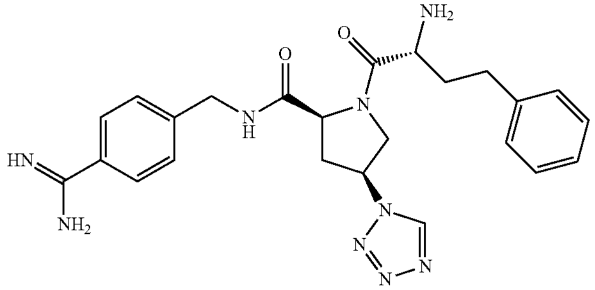 [SMILES: N=C(N)c1ccc(CNC(=O)[C@@H]2C[C@H](n3cnnn3)CN2C(=O)[C@H](N)CCc2ccccc2)cc1] | — | — | — |
| I-17 | 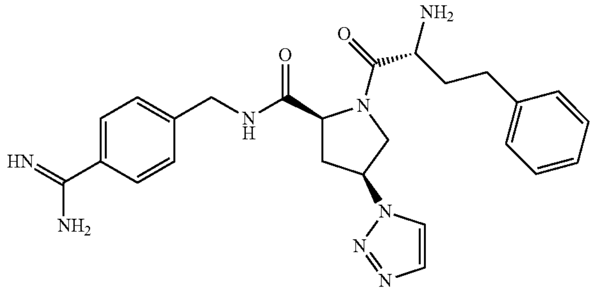 [SMILES: N=C(N)c1ccc(CNC(=O)[C@@H]2C[C@H](n3ccnn3)CN2C(=O)[C@H](N)CCc2ccccc2)cc1] | — | — | — |
| I-18 | 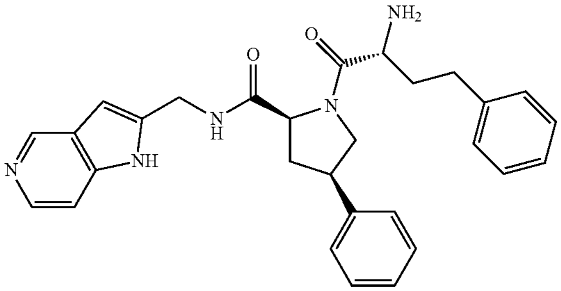 [SMILES: N[C@H](CCc1ccccc1)C(=O)N1C[C@@H](c2ccccc2)C[C@H]1C(=O)NCc1cc2cnccc2[nH]1] | — | — | — |

TABLE 1-continued
| Cmp No. | Structure | Salt | Exact Observed Mass (ES+; M + H) | Exact Calc. Mass |
|---|---|---|---|---|
| Exemplary compounds | | | | |
| I-19 | 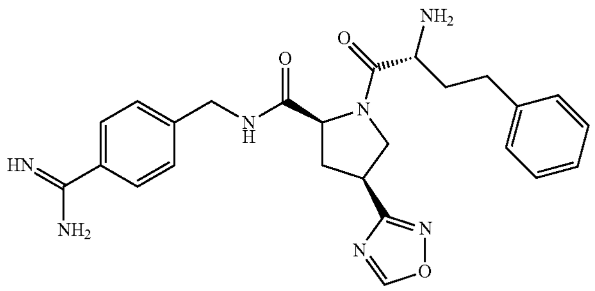 [SMILES: N=C(N)c1ccc(CNC(=O)[C@@H]2C[C@H](c3ncon3)CN2C(=O)[C@H](N)CCc2ccccc2)cc1] | — | — | — |
| I-20 | 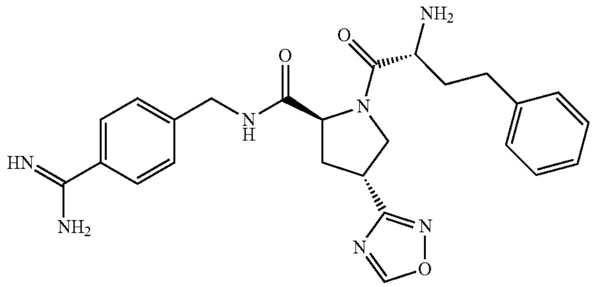 [SMILES: N=C(N)c1ccc(CNC(=O)[C@@H]2C[C@@H](c3ncon3)CN2C(=O)[C@H](N)CCc2ccccc2)cc1] | — | — | — |
| I-21 | 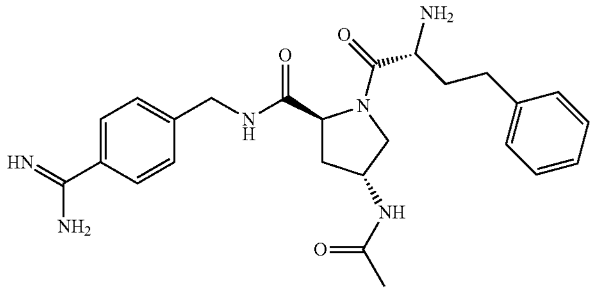 [SMILES: CC(=O)N[C@@H]1C[C@@H](C(=O)NCc2ccc(C(=N)N)cc2)N(C(=O)[C@H](N)CCc2ccccc2)C1] | — | — | — |
| I-22 | 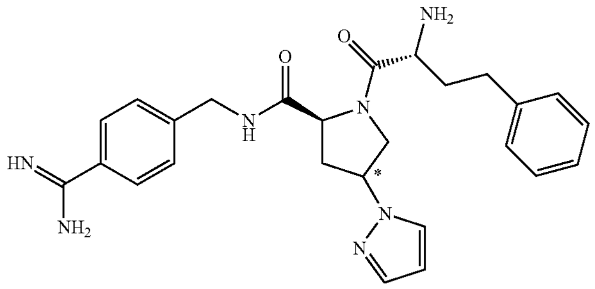 [SMILES: N=C(N)c1ccc(CNC(=O)[C@@H]2CC(n3cccn3)CN2C(=O)[C@H](N)CCc2ccccc2)cc1] | 2HCl | 474.5 | 473.25 |
| I-23 | 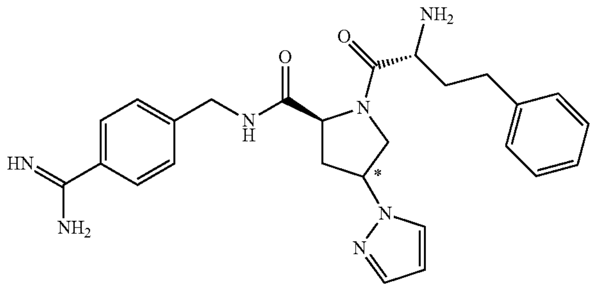 [SMILES: N=C(N)c1ccc(CNC(=O)[C@@H]2CC(n3cccn3)CN2C(=O)[C@H](N)CCc2ccccc2)cc1] | 2HCl | 474.5 | 473.25 |

TABLE 1-continued

| Exemplary compounds | | | | |
|---|---|---|---|---|
| Cmp No. | Structure | Salt | Exact Observed Mass (ES+; M + H) | Exact Calc. Mass |
| I-24 | 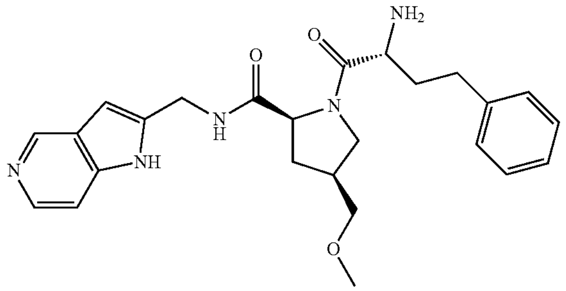 [SMILES: COC[C@H]1C[C@@H](C(=O)NCc2cc3cnccc3[nH]2)N(C(=O)[C@H](N)CCc2ccccc2)C1] | 2TFA | 450.4 | 449.24 |
| I-25 | 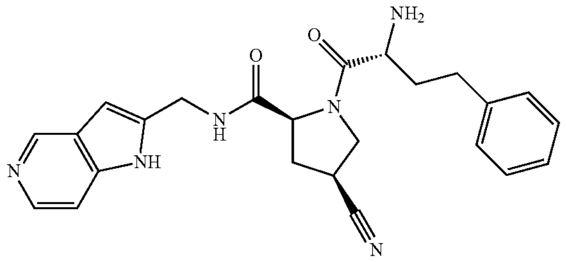 [SMILES: N#C[C@H]1C[C@@H](C(=O)NCc2cc3cnccc3[nH]2)N(C(=O)[C@H](N)CCc2ccccc2)C1] | 2TFA | 431.4 | 430.21 |

Example 10

Enzymatic Assay for MASP-2

The MASP-2 assay utilizes a fluorogenic substrate, based on the cleavage site for its natural substrate C2. The assay is run at room temperature in an assay buffer containing 20 mM HEPES, pH 7.4, 140 mM NaCl and 0.1% Tween 20. Assay parameters are adjusted such that the assay is linear with respect to time, enzyme, and substrate concentrations. Under these optimized assays conditions, $IC_{50}$ values are equivalent to Ki values, except in a few cases of "tight binding" inhibitors. Cases of "tight binding" or possible "slow binding" inhibitors are handled by the methods described in Copeland R. A. (2013) Evaluation of Enzyme Inhibitors in Drug Discovery. 2nd Ed., John Wiley and Sons, Inc., Chapters 5-7.

The MASP-2 assay protocol is carried out as follows. Test compounds are serially diluted in DMSO and then 100 nL of each dilution is transferred to the assay plate(s). 10 μL of Assay Buffer is added, followed by 15 μL of Enzyme MASP-2 (CCP1-CCP2-SP) in Assay Buffer. 15 μL of Substrate in Assay Buffer is then added and mixed to start the reactions. After 20 min at room temperature, 15 μL of a stop solution (0.1 M acetic acid) is added, mixed and the plates are read on a SpectraMax i3x Microplate Reader and exported as Excel files. Each assay plate included a "no inhibitor" (DMSO Only) control, a "no enzyme" control and a reference inhibitor control. % Activity values=100*(average test comp. fluorescence-average "no enzyme" fluorescence)/(average "DMSO only" fluorescence-average "no enzyme" fluorescence). $IC_{50}$ and Ki values are very reproducible, falling well within ±2-fold.

The results of biological assays for the compounds listed in Table 1 are listed in Table 2, below.

TABLE 2

| MASP-2 Inhibition for exemplary compounds | | | | | |
|---|---|---|---|---|---|
| Compound | MASP-2 $K_i$ (μM) | Compound | MASP-2 $K_i$ (μM) | Compound | MASP-2 $K_i$ (μM) |
| I-1 | **** | I-2 | **** | I-3 | **** |
| I-4 | — | I-5 | — | I-6 | **** |
| I-7 | — | I-8 | — | I-9 | — |
| I-10 | — | I-11 | **** | I-12 | — |
| I-13 | — | I-14 | — | I-15 | — |
| I-16 | — | I-17 | — | I-18 | — |
| I-19 | — | I-20 | — | I-21 | — |
| I-22 | **** | I-23 | — | I-24 | — |
| I-25 | — | I-26 | **** | I-27 | **** |
| I-28 | **** | I-29 | **** | — | — |

MASP-2 Inhibition Ki Values:
* $K_i$ greater than 10 μM
** $K_i$ between 2.5-10 μM
*** $K_i$ between 0.5-2.5 μM
**** $K_i$ of less than 0.5 μM
— not tested It is understood that the examples and embodiments described herein are for illustrative purposes only and that various modifications or changes in light thereof will be suggested to persons skilled in the art and are to be included within the spirit and purview of this application and scope of the appended claims. Each reference, including without limitation all patent, patent applications, and publications, cited in the present application is incorporated herein by reference in its entirety for all purposes.

The embodiments of the invention in which an exclusive property or privilege is claimed are defined as follows:

1. A compound having the following Structure (I):

(I)

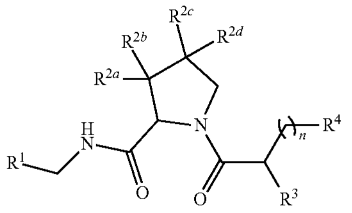

or a stereoisomer, tautomer, or pharmaceutically acceptable salt thereof, wherein:

$R^1$ is a substituted phenyl, a substituted or unsubstituted heteroaryl, a substituted or unsubstituted cycloalkyl, or a substituted or unsubstituted heterocyclyl;

wherein the substituted phenyl of $R^1$ is substituted with one or more of $R^{1a}$, $R^{1b}$, $R^{1c}$, $R^{1d}$ and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$ $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)NR^{13}R^{14}$, $OC(O)R^{13}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heteroaryl of $R^1$ is a 5-10 membered heteroaryl selected from the group consisting of:

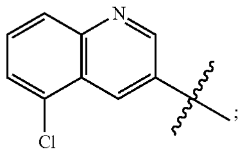
;
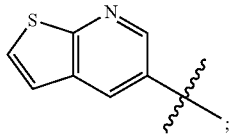
;
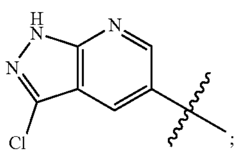
;
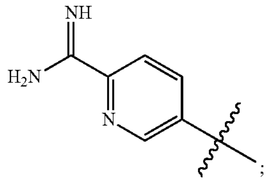
;
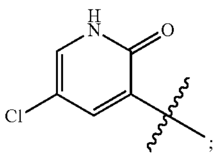
;
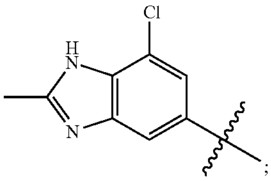
;

-continued

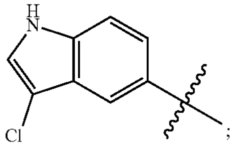 ; 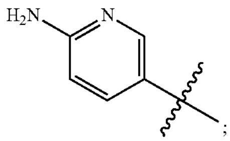 ;

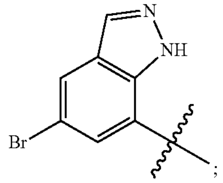 ; 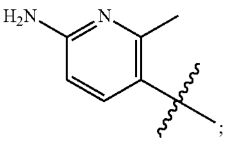 ;

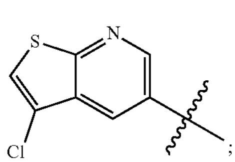 ; 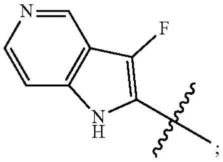 ;

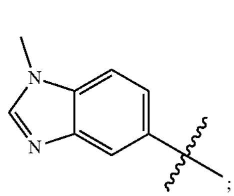 ; 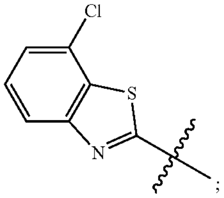 ;

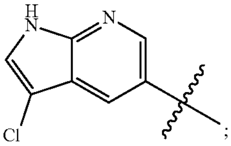 ; 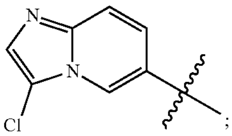 ;

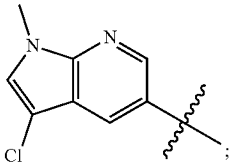 ; 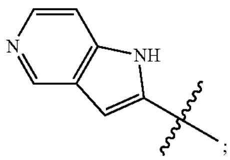 ;

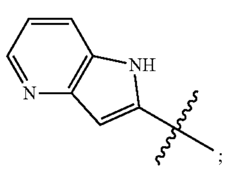 ; 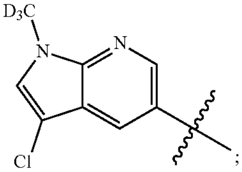 ;

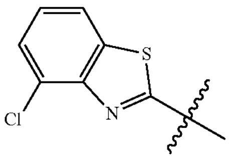 ; 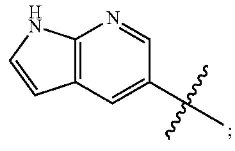 ;

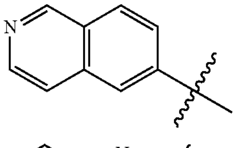 ; 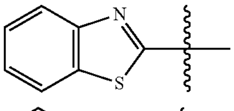 ;

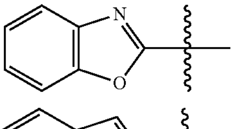 ; 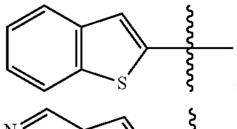 ;

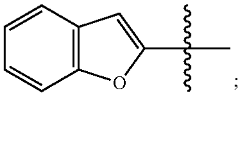 ; 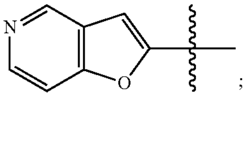 ;

-continued

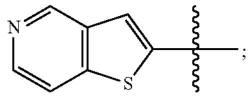 ; 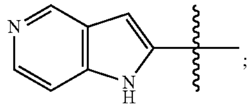 ;

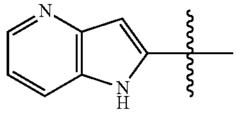 ; 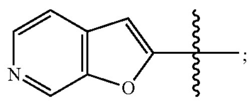 ;

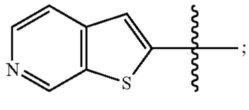 ; 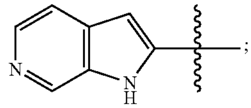 ;

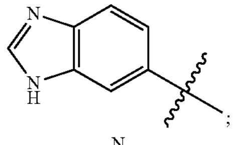 ; 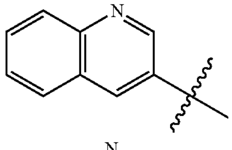 ;

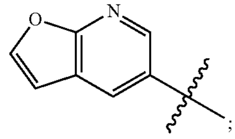 ; 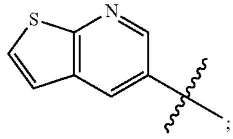 ;

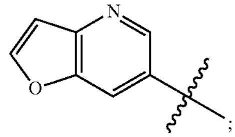 ; 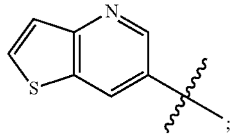 ;

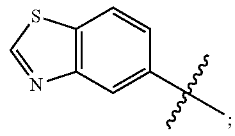 ; 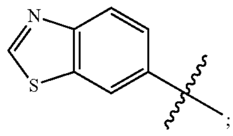 ;

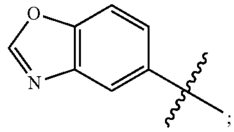 ; and 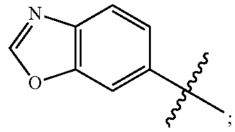 ;

wherein the substituted or unsubstituted cycloalkyl of $R^1$ is a $C_3$-$C_6$ cycloalkyl monocyclic or polycyclic ring system, which is saturated or unsaturated, and which can comprise fused or bridged ring systems, and the substituted cycloalkyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C({=}NR^{13})NR^{14}R^{15}$, $NR^{13}C({=}NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heterocyclyl of $R^1$ is a 4-10 membered monocyclic, bicyclic, tricyclic, or tetracyclic ring system consisting of carbon atoms and one to six heteroatoms selected from the group consisting of nitrogen, oxygen, and sulfur, and which can comprise fused, bridged, and spiro ring systems, and the substituted heterocyclyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C({=}NR^9)NR^{10}R^{11}$, $C({=}NOR^9)NR^{10}R^{11}$, $C({=}NOC(O)R^9)NR^{10}R^{11}$, $C({=}NR^9)N(R^{10})C(O)OR^{11}$, $N(R^9)C({=}NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)NR^{13}R^{14}$, $OC(O)R^{13}$, $NR^{13}R^{14}$, $NR^{13}C(O)R^{14}$, $NR^{13}C(O)NR^{14}R^{15}$, $NR^{13}C(O)OR^{14}$, $C({=}NR^{13})NR^{14}R^{15}$, $NR^{13}C({=}NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

$R^{2a}$, $R^{2b}$, $R^{2c}$, and $R^{2d}$ are each independently selected from the group consisting of hydrogen, halo, $C({=}O)OR^5$, $OC({=}O)R^5$, hydroxyalkyl, alkoxy, alkoxyalkyl, haloalkoxy, cyano, aminylalkyl, carboxyalkyl, $NR^5R^6$, $C({=}O)NR^5R^6$, $N(R^5)C({=}O)R^6$, $NR^5C({=}O)NR^6$, $S(O)_t$, $SR^5$, nitro, $N(R^5)C(O)OR^6$, $C({=}NR^5)NR^6R^7$, $N(R^5)C({=}NR^6)NR^7R^8$, $S(O)R^5$, $S(O)NR^5R^6$, $S(O)_2R^5$, $N(R^5)S(O)_2R^6$, $S(O)_2NR^5R^6$, aryl, heteroaryl, heterocyclyl, and cycloalkyl, or $R^{2a}$ and $R^{2b}$, or $R^{2c}$ and $R^{2d}$, together are oxo, and provided that at least one of $R^{2a}$, $R^{2b}$, $R^{2c}$, and $R^{2d}$ is not hydrogen;

$R^3$ is selected from the group consisting of:

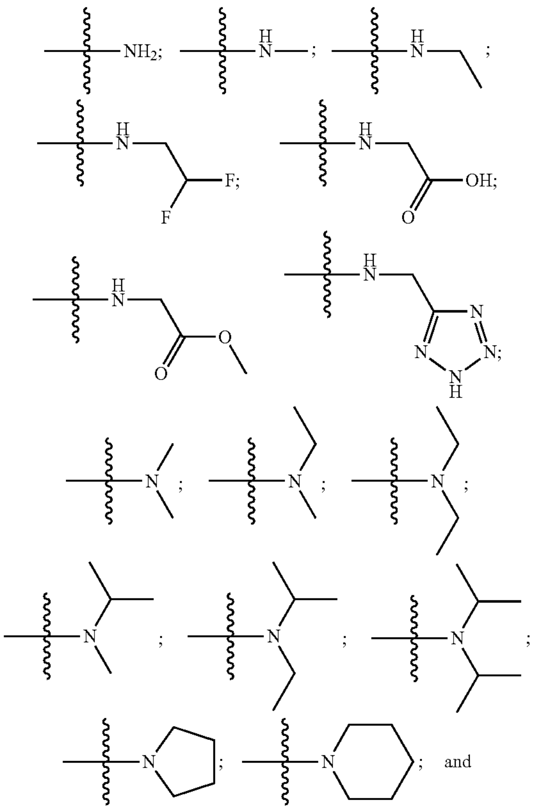

and

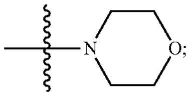

$R^4$ is an aryl, a heteroaryl, a cycloalkyl, or a heterocyclyl when n is 2, 3, 4, 5, or 6; or $R^4$ is a monocyclic heteroaryl, or a heterocyclyl when n is 0 or 1; or $R^4$ and $R^{3a}$ together with the carbon and nitrogen to which they are attached, respectively, form a 4-7 membered heterocyclyl;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3, and wherein the aryl of $R^{2a}$, $R^{2b}$, $R^{2c}$, $R^{2d}$, $R^4$ is a 6- to 18-membered monocyclic, bicyclic, tricyclic, or tetracyclic ring system comprising at least one aromatic ring, and which can comprise fused or bridged ring systems, wherein the heteroaryl of $R^{2a}$, $R^{2b}$, $R^{2c}$, $R^{2d}$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is a 5- to 14-membered monocyclic, bicyclic, tricyclic, or tetracyclic ring system comprising at least one aromatic ring and one to six heteroatoms selected from the group consisting of nitrogen, oxygen, and sulfur, and which can comprise fused or bridged ring systems, wherein the heterocyclyl of $R^{2a}$, $R^{2b}$, $R^{2c}$, $R^{2d}$, $R^4$, $R^5$, $R^6$, $R^7$, and $R^8$ is a 3- to 18-membered monocyclic, bicyclic, tricyclic, or tetracyclic ring system consisting of two to twelve carbon atoms and one to six heteroatoms selected from the group consisting of nitrogen, oxygen, and sulfur, and which can comprise fused, bridged, and spiro ring systems, and wherein the cycloalkyl of $R^{2a}$, $R^{2b}$, $R^{2c}$, $R^{2d}$, $R^4$, $R^5$, $R^6$, $R^7$, and $R^8$ is a 3- to 15-membered monocyclic or polycyclic ring system, which is saturated or unsaturated, and which can comprise fused or bridged ring systems.

2. The compound of claim 1, wherein $R^1$ is selected from the group consisting of:

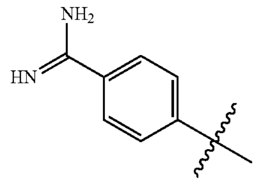 ; 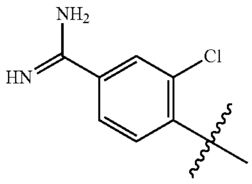 ;

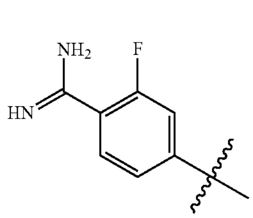 ; 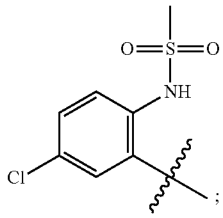 ;

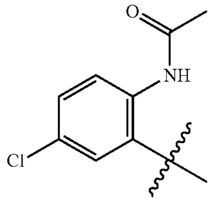 ; 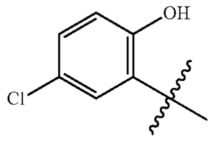 ;

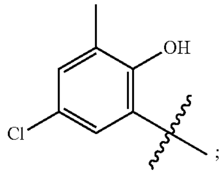 ; 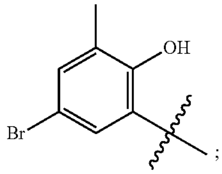 ;

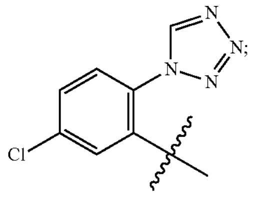 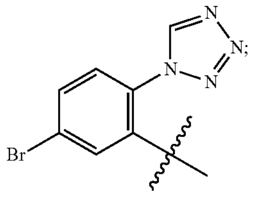

-continued

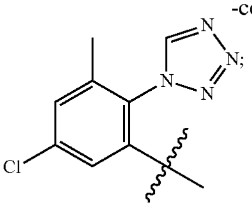 and 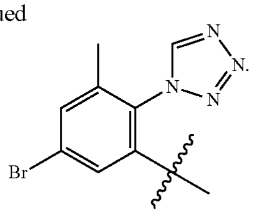

3. The compound of claim 1, wherein $R^1$ is a pyridinyl, pyrrolopyridinyl, or benzoimidazolyl.

4. The compound of claim 1, wherein the compound has one of the following structures:

(IA)

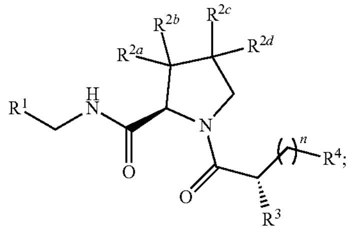

(IB)

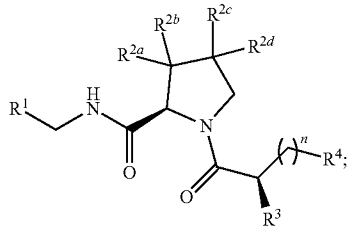

(IC)

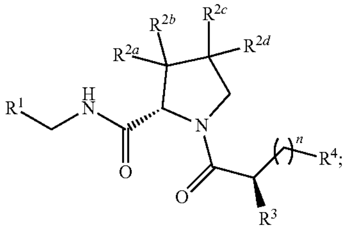 or (ID)

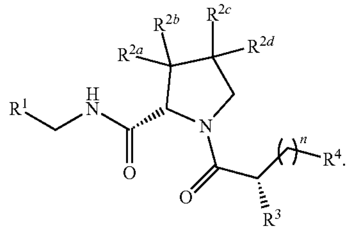

5. The compound of claim 1, wherein at least one of $R^{2a}$, $R^{2b}$, $R^{2c}$, and $R^{2d}$ is alkoxy, alkoxyalkyl, cyano, halo, $C(=O)OR^5$, $OC(=O)R^5$, $C(=O)NR^5R^6$, $N(R^5)C(=O)R^6$, aryl, heteroaryl, heterocyclyl, or $C(=O)N(R^5)$ heterocyclyl, wherein $R^5$ and $R^6$ are, at each occurrence, independently hydrogen or $C_1$-$C_6$ alkyl.

6. The compound of claim 1, wherein at least one of $R^{2a}$, $R^{2b}$, $R^{2c}$, and $R^{2d}$ has one of the following structures:

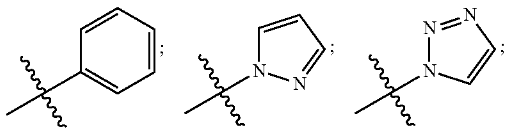
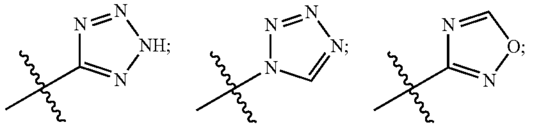
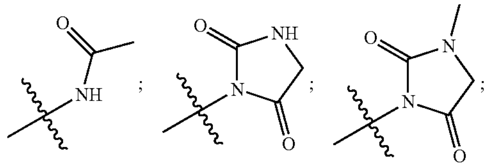
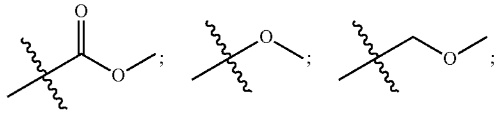
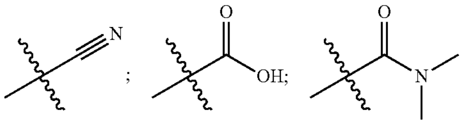
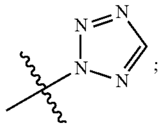
or
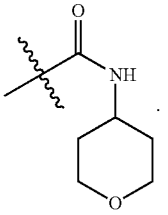
7. The compound of claim 1, wherein n is 0, 1, or 2.
8. The compound of claim 1, wherein n is 2 and $R^4$ is an aryl.
9. The compound of claim 8, wherein $R^4$ is selected from the group consisting of:
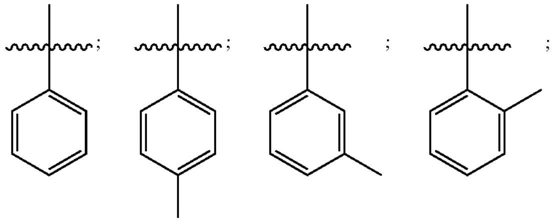
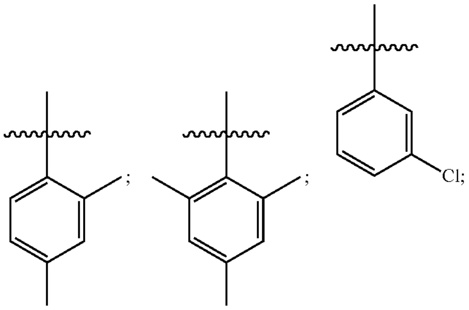
-continued
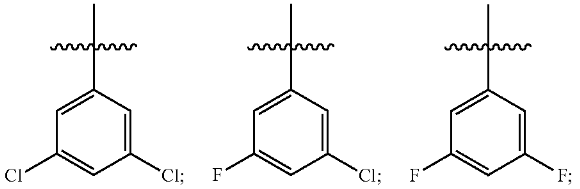
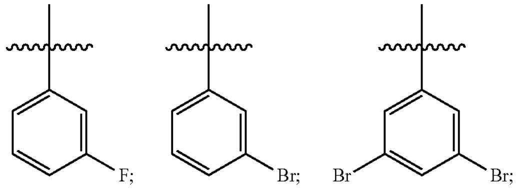
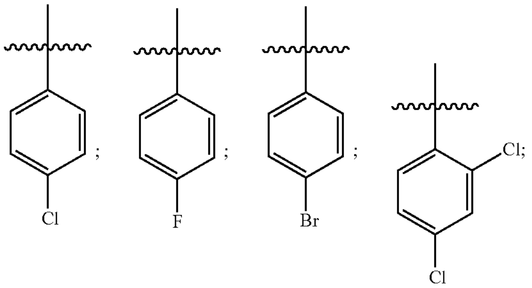
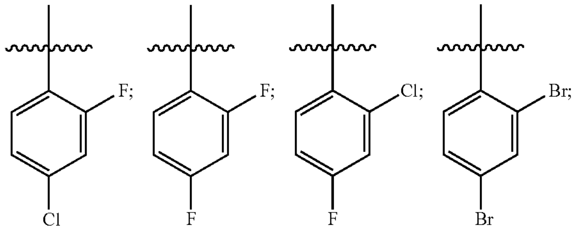
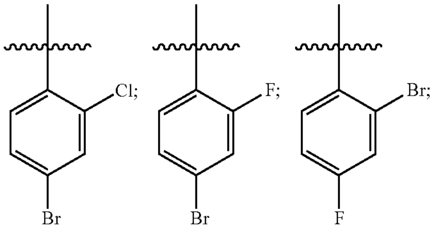
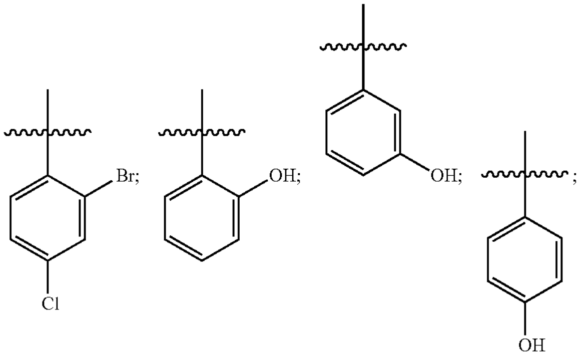
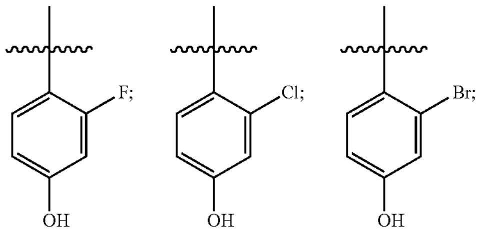

-continued
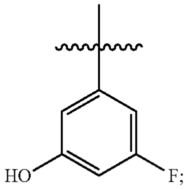
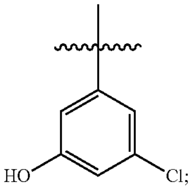
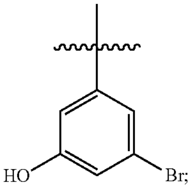
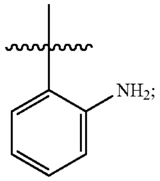
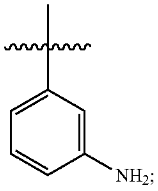
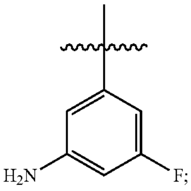
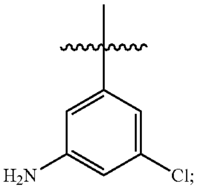
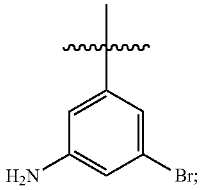
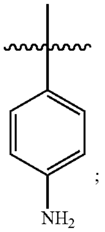
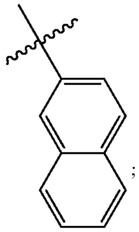
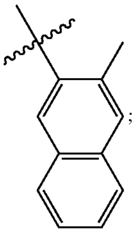
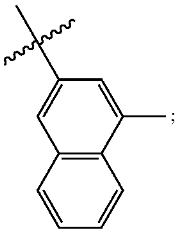
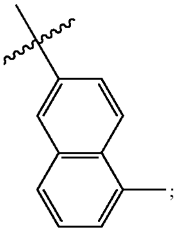
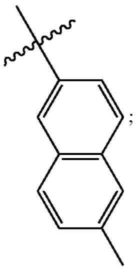
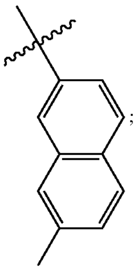
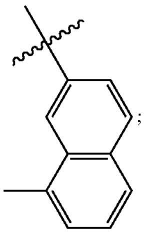
-continued
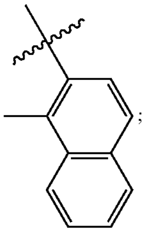
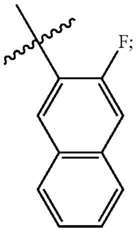
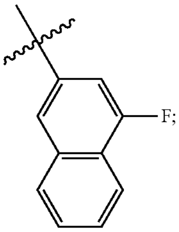
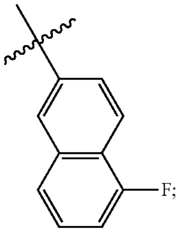
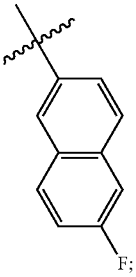
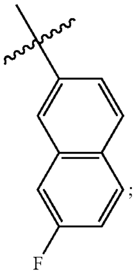
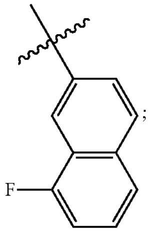
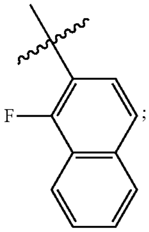
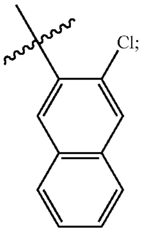
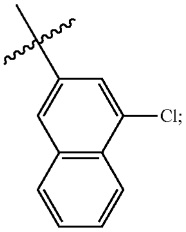
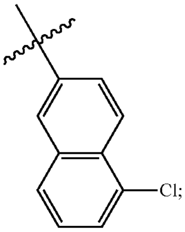
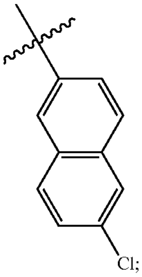
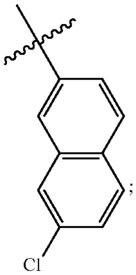
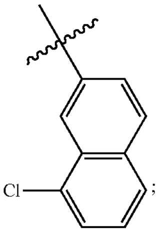
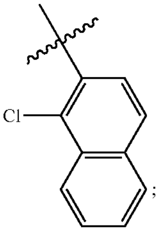

-continued
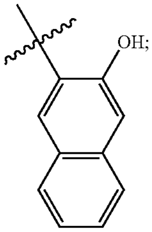;
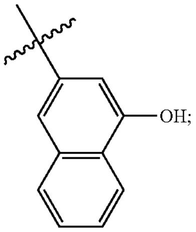;
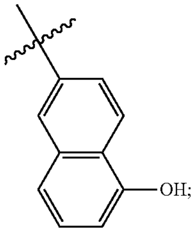;
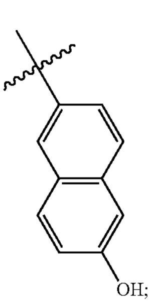;
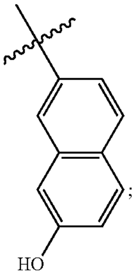;
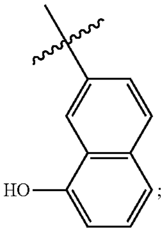;
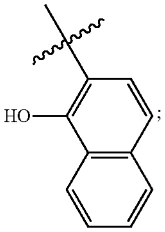;
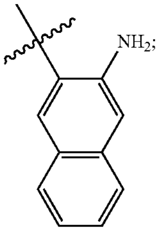;
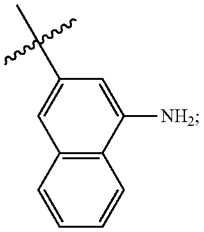;
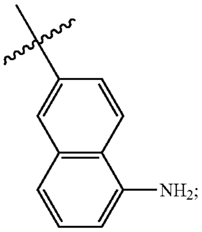;
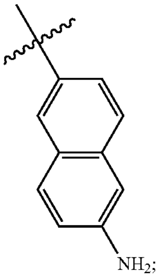;
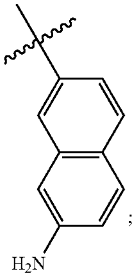;
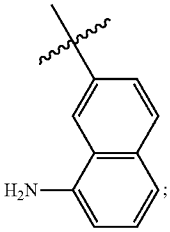;
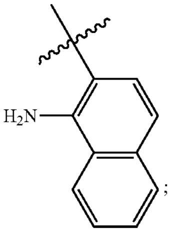;
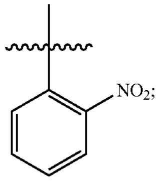;
-continued
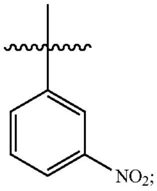; and 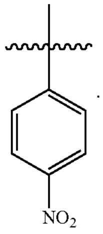.
10. The compound of claim 1, wherein n is 2 and $R^4$ is a heteroaryl.
11. The compound of claim 10, wherein $R^4$ is selected from the group consisting of:
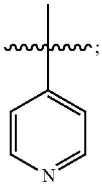;
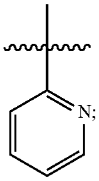;
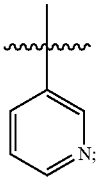;
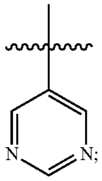;
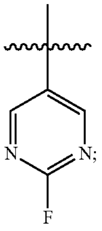;
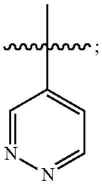;
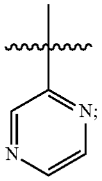;
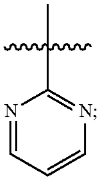;
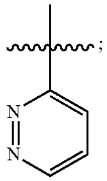;
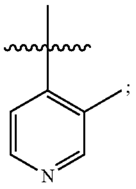;
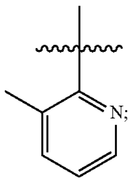;
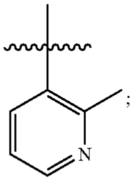;
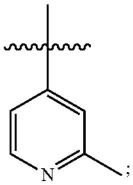;
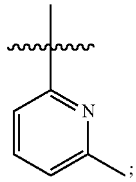;
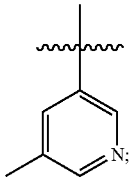;
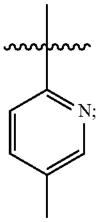;
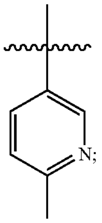;
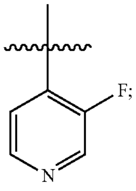;

-continued
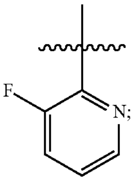
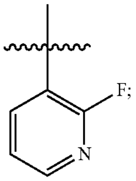
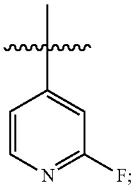
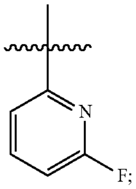
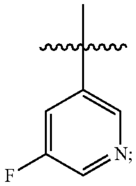
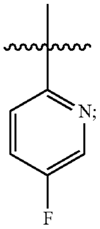
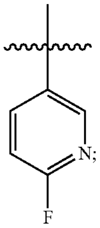
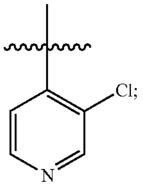
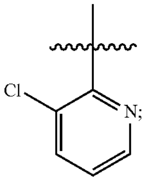
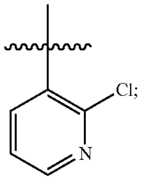
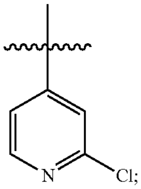
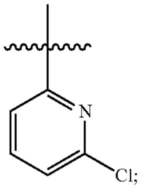
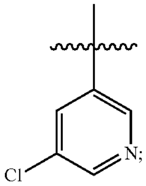
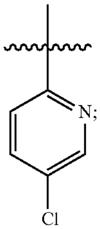
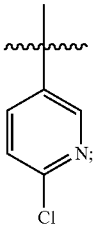
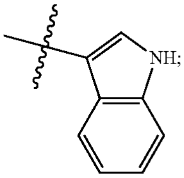
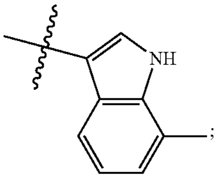
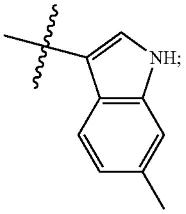
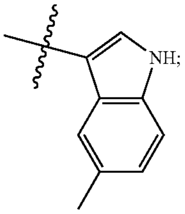
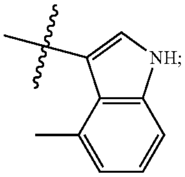
-continued
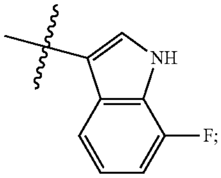
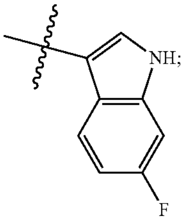
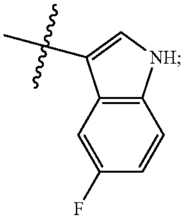
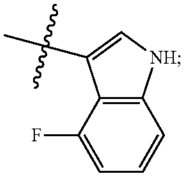
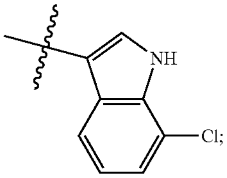
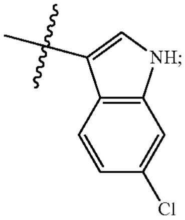
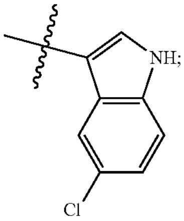
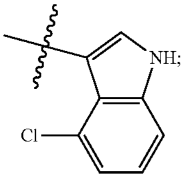
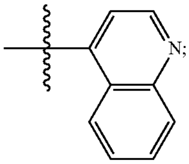
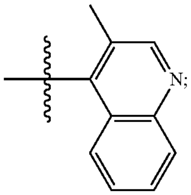
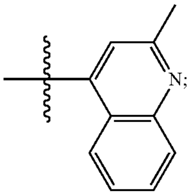
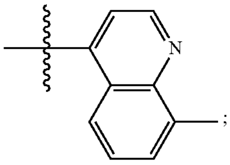
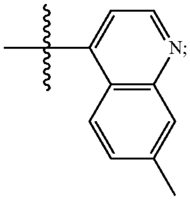
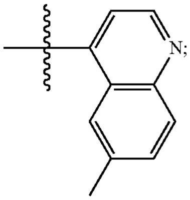
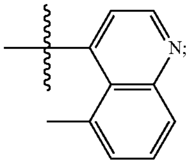

-continued
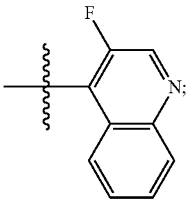
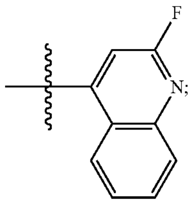
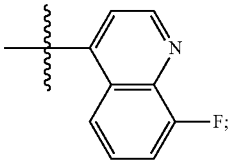
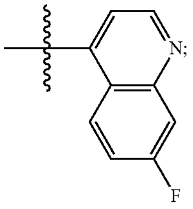
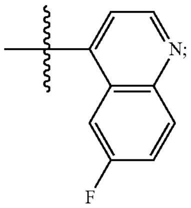
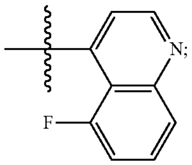
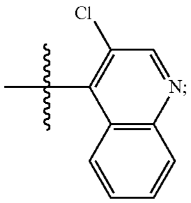
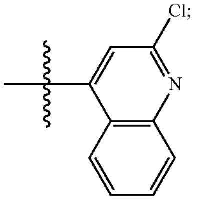
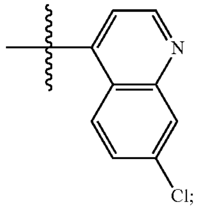
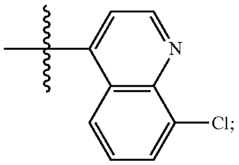
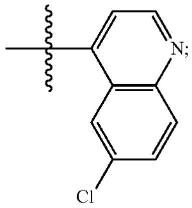
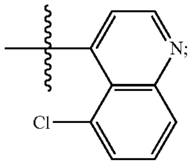
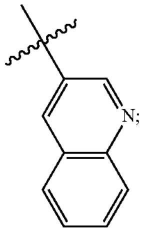
-continued
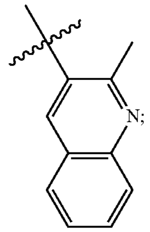
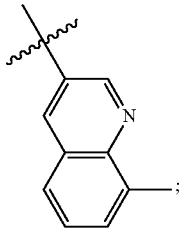
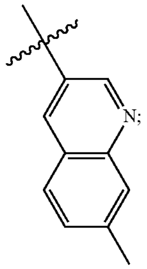
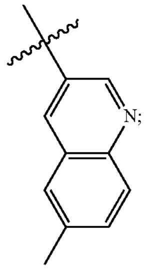
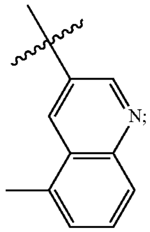
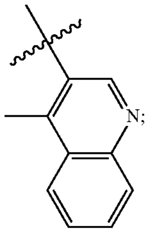
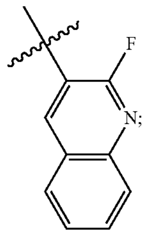
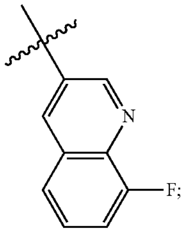
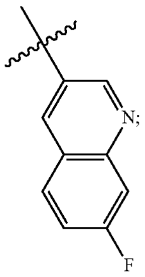
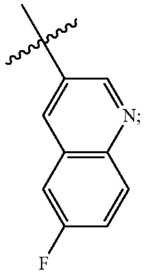
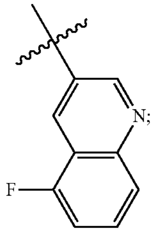
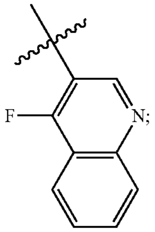
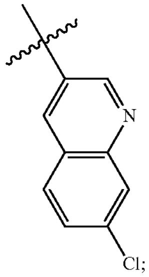
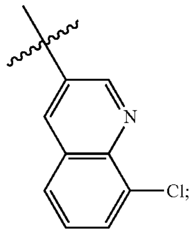
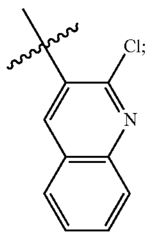

-continued
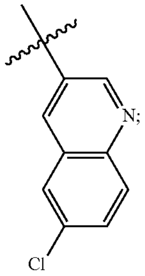
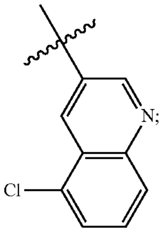
and
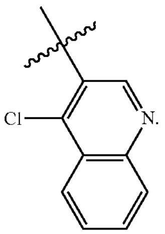
12. The compound of claim 1, wherein $R^4$ is selected from the group consisting of:
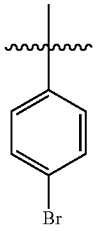
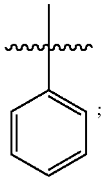
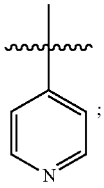
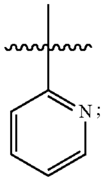
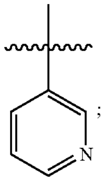
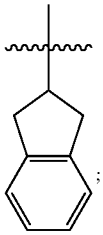
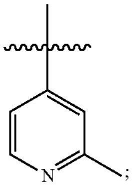
and
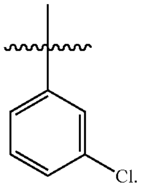
13. A compound of claim 1, having one of the structures:
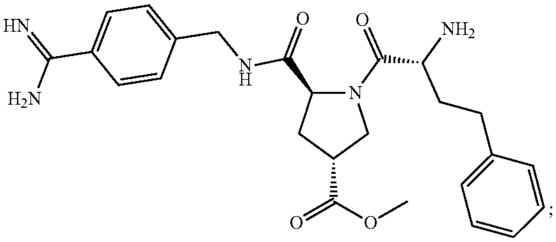
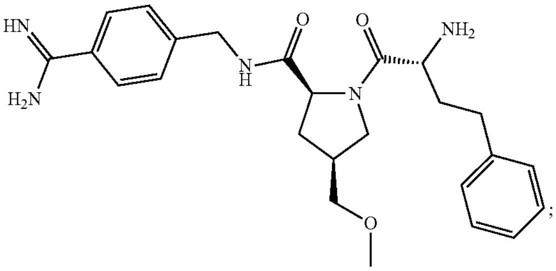
-continued
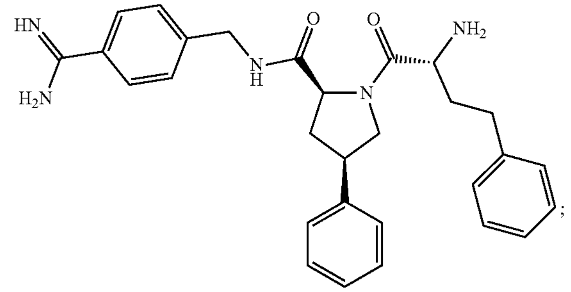
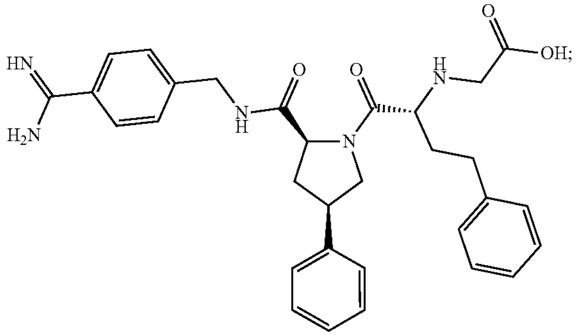
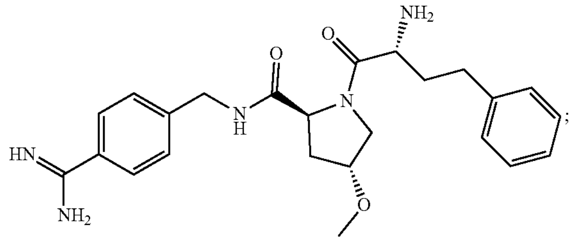
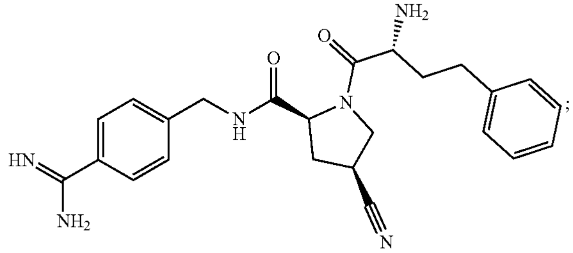
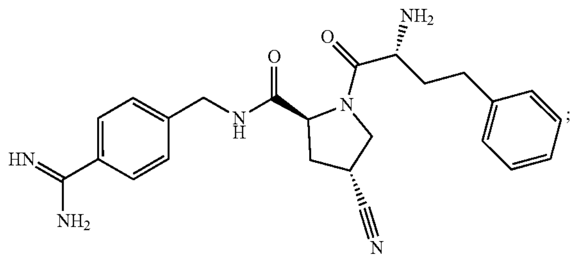
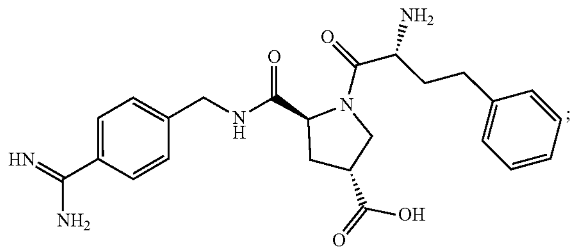

-continued
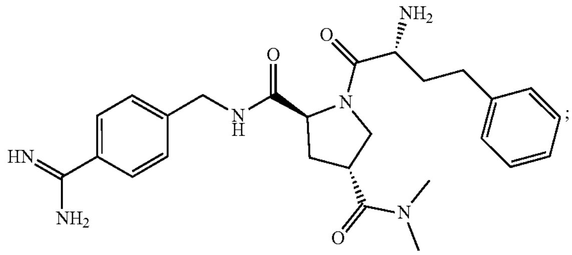
;
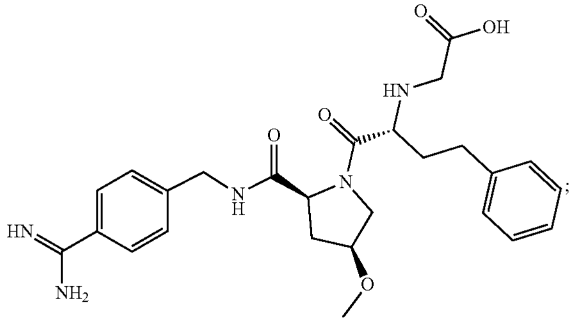
;
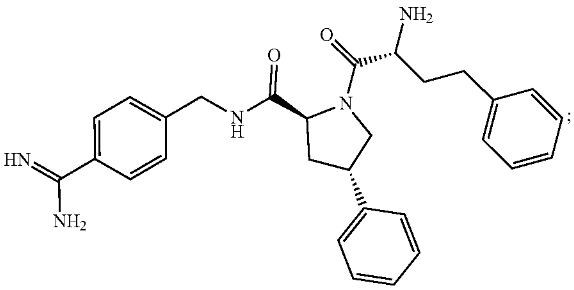
;
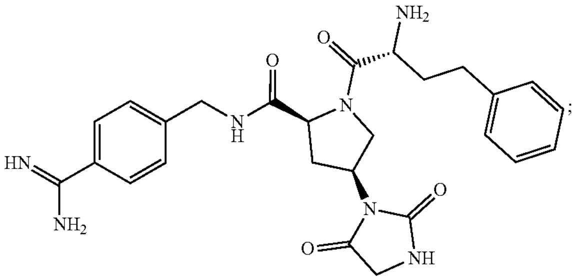
;
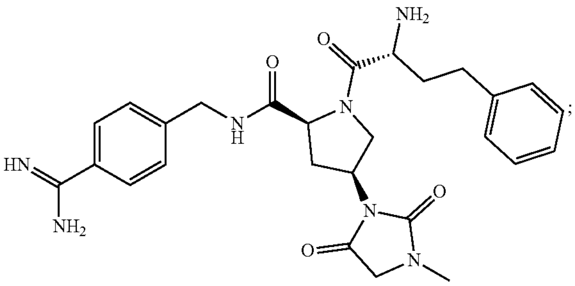
;
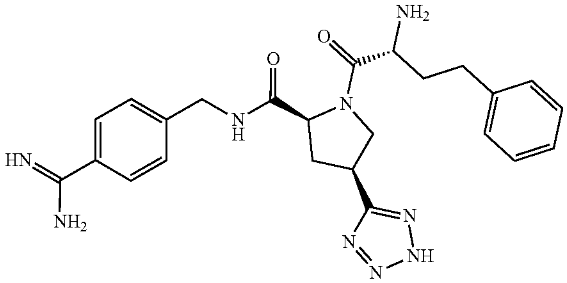
;
-continued
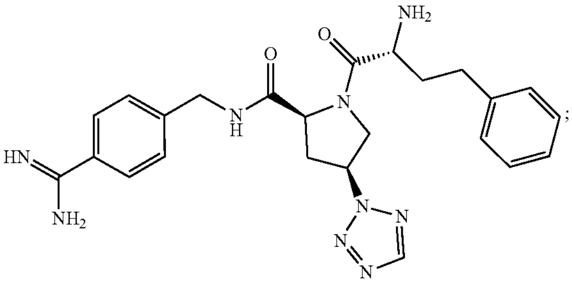
;
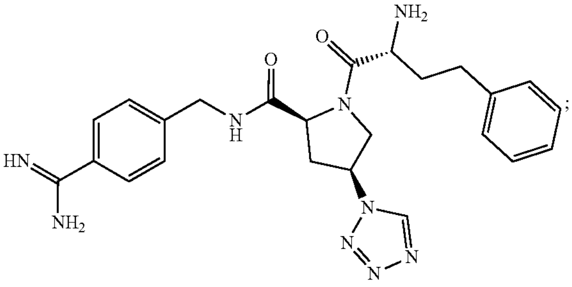
;
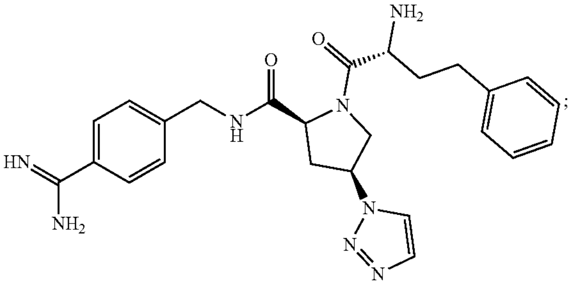
;
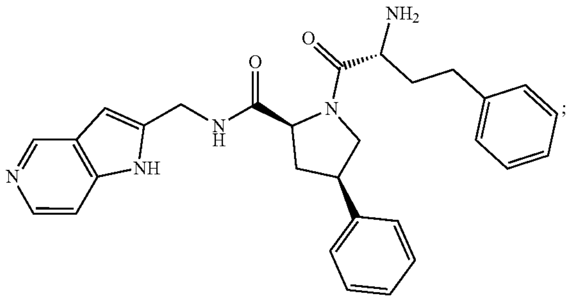
;
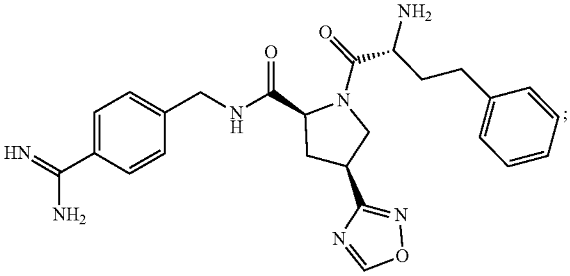
;
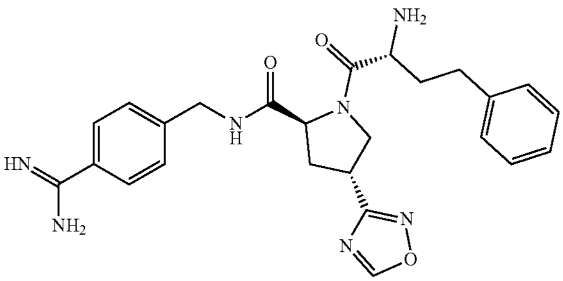
;

-continued

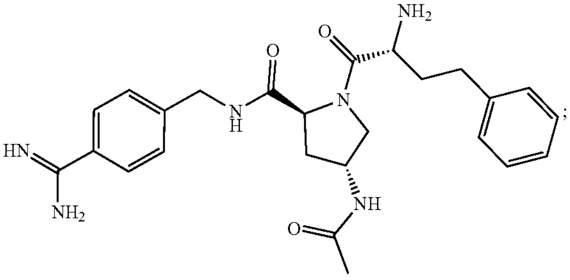
;

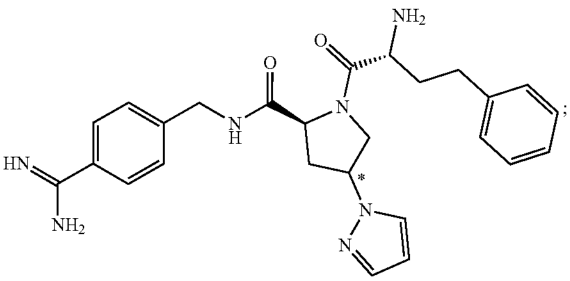
;

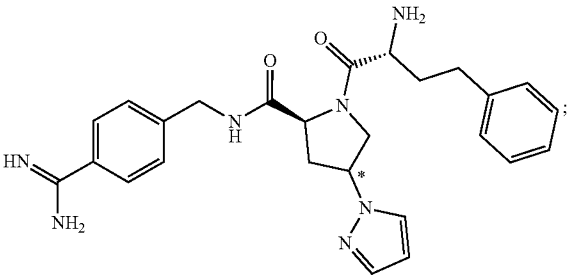
;

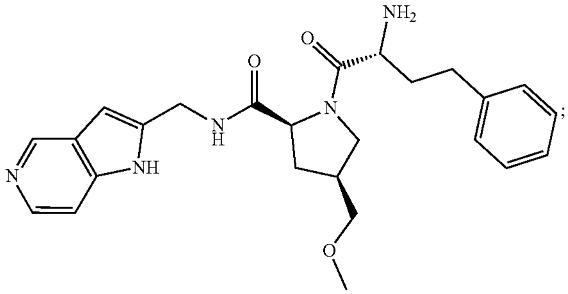
;

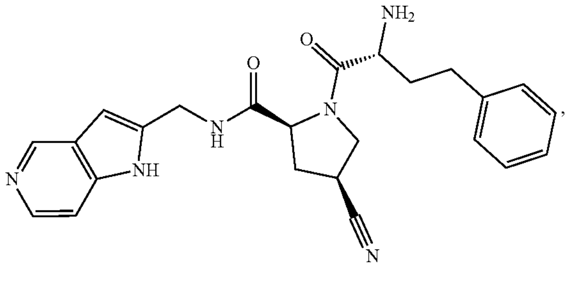
, or a stereoisomer, tautomer, or pharmaceutically acceptable salt thereof.

14. A pharmaceutical composition comprising a compound of claim 1, or a stereoisomer, tautomer, or pharmaceutically acceptable salt thereof, and a pharmaceutically acceptable carrier or excipient.

15. A compound having the following Structure (I'):

(I')

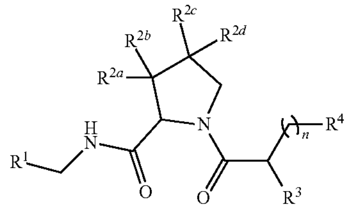

or a stereoisomer, tautomer, or pharmaceutically acceptable salt thereof, wherein:

$R^1$ is a substituted phenyl, a substituted or unsubstituted heteroaryl, a substituted or unsubstituted cycloalkyl, or a substituted or unsubstituted heterocyclyl;

wherein the substituted phenyl of $R^1$ is substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, OC(O)NR 13R 14, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heteroaryl of $R^1$ is a 5-10 membered heteroaryl selected from the group consisting of:

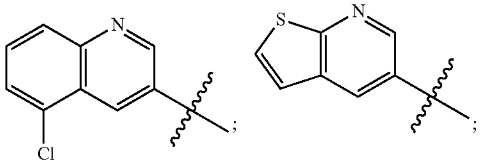
;
;

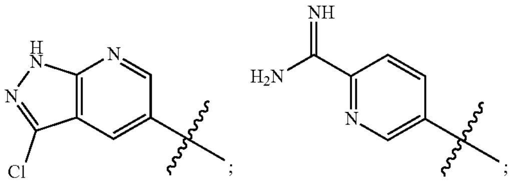
;
;

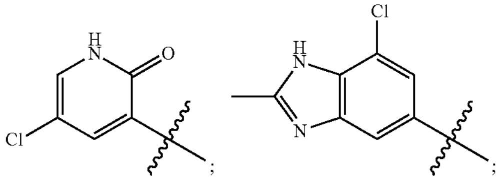
;
;

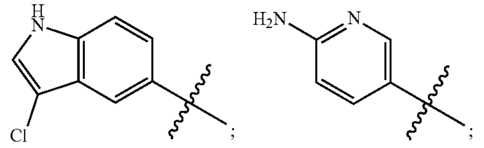
;
;

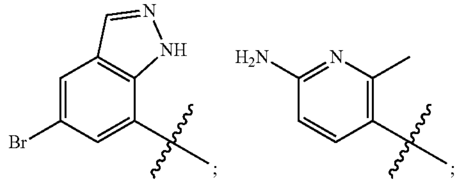
;
;

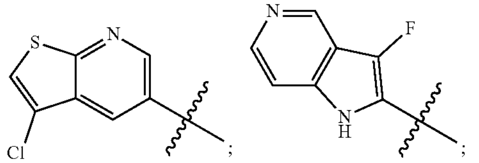
;
;

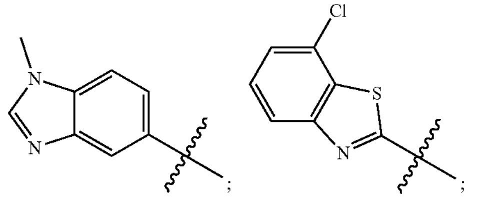
;
;

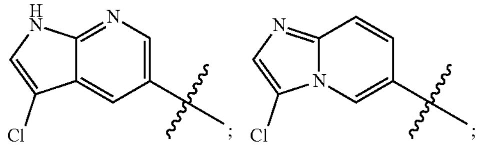
;
;

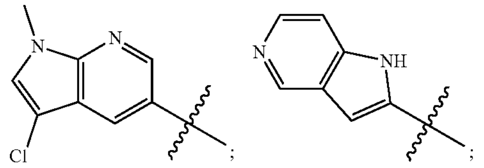
;
;

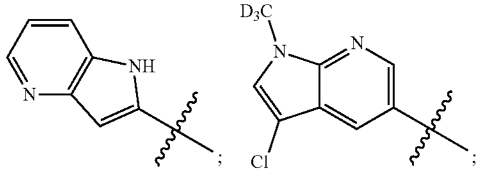
;
;

-continued

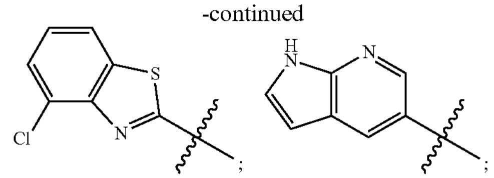
;
;

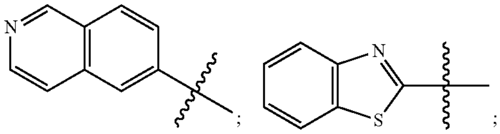
;
;

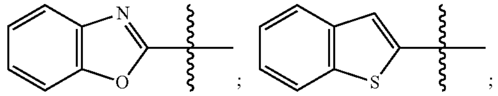
;
;

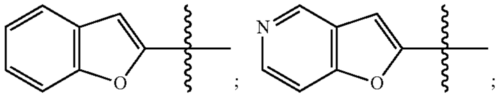
;
;

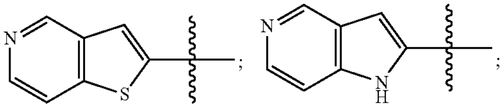
;
;

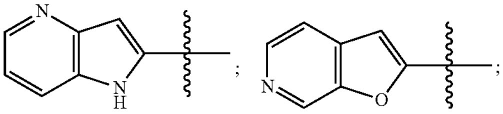
;
;

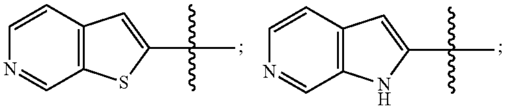
;
;

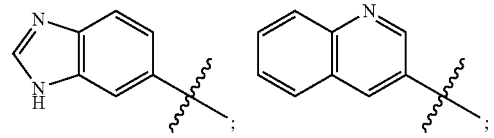
;
;

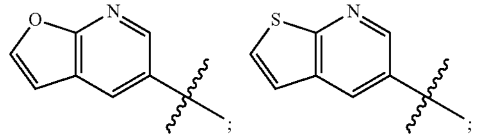
;
;

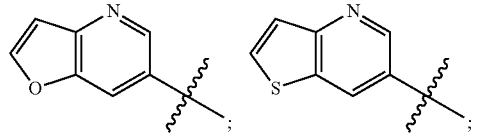
;
;

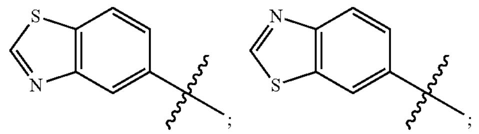
;
;

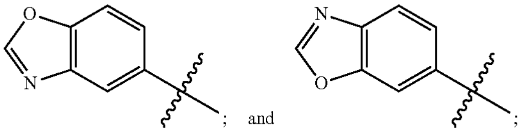
; and
;

wherein the substituted or unsubstituted cycloalkyl of $R^1$ is a C3-C6 cycloalkyl monocyclic or polycyclic ring system, which is saturated or unsaturated, and which can comprise fused or bridged ring systems, and the substituted cycloalkyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heterocyclyl of $R^1$ is a 4-10 membered monocyclic, bicyclic, tricyclic, or tetracyclic ring system consisting of carbon atoms and one to six heteroatoms selected from the group consisting of nitrogen, oxygen, and sulfur, and which can comprise fused, bridged, and spiro ring systems, and the substituted heterocyclyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

$R^{2a}$, $R^{2b}$, $R^{2c}$, and $R^{2d}$ are each independently selected from the group consisting of hydrogen, halo, $C(=O)OR^5$, $OC(=O)R^5$, hydroxyalkyl, alkoxy, alkoxyalkyl, haloalkoxy, cyano, aminylalkyl, carboxyalkyl, $NR^5R^6$, $C(=O)NR^5R^6$, $N(R^5)C(=O)R^6$, $NR^5C(=O)NR^6$, $S(O)_2SR^5$, nitro, $N(R^5)C(O)OR^6$, $C(=NR^5)NR_6R^7$, $N(R^5)C(=NR^6)NR^7R^8$, $S(O)R^5$, $S(O)NR^5R^6$, $S(O)_2R^5$, $N(R^5)S(O)_2R^6$, $S(O)_2NR^5R^6$, aryl, heteroaryl, heterocyclyl, and cycloalkyl, or $R^{2a}$ and $R^{2b}$, or $R^{2c}$ and $R^{2d}$, together are oxo, and provided that at least one of $R^{2a}$, $R^{2b}$, $R^{2c}$, and $R^{2d}$ is not hydrogen;

$R^3$ is $NR^{3a}R^{3b}$;

$R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)_2$; or $R^{3a}$ and $R^{3b}$, together with the nitrogen to which they are attached, form a 5-7 membered heteroaryl or a 4-7 membered heterocyclyl; or $R^{3a}$ and $R^4$ together with the nitrogen and carbon to which they are attached, respectively, form a 4-7 membered heterocyclyl, and $R^{3b}$ is hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)_2$;

$R^4$ is an aryl, a heteroaryl, a cycloalkyl, or a heterocyclyl when n is 2, 3, 4, 5, or 6, or $R^4$ is a monocyclic heteroaryl, or a heterocyclyl when n is 0 or 1, wherein the aryl of $R^4$ is selected from the group consisting of:

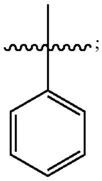;
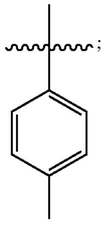;
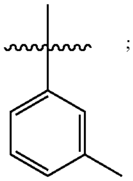;
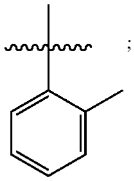;

-continued
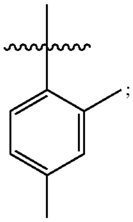
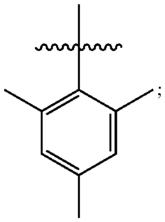
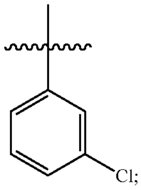
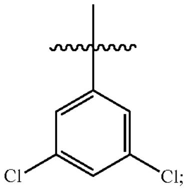
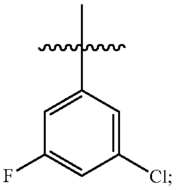
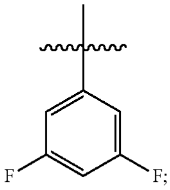
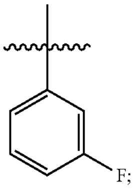
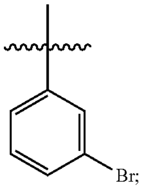
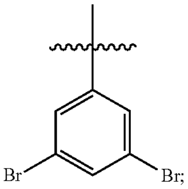
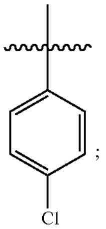
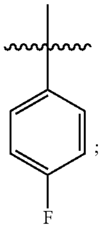
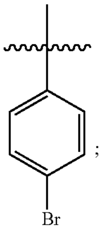
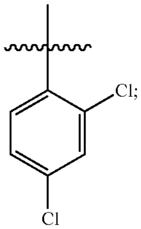
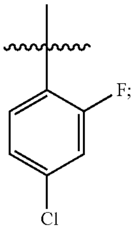
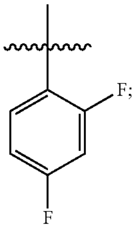
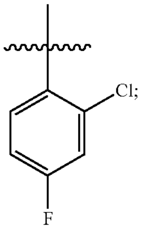
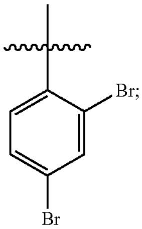
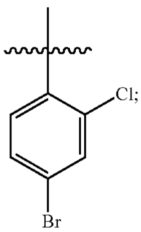
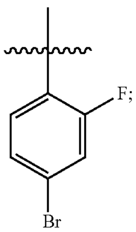
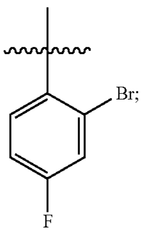
-continued
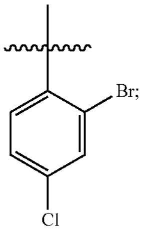
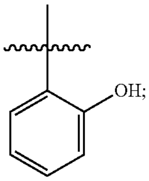
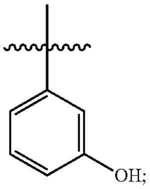
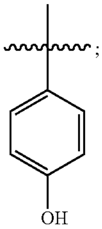
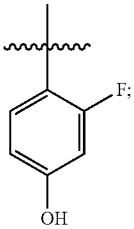
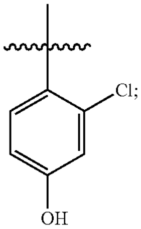
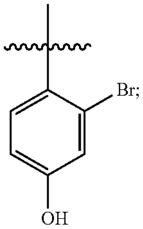
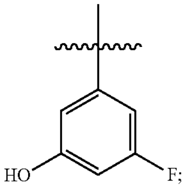
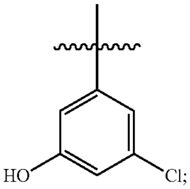
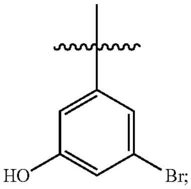
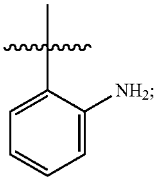
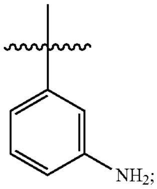
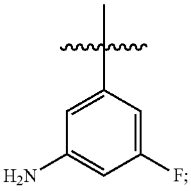
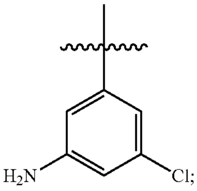
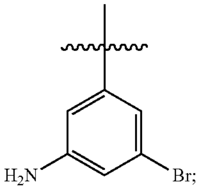
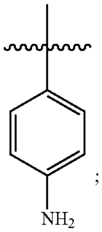
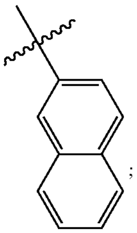

-continued
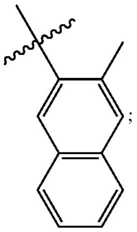
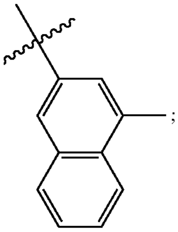
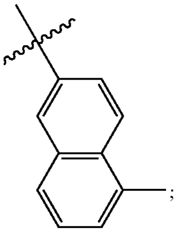
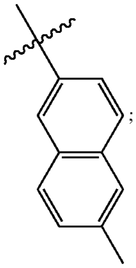
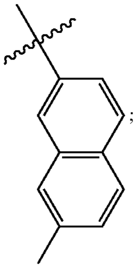
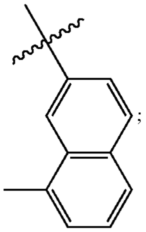
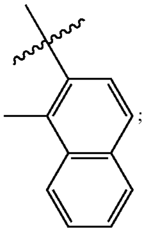
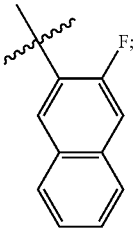
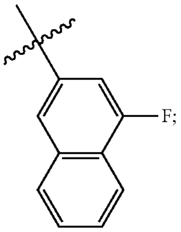
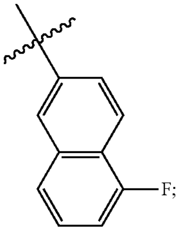
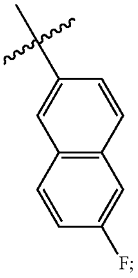
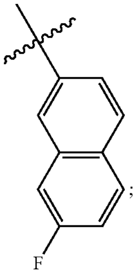
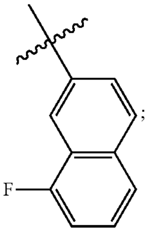
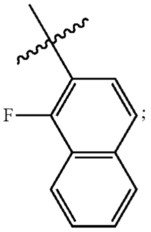
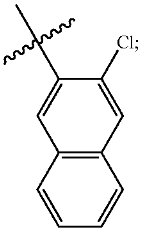
-continued
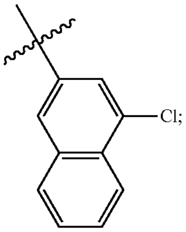
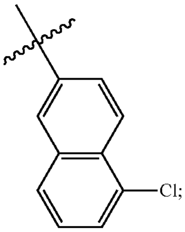
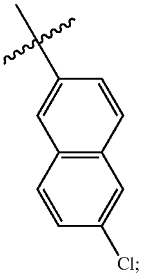
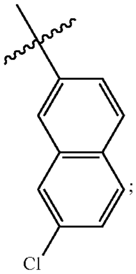
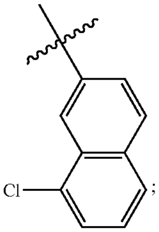
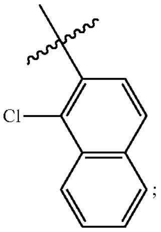
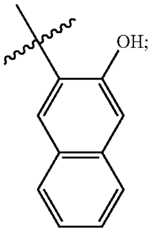
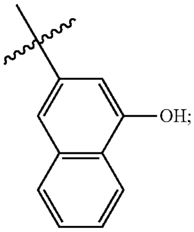
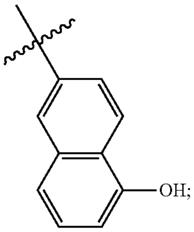
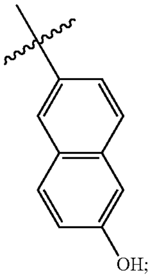
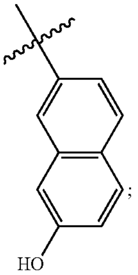
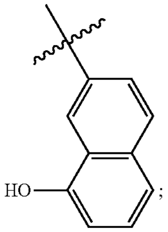
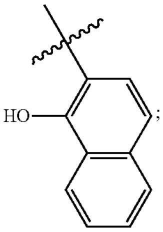
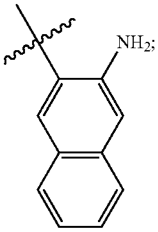
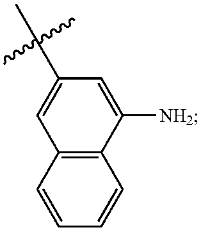

-continued

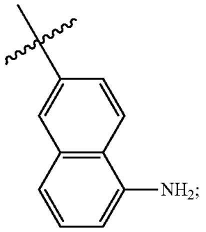;
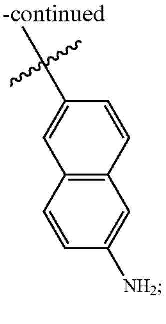;
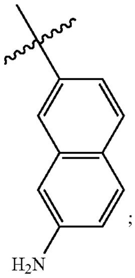;
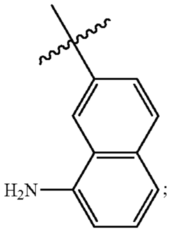;
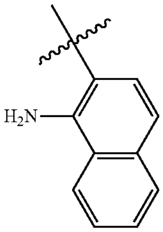;
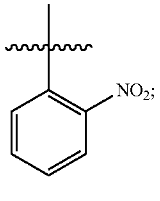;
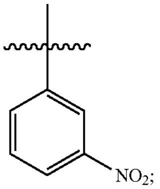; and
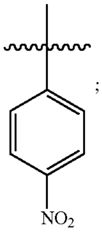;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3, and wherein the aryl of $R^{2a}$, $R^{2b}$, $R^{2c}$, and $R^{2d}$ is a 6- to 18-membered monocyclic, bicyclic, tricyclic, or tetracyclic ring system comprising at least one aromatic ring, and which can comprise fused or bridged ring systems, wherein the heteroaryl of $R^{2a}$, $R^{2b}$, $R^{2c}$, $R^{2d}$, $R^{3a}$, $R^{3b}$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is a 5- to 14-membered monocyclic, bicyclic, tricyclic, or tetracyclic ring system comprising at least one aromatic ring and one to six heteroatoms selected from the group consisting of nitrogen, oxygen, and sulfur, and which can comprise fused or bridged ring systems, wherein the heterocyclyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 18-membered monocyclic, bicyclic, tricyclic, or tetracyclic ring system consisting of two to twelve carbon atoms and one to six heteroatoms selected from the group consisting of nitrogen, oxygen, and sulfur, and which can comprise fused, bridged, and spiro ring systems, and wherein the cycloalkyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 15-membered monocyclic or polycyclic ring system, which is saturated or unsaturated, and which can comprise fused or bridged ring systems.

16. A compound having the following Structure (I"):

(I")

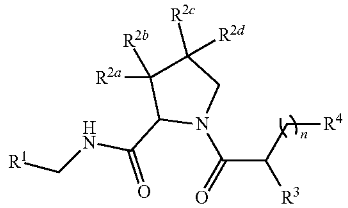

or a stereoisomer, tautomer, or pharmaceutically acceptable salt thereof, wherein:

$R^1$ is a substituted phenyl, a substituted or unsubstituted heteroaryl, a substituted or unsubstituted cycloalkyl, or a substituted or unsubstituted heterocyclyl;

wherein the substituted phenyl of $R^1$ is substituted with one or more of $R^{1a}$, $R^{1b}$, $R^{1c}$, $R^{1d}$ and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C({=}NR^9)NR^{10}R^{11}$, $C({=}NOR^9)NR^{10}R^{11}$, $C({=}NOC(O)R^9)NR^{10}R^{11}$, $C({=}NR^9)N(R^{10})C(O)OR^{11}$, $N(R^9)C({=}NR^{10})NR^{11}R^{12}$, $S(O)R^{-}$, $S(O)NR^9R^{10}$, $S(O)_2R^9$, $N(R^9)S(O)_2R^{10}$, $S(O)_2NR^9R^{10}$, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C({=}NR^{13})NR^{14}R^{15}$, $NR^{13}C({=}NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heteroaryl of $R^1$ is a 5-10 membered heteroaryl selected from the group consisting of:

-continued

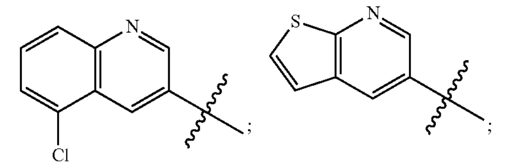

; ;

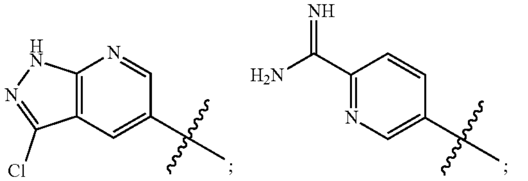

; ;

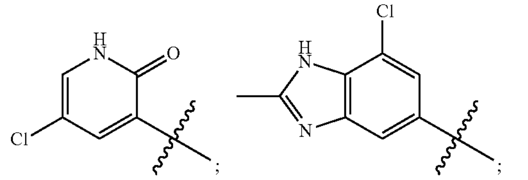

; ;

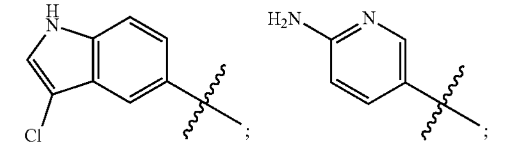

; ;

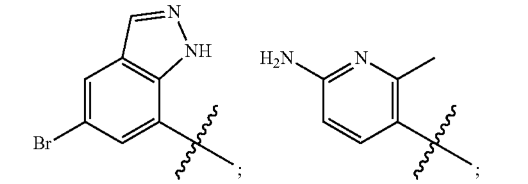

; ;

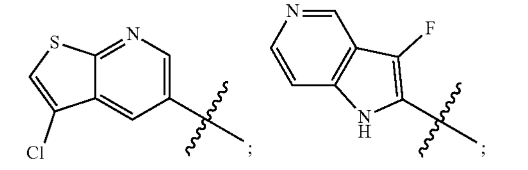

; ;

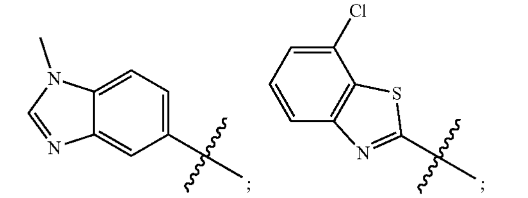

; ;

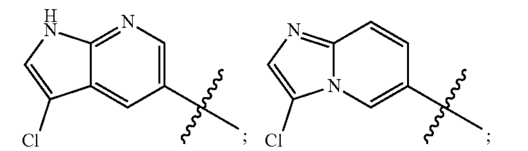

; ;

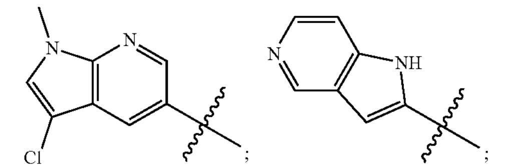

; ;

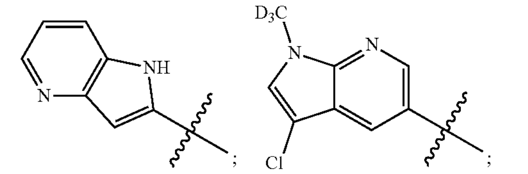

; ;

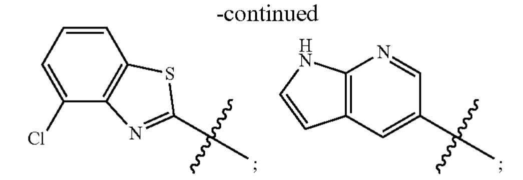

; ;

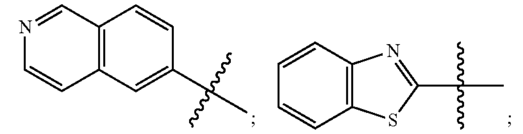

; ;

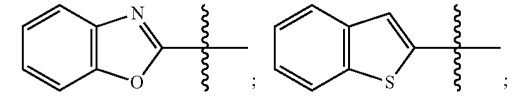

; ;

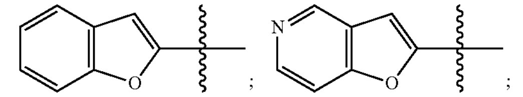

; ;

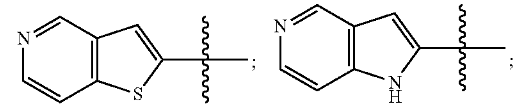

; ;

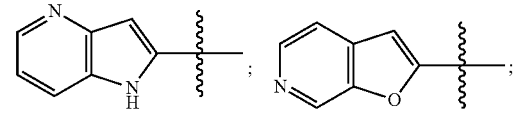

; ;

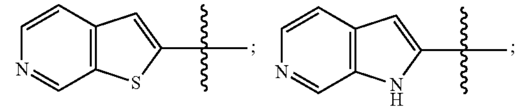

; ;

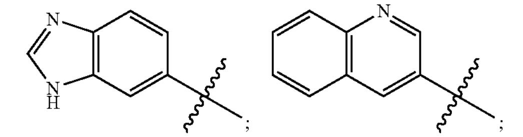

;

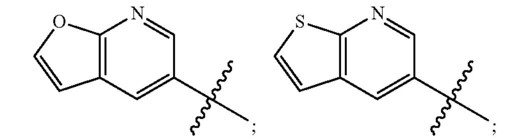

; ;

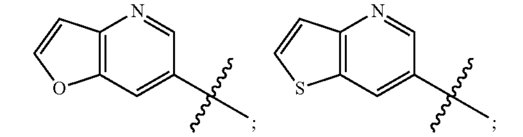

; ;

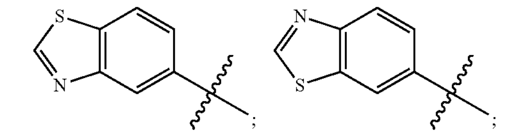

; ;

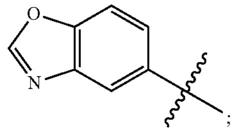

; and

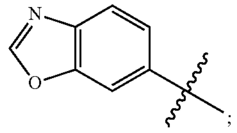

;

wherein the substituted or unsubstituted cycloalkyl of $R^1$ is a C3-C6 cycloalkyl monocyclic or polycyclic ring system, which is saturated or unsaturated, and which can comprise fused or bridged ring systems, and the substituted cycloalkyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heterocyclyl of $R^1$ is a 4-10 membered monocyclic, bicyclic, tricyclic, or tetracyclic ring system consisting of carbon atoms and one to six heteroatoms selected from the group consisting of nitrogen, oxygen, and sulfur, and which can comprise fused, bridged, and spiro ring systems, and the substituted heterocyclyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

$R^{2a}$, $R^{2b}$, $R^{2c}$, and $R^{2d}$ are each independently selected from the group consisting of hydrogen, halo, $C(=O)OR^5$, $OC(=O)R^5$, hydroxyalkyl, alkoxy, alkoxyalkyl, haloalkoxy, cyano, aminylalkyl, carboxyalkyl, $NR^5R^6$, $C(=O)NR^5R^6$, $N(R^5)C(=O)R^6$, $NR^5$, $C(=O)NR^6$, $S(O)_t$, $SR^5$, nitro, $N(R^5)C(O)OR^6$, $C(=NR^5)NR^6R^7$, $N(R^5)C(=NR^6)NR^7R^8$, $S(O)R^5$, $S(O)NR^5R^6$, $S(O)_2R^5$, $N(R^5)S(O)_2R^6$, $S(O)_2NR^5R^6$, aryl, heteroaryl, heterocyclyl, and cycloalkyl, or $R^{2a}$ and $R^{2b}$, or $R^{2c}$ and $R^{2d}$, together are oxo, and provided that at least one of $R^{2a}$, $R^{2b}$, $R^{2c}$, and $R^{2d}$ is not hydrogen;

$R^3$ is $NR^{3a}R^{3b}$;

$R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)_2$; or $R^{3a}$ and $R^{3b}$, together with the nitrogen to which they are attached, form a 5-7 membered heteroaryl or a 4-7 membered heterocyclyl; or $R^{3a}$ and $R^4$ together with the nitrogen and carbon to which they are attached, respectively, form a 4-7 membered heterocyclyl, and $R^{3b}$ is hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)$ 2;

$R^4$ is an aryl, a heteroaryl, a cycloalkyl, or a heterocyclyl when n is 2, 3, 4, 5, or 6; or $R^4$ is a monocyclic heteroaryl, or a heterocyclyl when n is 0 or 1; or $R^4$ and $R^{3a}$ together with the carbon and nitrogen to which they are attached, respectively, form a 4-7 membered heterocyclyl;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is 0, 1, or 2; and t is an integer from 1-3, and wherein the aryl of $R^{2a}$, $R^{2b}$, $R^{2c}$, $R^{2d}$, $R^4$ is a 6- to 18-membered monocyclic, bicyclic, tricyclic, or tetracyclic ring system comprising at least one aromatic ring, and which can comprise fused or bridged ring systems, wherein the heteroaryl of $R^{2a}$, $R^{2b}$, $R^{2c}$, $R^{2d}$, $R^{3a}$, $R^{3b}$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is a 5- to 14-membered monocyclic, bicyclic, tricyclic, or tetracyclic ring system comprising at least one aromatic ring and one to six heteroatoms selected from the group consisting of nitrogen, oxygen, and sulfur, and which can comprise fused or bridged ring systems, wherein the heterocyclyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 18-membered monocyclic, bicyclic, tricyclic, or tetracyclic ring system consisting of two to twelve carbon atoms and one to six heteroatoms selected from the group consisting of nitrogen, oxygen, and sulfur, and which can comprise fused, bridged, and spiro ring systems, and wherein the cycloalkyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 15-membered monocyclic or polycyclic ring system, which is saturated or unsaturated, and which can comprise fused or bridged ring systems.

17. A compound having one of the following structures:

(IA)

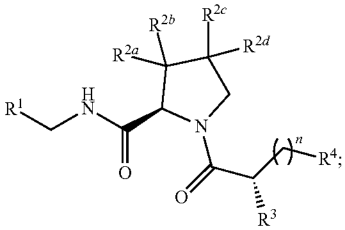

;

(IB)

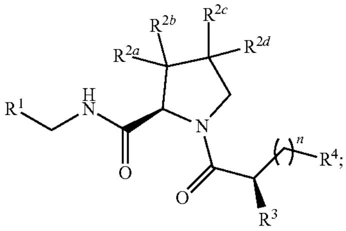

;

(IC)

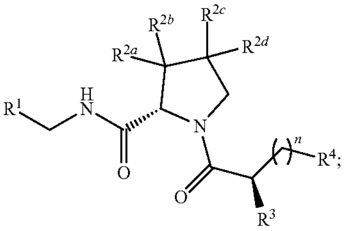

; or (ID)

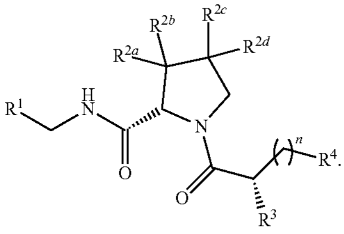

.

or a stereoisomer, tautomer, or pharmaceutically acceptable salt thereof, wherein:

$R^1$ is a substituted phenyl, a substituted or unsubstituted heteroaryl, a substituted or unsubstituted cycloalkyl, or a substituted or unsubstituted heterocyclyl;

wherein the substituted phenyl of $R^1$ is substituted with one or more of $R^{1a}$, $R^{1b}$, $R^{1c}$, $R^{1d}$ and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R$ 12, $S(O)R^9$, $S(O)NR^9R^{10}$, $S(O)_2R^9$, $N(R^9)S(O)_2R^{10}$, $S(O)_2NR^9R^{10}$, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}C(O)R^{14}$, $NR^{13}R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heteroaryl of $R^1$ is a 5-10 membered heteroaryl selected from the group consisting of:

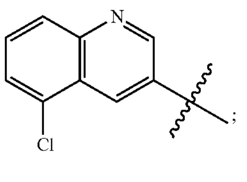

;

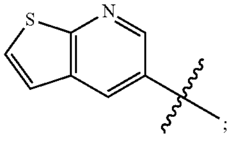

;

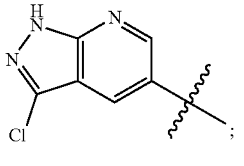

;

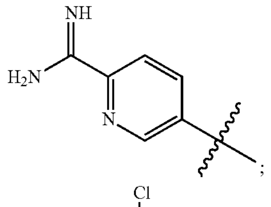

;

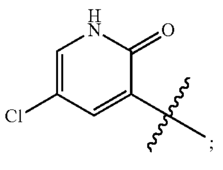

;

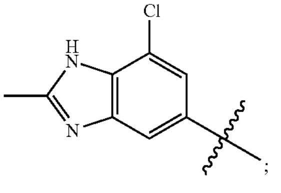

;

-continued

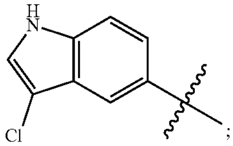 ; 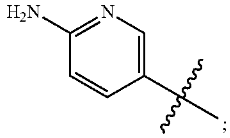 ;

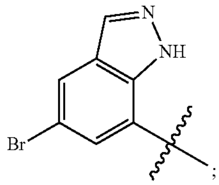 ; 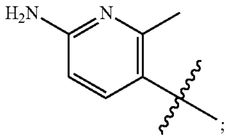 ;

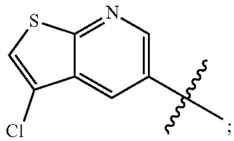 ; 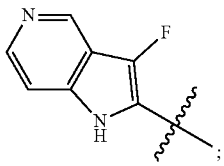 ;

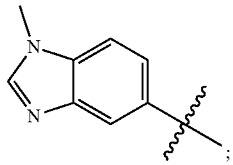 ; 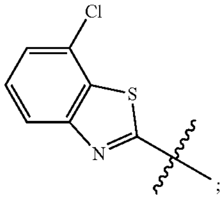 ;

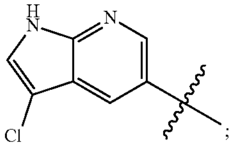 ; 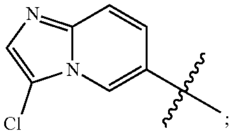 ;

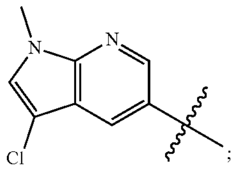 ; 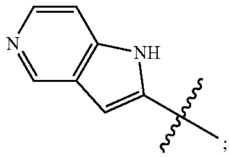 ;

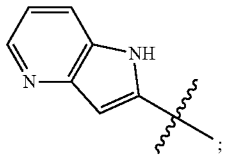 ; 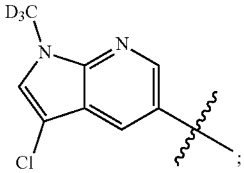 ;

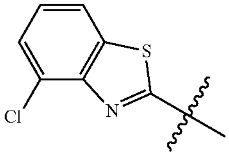 ; 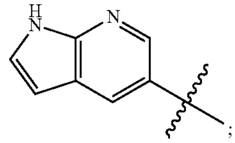 ;

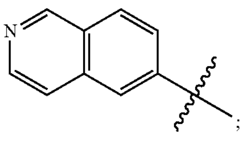 ; 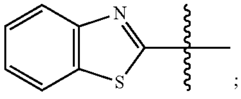 ;

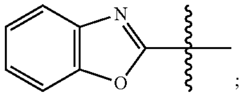 ; 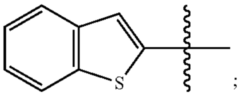 ;

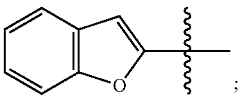 ; 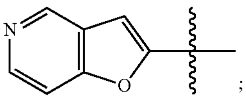 ;

-continued

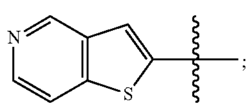 ; 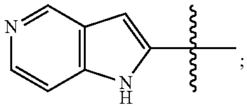 ;

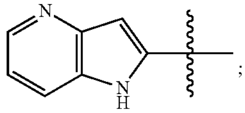 ; 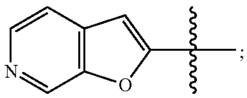 ;

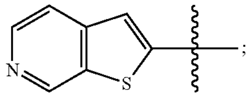 ; 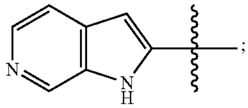 ;

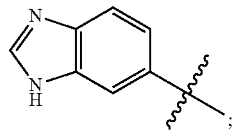 ; 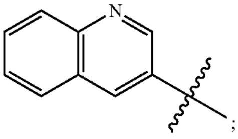 ;

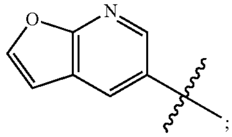 ; 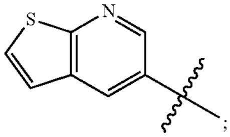 ;

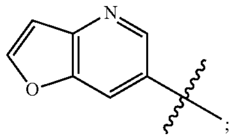 ; 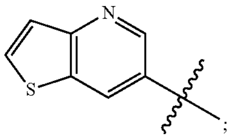 ;

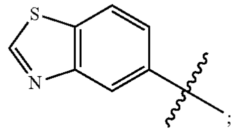 ; 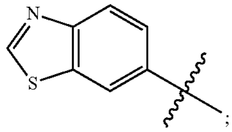 ;

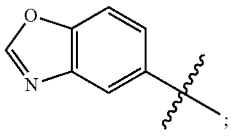 ; and 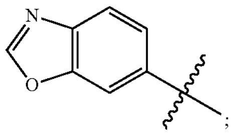 ;

wherein the substituted or unsubstituted cycloalkyl of $R^1$ is a C3-C6 cycloalkyl monocyclic or polycyclic ring system, which is saturated or unsaturated, and which can comprise fused or bridged ring systems, and the substituted cycloalkyl of $R^1$ is substituted with one or more of $R^{1a}$, $R^{1b}$, $R^{1c}$, $R^{1d}$, and $R^{1e}$, wherein $R^{1a}$, $R^{1b}$, $R^1$, $R^{1d}$, and $R^{1e}$ are independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR_9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C({=}NR^{13})NR^{14}R^{15}$, $NR^{13}C({=}NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heterocyclyl of $R^1$ is a 4-10 membered monocyclic, bicyclic, tricyclic, or tetracyclic ring system consisting of carbon atoms and one to six heteroatoms selected from the group consisting of nitrogen, oxygen, and sulfur, and which can comprise fused, bridged, and spiro ring systems, and the substituted heterocyclyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C({=}NR^9)NR^{10}R^{11}$, $C({=}NOR^9)NR^{10}R^{11}C({=}NOC(O)R^9)NR^{10}R^{11}$, $C({=}NR^9)N(R^{10})C(O)OR^{11}$, $N(R^9)C({=}NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)NR^{13}R^{14}$, $OC(O)R^{13}$, NR $13R^{14}$, $NR^{13}C(O)R^{14}$, $NR^{13}C(O)NR^{14}R^{15}$, $NR^{13}C(O)OR^{14}$, $C({=}NR^{13})NR^{14}R^{15}$, $NR^{13}C({=}NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

$R^{2a}$, $R^{2b}$, $R^{2c}$, and $R^{2d}$ are each independently selected from the group consisting of hydrogen, halo, $C({=}O)OR^5$, $OC({=}O)R^5$, hydroxyalkyl, alkoxy, alkoxyalkyl, haloalkoxy, cyano, aminylalkyl, carboxyalkyl, $NR^5R^6$, $C({=}O)NR^5R^6$, $N(R^5)C({=}O)R^6$, $NR^6$, $C({=}O)NR^6$, $S(O)_t$, $SR^5$, nitro, $N(R^5)C(O)OR^6$, $C({=}NR^5)NR^6R^7$, $N(R^5)C({=}NR^6)NR^7R^8$, $S(O)R^5$, $S(O)NR^5R^6$, $S(O)_2R^5$, $N(R^5)S(O)_2R^6$, $S(O)_2NR^5R^6$, aryl, heteroaryl, heterocyclyl, and cycloalkyl, or $R^{2a}$ and $R^{2b}$, or $R^{2c}$ and $R^{2d}$, together are oxo, and provided that at least one of $R^{2a}$, $R^{2b}$, $R^{2c}$, and $R^{2d}$ is not hydrogen;

$R^3$ is $NR^{3a}R^{3b}$;

$R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC({=}O)OR^6$, or $(CH_2)_nP({=}O)(OR^6)_2$; or $R^{3a}$ and $R^{3b}$, together with the nitrogen to which they are attached, form a 5-7 membered heteroaryl or a 4-7 membered heterocyclyl; or $R^{3a}$ and $R^4$ together with the nitrogen and carbon to which they are attached, respectively, form a 4-7 membered heterocyclyl, and $R^{3b}$ is hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC({=}O)OR^6$, or $(CH_2)_nP({=}O)(OR^6)_2$;

$R^4$ is an aryl, a heteroaryl, a cycloalkyl, or a heterocyclyl when n is 2, 3, 4, 5, or 6; or $R^4$ is a monocyclic heteroaryl, or a heterocyclyl when n is 0 or 1; or $R^4$ and $R^{3a}$ together with the carbon and nitrogen to which they are attached, respectively, form a 4-7 membered heterocyclyl;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3, and wherein the aryl of $R^{2a}$, $R^{2b}$, $R^{2c}$, $R^{2d}$, $R^4$ is a 6- to 18-membered monocyclic, bicyclic, tricyclic, or tetracyclic ring system comprising at least one aromatic ring, and which can comprise fused or bridged ring systems, wherein the heteroaryl of $R^{2a}$, $R^{2b}$, $R^{2c}$, $R^{2d}$, $R^{3a}$, $R^{3b}$, $R^4$, $R^5$, $R^6$, $R^7$, $R^8$, $R^9$, $R^{10}$, $R^{11}$, R 12, $R^{13}$, $R^{14}$, $R^{15}$, and $R^{16}$ is a 5- to 14-membered monocyclic, bicyclic, tricyclic, or tetracyclic ring system comprising at least one aromatic ring and one to six heteroatoms selected from the group consisting of nitrogen, oxygen, and sulfur, and which can comprise fused or bridged ring systems, wherein the heterocyclyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 18-membered monocyclic, bicyclic, tricyclic, or tetracyclic ring system consisting of two to twelve carbon atoms and one to six heteroatoms selected from the group consisting of nitrogen, oxygen, and sulfur, and which can comprise fused, bridged, and spiro ring systems, and wherein the cycloalkyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 15-membered monocyclic or polycyclic ring system, which is saturated or unsaturated, and which can comprise fused or bridged ring systems.

18. A compound having the following Structure (I"):

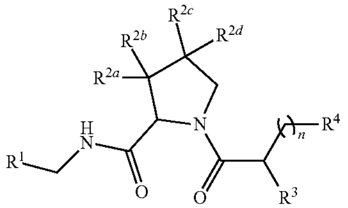

(I''')

or a stereoisomer, tautomer, or pharmaceutically acceptable salt thereof, wherein:

$R^1$ is a substituted phenyl, a substituted or unsubstituted heteroaryl, a substituted or unsubstituted cycloalkyl, or a substituted or unsubstituted heterocyclyl;

wherein the substituted phenyl of $R^1$ is substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)NR^{13}R^{14}$, $OC(O)R^{13}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heteroaryl of $R^1$ is a 5-10 membered heteroaryl selected from the group consisting of:

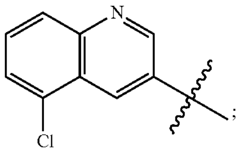 ; 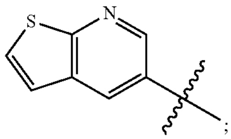 ;

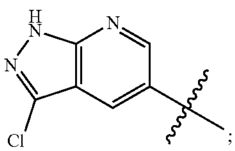 ; 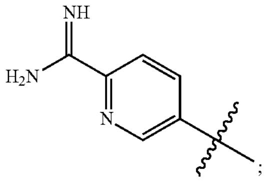 ;

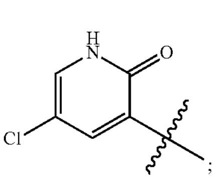 ; 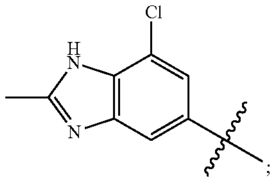 ;

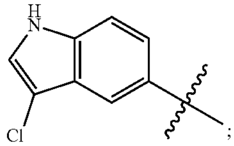 ; 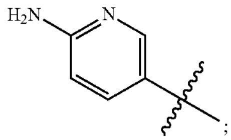 ;

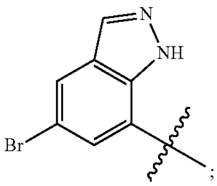 ; 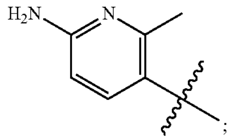 ;

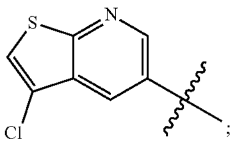 ; 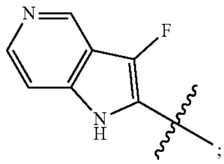 ;

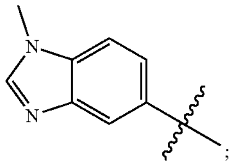 ; 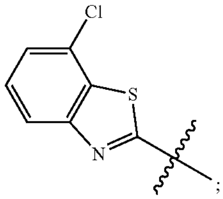 ;

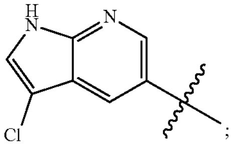 ; 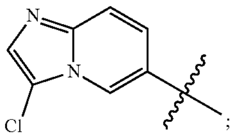 ;

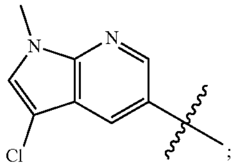 ; 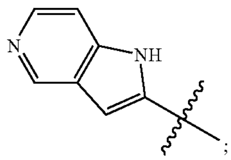 ;

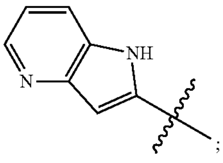 ; 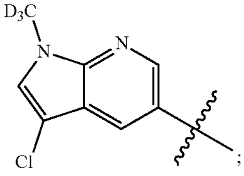 ;

-continued

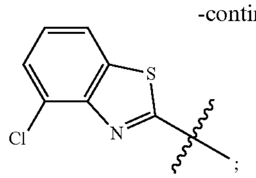 ; 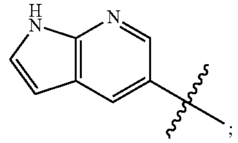 ;

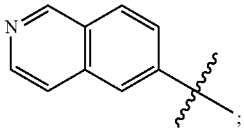 ; 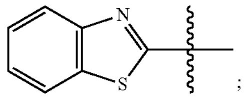 ;

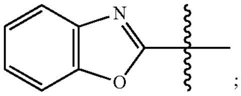 ; 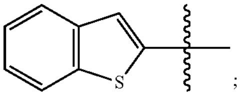 ;

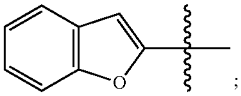 ; 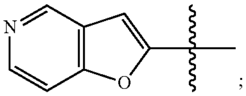 ;

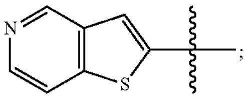 ; 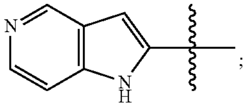 ;

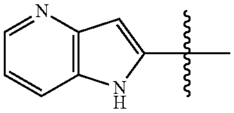 ; 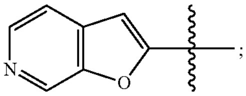 ;

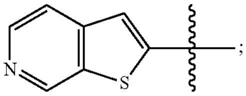 ; 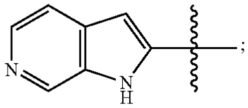 ;

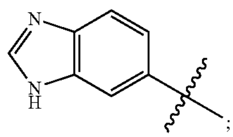 ; 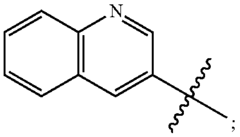 ;

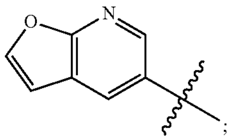 ; 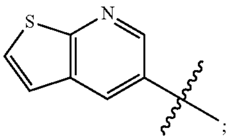 ;

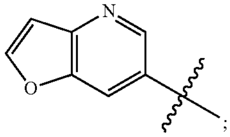 ; 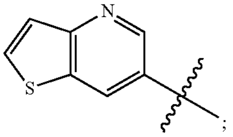 ;

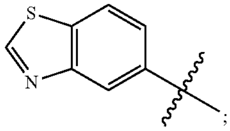 ; 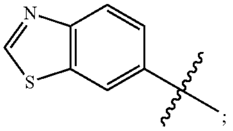 ;

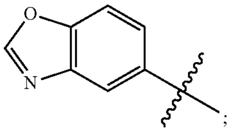 ; and 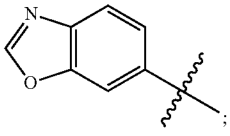 ;

wherein the substituted or unsubstituted cycloalkyl of $R^1$ is a C3-C6 cycloalkyl monocyclic or polycyclic ring system, which is saturated or unsaturated, and which can comprise fused or bridged ring systems, and the substituted cycloalkyl of $R^1$ is substituted with one or more of $R^{1a}$, $R^{1b}$, $R^{1c}$, $R^{1d}$, and $R^{1e}$, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}S(O)R^9$, $S(O)NR^9R^{10}$, $S(O)_2R^9$, $N(R^9)S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

wherein the substituted or unsubstituted heterocyclyl of $R^1$ is a 4-10 membered monocyclic, bicyclic, tricyclic, or tetracyclic ring system consisting of carbon atoms and one to six heteroatoms selected from the group consisting of nitrogen, oxygen, and sulfur, and which can comprise fused, bridged, and spiro ring systems, and the substituted heterocyclyl of $R^1$ is substituted with one or more of $R^{1a}$, $R^{1b}$, $R^{1c}$, $R^{1d}$, and Rle, wherein $R^{1a}$, $R^{1b}$, $R^{1c}$, $R^{1d}$, and $R^{1e}$ are independently selected from the group consisting of $C_{1-6}$ alkyl, $C_{2-6}$ alkenyl, $C_{2-6}$ alkynyl, halo, C-6 haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)$ $S(O)_2R^{10}$, $S(O)_2NR^9R^{10}$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the $R^{1a}$, $R^{1b}$, $R^{1c}$, $R^{1d}$, and $R^{1e}$ are independently unsubstituted or substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$ $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, and $S(O)_2NR^{13}R^{14}$ when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, and wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

at least one of $R^{2a}$, $R^{2b}$, $R^{2c}$, and $R^{2d}$ is alkoxy, alkoxyalkyl, cyano, halo, $C(=O)OR^5$, $OC(=O)R^5$, $C(=O)NR^5R^6$, $N(R^5)C(=O)R^6$, aryl, heteroaryl, heterocyclyl, or $C(=O)N(R^5)$ heterocyclyl, wherein $R^5$ and $R^6$ are, at each occurrence, independently hydrogen or $C_1$-$C_6$ alkyl;

$R^3$ is $NR^{3a}R$ 3b, $R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)$ 2; or $R^{3a}$ and $R^{3b}$, together with the nitrogen to which they are attached, form a 5-7 membered heteroaryl or a 4-7 membered heterocyclyl; or $R^{3a}$ and $R^4$ together with the nitrogen and carbon to which they are attached, respectively, form a 4-7 membered heterocyclyl, and $R^{3b}$ is hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^6$, or $(CH_2)_nP(=O)(OR^6)_2$;

$R^4$ is an aryl, a heteroaryl, a cycloalkyl, or a heterocyclyl when n is 2, 3, 4, 5, or 6; or $R^4$ is a monocyclic heteroaryl, or a heterocyclyl when n is 0 or 1; or $R^4$ and $R^{3a}$ together with the carbon and nitrogen to which they are attached, respectively, form a 4-7 membered heterocyclyl;

$R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;

n is an integer from 0-6; and t is an integer from 1-3, and wherein the aryl of $R^{2a}$, $R^{2b}$, $R^{2c}$, $R^{2d}$, $R^4$ is a 6- to 18-membered monocyclic, bicyclic, tricyclic, or tetracyclic ring system comprising at least one aromatic ring, and which can comprise fused or bridged ring systems, wherein the heteroaryl of $R^{2a}$, $R^{2b}$, $R^{2c}$, $R^{2d}$, $R^{3a}$, $R^{3b}$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is a 5- to 14-membered monocyclic, bicyclic, tricyclic, or tetracyclic ring system comprising at least one aromatic ring and one to six heteroatoms selected from the group consisting of nitrogen, oxygen, and sulfur, and which can comprise fused or bridged ring systems, wherein the heterocyclyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 18-membered monocyclic, bicyclic, tricyclic, or tetracyclic ring system consisting of two to twelve carbon atoms and one to six heteroatoms selected from the group consisting of nitrogen, oxygen, and sulfur, and which can comprise fused, bridged, and spiro ring systems, and wherein the cycloalkyl of $R^{2a}$, $R^{2b}$, $R^{2c}$, $R^{2d}$, $R^{3a}$, $R^{3b}$, $R^4$, $R^5$, $R^6$, $R^7$, and $R^8$ is a 3- to 15-membered monocyclic or polycyclic ring system, which is saturated or unsaturated, and which can comprise fused or bridged ring systems.

* * * * *